US010624351B2

(12) United States Patent
Riley et al.

(10) Patent No.: US 10,624,351 B2
(45) Date of Patent: Apr. 21, 2020

(54) MODULATED NUTRITIONAL QUALITY TRAITS IN SEEDS

(71) Applicant: Indigo Ag, Inc., Boston, MA (US)

(72) Inventors: Raymond Riley, Woodbury, MN (US); Slavica Djonovic, Malden, MA (US); Nancy Vosnidou, West Des Moines, IA (US); Vasileios Bitas, Somerville, MA (US)

(73) Assignee: Indigo Ag, Inc., Boston, MA (US)

( * ) Notice: Subject to any disclaimer, the term of this patent is extended or adjusted under 35 U.S.C. 154(b) by 122 days.

(21) Appl. No.: 15/829,631

(22) Filed: Dec. 1, 2017

(65) Prior Publication Data

US 2018/0153174 A1 Jun. 7, 2018

Related U.S. Application Data

(60) Provisional application No. 62/429,014, filed on Dec. 1, 2016, provisional application No. 62/429,009, filed on Dec. 1, 2016, provisional application No. 62/429,007, filed on Dec. 1, 2016, provisional application No. 62/429,004, filed on Dec. 1, 2016, provisional application No. 62/433,095, filed on Dec. 12, 2016.

(51) Int. Cl.
C12N 15/82 (2006.01)
A01N 63/04 (2006.01)
A01H 17/00 (2006.01)
A01H 3/00 (2006.01)
A01H 5/10 (2018.01)

(52) U.S. Cl.
CPC ............... *A01N 63/04* (2013.01); *A01H 3/00* (2013.01); *A01H 5/10* (2013.01); *A01H 17/00* (2013.01)

(58) Field of Classification Search
None
See application file for complete search history.

(56) References Cited

U.S. PATENT DOCUMENTS

| | | | |
|---|---|---|---|
| 2,200,532 A | 5/1940 | Sherman | |
| 4,940,834 A | 7/1990 | Hurley et al. | |
| 5,041,290 A | 8/1991 | Gindrat et al. | |
| 5,113,619 A | 5/1992 | Leps et al. | |
| 5,229,291 A | 7/1993 | Nielsen et al. | |
| 5,292,507 A | 3/1994 | Charley | |
| 5,415,672 A | 5/1995 | Fahey et al. | |
| 5,730,973 A | 3/1998 | Morales et al. | |
| 5,919,447 A | 7/1999 | Marrone et al. | |
| 5,994,117 A | 11/1999 | Bacon et al. | |
| 6,072,107 A | 6/2000 | Latch et al. | |
| 6,077,505 A | 6/2000 | Parke et al. | |
| 6,337,431 B1 | 1/2002 | Tricoli et al. | |
| 6,495,133 B1 | 12/2002 | Xue | |
| 6,602,500 B1 | 8/2003 | Kharbanda et al. | |
| 6,681,186 B1 | 1/2004 | Denisov et al. | |
| 6,689,880 B2 | 2/2004 | Chen et al. | |
| 6,823,623 B2 | 11/2004 | Minato et al. | |
| 7,037,879 B2 | 5/2006 | Imada et al. | |
| 7,084,331 B2 | 8/2006 | Isawa et al. | |
| 7,335,816 B2 | 2/2008 | Kraus et al. | |
| 7,341,868 B2 | 3/2008 | Chopade et al. | |
| 7,485,451 B2 | 2/2009 | VanderGheynst et al. | |
| 7,555,990 B2 | 7/2009 | Beaujot | |
| 7,632,985 B2 | 12/2009 | Malven et al. | |
| 7,763,420 B2 | 7/2010 | Stritzker et al. | |
| 7,906,313 B2 | 3/2011 | Henson et al. | |
| 7,977,550 B2 | 7/2011 | West et al. | |
| 8,143,045 B2 | 3/2012 | Miansnikov et al. | |
| 8,455,198 B2 | 6/2013 | Gao et al. | |
| 8,455,395 B2 | 6/2013 | Miller et al. | |
| 8,465,963 B2 | 6/2013 | Rolston et al. | |
| 8,728,459 B2 | 5/2014 | Isawa et al. | |
| 8,975,489 B2 | 3/2015 | Craven | |
| 9,049,814 B2 | 6/2015 | Marx et al. | |
| 9,113,636 B2 | 8/2015 | von Maltzahn et al. | |
| 9,277,751 B2 | 3/2016 | Sword | |
| 9,288,995 B2 | 3/2016 | von Maltzahn et al. | |
| 9,295,263 B2 | 3/2016 | von Maltzahn et al. | |
| 9,364,005 B2 | 6/2016 | Mitter et al. | |
| 9,408,394 B2 | 8/2016 | von Maltzahn et al. | |
| 9,532,572 B2 | 1/2017 | von Maltzahn et al. | |
| 9,532,573 B2 | 1/2017 | von Maltzahn et al. | |
| 9,545,111 B2 | 1/2017 | Sword | |
| 9,622,485 B2 | 4/2017 | von Maltzahn et al. | |
| 9,652,840 B1 | 5/2017 | Shriver et al. | |
| 9,687,001 B2 | 6/2017 | Vujanovic et al. | |
| 9,756,865 B2 | 9/2017 | Sword | |

(Continued)

FOREIGN PATENT DOCUMENTS

| | | |
|---|---|---|
| CA | 1041788 | 11/1978 |
| CA | 1229497 | 11/1987 |

(Continued)

OTHER PUBLICATIONS

Pacovsky (Physiologia Pantarium; 75:346-354, 1989).*
Gabor et al. (Journal of Plant Nutrition, 20:4-5, 581-591, 1997).*
Gropper et al. (Mol Ecol., 8:1827-1835, 1999).*
PCT Invitation to Pay Additional Fees, PCT Application No. PCT/CA2013/000091, dated Mar. 27, 2013, 2 Pages.
PCT International Search Report and Written Opinion for PCT/CA2013/000091, dated Sep. 20, 2013, 17 Pages.

(Continued)

Primary Examiner — Vinod Kumar
(74) Attorney, Agent, or Firm — Goodwin Procter LLP

(57) ABSTRACT

This invention relates to methods and materials for modulating seed nutritional quality traits of seeds produced by a wheat, cotton, soybean, or maize plant, said plant having been heterologously disposed to, or grown from, a plant element treated with an endophyte.

2 Claims, 11 Drawing Sheets
Specification includes a Sequence Listing.

(56) References Cited

U.S. PATENT DOCUMENTS

| | | |
|---|---|---|
| 10,058,101 B2 | 8/2018 | von Maltzahn et al. |
| 10,076,120 B2 | 9/2018 | von Maltzahn et al. |
| 10,104,862 B2 | 10/2018 | Vujanovic et al. |
| 2005/0072047 A1 | 4/2005 | Conkling et al. |
| 2006/0046246 A1 | 3/2006 | Zeng et al. |
| 2007/0028318 A1 | 2/2007 | Livore et al. |
| 2007/0055456 A1 | 3/2007 | Raftery et al. |
| 2007/0142226 A1 | 6/2007 | Franco |
| 2007/0292953 A1 | 12/2007 | Mankin et al. |
| 2008/0229441 A1 | 9/2008 | Young et al. |
| 2008/0289060 A1 | 11/2008 | De Beuckeleer et al. |
| 2009/0155214 A1 | 6/2009 | Isawa et al. |
| 2010/0064392 A1 | 3/2010 | Yang et al. |
| 2010/0095396 A1 | 4/2010 | Voeste et al. |
| 2010/0205690 A1 | 8/2010 | Blasing et al. |
| 2010/0227357 A1 | 9/2010 | Redman et al. |
| 2011/0182862 A1 | 7/2011 | Green et al. |
| 2012/0108431 A1 | 5/2012 | Williams et al. |
| 2012/0131696 A1 | 5/2012 | Aayal et al. |
| 2012/0144533 A1 | 6/2012 | Craven |
| 2012/0149571 A1 | 6/2012 | Kloepper et al. |
| 2012/0178624 A1 | 7/2012 | Kaminskyj et al. |
| 2012/0324599 A1 | 12/2012 | Kerns et al. |
| 2013/0031673 A1 | 1/2013 | Grandlic et al. |
| 2013/0071425 A1 | 3/2013 | Vidal et al. |
| 2013/0079225 A1 | 3/2013 | Smith et al. |
| 2013/0150240 A1 | 6/2013 | Newman et al. |
| 2013/0233501 A1 | 9/2013 | Van Zyl et al. |
| 2014/0020136 A1 | 1/2014 | Van Der Wolf et al. |
| 2014/0109249 A1 | 4/2014 | Turner et al. |
| 2014/0115731 A1 | 4/2014 | Turner et al. |
| 2014/0147425 A1 | 5/2014 | Henn et al. |
| 2014/0342905 A1 | 11/2014 | Bullis et al. |
| 2015/0020239 A1 | 1/2015 | von Maltzahn et al. |
| 2015/0033420 A1 | 1/2015 | Rodriguez et al. |
| 2015/0126365 A1 | 5/2015 | Sword |
| 2015/0230478 A1 | 8/2015 | Vujanovic et al. |
| 2015/0242970 A1 | 8/2015 | Avey et al. |
| 2015/0335029 A1 | 11/2015 | Mitter et al. |
| 2015/0366217 A1 | 12/2015 | Vujanovic et al. |
| 2015/0368607 A1 | 12/2015 | Arnold et al. |
| 2015/0370935 A1 | 12/2015 | Starr |
| 2015/0373993 A1 | 12/2015 | von Maltzahn et al. |
| 2016/0021891 A1 | 1/2016 | von Maltzahn et al. |
| 2016/0150796 A1 | 6/2016 | von Maltzahn et al. |
| 2016/0174570 A1 | 6/2016 | Vujanovic et al. |
| 2016/0192662 A1 | 7/2016 | Sword |
| 2016/0205947 A1 | 7/2016 | Sword |
| 2016/0235074 A1 | 8/2016 | von Maltzahn et al. |
| 2016/0255844 A1 | 9/2016 | Mitter et al. |
| 2016/0260021 A1 | 9/2016 | Marek |
| 2016/0286821 A1 | 10/2016 | Sword |
| 2016/0290918 A1 | 10/2016 | Xu et al. |
| 2016/0316760 A1 | 11/2016 | Ambrose et al. |
| 2016/0316763 A1 | 11/2016 | Sword |
| 2016/0330976 A1 | 11/2016 | Mitter et al. |
| 2016/0338360 A1 | 11/2016 | Mitter et al. |
| 2016/0366892 A1 | 12/2016 | Ambrose et al. |
| 2017/0020138 A1 | 1/2017 | Von Maltzahn et al. |
| 2017/0164619 A1 | 6/2017 | von Maltzahn et al. |
| 2017/0164620 A1 | 6/2017 | von Maltzahn et al. |
| 2017/0215358 A1 | 8/2017 | Franco et al. |
| 2017/0223967 A1 | 8/2017 | Mitter et al. |
| 2018/0020677 A1 | 1/2018 | Ambrose et al. |
| 2018/0092365 A1 | 4/2018 | Sword |
| 2018/0177196 A1 | 6/2018 | Sword |
| 2018/0213800 A1 | 8/2018 | Djonovic et al. |
| 2018/0249716 A1 | 9/2018 | Riley |
| 2018/0251776 A1 | 9/2018 | Riley |

FOREIGN PATENT DOCUMENTS

| | | |
|---|---|---|
| CA | 2562175 | 1/2013 |
| CN | 1604732 | 4/2005 |
| CN | 101311262 A | 11/2008 |
| CN | 101423810 A | 5/2009 |
| CN | 101570738 | 11/2009 |
| CN | 101693881 A | 4/2010 |
| CN | 102168022 A | 8/2011 |
| CN | 102352327 A | 2/2012 |
| CN | 102010835 B | 4/2012 |
| CN | 102533601 B | 10/2013 |
| CN | 103642725 A | 3/2014 |
| CN | 104560742 A | 1/2015 |
| CN | 104388356 A | 3/2015 |
| EP | 0192342 | 8/1986 |
| EP | 0223662 | 5/1987 |
| EP | 0378000 | 7/1990 |
| EP | 0494802 | 7/1992 |
| EP | 0818135 | 1/1998 |
| EP | 1621632 | 2/2006 |
| EP | 1935245 | 6/2008 |
| EP | 2676536 | 12/2013 |
| JP | 2009/072168 | 4/2009 |
| KR | 20100114806 A | 10/2010 |
| KR | 101091151 | 12/2011 |
| KR | 20130023491 | 3/2013 |
| WO | WO 1988/009114 | 1/1988 |
| WO | WO 1994/016076 | 7/1994 |
| WO | WO 2000/029607 | 5/2000 |
| WO | WO 2001/083697 | 11/2001 |
| WO | WO 2001/083818 | 11/2001 |
| WO | WO 2002/065836 | 8/2002 |
| WO | WO 2004/046357 | 6/2004 |
| WO | WO 2005/003328 | 1/2005 |
| WO | WO 2007/021200 | 2/2007 |
| WO | WO 2007/107000 | 9/2007 |
| WO | WO 2008/103422 | 8/2008 |
| WO | WO 2009/012480 A2 | 1/2009 |
| WO | WO 2009/078710 A1 | 6/2009 |
| WO | WO 2009/126473 A1 | 10/2009 |
| WO | WO 2010/109436 | 9/2010 |
| WO | WO 2010/115156 | 10/2010 |
| WO | WO 2011/001127 | 1/2011 |
| WO | WO 2011/082455 | 7/2011 |
| WO | WO 2011/112781 | 9/2011 |
| WO | WO 2011/117351 | 9/2011 |
| WO | WO 2012/034996 | 3/2012 |
| WO | WO 2013/016361 | 1/2013 |
| WO | WO 2013/029112 | 3/2013 |
| WO | WO 2013/090628 | 6/2013 |
| WO | WO 2013/122473 | 8/2013 |
| WO | WO 2013/177615 | 12/2013 |
| WO | WO 2013/190082 | 12/2013 |
| WO | WO 2014/046553 | 3/2014 |
| WO | WO 2014/082950 | 6/2014 |
| WO | WO 2014/121366 | 8/2014 |
| WO | WO 2014/206953 | 12/2014 |
| WO | WO 2014/210372 | 12/2014 |
| WO | WO 2015/035099 | 3/2015 |
| WO | WO 2015/069938 | 5/2015 |
| WO | WO 2015/100431 | 7/2015 |
| WO | WO 2015/100432 | 7/2015 |
| WO | WO 2015/192172 | 12/2015 |
| WO | WO 2015/200852 | 12/2015 |
| WO | WO 2015/200902 | 12/2015 |
| WO | WO-2015200902 A2 * | 12/2015 ............. A01N 63/02 |
| WO | WO 2016/090212 | 6/2016 |
| WO | WO 2016/109758 | 7/2016 |
| WO | WO 2016/179046 | 11/2016 |
| WO | WO 2016/179047 | 11/2016 |
| WO | WO 2016/200987 | 12/2016 |
| WO | WO 2016/057991 | 3/2019 |

OTHER PUBLICATIONS

PCT International Search Report and Written Opinion for PCT/EP2013/062976, dated Dec. 22, 2014, 9 Pages.

PCT International Search Report, Application No. PCT/US2014/044427, dated Dec. 3, 2014, 9 Pages.

PCT International Search Report and Written Opinion, Application No. PCT/US2014/054160, dated Dec. 9, 2014, 21 Pages.

(56) References Cited

OTHER PUBLICATIONS

PCT Invitation to Pay Additional Fees, PCT Application No. PCT/US2014/064411, dated Feb. 5, 2015, 2 Pages.
PCT International Search Report and Written Opinion, International Application No. PCT/US2014/064411, dated Mar. 27, 2015, 15 Pages.
PCT Invitation to Pay Additional Fees, PCT Application No. PCT/US2014/072399, dated Apr. 14, 2015, 2 Pages.
PCT International Search Report and Written Opinion, International Application No. PCT/US2014/072399, dated Jun. 26, 2015, 22 Pages.
PCT Invitation to Pay Additional Fees, PCT Application No. PCT/US2014/072400, dated Apr. 16, 2015, 6 Pages.
PCT International Search Report and Written Opinion, Application No. PCT/US2014/072400, dated Jul. 8, 2015, 38 Pages.
PCT International Search Report and Written Opinion, Application No. PCT/AU2014/000360, dated Aug. 5, 2015, 12 Pages.
PCT Invitation to Pay Additional Fees, PCT Application No. PCT/US2015/038110, dated Sep. 22, 2015, 8 Pages.
PCT Invitation to Pay Additional Fees, PCT Application No. PCT/US2015/038187, dated Oct. 14, 2015, 5 Pages.
PCT International Search Report and Written Opinion, PCT Application No. PCT/US2015/038110, dated Dec. 11, 2015, 36 Pages.
PCT International Search Report and Written Opinion, PCT Application No. PCT/US2015/038187, dated Jan. 22, 2016, 36 Pages.
PCT Invitation to Pay Additional Fees, PCT Application No. PCT/US2015/068206, dated Apr. 12, 2016, 5 Pages.
PCT International Search Report and Written Opinion, PCT Application No. PCT/US2015/068206, dated Jun. 27, 2016, 20 Pages.
PCT International Search Report and Written Opinion, PCT Application No. PCT/US2016/030292, dated Aug. 12, 2016, 20 Pages.
PCT International Preliminary Report on Patentability, PCT Application No. PCT/US2016/030292, dated Aug. 2, 2017, 23 Pages.
PCT International Search Report and Written Opinion, PCT Application No. PCT/US2016/030293, dated Aug. 11, 2016, 23 Pages.
PCT International Search Report and Written Opinion, PCT Application No. PCT/US2016/036504, dated Nov. 4, 2016, 18 Pages.
PCT International Search Report and Written Opinion, PCT Application No. PCT/US2016/039191, dated Nov. 29, 2016, 20 Pages.
PCT International Search Report and Written Opinion, PCT Application No. PCT/US2016/068144, dated May 18, 2017, 30 Pages.
PCT Invitation to Pay Additional Fees, PCT Application No. PCT/US2017/064351, dated Feb. 9, 2018, 18 Pages.
PCT International Search Report and Written Opinion, PCT Application No. PCT/US2017/064351, dated Apr. 9, 2018, 25 Pages.
PCT Invitation to Pay Additional Fees, PCT Application No. PCT/US2017/064361, dated Mar. 7, 2018, 18 Pages.
PCT Invitation to Pay Additional Fees, PCT Application No. PCT/US2017/064292, dated Mar. 5, 2018, 15 Pages.
PCT International Search Report and Written Opinion, PCT Application No. PCT/USS2017/068255, dated Mar. 19, 2018, 14 Pages.
Canadian Patent Office, Office Action, Canadian Patent Application No. CA 2,953,466, dated Dec. 11, 2017, 7 Pages.
Canadian Patent Office, Office Action, Canadian Patent Application No. 2,916,678, dated Feb. 8, 2017, 8 Pages.
Canadian Patent Office, Office Action, Canadian Patent Application No. 2,935,218, dated Jun. 13, 2017, 5 Pages.
Canadian Patent Office, Office Action, Canadian Patent Application No. 2,935,218, dated May 8, 2018, 5 Pages.
Canadian Patent Office, Office Action, Canadian Patent Application No. CA 2,953,697, dated Oct. 12, 2017, 6 Pages.
Canadian Patent Office, Office Action, Canadian Patent Application No. CA 2,952,057, dated Oct. 12, 2017, 4 Pages.
Canadian Patent Office, Office Action, Canadian Patent Application No. CA 2,929,487, dated Dec. 7, 2017, 4 Pages.
Chinese Patent Office, Office Action, Chinese Patent Application No. 201480072142.7, dated Apr. 25, 2017, 14 Pages (with English translation).
Chinese Patent Office, 2nd Office Action for Chinese Patent Application No. CN 201480072142.7, dated Oct. 30, 2017, 13 Pages, (with English translation).
European Patent Office, Supplementary Partial European Search Report, European Patent Application No. 13874703.5, dated Jun. 21, 2016, 3 Pages.
European Patent Office, Supplementary European Search Report, European Patent Application No. 13874703.5, dated Oct. 21, 2016, 16 Pages.
European Patent Office, Communication Pursuant to Article 94(3) EPC for European Patent Application No. 13874703.5, dated Jan. 5, 2018, 4 Pages.
European Patent Office, Supplementary European Search Report, European Patent Application No. 14860187.5, dated May 24, 2017, 9 Pages.
European Patent Office, Supplementary European Search Report, European Patent Application No. 14874589.6, dated Jul. 11, 2017, 9 Pages.
European Patent Office, Communication Pursuant to Article 94(3) EPC for European Patent Application No. EP 14748326.7, dated Feb. 15, 2018, 7 Pages.
European Patent Office, Examination Report, European Patent Application No. 14748326.7, dated Jul. 19, 2017, 4 Pages.
European Patent Office, Examination Report for European Patent Application No. EP 14777213.1, dated Oct. 20, 2017, 12 Pages.
European Patent Office, Supplementary European Search Report, European Patent Application No. EP 15809264.3, dated Dec. 4, 2017, 16 Pages.
European Patent Office, Communication Pursuant to Article 94(3) EPC for European Patent Application No. 15810847.2, dated Nov. 17, 2017, 17 Pages.
European Patent Office, Supplementary European Search Report for European Patent Application No. 15810847.2, dated Feb. 28, 2018, 19 Pages.
European Patent Office, Supplementary European Search Report, European Patent Application No. EP 15812324.0, dated Nov. 2, 2017, 19 Pages.
European Patent Office, Extended European Search Report, European Patent Application No. EP 15812324.0, dated Feb. 21, 2018, 23 Pages.
European Patent Office, Extended European Search Report, European Patent Application No. EP 15809264.3, dated Mar. 12, 2018, 14 Pages.
Intellectual Property Australia, Examination Report for Australian Patent Application No. 2016202480, dated Apr. 28, 2016, 2 Pages.
Intellectual Property Australia, Examination Report for Australian Patent Application No. 2014346664, dated Nov. 24, 2016, 3 Pages.
Intellectual Property Australia, Examination Report for Australian Patent Application No. 2014315191, dated Jul. 15, 2017, 6 Pages.
Intellectual Property Australia, Examination Report for Australian Patent Application No. 2015279600, dated Jul. 21, 2017, 7 Pages.
Intellectual Property Australia, Examination Report for Australian Patent Application No. 2015278238, dated Jul. 24, 2017, 3 Pages.
Intellectual Property Australia, Examination Report No. 1 for Australian Patent Application No. AU 2017254880, dated Nov. 15, 2017, 2 Pages.
Intellectual Property Australia, Examination Report No. 1 for Australian Patent Application No. AU 2017201009, dated Apr. 4, 2018, 3 Pages.
Intellectual Property Australia, Examination Report No. 1 for Australian Patent Application No. AU 2017210482, dated May 15, 2018, 4 Pages.
New Zealand Intellectual Property Office, First Examination Report, New Zealand Patent Application No. 715728, dated May 10, 2016, 4 Pages.
New Zealand Intellectual Property Office, First Examination Report, New Zealand Patent Application No. 715728, dated Dec. 5, 2016, 3 Pages.
New Zealand Intellectual Property Office, First Examination Report, New Zealand Patent Application No. 727449, dated Jun. 8, 2017, 7 Pages.
New Zealand Intellectual Property Office, First Examination Report, New Zealand Patent Application No. 726116, dated Jun. 29, 2017, 2 Pages.

(56) References Cited

OTHER PUBLICATIONS

New Zealand Intellectual Property Office, First Examination Report, New Zealand Patent Application No. 726116, dated Sep. 26, 2017, 5 Pages.
New Zealand Intellectual Property Office, Further Examination Report, New Zealand Patent Application No. 726116, dated Feb. 27, 2018, 6 Pages.
New Zealand Intellectual Property Office, First Examination Report, New Zealand Patent Application No. 728495, dated Jul. 12, 2017, 5 Pages.
New Zealand Intellectual Property Office, First Examination Report for New Zealand Patent Application No. NZ 728483, dated Dec. 8, 2017, 2 Pages.
Russian Patent Office, Office Action for Russian Patent Application No. RU 2017127214, dated Nov. 22, 2017, 4 Pages, (with English translation).
Russian Patent Office, Office Action for Russian Patent Application No. RU 2015137613, dated Jun. 7, 2017, 14 Pages (with English translation).
Ukraine Patent Office, Office Action for Ukrainian Patent Application No. a201508515, dated May 19, 2017, 14 Pages (with English translation).
Ukraine Patent Office, Office Action for Ukrainian Patent Application No. a201508515, dated Feb. 20, 2018, 9 Pages (with English translation).
Office Action for Israel Patent Application No. IL 255682, dated Mar. 15, 2018, 2 Pages (Translation).
Office Action for Israel Patent Application No. IL 255684, dated Mar. 19, 2018, 2 Pages (Translation).
Office Action for Israel Patent Application No. IL 255685, dated Mar. 20, 2018, 2 Pages (Translation).
Office Action for Israel Patent Application No. IL 255688, dated Mar. 22, 2018, 2 Pages (Translation).
Office Action for Israel Patent Application No. IL 245385, dated Mar. 23, 2018, 3 Pages (With Concise Explanation of Relevance).
Abarenkov, K., et al., "PlutoF—A Web Based Workbench for Ecological and Taxonomic Research, with an Online Implementation for Fungal ITS Sequences," Evol Bioinform Online, 2010, pp. 189-196, vol. 6.
Abarenkov, K., et al., "The UNITE Database for Molecular Identification of Fungi—Recent Updates and Future Perspectives," New Phytol., 2010, pp. 281-285, vol. 186.
Abdellatif, L., et al., "Endophytic hyphal compartmentalization is required for successful symbiotic Ascomycota association with root cells," Mycological Research, 2009, pp. 782-791, vol. 113.
Abdellatif, L., et al., "Characterization of virulence and PCR-DGGE profiles of Fusarium avenaceum from western Canadian Prairie Ecozone of Saskatchewan,"Canadian Journal of Plant Pathology, 2010, pp. 468-480.
Abdou, R., et al., "Botryorhodines A-D, antifungal and cytotoxic depsidones from *Botryosphaeria rhodina*, an endophyte of the medicinal plant *Bidens pilosa*," Phytochemistry, 2010, vol. 71, pp. 110-116.
Abou-Shanab, R. A., et al: "Characterization of Ni-resistant bacteria in the rhizosphere of the hyperaccumulator Alyssum murale by 16S rRNA gene sequence analysis", World Journal of Microbiology and Biotechnology, vol. 26, No. 1, Aug. 15, 2009, pp. 101-108.
Adhikari, M., et al., "A New Record of Pseudeurotium bakeri from Crop Field Soil in Korea," The Korean Journal of Mycology, 2016, pp. 145-149, vol. 44.
Ahmad, F., et al., "Screening of Free-Living Rhizospheric Bacteria for Their Multiple Plant Growth Promoting Activities," Microbiol Res., 2008, pp. 173-181, vol. 163.
Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.
Amann, R., et al., "The Identification of Microorganisms by Fluorescence in Situ Hybridisation," Curr Opin Biotechnol., 2001, pp. 231-236, vol. 12.

Amatuzzi, R.F., et al., "Univers1dade Federal Do Parana," Jan. 1, 2014, 52 Pages. (With English Abstract).
Amatuzzi, R.F., et al., "Potential of endophytic fungi as biocontrol agents of *Duponchelia fovealis* (Zeller) (Lepidoptera:Crambidae," Brazilian Journal of Biology, Nov. 9, 2017, 7 Pages.
Apel, K., et al., "Reactive Oxygen Species: Metabolism, Oxidative Stress, and Signal Transduction," Annu Rev Plant Biol., 2004, pp. 373-399, vol. 55.
Arendt, K. R., et al., "Isolation of endohyphal bacteria from foliar Ascomycota and in vitro establishment of their symbiotic associations," Appl. Environ. Microbiol., 2016, pp. 2943-2949, vol. 82, No. 10.
Ashrafuzzaman, M., et al., "Efficiency of plant growth-promoting rhizobacteria (PGPR) for the enhancement of rice growth," African Journal of Biotechnology, 2009, pp. 1247-1252, vol. 8, No. 7.
Aveskamp, M., et al., "DNA phylogeny reveals polyphyly of Phoma section Peyronellaea and multiple taxonomic novelties," Mycologia, 2009, vol. 101, No. 3, pp. 363-382.
Bacon, C. W., et al., "Isolation, In Planta Detection, and Uses of Endophytic Bacteria for Plant Protection," Manual of Environmental Microbiology, 2007, pp. 638-647.
Baker, K. F., et al., "Dynamics of Seed Transmission of Plant Pathogens," Annu Rev Phytopathol., 1966, pp. 311-334,vol. 4.
Baltruschat, H., et al., "Salt tolerance of barley induced by the root endophyte Piriformospora indica is associated with a strong increase in antioxidants," New Phytologist., 2008, pp. 501-510, vol. 180.
Bensch, K., et al., "Species and ecological diversity within the *Cladosporium cladosporioides* complex (Davidiellaceae, Capnodiales)," Studies in Mycology, 2010, pp. 1-94, vol. 67.
Bethlenfalvay, G., et al., "Mycorrhizal fungi effects on nutrient composition and yield of soybean seeds", Journal of Plant Nutrition, vol. 20, No. 4-5, Apr. 1, 1997, pp. 581-591.
Block, C. C., et al., "Seed Transmission of Pantoea stewartii in Field and Sweet Corn," Plant Disease, 1998, pp. 775-780, vol. 82.
Brinkmeyer, R., et al., "Uncultured Bacterium Clone ARKMP-100 16S Ribosomal RNA Gene, Partial Sequence," NCBI GenBank Accession No. AF468334, Submitted Jan. 14, 2002.
Brodie, E.L., et al., "Uncultured Bacterium Clone BANW722 16S Ribosomal RNA Gene, Partial Sequence," NCBI GenBank Accession No. DQ264636, Submitted Oct. 25, 2005.
Bulgarelli, D., et al., "Structure and Functions of the Bacterial Microbiota of Plants," Annu Rev Plant Biol., 2013, pp. 807-838, vol. 64.
Buttner, D., et al., "Regulation and secretion of Xanthomonas virulence factors," FEMS Microbiology Reviews, 2010, pp. 107-133, vol. 34, No. 2.
Caporaso, J.G., et al., "Ultra-High-Throughput Microbial Community Analysis on the Illumina HiSeq and MiSeq Platforms," ISME J., 2012, pp. 1621-1624, vol. 6.
Castillo, D., et al., "Fungal Entomopathogenic Endophytes: Negative Effects on Cotton Aphid Reproduction in Greenhouse and Field Conditions," Power Point Presentation dated Mar. 23, 2013.
Castillo, D., et al., "Fungal Endophytes: Plant Protective Agents Against Herbivores," Power Point Presentation dated Aug. 4, 2013.
Cavalier-Smith, T., "A Revised Six-Kingdom System of Life," Biol Rev Camb Philos Soc., 1998, pp. 203-266, vol. 73.
Cha, C., et al., "Production of Acyl-Homoserine Lactone Quorum-Sensing Signals by Gram-Negative Plant Associated Bacteria," Mol Plant Microbe Interact., 1998, pp. 1119-1129, vol. 11, No. 11.
Chagas, F., et al., "A Mixed Culture of Endophytic Fungi Increases Production of Antifungal Polyketides," J. Chem Ecol., Oct. 2013, pp. 1335-1342, vol. 39.
Chernin, L. S., et al., "Chitinolytic Activity in Chromobacterium violaceum: Substrate Analysis and Regulation by Quorum Sensing," J Bacteriol., 1998, pp. 4435-4441, vol. 180, No. 17.
Clark, E. M., et al., "Improved Histochemical Techniques for the Detection of Acremonium coenophilum in Tall Fescue and Methods of in vitro Culture of the Fungus," J. Microbiol Methods, 1983, pp. 149-155, vol. 1.
Clarridge, J., "Impact of 16S rRNA Gene Sequence Analysis for Identification of Bacteria on Clinical Microbiology and Infectious Diseases," Clinical Microbiology Reviews, Oct. 2004, pp. 840-862, vol. 17, No. 4.

(56) References Cited

OTHER PUBLICATIONS

Clay, K., "Effects of fungal endophytes on the seed and seedling biology of Lolium perenne and Festuca arundinacea," Oecologia, 1987, pp. 358-362, vol. 73.

Clough, S. J., et al., "Floral Dip: A Simplified Method for Agrobacterium-mediated Transformation of *Arabidopsis thaliana*," Plant J., 1998, pp. 735-743, vol. 16, No. 6.

Compant, S., et al., "Endophytes of Grapevines Flowers, Berries, and Seeds: Identification of Cultivable Bacteria, Comparison with Other Plant Parts, and Visualization of Niches of Colonization," Microbial Ecology, 2011, pp. 188-197, vol. 62.

Coombs, J. T., et al., "Isolation and Identification of Actinobacteria from Surface-Sterilized Wheat Roots," Applied and Environmental Microbiology, 2003, pp. 5603-5608, vol. 69, No. 9.

Conn, V. M., "Effect of Microbial Inoculants on the Indigenous Actinobacterial Endophyte Population in the Roots of Wheats as Determined by Terminal Restriction Fragment Length Polymorphism," Applied and Environmental Microbiology, 2004, pp. 6407-6413, vol. 70, No. 11.

Cottyn, B., et al., "Phenotypic and genetic diversity of rice seed-associated bacteria and their role in pathogenicity and biological control," Journal of Applied Microbiology, 2009, pp. 885-897, vol. 107.

Cox, C. D., "Deferration of Laboratory Media and Assays for Ferric and Ferrous Ions," Methods Enzymol., 1994, pp. 315-329, vol. 235.

Craine, J. M., et al., "Global Diversity of Drought Tolerance and Grassland Climate-Change Resilience," Nature Climate Change, 2013, pp. 63-67, vol. 3.

Dalal, J.M., et al., "Utilization of Endophytic Microbes for Induction of Systemic Resistance (ISR) in Soybean (*Glycine max* (L) Merril) Against Challenge Inoculation with R. solani," Journal of Applied Science and Research, 2014, pp. 70-84, vol. 2, No. 5.

Danhorn, T., et al., "Biofilm Formation by Plant-Associated Bacteria," Annu Rev Microbiol., 2007, pp. 401-422, vol. 61.

Daniels, R., et al., "Quorum Signal Molecules as Biosurfactants Affecting Swarming in Rhizobium etli," PNAS, 2006, pp. 14965-14970, vol. 103, No. 40.

Darsonval, A., et al., "Adhesion and Fitness in the Bean Phyllosphere and Transmission to Seed of *Xanthomonas fuscans* subsp. *fuscans*," Molecular Plant-Microbe Interactions, 2009, pp. 747-757, vol. 22, No. 6.

Darsonval, A., et al., "The Type III Secretion System of *Xanthomonas fuscans* subsp. *fuscans* is involved in the Phyllosphere Colonization Process and in Transmission to Seeds of Susceptible Beans," Applied and Envioronmental Mirobiology, 2008, pp. 2669-2678, vol. 74, No. 9.

Dbget, "Orthology: K14454," 2005, 2 pages, can be retrieved at <URL:http://www.genome.jp/dbget-bin/www_bget?ko:K14454>.

De Freitas, J. R., et al., "Phosphate-Solubilizing Rhizobacteria Enhance the Growth and Yield but not Phosphorus Uptake of Canola (*Brassica napus* L.)," Biol Fertil Soils, 1997, pp. 358-364, vol. 24.

De Lima Favaro, L. C., et al., "Epicoccum nigrum P16, a Sugarcane Endophyte, Produces Antifungal Compounds and Induces Root Growth," PLoS One, 2012, pp. 1-10, vol. 7, No. 6.

De Melo Pereira, G. V., et al. "A Multiphasic Approach for the Identification of Endophytic Bacterial in Strawberry Fruit and their Potential for Plant Growth Promotion," Microbial Ecology, 2012, pp. 405-417, vol. 63, No. 2.

De Souza, J. J., et al., "Terpenoids from Endophytic Fungi," Molecules, 2011, pp. 10604-10618, vol. 16, No. 12.

Dennis, C., et al., "Antagonistic Properties of Species Groups of Trichoderma," Trans Brit Mycol Soc, 1971, pp. 25-39, vol. 57, No. 1.

Desiro, A., et al., "Detection of a novel intracellular microbiome hosted in arbuscular mycorrhizal fungi," ISME Journal, 2014, pp. 257-270, vol. 8.

Djordjevic, D., et al., "Microtiter Plate Assay for Assessment of Listeria monocytogenes Biofilm Formation," Annl Environ Microbiol., 2002, pp. 2950-2958, vol. 68, No. 6.

Don, R. H., et al., "Properties of Six Pesticide Degradation Plasmids Isolated From Alcaligenes Paradoxus and Alcaligenes eutrophus," J Bacteriol., 1981, pp. 681-686, vol. 145, No. 2.

Dunbar, J, et al., "Uncultured Bacterium Clone NT42a2_20488 16S Ribosomal RNA Gene, Partial Sequence," NCBI GenBank Accession No. JQ378705. Submitted Nov. 8, 2012, 1 Page.

Eberhard, A., et al., "Structural Identification of Autoinducer of Photobacterium fischeri Luciferase," Biochem., 1981, pp. 2444-2449, vol. 20.

Edgar, R. C., "Search and Clustering Orders of Magnitude Faster than BLAST," Bioinformatics, 2010, pp. 2460-2461, vol. 26, No. 19.

Edgar, R. C., "UPARSE: Highly Accurate OTU Sequences From Microbial Amplicon Reads," Nat Methods, 2013, pp. 996-998, vol. 10, No. 10.

Ek-Ramos, M. J., "Ecology, Distribution and Benefits of Fungal Endophytes Isolated from Cultivated Cotton (*Gossypium hirsutum*) in Texas," Power Point Presentation dated Nov. 7, 2012, 27 Pages.

Ek-Ramos, M. J., et al., "Spatial and Temporal Variation in Fungal Endophyte Communities Isolated from Cultivated Cotton (*Gossypium hirsutum*)," PLoS One, 2013, vol. 8, No. 6, 13 Pages, e66049.

Ek-Ramos, M. J., et al., "Spatial and Temporal Variation in Fungal Endophyte Communities Isolated from Cultivated Cotton (*Gossypium hirsutum*)," Power Point Presentation dated Jan. 7, 2013, 18 Pages.

El-Shanshoury, a. R., "Growth Promotion of Wheat Seedlings by Streptomyces atroolivaceus," Journal of Agronomy and Crop Science, 1989, pp. 109-114, vol. 163.

Emerson, D., et al., Identifying and Characterizing Bacteria in an Era of Genomics and Proteomics, BioScience, 2008, pp. 925-936, vol. 58, No. 10.

Endre, G., et al., "A Receptor Kinase Gene Regulating Symbiotic Nodule Development," Nature, 2002, pp. 962-966, vol. 417.

Faria, D. C., et al., "Endophytic Bacteria Isolated from Orchid and Their Potential to Promote Plant Growth," World J Microbiol Biotechnol., 2013, pp. 217-221, vol. 29.

Ferrando, L., et al., "Molecular and Culture-Dependent Analyses Revealed Similarities in the Endophytic Bacterial Community Composition of Leaves from Three Rice (*Oryza sativa*) Varieties," FEMS Microbiol Ecol., 2012, pp. 696-708, vol. 80.

Fiehn, O., et al., "Metabolite Profiling for Plant Functional Genomics," Nature Biotechnol., 2000, pp. 1157-1161, vol. 8.

Fierer, N., et al., "Cross-Biome Metagenomic Analyses of Soil Microbial Communities and Their Functional Attributes," Proc Natl Acad Sci USA, 2012, pp. 21390-21395, vol. 109, No. 52.

Fincher, G. B., "Molecular and Cellular Biology Associated with Endosperm Mobilization in Germinating Cereal Grains," Annu Rev Plant Phvsiol Plant Mol Biol., 1989, pp. 305-346, vol. 40.

Fisher, P. J., et al., "Fungal saprobes and pathogens as endophytes of rice (*Oryza sativa* L.)," New Phytol., 1992, pp. 137-143, vol. 120.

Fisher, P. R., et al., "Isolation and Characterization of the Pesticide-Degrading Plasmid pJP1 from Alcaligenes paradoxus," J Bacteriol., 1978, pp. 798-804, vol. 135, No. 3.

Franco, C., et al., "Actinobacterial Endophytes for Improved Crop Performance," Australasian Plant Pathology, 2007, pp. 524-531, vol. 36.

Fulthorpe, R. R., et al., "Distantly Sampled Soils Carry Few Species in Common," ISME J., 2008, pp. 901-910, vol. 2.

Gantner, S., et al., "Novel Primers for 16S rRNA-based Archaeal Community Analyses in Environmental Samples," J Microbiol Methods, 2011, pp. 12-18, vol. 84.

Gao, Z., et al., "Quantitation of Major Human Cutaneous Bacterial and Fungal Populations," J Clin Microbiol., 2010, pp. 3575-3581, vol. 48, No. 10.

Garazzino, S., et al., "Osteomyelitis Caused by Enterobacter cancerogenus Infection following a Traumatic Injury: Case Report and Review of the Literature," J Clin Microbiol., Mar. 2005, vol. 43, No. 3, pp. 1459-1461.

Gasser, I., et al., "Ecology and Characterization of Polyhydroxyalkanoate-Producing Microorganisms on and in Plants," FEMS Microbiol Ecol., 2010, pp. 142-150, vol. 70.

(56) References Cited

OTHER PUBLICATIONS

Gavrish, E, et al., "*Lentzea* sp. MS6 16S Ribosomal RNA Gene, Partial Sequence," NCBI GenBank Accession No. EF599958. Submitted May 9, 2007, 1 Page.
Gebhardt, J., et al., "Characterization of a single soybean cDNA encoding cytosolic and glyoxysomal isozymes of aspartate aminostransferase," Plant Molecular Biology, 1998, pp. 99-108, vol. 37.
GenBank: AF034210.1 "Glycine max aspartate aminotransferase glyoxysomal isozyme AAT1 precursor and aspartate aminotransferase cytosolic isozyme AAT2 (AAT) mRNA, complete cds," NCBI, May 26, 1998, 2 Pages, can be retrieved at <URL:https://www.ncbi.nlm.nih.gov/nuccore/AF034210>.
GenBank: JN210900.1, "*Enterobacter* sp. WS05 16S ribosomal RNA gene, partial sequence," NCBI, Sep. 24, 2012, 1 Page, can be retrieved at <URL:https://www.ncbi.nlm.nih.gov/nuccore/jn210900>.
GenBank: NP_001237541.1, "aspartate aminotransferase glyoxysomal isozyme AAT1 precursor [*Glycine max*]," NCBI, Oct. 29, 2016, 2 Pages, can be retrieved at <URL:https://www.ncbi.nlm.nih.gov/protein/NP_001237541.1>.
NCBI GenBank: CP000653.1 "*Enterobacter* sp. 638, complete genome" Jan. 28, 2014, 5 Pages, Can be retrieved at <URL:https://www.ncbi.nlm.nih.gov/nuccore/CP000653.1>.
NCBI GenBank: CP000653.1 "*Enterobacter* sp. 638, complete genome" ASM1632v1, Apr. 18, 2007, 2 Pages, Can be retrieved at <URL:https://www.ncbi.nlm.nih.gov/assembly/GCA_000016325.1>.
NCBI GenBank: EU340965.1 "*Enterobacter* sp. 638 16S ribosomal RNA gene, partial sequence" Jan. 30, 2009, 1 Page, Can be retrieved at <URL:https://www.ncbi.nlm.nih.gov/nuccore/EU340965.1>.
NCBI GenBank: EBI accession No. EM STD:JQ759988, "*Dothideomycetes* sp. genotype 226 isolate FL0175 internal transcribed spacer 1, partial sequence; 5.8S ribosomal RNA gene and internal transcribed spacer 2, complete sequence; and 28S ribosomal RNA gene, partial sequence," May 17, 2012, 2 Pages.
NCBI GenBank: EBI accession No. EM STD:GU055658, "Uncultured Periconia clone NG R 806 18S ribosomal RNA gene, partial sequence; internal transcribed spacer 1, 5.8S ribosomal RNA gene, and internal transcribed spacer 2, complete sequence; and 28S ribosomal RNA gene, partial sequence," Oct. 27, 2009, 2 Pages.
GenEmbl Database, GenEmbl Record No. KF673660, Sandberg, et al., "Fungal endophytes of aquatic macrophytes: diverse host-generalists characterized by tissue preferences and geographic structure," 2013, 35 Pages.
GenEmbl Database, GenEmbl Record No. KP991588, Huang, et al., "Pervasive effects of wildfire on foliar endophyte communities in montane forest trees," Mar. 2015, 35 Pages.
GenEmbl Database, GenEmbl Record No. JN872548, 38 Pages, Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.
GenEmbl database, GenEmbl Record No. EU 977189, Jan. 21, 2009, 4 pages, Smith, S.A., et al., "Bioactive endophytes warrant intensified exploration and conservation," PloS One 3(8):E3052, 2008.
GenEmbl database, GenEmbl Record No. KF011597, Paenibacillus strain No. HA 13, Aug. 26, 2013, 5 Pages, Park, H.J., et al., "Isolation and characterization of humic substances-degrading bacteria from the subarctic Alaska grasslands," J Basic Microbiol, 2013.
Database Geneseq Database accession No. BAP97938 "Pantoea dispersa strain KACC91642P 16S rDNA sequence, Seq ID 1." Aug. 15, 2013, 1 Page.
Gilmour, S. J., et al., "Overexpression of the *Arabidopsis* CBF3 Transcriptional Activator Mimics Multiple Biochemical Changes Associated with Cold Acclimation," Plant Physiol., 2000, pp. 1854-1865, vol. 124.
Giraldo, A., et al., "Phylogeny of *Sarocladium* (Hypocreales)," Persoonia, 2015, pp. 10-24, vol. 34.
Gitaitis, R., et al., "The Epidemiology and Management of Seedborne Bacterial Diseases," Annu Rev Phytopathol., 2007, pp. 371-397, vol. 45.
Grondona, I., et al., "TUSAL®, a commercial biocontrol formulation based on Trichoderma," Bulletin OILB/SROP, 2004, pp. 285-288, vol. 27, No. 8.
Gu, O., et al., "*Glycomyces sambucus* sp. nov., an endophytic actinomycete islolated from the stem of Sambucus adnata Wall," International Journal of Systematic and Evolutionary Microbiology, 2007, pp. 1995-1998, vol. 57.
Haake, V., et al., "Transcription Factor CBF4 is a Regulator of Drought Adaptation in *Arabidopsis*," Plant Physiol., 2002, pp. 639-648, vol. 130.
Haas, D., et al., "R Factor Variants with Enhanced Sex Factor Activity in Pseudomonas aeruginosa," Mol Gen Genet., 1976, pp. 243-251, vol. 144.
Hahm, M-S., et al., "Biological Control and Plant Growth Promoting Capacity of Rhizobacteria and Pepper Under Greenhouse and Field Conditions," The Journal of Microbiology, The Microbiological Society of Korea, Heidelberg, Jun. 30, 2012, pp. 380-385, vol. 50, No. 3.
Hallman, J., et al., "Bacterial Endophytes in Agricultural Crops," Canadian J Microbiol., 1997, pp. 895-914, vol. 43.
Hamayun, M., et al., "Cladosporium sphaerospermum as a new plant growth-promoting endophyte from the roots of *Glycine max* (L.) *Merr*," World Journal of Microbiology and Biotechnology, Kluwer Academic Publishers, Feb. 15, 2009, pp. 627-632, vol. 25, No. 4.
Hanson, L.E., "Reduction of Verticillium Wilt Symptoms in Cotton Following Seed Treatment with Trichoderma virens," The Journal of Cotton Science, 2000, pp. 224-231, vol. 4, No. 4.
Hanson, L.E., "Reduction of Verticillium Wilt Symptoms in Cotton Following Seed Treatment with Trichoderma virens," Proceedings Beltwide Cotton Conferences, 2000, vol. 1. (Abstract), 1 Page.
Hardegree, S. P. et al., "Effect of Polyethylene Glycol Exclusion on the Water Potential of Solution-Saturated Filter Paper," Plant Physiol., 1990, pp. 462-466, vol. 92.
Hardoim, P. R., et al., "Assessment of Rice Root Endophytes and Their Potential for Plant Growth Promotion," In: Hardoim, P.R., Bacterial Endophytes of Rice—Their Diversity, Characteristics and Perspectives, Groningen, 2011, pp. 77-100.
Hardoim, P. R., et al., "Dynamics of Seed-Borne Rice Endophytes on Early Plant Growth Stages," PLoS One, 2012, vol. 7, No. 2, 13 Pages.
Harman, G.E., et al., "Symposium: biocontrol and biotechnological methods for controlling cotton pests," Proceedings of the Beltwide Cotton Production Research Conf., 1989, Memphis, Tennessee, USA, pp. 15-20. (Abstract).
Hepler, P. K., et al., "Polarized Cell Growth in Higher Plants," Annu Rev Cell Dev Biol., 2001, pp. 159-187, vol. 17.
Hiatt, E. E., et al., "Tall Fescue Endophyte Detection: Commerical Immunoblot Test Kit Compared with Microscopic Analysis," Crop Science, 1999, pp. 796-799, vol. 39.
Hibbett, D. S., et al., "A Higher-Level Phylogenetic Classification of the Fungi," Mycol Res., 2007, pp. 509-547, vol. 111.
Hill, N. S., et al., "Endophyte Survival during Seed Storage: Endophyte-Host Interactions and Heritability," Crop Sci., 2009, pp. 1425-1430, vol. 49.
Hill N. S., et al., "Endophyte Survival during Seed Storage: Endophyte-Host Interactions and Heritability," PowerPoint, Dept. Crop Soil Sciences, University of Georgia, Nov. 16, 2012, 3 Pages.
Hinton, D. M., et al., "Enterobacter cloacae is an endophytic symbiont of corn," Mycopathologia, 1995, pp. 117-125, vol. 129.
Hoffman, M., et al., "Diverse Bacteria Inhabit Living Hyphae of Phylogenetically Diverse Fungal Endophytes," Applied and Environmental Microbiology, Jun. 2010, pp. 4063-4075, vol. 76, No. 12.
Hoffman, M., et al., "Endohyphal Bacterium Enhances Production of Indole-3-Acetic Acid by a Foliar Fungal Endophyte," PLOS One, Sep. 24, 2013, pp. 1-8, vol. 8, Issue 9, e73132.
Howell, C.R., et al., "Induction of Terpenoid Synthesis in Cotton Roots and Control of Rhizoctonia solani by Seed Treatment with Trichoderma virens," Phytopathology, 2000, pp. 248-252, vol. 90, No. 3.

(56) References Cited

OTHER PUBLICATIONS

Hubbard, M., et al., "Fungal Endophytes Improve Wheat Seed Germination Under Heat and Drought Stress," Botany, 2012, pp. 137-149, vol. 90.

Humann, J., et al., "Complete genome of the onion pathogen Enterobacter cloacae EcWSU1," Standard in Genomic Sciences, Dec. 31, 2011, vol. 5, No. 3, pp. 279-286.

Hung, P.Q., et al., "Isolation and Characterization of Endophytic Bacteria in Soybean (*Glycine* Sp.)," Omonrice, 2004, pp. 92-101, vol. 12.

Idris, A., et al., "Efficacy of Rhizobacteria for Growth Promotion in Sorghum Under Greenhouse Conditions and Selected Modes of Action Studies," J Agr Sci., 2009, pp. 17-30, vol. 147.

Ikeda, S., et al., "The Genotype of The Calcium/Calmodulin-Dependent Protein Kinase Gene (CCaMK) Determines Bacterial Community Diversity in Rice Roots Under Paddy and Upland Field Conditions," Applied and Environmental Microbiology, 2011, pp. 4399-4405, vol. 77, No. 13.

Imoto, K., et al., "Comprehensive Approach to Genes Involved in Cell Wall Modifications in *Arabidopsis thaliana*," Plant Mol Biol., 2005, pp. 177-192, vol. 58.

Jalgaonwala, R., et al., "A Review on Microbial Endophytes from Plants: A Treasure Search for Biologically Active Metabolites," Global Journal of Research on Medicinal Plants & Indigenous Medicine, 2014, pp. 263-277, vol. 3, No. 6.

Janda, J. M., et al., "16S rRNA Gene Sequencing for Bacterial Identification in the Diagnostic Laboratory: Pluses, Perils, and Pitfalls," Journal of Clinical Microbiology, 2007, pp. 2761-2764, vol. 45, No. 9.

Johnston-Monje, D., et al., "Conservation and Diversity of Seed Associated Endophytes in Zea Across Boundaries of Evolution, Ethnography and Ecology," PLOS One, vol. 6, No. 6, Jun. 3, 2011, p. e20396, 22 Pages.

Johnston-Monje, D., et al., "Plant and Endophyte Relationships: Nutrient Management," Comprehensive Biotechnol., 2011, pp. 713-727, vol. 4.

Johnston-Monje, D., "Microbial Ecology of Endophytic Bacteria in Zea Species as Influenced by Plant Genotype, Seed Origin, and Soil Environment," Thesis, University of Guelph, 2011, 230 Pages.

Jones, K.L., "Fresh Isolates of Actinomycetes in which the Presence of Sporogenous Aerial Mycelia is a Fluctuating Characteristic," J Bacteriol., 1949, pp. 141-145, vol. 57, No. 2.

Jung, C., et al., "The Effects of Endohyphal Bacteria on Anti-Cancer and Anti-Malaria Metabolites of Endophytic Fungi," Honors Thesis, University of Arizona, May 2012, 15 Pages.

Kaga, H., et al., "Rice Seeds as Sources of Endophytic Bacteria," Microbes Environ., 2009, pp. 154-162, vol. 24, No. 2.

Kalns, L., et al., "The Effects of Cotton Fungal Endophytes in the Field on Arthropod Community Structure," Power Point Presentation dated Jan. 7, 2013.

Kang, B. H., et al., "Members of the *Arabidopsis* Dynamin-Like Gene Family, ADL1, are Essential for Plant Cytokinesis and Polarized Cell Growth," Plant Cell, 2003, pp. 899-913, vol. 15.

Kasana, R. C., et al., "A Rapid and Easy Method for the Detection of Microbial Cellulases on Agar Plates Using Gram's Iodine," Curr Microbiol., 2008, pp. 503-507, vol. 57.

Khan, A.L., et al., "Salinity Stress Resistance Offered by Endophytic Fungal Interaction Between Penicillium minioluteum LHL09 and *Glycine max*. L," J. Microbiol. Biotechnol., 2011, pp. 893-902, vol. 21, No. 9.

Kim, M., et al., "Towards a taxonomic coherence between average nucleotide identity and 16S rRNA gene sequence similarity for species demarcation of prokaryotes", Int J Systematic Evolutionary Microbial., 2014, vol. 64, pp. 346-351.

Klaubauf, S., et al., "Molecular diversity of fungal conmunities in agricultural soils from Lower Austria," Fungal Diversity, Aug. 13, 2010, pp. 65-75, vol. 44, No. 1.

Knapp, D., et al., "Inter- and intraspecific functional diversity of fungal root endophytes of semiarid sandy grasslands," Acta Microbiologica et Immunologica Hungarica, Nov. 2017, pp. 1-101, vol. 64, Issue Supplement 1.

Kruger, M., et al., "DNA-Based Species Level Detection of Glomeromycota: One PCR Primer Set for All Arbuscular Mycorrhizal Fungi," New Phvtol., 2009, pp. 212-223, vol. 183.

Kuklinsky-Sobral, J., et al., "Isolation and Characterization of Endophytic Bacteria from Soybean (*Glycine max*) Grown in Soil Treated with Glyphosate Herbicide," Plant and Soil, 2005, pp. 91-99, vol. 273.

Kuklinsky-Sobral, J., et al., "Isolation and characterization of soybean-associated bacteria and their potential for plant growth promotion," Environmental Microbiology, 2004, pp. 1244-1251, vol. 6, No. 12.

Kumar, S., et al., "MEGA7: Molecular Evolutionary Genetics Analysis version 7.0 for bigger datasets," Molecular Biology and Evolution, Mar. 22, 2016, vol. 33, pp. 1870-1874.

Kumar, A., et al., "Bio-control potential of *Cladosporium* sp. (MCPL-461), against a noxious weed *Parthenium hysterophorus* L.," J. Environ Biol., Mar. 2009, pp. 307-312, vol. 30, Issue 2.

Kusari, S., et al. "Chemical ecology of endophytic fungi: origins of secondary metabolites," Cell Press, Chem & Biol., 2012, pp. 792-798, vol. 19.

Labeda, D.P., et al., "Phylogenetic study of the species within the family Streptomycetaceae," Antonie van Leeuwenhoek, 2012, vol. 101, pp. 73-104, Springer.

Lanver, D., et al., "Shot and Msb2-Related Proteins Regulate Appressorium Development in the Smut Fungus Ustilago aydis," Plant Cell, 2010, pp. 2085-2101, vol. 22.

Laus, M. C., et al., "Role of Cellulose Fibrils and Exopolysaccharides of Rhizobium leguminosarum in Attachment to and Infection of Vicia sativa Root Hairs," Mol Plant Microbe Interact., 2005, pp. 533-538, vol. 18, No. 6.

Le, X.H., et al., "Effects of endophytic Streptomyces on the lucerne (*Medicago sativa* L.) symbiosis at different levels of nitrogen," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 66-67.

Le, X.H., et al., "Isolation and characterisation of endophytic actinobacteria and their effect on the early growth and nodulation of lucerne (*Medicago sativa* L.)," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 134-136.

Lehman, S.G., "Treat Cotton Seed," Review of Applied Mycology, 1945, 24, 369, 16 Pages.

Lehman, S.G., "Treat Cotton Seed," Research and Farming III, Progr. Rept., 1945, 3, 5, 16 Pages.

Leonard, C. A., et al., "Random Mutagenesis of the Aspergillus oryzae Genome Results in Fungal Antibacterial Activity," Int J Microbiol., 2013, vol. 2013, Article ID 901697, 6 Pages.

Li, H. M., et al., "Expression of a Novel Chitinase by the Fungal Endophyte in Poa ampla," Mycologia, 2004, pp. 526-536, vol. 96, No. 3.

Li, H., et al., "Endophytes and their role in phytoremediation," Fungal Diversity, 2012, pp. 11-18, vol. 54.

Li, Q., "Agrobacterium tumefaciens Strain TA-AT-10 16S Ribosomal RNA Gene, Partial Sequence: GenBank: KF673157.1," Submitted Sep. 17, 2013.

Liu, M., et al., "A Novel Screening Method for Isolating Exopolysaccharide-Deficient Mutants," Appl Environ Microbiol., 1998, pp. 4600-4602, vol. 64, No. 11.

Liu, Y., et al., "Investigation on Diversity and Population Succession Dynamics of Endophytic Bacteria from Seeds of Maize (Zea mays L., Nongda108) at Different Growth Stages," Ann Microbiol., 2013, pp. 71-79, vol. 63.

Liu, D., et al., "Osmotin Overexpression in Potato Delays Development of Disease Symptoms," Proc Natl Acad Sci USA, 1994, pp. 1888-1892, vol. 91.

Liu, Y., et al., "Phylogenetic relationships among ascomycetes: evidence from an RNA polymerase II subunit," Mol. Biol. Evol. 1999. vol. 16, No. 12, pp. 1799-1808.

(56) References Cited

OTHER PUBLICATIONS

Liu, Y., et al., "Study on Diversity of Endophytic Bacterial Communities in Seeds of Hybrid Maize and their Parental Lines," Arch Microbiol., 2012, pp. 1001-1012, vol. 194.
Long, H. H., et al., "The Structure of the Culturable Root Bacterial Endophyte Community of Nicotiana attenuata is Organized by Soil Composition and Host Plant Ethylene Production and Perception," New Phytol., 2010, pp. 554-567, vol. 185.
Lopez-Lopez, A., et al., "Phaseolus vulgaris Seed-Borne Endophytic Community with Novel Bacterial Species such as *Rhizobium endophyticum* sp. nov.," Systematic Appl Microbiol., 2010, pp. 322-327, vol. 33.
Lorck, H., "Production of Hydrocyanic Acid by Bacteria," Physiol Plant, 1948, pp. 142-146, vol. 1.
Lugtenberg, B., et al., "Plant-Growth-Promoting Rhizobacteria," Ann. Rev. Microbiol., 2009, pp. 541-556, vol. 63.
Lundberg, D. S., et al., "Defining the Core *Arabidopsis thaliana* Root Microbiome," Nature, 2012, pp. 86-90, vol. 488, No. 7409.
Lundberg, D. S., et al., "Practical Innovations for High-Throughput Amplicon Sequencing," Nat Methods, 2013, pp. 999-1002, vol. 10, No. 10.
Ma, Y., et al., "Plant Growth Promoting Rhizobacteria and Endophytes Accelerate Phytoremediation of Metalliferous Soils," Biotechnology Advances, 2011, pp. 248-258, vol. 29.
Madi, L. et al., "Aggregation in Azospirillum brasilense Cd: Conditions and Factors Involved in Cell-to-Cell Adhesion," Plant Soil, 1989, pp. 89-98, vol. 115.
Mandyam, K., et al., "Mutualism-parasitism paradigm synthesized from results of root-endophyte models", Frontiers in Microbiology, Jan. 12, 2015, pp. 1-14, vol. 5.
Mannisto, M.K., et al., "Characterization of Psychrotolerant Heterotrophic Bacteria From Finnish Lapland," Svst Appl Microbiol., 2006, pp. 229-243, vol. 29.
Mano, H., et al., "Culturable Surface and Endophytic Bacterial Flora of the Maturing Seeds of Rice Plants (*Oryza sativa*) Cultivated in a Paddy Field," Microbes Environ., 2006, vol. 21, No. 2.
Manter, D. K., et al., "Use of the ITS Primers, ITSIF and ITS4, to Characterize Fungal Abundance and Diversity in Mixed-Template Samples by qPCR and Length Heterogeneity Analysis," J Microbiol Methods, 2007, pp. 7-14, vol. 71.
Mao, W., et al., "Seed Treatment with a Fungal or a Bacterial Antagonist for Reducing Corn Damping-off Caused by Species of Pythium and Fusarium," Plant Disease, 1997, pp. 450-454, vol. 81, No. 5.
Marasco, R., et al., "A Drought Resistance-Promoting Microbiome is Selected by Root System Under Desert Farming," PLoS One, 2012, vol. 7, No. 10, 14 Pages.
Marquez, L. M., et al., "A Virus in a Fungus in a Plant: Three-Way Symbiosis Required for Thermal Tolerance," Science, 2007, pp. 513-515, vol. 315.
Mastretta, C., et al., "Endophytic Bacteria from Seeds of Nicotiana Tabacum Can Reduce Cadmium Phytotoxicity," Intl J Phytoremediation, 2009, pp. 251-267, vol. 11.
Mateos, P. F., et al., "Cell-Associated Pectinolytic and Cellulolytic Enzymes in Rhizobium leguminosarum biovar trifolii," Appl Environ Microbiol., 1992, pp. 816-1822, vol. 58, No. 6.
McDonald, D., et al., "An Improved Greengenes Taxonomy with Explicit Ranks for Ecological and Evolutionary Analyses of Bacteria and Archaea," ISME J., 2012, pp. 610-618, vol. 6.
McGuire, K.L., et al., "Digging the New York City Skyline: Soil Fungal Communities in Green Roofs and City Parks," PloS One, 2013, vol. 8, No. 3, 13 Pages.
Medina, P., et al., "Rapid Identification of Gelatin and Casein Hydrolysis Using TCA," J Microbiol Methods, 2007, pp. 391-393, vol. 69.
Mehnaz, S., et al., "Growth Promoting Effects of Corn (*Zea mays*) Bacterial Isolates Under Greenhouse and Field Conditions," Soil Biology and Biochemistry, 2010, pp. 1848-1856, vol. 42.

Mehnaz, S., et al., "Isolation and 16S rRNA sequence analysis of the beneficial bacteria from the rhizosphere of rice," Canada Journal of Microbiology, 2001, pp. 110-117, vol. 47, No. 2.
Mei, C., et al., "The Use of Beneficial Microbial Endophytes for Plant Biomass and Stress Tolerance Improvement," Recent Patents on Biotechnology, 2010, pp. 81-95, vol. 4.
Michel, B. E., et al., "The Osmotic Potential of Polyethylene Glycol 6000," Plant Physiol., 1973, pp. 914-916, vol. 51.
Misk, A., et al., "Biocontrol of chickpea root rot using endophytic actinobacteria", Biocontrol, vol. 56, No. 5, Mar. 12, 2011, pp. 811-822, XP036215297.
Miyoshi-Akiyama, T., et al., "Multilocus Sequence Typing (MLST) for Characterization of Enterobacter cloacae," PLoS One, 2013, vol. 8, No. 6, 10 Pages, e66358.
Moe, L. A., "Amino Acids in the Rhizosphere: From Plants to Microbes," American Journal of Botany, 2013, pp. 1692-1705, vol. 100, No. 9.
Mohiddin, F. A., et al., "Tolerance of Fungal and Bacterial Biocontrol Agents to Six Pesticides Commonly Used in the Control of Soil Borne Plant Pathogens," African Journal of Agricultural Research, 2013, pp. 5331-5334, vol. 8, No. 43.
Mousa, W. K., et al., "The Diversity of Anti-Microbial Secondary Metabolites Produced by Fungal Endophytes: An Interdisciplinary Perspective," Front Microbiol., 2013, vol. 4, No. 65, 18 Pages.
Mundt, J.O., et al., "Bacteria Within Ovules and Seeds," Appl Environ Microbiol., 1976, pp. 694-698, vol. 32, No. 5.
Naik, B. S., et al., "Study on the diversity of endophytic communities from rice (*Oryza sativa* L.) and their antagonistic activities in vitro," Microbiological Research, 2009, pp. 290-296, vol. 164.
Naveed, M., "Maize Endophytes—Diversity, Functionality and Application Potential," University of Natural Resources and Life Sciences, 2013, pp. 1-266 and 81-87; Tables 1-3; Figure 2.
Nejad, P. et al., "Endophytic Bacteria Induce Growth Promotion and Wilt Disease Suppression in Oilseed Rape and Tomato," Biological Control, 2000, pp. 208-215, vol. 18.
Neslon, E.B., "Microbial Dynamics and Interactions in the Spermosphere," Ann. Rev. Phytopathol., 2004, pp. 271-309, vol. 42.
Nikolcheva, L.G., et al., "Taxon-Specific Fungal Primers Reveal Unexpectedly High Diversity During Leaf Decomposition in a Stream," Mycological Progress, 2004, pp. 41-49, vol. 3, No. 1.
Nimnoi, P., et al., "Co-Inoculation of Soybean (*Glycin Max*) with Actinomycetes and Bradyrhizobium Japonicum Enhances Plant Growth, Nitrogenase Activity and Plant Nutrition," Journal of Plant Nutrition, 2014, pp. 432-446, vol. 37.
Nishijima, K.A., et al., "Demonstrating Pathogenicity of Enterobacter cloacae on Macadamia and Identifying Associated Volatiles of Gray Kernel of Macadamia in Hawaii," Plant Disease, Oct. 2007, vol. 91, No. 10, pp. 1221-1228.
Normander, B., et al., "Bacterial Origin and Community Composition in the Barley Phytosphere as a Function of Habitat and Presowing Conditions," Appl Environ Microbiol., Oct. 2000, pp. 4372-4377, vol. 66, No. 10.
Okunishi, S., et al., "Bacterial Flora of Endophytes in the Maturing Seeds of Cultivated Rice (*Oryza sativa*)," Microbes and Environment, 2005, pp. 168-177, vol. 20, No. 3.
Op De Beeck, M., et al., "Comparison and Validation of Some ITS Primer Pairs Useful for Fungal Metabarcoding Studies," PLOS One, Jun. 2014, vol. 9, Issue 6, e97629, pp. 1-11.
Orole, O. O., et al., "Bacterial and fungal endophytes associated with grains and roots of maize," Journal of Ecology and the Natural Enviornment, 2011, pp. 298-303, vol. 3, No. 9.
Partida-Martinez, L.P., et al., "The Microbe-Free Plant: Fact or Artifact?" Front Plant Sci., 2011, vol. 2, No. 100, 16 Pages.
Pearson, W.R., et al., "Rapid and Sensitive Sequence Comparison With FASTP and FASTA," Methods Enzymol., 2011, pp. 63-98, vol. 183.
Pedraza, R. O., et al., "Azospirillum inoculation and nitrogen fertilization effect on grain yield and on the diversity of endophytic bacteria in the phyllosphere of rice rainfed crop," European Journal of Soil Biology, 2009, pp. 36-43, vol. 45.
Perez-Fernandez, M. A., et al., "Simulation of Germination of Pioneer Species Along an Experimental Drought Gradient," J Environ Biol., 2006, pp. 669-685, vol. 27, No. 4.

(56) References Cited

OTHER PUBLICATIONS

Perez-Miranda, S., et al., "O-CAS, A Fast and Universal Method for Siderophore Detection," J Microbiol Methods, 2007, pp. 127-131, vol. 70.
Petti, C. A., "Detection and Identification of Microorganisms by Gene Amplification and Sequencing," Clinical Infectious Diseases, 2007, pp. 1108-1114, vol. 44.
Phalip, V., et al., "A Method for Screening Diacetyl and Acetoin-Producing Bacteria on Agar Plates," J Basic Microbiol., 1994, pp. 277-280, vol. 34.
Philippot, L., et al., "Going Back to the Roots: The Microbial Ecology of the Rhizosphere," Nat Rev Microbiol., Nov. 2013, pp. 789-799, vol. 11.
Philrice Batac, Philippine Rice R&D Highlights, 2012, Area-Based R&D Projects, 52 Pages, [online][Retrieved Aug. 11, 2016] Retrieved from the Internet <URL:http://www.philrice.gov.ph/2012-rd-highlights/>.
Pillay, V. K., et al., "Inoculum Density, Temperature, and Genotype Effects on in vitro Growth Promotion and Epiphytic and Endophytic Colonization of Tomato (*Lycopersicon esculentum* L.) Seedlings Inoculated with a Pseudomonad Bacterium," Can J Microbiol., 1997, pp. 354-361, vol. 43.
Powell, W. A., et al., "Evidence of Endophytic Beauveria Bassiana in Seed-Treated Tomato Plants Acting as a Systemic Entomopathogen to Larval *Helicoverpa zea* (Lepidoptera: Noctuidae)," J. Entomol. Sci., 2009, pp. 391-396, vol. 44, No. 4.
Quadt-Hallmann, A., et al., "Bacterial Endophytes in Cotton: Mechanisms of Entering the Plant," Can J Microbiol., 1997, pp. 577-582, vol. 43.
R Core Team, "R: A Language and Environment for Statistical Computing," R Foundation for Statistical Computing, Vienna, Austria, May 2013, ISBN: 3-900051-07-0. Available online at http://www.R- 25 project.org/, 3604 Pages.
Rae, R., et al., "A subset of naturally isolated Bacillus strains show extreme virulence to the free-living nematodes Caenorhabditis elegans and Pristionchus pacificus", Environmental Microbiology, 2010, pp. 3007-3021, vol. 12, No. 11.
Rasmussen, S., et al., "Grass-endophyte interactions: a note on the role of monosaccharide transport in the Neotyphodium lolii-Lolium perenne symbiosis," New Phytologist, 2012, pp. 7-12, vol. 196.
Ravel, C., et al., "Beneficial effects of Neotyphodium lolii on the growth and the water status in perennial ryegrass cultivated under nitrogen deficiency or drought stress," Agronomie, 1997, pp. 173-181, vol. 17.
Redman, R. S., et al., "Thermotolerance Generated by Plant/Fungal Symbiosis," Science, Nov. 2002, vol. 298, 1 Page (with 4 pages of supplemental material).
Reiter, B., et al., "Response of Endophytic Bacterial Communities in Potato Plants to Infection with *Erwinia carotovora* subsp. *atroseptica*," Appl Environ Microbiol., 2001, pp. 2261-2268, vol. 68, No. 5.
Ren, Y., et al., "Complete Genome Sequence of *Enterobacter cloacae* subsp. *cloacae* Type Strain ATCC 13047," J. Bacteriol. May 2010, vol. 192, No. 9, pp. 2463-2464.
Riess, K., et al., "High genetic diversity at the regional scale and possible speciation in Sebacina epigaea and S. incrustans," BMC Evolutionary Biology, 2013, vol. 13, No. 102, 17 Pages.
Riken, GI No. GMFL01-01-D03, 2 Pages, [online] [Retrieved on Dec. 18, 2017] Retrieved from the internet <URL:http://spectra.psc.riken.jp/menta.cgi/rsoy/datail?id=GMFL01-01-D03>.
Rodriguez, H., et al., "Expression of a Mineral Phosphate Solubilizing Gene From Erwinia herbicola in Two Rhizobacterial Strains," J Biotechnol., 2001, pp. 155-161, vol. 84.
Rodriguez, R.J., et al., "Stress Tolerance in Plants via Habitat-Adapted Symbiosis," ISME J., 2008, pp. 404-416, vol. 2.
Rodriguez-Navarro, D., et al., "Soybean Interactions with Soil Microbes, Agronomical and Molecular Aspects," Agronomy for Sustainable Development, 2011, pp. 173-190, vol. 31, No. 1.
Roessner, U., et al., "Metabolic Profiling Allows Comprehensive Phenotyping of Genetically or Environmentally Modified Plant Systems," Plant Cell, 2001,pp. 11-29, vol. 13.
Rosado, A. S., et al., "Phenotypic and Genetic Diversity of Paenibacillus azotofixans Strains Isolated from the Rhizoplane or Rhizosphere Soil of Different Grasses," J App Microbiol., 1998, pp. 216-226, vol. 84.
Rosenblueth, A., et al., "Seed Bacterial Endophytes: Common Genera, Seed-to-Seed Variability and Their Possible Role in Plants," Acta Hort., 2012, pp. 39-48, vol. 938.
Rosenblueth, M., et al., "Bacterial Endophytes and Their Interactions With Host," Molecular Plant-Microbe Interactions, 2006, pp. 827-837, vol. 19, No. 8.
Ross, P.L., et al., "Multiplexed Protein Quantitation in *Saccharomyces cerevisiae* Using Amine-Reactive Isobaric Tagging Reagents," Mol Cell Proteomics, 2004, pp. 1154-1169, vol. 3, No. 12.
Saleem, M., et al., "Perspective of Plant Growth Promoting Rhizobacteria (PGPR) Containing ACC Deaminase in Stress Agriculture," J Ind Microbiol Biotechnol., Oct. 2007, pp. 635-648, vol. 34.
Samac, D.A., et al., "Recent Advances in Legume-Microbe Interactions: Recognition, Defense Response, and Symbiosis from a Genomic Perspective," Plant Physiol., 2007, pp. 582-587, vol. 144.
Samways, M.J., et al., "Assessment of the Fungus Cladosporium Oxyspoum (BERK. And CURT.) As a Potential BioControl Agent Against Certain Homoptera," Elsevier Science Publioshers B.V., Jan. 1, 1986, pp. 231-239.
Sardi, P., et al., "Isolation of Endophytic Streptomyces Strains from Surface Sterilized Roots," Applied and Environmental Microbiology, 1992, pp. 2691-2693, vol. 58, No. 8.
Sarwar, M., et al., "Tryptophan Dependent Biosynthesis of Auxins in Soil," Plant Soil, 1992, pp. 207-215, vol. 147.
Saunders, M., et al., "Host-Synthesized Secondary Compounds Influence the In Vitro Interactions between Fungal Endophytes of Maize", Applied and Environmental Microbiology, Nov. 9, 2007, pp. 136-142, vol. 74 , No. 1.
Schmieder, R., et al., "Quality Control and Preprocessing of Metagenomic Datasets," Bioinformatics, 2011, pp. 863-864, vol. 27, No. 6.
Schneider, C., et al., "Endophytes for plant protection: the state of the art Proceedings," DPG Spectrum Phytomedizin, Proceedings of the 5th International Symposium on Plant Protection and Plant Health in Europe, May 26-29, 2013, 347 Pages.
Schoch, C. L., et al., "Nuclear Ribosomal Internal Transcribed Spacer (ITS) Region as a Universal DNA Barcode Marker for Fungi," Proc Natl Acad Sci USA, 2012, pp. 6241-6246, vol. 109, No. 16.
Schwyn, B. et al., "Universal Chemical Assay for the Detection and Determination of Siderophores," Analytical Biochemistry, 1987, pp. 47-56, vol. 160.
Senthilkumar, M., et al., "Biocontrol Potential of Soybean Bacterial Endophytes Against Charcoal Rot Fungus, *Rhizoctonia batatiola*," Current Microbiology, 2009, vol. 58, pp. 288-293.
Sessitsch, A., et al., "*Burkholderia phytofirmans* sp. Nov., a novel plant-associated bacterium with plant-beneficial properties," International Journal of Systematic and Evoluntary Microbiology, 2005, pp. 1187-1192, vol. 55.
Shapiro-Ilan, D.I., et al., "The Potential for Enhanced Fungicide Resistance in Beauveria Bassiana Through Strain Discovery and Artificial Selection," Journal of Invertebrate Pathology, 2002, pp. 86-93, vol. 81.
Shankar, M., et al.,"Root colonization of a rice growth promoting strain of Enterobacter cloacae," Journal of Basic Microbiology, 2011, pp. 523-530, vol. 51.
Shiraishi, A., et al., "Nodulation in black locust by the ammaproteobacteria *Pseudomonas sp.* and the *Betaproteobacteria Burkholderia* sp", Systematic and Applied Microbiology, Aug. 2010, pp. 269-274, vol. 33, No. 5.
Simola, L., et al., "The Effect of Some Protein and Non-Protein Amino Acids on the Growth of Cladosporium herbarum and Trichotheeium roseum," Effect of Amino Acids on Fungi, Physiologia Plantarum, 1979, pp. 381-387, vol. 46.
Singh, A. K., et al., "Uncultured *Actinomyces* sp. Clone EMLACT 80 IV (New) 16S Ribosomal RNA Gene, Partial Sequence," NCBI GenBank Accession No. JQ285908. Submitted Dec. 13, 2011.

(56) References Cited

OTHER PUBLICATIONS

Soares, M. M. C. N., et al., "Screening of Bacterial Strains for Pectinolytic Activity: Characterization of the Polygalacturonase Produced by *Bacillus* Sp," Revista de Microbiolgia, 1999, pp. 299-303, vol. 30.

Soe, K.M., et al., "Effects of endophytic actinomycetes and Bradyrhizobium japonicum strains on growth, nodulation, nitrogen fixation and seed weight of different soybean varieties," Soil Science and Plant Nutrition, 2012, pp. 319-325, vol. 58, No. 3.

Soe, K.M., et al., "Low-Density Co-Inoculation of Myanmar Bradyrhizobium yuanmingense MAS34 and Streptomyces griseoflavus P4 to Enhance Symbiosis and Seed Yield in Soybean Varieties," American Journal of Plant Sciences, 2013, pp. 1879-1892, vol. 4.

Sogonov, M.V., et al., "The hyphomycete *Teberdinia hygrophila* gen. nov., sp. nov. and related anamorphs of *Pseudeurotium* species," Mycologia, May 2005, pp. 695-709, vol. 97, No. 3.

Song, M., et al., "Effects of Neotyphodium Endophyte on Germination of Hordeum brevisubulatum under Temperature and Water Stress Conditions," Acta Agrestia Sinica, 2010, pp. 834-837, vol. 18, No. 6. (English Abstract).

Souleimanov, A., et al., "The Major Nod Factor of Bradyrhizobium japonicum Promotes Early Growth of Soybean and Corn," J. Exp. Bot., 2002, pp. 1929-1934, vol. 53, No. 376.

Spiekermann, P., et al., "A Sensitive, Viable-Colony Staining Method Using Nile Red for Direct Screening of Bacteria that Accumulate Polyhydroxyalkanoic Acids and Other Lipid Storage Compounds," Arch Microbiol., 1999, pp. 73-80, vol. 171.

Staudt, A. K., et al., "Variations in Exopolysaccharide Production by Rhizobium tropici," Arch Microbiol., 2012, pp. 197-206, vol. 194.

Stielow, J.B., et al., "One fungus, which genes? Development and assessment of universal primers for potential secondary fungal DNA barcodes," Persoonia: Molecular Phylogeny and Evolution of Fungi, 2015, vol. 35, pp. 242-263.

Strobel, G. A., "Endophytes as Sources of Bioactive Products," Microbes and Infection, 2003, pp. 535-544, vol. 5.

Sturz, A. V., et al., "Weeds as a Source of Plant Growth Promoting Rhizobacteria in Agricultural Soils," Can J Microbiol., 2001, pp. 1013-1024, vol. 47, No. 11.

Surette, M. A., et al. "Bacterial Endophytes in Processing Carrots (*Daucus carota* L. var. *sativus*): Their Localization, Population Density, Biodiversity and Their Effects on Plant Growth," Plant and Soil, 2003, pp. 381-390, vol. 253, No. 2.

Suto, M., et al., "Endophytes as Producers of Xylanase," J Biosci Bioeng., 2002, pp. 88-90, vol. 93, No. 1.

Sword, G., "Manipulating Fungal Endophytes to Protect Plants from Insects and Nematodes," Power Point Presentation dated Aug. 7, 2013.

Sword, G., et al., "Manipulating Fungal Endophytes for the Protection of Cotton in the Field," Power Point Presentation dated Jan. 7, 2013.

Sword, G., et al., "Field Trials of Potentially Beneficial Fungal Endophytes in Cotton," Power Point Presentation dated Jan. 7, 2013.

Sword, G., "Fungal Endophytes to Protect Cotton from Insects and Nematodes," Power Point Presentation dated Dec. 7, 2012, 20 Pages.

Sword, G., "Natural Enemies—The Forgotten Basis of IPM?," Power Point Presentation dated Sep. 6, 2013.

Taghavi, S., et al., "Genome Survey and Characterization of Endophytic Bacteria Exhibiting a Beneficial Effect on Growth and Development of Poplar Trees," Applied and Environmental Microbiology, 2009, pp. 748-757, vol. 75, No. 3.

Taghavi, S., et al., "Genome Sequence of the Plant Growth promoting Endophytic Bacterium *Enterobacter* sp. 638", PLoS Genet., May 2010, pp. 1-15, vol. 6, Issue 5, e1000943.

Tamura, K., et al., "Estimation of the number of nucleotide substitutions in the control region of mitochondrial DNA in humans and chimpanzees," Molecular Biology and Evolution, 1993, vol. 10, No. 3, pp. 512-526.

Taylor, A. G., et al., "Concepts and Technologies of Selected Seed Treatments," Annu. Rev. Phytopathol., 1990, pp. 321-339, vol. 28.

Teather, R. M., et al., "Use of Congo Red-Polysaccharide Interactions in Enumeration and Characterization of Cellulolytic Bacteria from the Bovine Rumen," Appl Environ Microbiol., 1982, pp. 777-780, vol. 43, No. 4.

Thakur, A., et al., "Detrimental effects of endophytic fungus *Nigrospora* sp. on survival and development of Spodoptera litura," Biocontrol Science and Technology, Feb. 1, 2012, pp. 151-161, vol. 22, No. 2.

Thakur, A., et al., "Enhanced Resistance to Spodoptera litura in Endophyte Infected Cauliflower Plants," Environmental Entomology, Apr. 1, 2013, pp. 240-246, vol. 42, No. 2.

Thakur, A., et al., "Suppression of Cellular Immune Response in *Spodoptera litura* (Lepidoptera: Noctuidae) Larvae by Endophytic Fungi Nigrospora oryzae and Cladosporium uredinicola,", Annals of the Entomological Society of America, May 1, 2014, pp. 674-679, vol. 107, No. 3.

Theis, K. R., et al., "Uncultured Bacterium Clone GM2GI8201A64RC 16S Ribosomal RNA Gene, Partial Sequence," NCBI GenBank Accession No. JX051943, Submitted May 14, 2012.

Thomas, L., et al., "Development of Resistance to Chlorhexidine Diacetate in Pseudomonas aeruginosa and the Effect of a "Residual" Concentration," J Hosp Infect., 2000, pp. 297-303, vol. 46.

Thomashow, M. F., "So What's New in the Field of Plant Cold Acclimation? Lots!," Plant Physiol., 2001, pp. 89-93, vol. 125.

Tokala, R. T., et al., "Novel Plant-Microbe Rhizosphere Interaction Involving Streptomyces Lydicus WYEC108 and the Pea Plant (*Pisum sativum*)," Applied and Environmental Microbiology, May 2002, pp. 2161-2171, vol. 68, No. 5.

Trichoderma definition, 2016, 6 Pages, [online] [Retrieved on Sep. 16, 2016,] Retrieved from the Internet <URL:https://en.wikipedia.org/wiki/Trichoderma>.

Trotel-Aziz, P., et al., "Characterization of New Bacterial Biocontrol Agents Acinetobacter, Bacillus, Pantoea and *Pseudomonas* spp. Mediating Grapevine Resistance Against Botrytis cinerea," Environmental and Experimental Botany, 2008, pp. 21-32, vol. 64.

Truyens, S., et al., "Changes in the Population of Seed Bacteria of Transgenerationally Cd-Exposed *Arabidopsis thaliana*," Plant Biol., 2013, pp. 971-981, vol. 15.

U'Ren, J.M., et al., "Host and geographic structure of endophytic and endolichenic fungi at the continental scale," American Journal of Botany, May 1, 2012, pp. 898-914, vol. 99, No. 5.

Usadel, B., et al., "The Plant Transcriptome—From Integrating Observations to Models," Front Plant Sci., 2013, pp. 1-3, vol. 4., Article 48, 3 Pages.

Vacheron, J., et al., "Plant Growth-Promoting Rhizobacteria and Root System Functioning," Frontiers Plant Sci., 2013, vol. 4, Article 356, 19 Pages.

Valencia, C. U., et al., "Endophytic Establishment as an Unintended Consequence of Biocontrol with Fungal Entomopathogens," Power Point Presentation dated Jan. 7, 2013, 10 Pages.

Valencia, E., et al., "Mini-review: Brazilian fungi diversity for biomass degradation," Fungal Genetics and Biology, 2013, pp. 9-18, vol. 60.

Van Der Lelie, D., et al., "Poplar and its Bacterial Endophytes: Coexistence and Harmony," Critical Rev Plant Sci., 2009, pp. 346-358, vol. 28.

Verkley, G., et al., "*Paraconiothyrium*, a new genus to accommodate the mycoparasite Coniothyrium minitans, anamorphs of Paraphaeosphaeria, and four new species," Studies in Mycology, 2004, pp. 323-335, vol. 50.

Vining, K., et al., "Methylome Reorganization During in vitro Dedifferentiation and Regeneration of Populus trichocarpa," BMC Plant Biol., 2013, vol. 13, No. 92, 15 Pages.

Viruel, E., et al., "Pseudomonas thiveralensis Strain IEHa 16S Ribosomal RNA Fene, Partial Sequence," NCBI GenBank Accession No. GQ169380.1, Submitted May 15, 2009.

Visagie, C.M., et al., "Identification and nomenclature of the genus *Penicillium*," Studies in Mycology, Jun. 2014, pp. 343-371, vol. 78.

Vujanovic, V., et al., "Viability Testing of Orchid Seed and the Promotion of Colouration and Germination," Annals of Botany, Mar. 17, 2000, pp. 79-86, vol. 86.

(56) References Cited

OTHER PUBLICATIONS

Vujanovic, V., et al., "Endophytic hyphal compartmentalization is required for successful mycobiont-wheat interaction as revealed by confocal laser microscopy," The proceedings of the Soils and Crops conference in Saskatoon (2008) published 2009, 7 Pages.
Vujanovic, V., et al., "A comparative study of endophytic mycobiota in leaves of Acer saccharum in eastern North America," Mycological Progress, May 2002, pp. 147-154, vol. 1, Issue 2.
Vujanovic, V., et al., "Orchid seed viability testing by fungal bioassays and molecular phylogeny," Floriculture, ornamental and plant biotechnology, 2006, vol. 63, pp. 563-569.
Vujanovic, V., et al., "Mycovitality—a new concept of plant biotechnology," Canadian Journal Plant Pathol, 2007, vol. 29, p. 451.
Vujanovic, V., et al., "19th International Conference on *Arabidopsis*. Research Proceedings—ICAR13," Jul. 23-27, 2008, 264 Pages, Montreal, QC, Canada.
Vujanovic, V., et al., "Mycovitality and mycoheterotrophy: where lies dormancy in terrestrial orchid and plants with minute seeds?" Symbiosis, 2007, vol. 44, pp. 93-99.
Vujanovic, V., et al., "Seed endosymbiosis: a vital relationship in providing prenatal care to plants," Can. J. Plant Sci., NRC Research Press, Feb. 6, 2017, pp. 972-981, vol. 97.
Waller, F., et al., "The Endophytic Fungus Piriformospora indica Reprograms Barley to Salt-Stress Tolerance, Disease Resistance, and Higher Yield," PNAS, 2005, pp. 13386-13391, vol. 102, No. 38.
Wang, B., et al., "Fungal endophytes of native *Gossypium* species in Australia," Mycological Research, 2007, pp. 347-354, vol. 111, No. 3.
Wang, K., et al., "Monitoring in Planta Bacterial Infection at Both Cellular and Whole-Plant Levels Using the Green Fluorescent Protein Variant GFPuv," New Phytol., 2007, pp. 212-223, vol. 174.
Wang, Q., et al., "Naive Bayesian Classifier for Rapid Assignment of rRNA Sequences into the New Bacterial Taxonomy," Appl. Environ. Microbiol., 2007, pp. 5261-5267, vol. 73, No. 16.
Waqas, M., et al., "Endophytic Fungi Produce Gibberellins and Indoleacetic Acid and Promotes Host-Plant Growth during Stress," Molecules, 2012, pp. 10754-10773, vol. 17.
Weaver, P.F., et al., "Characterization of Rhodopseudomonas capsulata," Arch Microbiol., 1975, pp. 207-216, vol. 105.
Weindling, R., "Relation of dosage to control of cotton seedling diseases by seed treatment," Plant Disease Reporter, 1943, 27, pp. 68-70.
Welty, R.E., et al., "Influence of Moisture Content, Temperature, and Length of Storage on Seed Germination and Survival of Endophytic Fungi in Seeds of Tall Fescue and Perennial Ryegrass," Phytopathyol., 1987, pp. 893-900, vol. 77, No. 6.
White, J. F., et al., "A Proposed Mechanism for Nitrogen Acquisition by Grass Seedlings Through Oxidation of Symbiotic Bacteria," Symbiosis, 2012, pp. 161-171, vol. 57.
Wiegand, I., et al., "Agar and Broth Dilution Methods to Determine the Minimal Inhibitory Concentration (MIC) of Antimicrobial Substances," Nature Protocols, 2008, pp. 163-175, vol. 3, No. 2.
Xu, M., et al., "Bacterial Community Compositions of Tomato (*Lycopersicum esculentum* Mill.) Seeds and Plant Growth Promoting Activity of ACC Deaminase Producing Bacillus subtilis (HYT-12-1) on Tomato Seedlings," World J Microbiol Biotechnol., 2014, pp. 835-845, vol. 30.
Xu, Y., et al., "Biosynthesis of the Cyclooligomer Despipeptide bassianolide, an Insecticidal Virulence Factor of Beauveria bassiana," Fungal Genetics and Biology, 2009, pp. 353-364, vol. 46.
Xue, Q.Y., et al., "Evaluation of the Strains of Acinetobacter and Enterobacter as potential Biocontrol Agents Against Ralstonia Wilt of Tomato," Biological Control, 2009, vol. 48, pp. 252-258.
Yandigeri, M. S., et al., "Drought-tolerant endophytic actinobacteria promote growth of wheat (*Triticum aestivum*) under water stress conditions," Plant Growth Regulation, 2012, pp. 411-420, vol. 68.
Yennamalli, R., et al., "Endoglucanases: insights into thermostability for biofuel applications", Biotech Biofuels, 2013, vol. 6, Issue 136, pp. 1-9.
Yezerski, A., et al., "The Effects of the Presence of Stored Product Pests on the Microfauna of a Flour Community," Journal of Applied Microbiology, 2005, pp. 507-515, vol. 98.
You, Y., et al., "Analysis of Genomic Diversity of Endophytic Fungal Strains Isolated from the Roots of Suaeda japonica and S. maritima for the Restoration of Ecosystems in Buan Salt Marsh," Korean Journal of Microbiology and Biotechnology, 2012, pp. 287-295, vol. 40, No. 4. (with English Abstract).
Youssef, Y.A., et al., "Production of Plant Growth Substances by Rhizosphere Myoflora of Broad Bean and Cotton," Biologia Plantarum, 1975, pp. 175-181, vol. 17, No. 3.
Zhang, J., et al: "Isolation and Characterization of Plant Growth-Promoting Rhizobacteria from Wheat Roots by Wheat Germ Agglutinin Labeled with Fluorescein Isothiocyanate", The Journal of Microbiology, Apr. 27, 2012, vol. 50, No. 2, pp. 191-198, GenBank Accession No: JN210900.
Zhao, J.H., et al., "Bioactive secondary metabolites from *Nigrospora* sp. LLGLM003, an endophytic fungus of the medicinal plant *Moringa oleifera* Lam." World Journal of Microbiology and Biotechnology, Kluwer Academic Publishers, Feb. 12, 2012, pp. 2107-2112, vol. 28, No. 5.
Zhou, W., et al., "Effects of the Fungal Endophyte *Paecilomyces* sp. in Cotton on the Roo-Knot Nematode Meloidogyne incognita," poster dated Jan. 7, 2013.
Zhu et al., Helminthosporium velutinum and *H. aquaticum* sp. nov. from aquatic habitats in Yunnan Province, China. Phytotaxa, 2016, vol. 253, No. 3, pp. 179-190.
Zimmerman, N. B., et al., "Fungal Endophyte Communities Reflect Environmental Structuring Across a Hawaiian Landscape," Proc Natl Acad Sci USA, 2012, pp. 13022-13027, vol. 109, No. 32.
Zuccaro, a., et al., "Endophytic Life Strategies Decoded by Genome and Transcriptome Analyses of the Mutualistic Root Symbiont Piriformospora indica," PLOS Pathogens, 2011, vol. 7, No. 10, e1002290.
Zuniga, A., et al., "Quorum Sensing and Indole-3-Acetic Acid Degradation Play a Role in Colonization and Plant Growth Promotion of *Arabidopsis thaliana* by Burkholderia phytofirmans PsJN," Mol Plant Microbe Interact., 2013, pp., 546-553, vol. 26, No. 5.
PCT International Search Report and Written Opinion for PCT/US2017/064292, dated May 11, 2018, 20 Pages.
PCT International Search Report and Written Opinion for PCT/US2017/064361, dated May 11, 2018, 22 Pages.
Database EMBL [Online] Oct. 1, 2001, "Setosphaeria monoceras 28S ribosomal RNA gene, partial sequence," XP002777918, retrieved from EBI accession No. EM_STD:AY016368 Database accession No. AY016368 sequence.
Amr H Nassar et al., "Promotion of plant growth by an auxin-producing isolate of the yeast Williopsis saturnus endophytic in maize (*Zea mays* L.) roots", Biology and Fertility of Soils; Cooperating Journal of International Society of Soil Science, Springer, Berlin, DE, vol. 42, No. 2, Nov. 1, 2005, pp. 97-108.
Bing Lori Anderson et al., "Suppression of *Ostrinia nubilalis* (Huebner) (Lepidoptera: Pyralidae) by Endophytic *Beauveria bassiana* (Balsamo) Vui 11 emi n", Environmental Entomol, Entomological Society of America, College Park, MD, US, vol. 20, Jan. 1, 1991, pp. 1207-1211.
O'Hanlon Karen A et al., "Exploring the potential of symbiotic fungal endophytes in cereal disease suppression", Biological Control, vol. 63, No. 2, Sep. 5, 2012, pp. 69-78.
A.E. Impullitti et al.,"Fungal endophyte diversity in soybean", Journal of Applied Microbiolog, vol. 114, No. 5, May 1, 2013, pp. 1500-1506.
Vladimir Vujanovic et al: "Fungal communities associated with durum wheat production system: a characterization by growth stage, plant organ and preceding crop", Crop Protection, Elsevier Science, GB, vol. 37, Feb. 19, 2012, pp. 26-34.
Wenming Zhang et al., Host range of Exserohilum monoceras, a potential bioherbicide for the control of *Echinochloa* species, Canadian Journal of Botany/ Journal Canadien De Botan, National Research Council, Ottawa, CA, vol. 75, Jan. 1, 1997, pp. 685-692.
United States Patent Office, Non-Final Office Action, U.S. Appl. No. 14/766,065, dated Oct. 27, 2017, 11 Pages.

(56) References Cited

OTHER PUBLICATIONS

United States Patent Office, Non-Final Office Action, U.S. Appl. No. 14/964,429, dated Aug. 9, 2016, 6 Pages.
United States Patent Office, Final Office Action, U.S. Appl. No. 14/964,429, dated May 31, 2017, 9 Pages.
United States Patent Office, Non-Final Office Action, U.S. Appl. No. 15/212,038, dated Sep. 21, 2016, 10 Pages.
United States Patent Office, Non-Final Office Action, U.S. Appl. No. 15/063,350, dated Nov. 10, 2016, 18 Pages.
United States Patent Office, Final Office Action, U.S. Appl. No. 14/614,193, dated Dec. 22, 2016, 13 Pages.
United States Patent Office, Final Office Action, U.S. Appl. No. 14/614,193, dated Jul. 18, 2017, 14 Pages.
United States Patent Office, Final Office Action, U.S. Appl. No. 14/614,193, dated May 3, 2018, 10 Pages.
United States Patent Office, Non-Final Office Action, U.S. Appl. No. 15/107,973, dated Apr. 10, 2017, 39 Pages.
United States Patent Office, Final Office Action, U.S. Appl. No. 15/107,973, dated Jan. 26, 2018, 20 Pages.
United States Patent Office, Final Office Action, U.S. Appl. No. 14/410,537, dated May 5, 2017, 9 Pages.
United States Patent Office, Non-Final Office Action, U.S. Appl. No. 15/034,862, dated May 19, 2017, 8 Pages.
United States Patent Office, Final Office Action, U.S. Appl. No. 15/034,862, dated Jan. 12, 2018, 14 Pages.
United States Patent Office, Non-Final Office Action, U.S. Appl. No. 15/436,592, dated Aug. 30, 2017, 17 Pages.
United States Patent Office, Non-Final Office Action, U.S. Appl. No. 15/436,609, dated Aug. 30, 2017, 21 Pages.
United States Patent Office, Non-Final Office Action, U.S. Appl. No. 14/916,514, dated Sep. 20, 2017, 31 Pages.
United States Patent Office, Non-Final Office Action, U.S. Appl. No. 15/143,398, dated Sep. 22, 2017, 17 Pages.
United States Patent Office, Non-Final Office Action, U.S. Appl. No. 15/143,394, dated Sep. 25, 2017, 15 Pages.
United States Patent Office, Non-Final Office Action, U.S. Appl. No. 15/107,965, dated Jun. 21, 2018, 27 Pages.
Abello, J., et al., "Agrobacterium-mediated transformation of the endophytic fungus Acremonium implicatum associated with Brachiaria grasses", Mycological Research, pp. 407-413, vol. 112, Pt 3.
Al-Askar AA, "Microbiological studies on the in vitro inhibitory effect of Streptomyces collinus albescens against some phytopathogenic fungi", African Journal of Microbiology Research, 2012, 6: 3277-3283 & GenBank Accession No. AB184101, May 20, 2008.
Antony-Badu, S., et al., "Multiple *Streptomyces* species with distinct secondary metabolomes have identical 16S rRNA gene sequences." Scientific Reports 7.1, Sep. 2017, No. 7, 11089, pp. 1-8.
Ardakani, M.R. et al., "Absorption of N, P, K through triple inoculation of wheat (*Triticum aestivum* L.) by Azospirillum brasilense, *streptomyces* sp., Glomus intraradices and manure application," Physiol Mol Biol Plants, 2011, vol. 17, No. 2, pp. 181-192.
Artusson, V., et al., "Interactions between arbuscular mycorrhizal fungi and bacteria and their potential for stimulating plant growth", Environmental Microbiology, vol. 8, No. 1, Jan. 1, 2006, pp. 1-10.
Azcon, R., et al., "Selective interactions between different species of mycorrhizal fungi and Rhizobium meliloti strains, and their effects on growth, N2-fixation (15N) and nutrition of *Medicago sativa* L.," New PhytoL., 1991, vol. 117, pp. 399-404.
Bandara, W.M.M.S., et al., "Interactions among endophytic bacteria and fungi: effects and potentials", Journal of Biosciences, Dec. 2006, vol. 31, No. 5, pp. 645-650.
Barnett, S., et al., "Selection of microbes for control of Rhizoctonia root rot on wheat using a high throughput pathosystem", Biological Control, Jul. 6, 2017, 113: 45-57.
Bashan, Yoav Ed, et al., "Inoculants of plant growth-promoting bacteria for use in agriculture," Biotechnology Advances, Elsevier Publishing, Barking, GB, vol. 16, No. 4, Jul. 1, 1998, pp. 729-770, XP004123985.
Bashan, Yoav E., et al., "Alginate Beads as Synthetic Inoculant Carriers for Slow Release of Bacteria that Affect Plant Growth," Applied and Environmental Microbiology, pp. 1089-1098, May 1986.
Bing, LA, et al., "Suppression of *Ostrinia nubilalis* (Hübner) (Lepidoptera: Pyralidae) by endophytic *Beauveria bassiana* (Balsamo) Vuillemin", Environmental Entomol, Entomological Society of America, College Park, MD, US, vol. 20, Jan. 1, 1991, pp. 1207-1211.
Bragantia, et al: "Identificaqao E Avaliaqao De Rizobacterias Isoladas De Raizes De Milho," Jan. 1, 2010, pp. 905-911, Retrieved from the Internet: URL:http://www.scielo.br/pdf/brag/v69n4/v69n4a17.pdf (With English Abstract).
Chenhua Li, et al., "Change in deep soil microbial communities due to long-term fertilization," Soil Biology and Biochemistry, vol. 75, Mar. 5, 2014, pp. 264-272, XP055530941.
Cheow, W.S., et al., "Biofilm-like Lactobacillus rhamnosus Probiotices Encapsulated in Algiinate and Carrageenan Microcapsules Exhibiting Enhanced Thermotolerance and Freeze-drying Resistance," Biomacromolecules 2013, vol. 14(9):3214-3222.
Compant, S., et al., "Endophytic colonization of *Vitis vinfera* L. by Burkholderia phytofirmans strain PsJN: from the rhizosphere to inflorescence tissues," FEMS Microbiol Ecol, 2008, pp. 84-93, vol. 63.
De Medeiros, L., et al., "Evaluation of Herbicidal Potential of Depsides from Cladosporium uredinicola an Endophytic Fungus found in Guava Fruit," J. Braz. Chem. Soc., 2012, vol. 23, No. 8, p. 1551-1557.
De Santi, M. et al., "A combined morphologic and molecular approach for characterizing fungal microflora from a traditional Italian cheese (Fossa cheese)," Inter. Dairy J., 2010, vol. 10, No. 7, pp. 465-471.
Fatima Z et al, "Antifungal activity of plant growth-promoting rhizobacteria isolates against Rhizoctonia solani in wheat", African Journal of Biotechnology, 2009, 8: 219-225.
Fox, G., et al., "How close is close: 16S rRNA sequence identity may not be sufficient to guarantee species identity." International Journal of Systematic and Evolutionary Microbiology 42.1, 1992, pp. 166-170.
NCBI GenBank: Accession No. JX880250.1, "Enterobacteriaceae bacterium Clero1 16S ribosomal RNA gene, partial sequence," NIH, Jun. 24, 2015, 2 Pages, can be retreived at <URL:https://www.ncbi.nlm.nih.gov/nucleotide/JX880250.1?report=genbank&log$=nuclalign&blast_rank=80&RID=KWUPBV08015>.
GenBank Accession No. KY643705, Feb. 27, 2017.
GenBank Accession No. KF951483, Jan. 5, 2014.
GenBank Accession No. KJ152029, May 6, 2015.
GenBank Accession No. KJ162248, Apr. 8, 2014.
Database EMBL [Online] Oct. 1, 2001, 2 Pages, "Setosphaeria monoceras 28S ribosomal RNA gene, partial sequence," XP002777918, retrieved from EBI accession No. EM_STD:AY016368 Database accession No. AY016368 sequence.
NCBI, GenBank Accession No. XP_002568042, Aug. 14, 2009, 4 Pages, Berg, V.D., et al., "Genome sequencing and analysis of the filamentous fungus," Nat. Biotechnol. 26 (10), 1161-1168 (2008).
Goudjal, Y., et al., "Biocontrol of Rhizoctonia solanidamping-off and promotion of tomato plant growth by endophytic actinomycetes isolated from native plants of *Algerian sahara*", Microbiological Research, 2014, vol. 169, No. 1, pp. 59-65.
Govindarajan, M. et al., "Effects of the Inoculation of Burkholderia vietnamensis and Related Endophytic Diaztrophic Bacteria on Grain Yield of Rice", Mircobial Ecology, Apr. 4, 2007, 17 pages.
Guo, X., et al., "Red Soils Harbor Diverse Culturable Actinomycetes That Are Promising Sources of Novel Secondary Metabolites", Applied and Environmental Microbiology, Feb. 27, 2015, vol. 81, No. 9, pp. 3086-3103.
Hain, T., et al., "Chitinolytic transgenes from Streptomyces albidoflavus as phytochemicals defences against herbivorous insects, use in transgenic plants and effect in plant development", International Journal of Systematic Bacteriology, Jan. 1997, vol. 47, No. 1, pp. 202-206.

(56) References Cited

OTHER PUBLICATIONS

Hanshew, A., et al., "Characterization of Actinobacteria Associated with Three Ant-Plant Mutualisms", Microbial Ecology, Aug. 6, 2017, vol. 69, No. 1, pp. 192-203.
Hjort, K., et al., "Chitinase genes revealed and compared in bacterial isolates, DNA extracts and a metagenomic library from a phytopathogen-suppressive soil", FEMS Microbiology Ecology, Feb. 2010, vol. 71, No. 2, pp. 197-207.
Hubbard, M., et al., 2011. "Agricultural Potential of Fungal Endophytes of Grasses, Cereals and Wheat," In: Wheat: Genetics, Crops and Food Production. Nova Science Publishers Hauppauge, NY, USA. pp. 333-345.
Impullitti, A.E., et al., "Fungal endophyte diversity in soybean", Journal of Applied Microbiolog, vol. 114, No. 5, May 1, 2013, pp. 1500-1506.
Iverson, C., et al, "The taxonomy of Enterobacter sakazakii: proposal of a new genus *Cronobacter* gen. nov. and descriptions of *Cronobacter sakazakii* comb. nov. *Cronobacter sakazakii* subsp. *sakazakii*, comb. nov., *Cronobacter sakazakii* subsp. *malonaticus* subsp. nov., *Cronobacter turicensis* sp. nov., *Cronobacter muytjensii* sp. nov., *Cronobacter dublinensis* sp. nov. and Cronobacter genomospecies I", BMC Evolutionary Biology 2007, Apr. 17, 2017, 11 pages.
Joe, M.M. et al., "Development of alginate-based aggregate inoculants of *methylobacterium* sp. and Azospirillum brasilense tested under in vitro conditions to promote plant growth," Journal of Applied Microbiology 2013, 116(2):408-423, XP055225426, Nov. 22, 2013.
Kanbar, A., et al., "Relationship between Root and Yield Morphological Characters in Rainfed Low Land Rice (*Oryza sativa* L.)," Cereal Research Communications, 2009, vol. 37, No. 2, pp. 261-268.
Li, M., et al., "ATP Modulates the Growth of Specific Microbial Strains", Current Microbiology, May 30, 2010, vol. 62, No. 1, pp. 84-89.
Lind, A., et al., "Drivers of genetic diversity in secondary metabolic gene clusters within a fungal species", PLOS Biology, Nov. 17, 2017, 26 pages.
Manoharan, M. J. et. Al., "Survival of flocculated cells in alginate and its inoculatin effect on growth and yield of maize under water deficit conditions," Ep J of Siil Biology, Gauthier-Villars, Montrouge, FR, vol. 50, Mar. 7, 2012, pp. 198-206, XP028421147.
Nassar, A., et al., "Promotion of plant growth by an auxin-producing isolate of the yeast Williopsis saturnus endophytic in maize (*Zea mays* L.) roots", Biology and Fertility of Soils; Cooperating Journal of International Society of Soil Science, Springer, Berlin, DE, vol. 42, No. 2, Nov. 1, 2005, pp. 97-108.
Murali, Gopal, et al., "Microbiome Selection Could Spur Next-Generation Plant Breeding Strategies," Frontiers in Microbiology, vol. 7, Dec. 7, 2016, XP055531064.
Ogbo, F., et al., "Some Characteristics of a Plant Growth Promoting iEnterobacter/isp. Isolated from the Roots of Maize", Advances in Microbiology, Jan. 1, 2012, vol. 02, No. 03, pp. 368-374.
O'Hanlon, K., et al., "Exploring the potential of symbiotic fungal endophytes in cereal disease suppression", Biological Control, vol. 63, No. 2, Sep. 5, 2012, pp. 69-78.
Orakçi GE et al, "Selection of antagonistic actinomycete isolates as biocontrol agents against root-rot fungi", Fresenius Environmental Bulletin, 2010, 19: 417-424 & GenBank Accession No. GQ475299, Oct. 5, 2009.
Partida-Martinez, L.P., et al., "Endosymbiont-Dependent Host Reproduction Maintains Bacterial-Fungal Mutualism", Current Biology, May 1, 2007, vol. 17, No. 9, pp. 773-777.
Sarkar, S., et al., "New report of additional enterobacterial species causing wilt in West Bengal, India," Canadian Journal of Microbiology, 2015, vol. 61, No. 7, pp. 477-486.
NCBI, GenBank Accession No. KX641980.1, Jul. 29, 2017, Scott, M., et al., "*Dothideomycetes* sp. isolate FT14-6 internal transcribed spacer 1, partial sequence; 5.8S ribosomal RNA gene and internal transcribed spacer 2, complete sequence; and large subunit ribosomal RNA gene, partial sequence," 2 Pages.

"Sequence Alignment of JQ047949 with Instant Seq ID No. 2," Search conducted on Jan. 2, 2019. 2 pages.
Sha, T. et al., "Genetic diversity of the endemic gourmet mushroom Thelephora ganbajun from southwestern China", Microbiology (2008), 154, 3460-3468.
Sharma et al., "Detection and identification of bacteria intimately associated with fungi of the order Sebacinales", Cellular Microbiology, Aug. 5, 2008, pp. 2235-2246, vol. 10, No. 11.
Sugita, T. et al., "Intraspecies Diversity of Cryptococcus laurentii as Revealed by Sequences of Internal Transcribed Spacer Regions and 28S rRNA Gene and Taxonomic Position of C. laurentii Clinical Isolates", Journal of Clinical Microbiology, Apr. 2000, p. 1468-1471.
Vujanovic, V., et al: "Fungal communities associated with durum wheat production system: a characterization by growth stage, plant organ and preceding crop", Crop Protection, Elsevier Science, GB, vol. 37, Feb. 19, 2012, pp. 26-34.
Wang, L. et al. Application of Bioorganic Fertilizer Significantly Increased Apple Yields and Shaped Bacterial Community Structure in Orchard Soil.
Whelehan, et al., "Microencapsulation using vibrating technology," Journal of Microencapsulation 2011, vol. 28(8), pp. 669-688.
Yashiro et al., "Effect of Streptomycin Treatment on Bacterial Community Structure in the Apple Phyllosphere," PLOS One, May 21 2012, vol. 7, No. 5, 10 pages.
Zhang, Y., et al., "BcGsl, a glycoprotein from Botrytis cinerea, elicits defence response and improves disease resistance in host plants," Biochemical and Biophysical Research Communications, 2015, vol. 457, No. 4, pp. 627-634.
Zhang, W., et al., Host range of Exserohilum monoceras, a potential bioherbicide for the control of *Echinochloa* species, Canadian Journal of Botany/ Journal Canadien De Botan, National Research Council, Ottawa, CA, vol. 75, Jan. 1, 1997, pp. 685-692.
Zhao, Jun, et al., "Effects of organic-inorganic compound fertilizer with reduced chemical fertilizer application on crop yields, soil biological activity and bacterial community structure in a rice-wheat cropping system," Applied Soil Ecology, vol. 99, Nov. 28, 2015, pp. 1-12, XP055530937.
Bently, S.D., et al, "Complete genome sequence of the model actinomycete Streptomyces coelicolor A3(2)," Nature. May 9, 2002;417(6885):141-7. (Year: 2002).
Gabor, J., et al., "Mycorrhizal fungi effects on nutrient composition and yield of soybean seeds," Journal of Plant Nutrition, 20:4-5, 581-591, 1997.
Gopalakrishnan, S. et al., "Plant growth-promoting activities of *Streptomyces* spp. In sorghum and rice", SpringerPlus, 2/1/574, pp. 1-8, http://www.springerplus.com/content/2/1/574, 2013.
Groppe, K., et al., "Interaction between the endophytic fungus Epichloë bromicola and the grass Bromus erectus: effects of endophyte infection, fungal concentration and environment on grass growth and flowering," Mol Ecol., 8:1827-1835, 1999.
Hubbard, M., "Fungal Endophytes that Confer Heat and Drought Tolerance to Wheat," Doctoral dissertation, University of Saskatchewan, 2012.
Ikeda, H., et al., "Complete genome sequence and comparative analysis of the industrial microorganism Streptomyces avermitilis," Nat Biotechnol. May 2003;21 (5) :526-31. Epub Apr. 14, 2003. (Year: 2003).
Langille, M., et al., "Predictive functional profiling of microbial communities, using 16S rRNA marker gene sequences", Nature Biotechnology, vol. 31, No. 9, Sep. 2013, 11 pages.
Lee, J., et al., "*Streptomyces koyangensis* sp. nov., a novel actinomycete that produces 4-phenyl-3-butenoic acid," Int J Syst Evol Microbial. Jan. 2005;55(Pt 1):257-62. (Year: 2005).
Pacovsky, R., "Carbohydrate, protein and amino acid status of Glycine-Glomus-Bradyrhizobium symbioses," Physiologia Pantarium; 75:346-354, 1989).
Wiebold, M., et al., "Agriculture Experiment Station, College of Agriculture, Food & Natural Resources, University of Missouri, Special Report 589, pp. 1-124)."

* cited by examiner

MODULATED NUTRITIONAL QUALITY TRAITS IN SEEDS

CROSS REFERENCE TO RELATED APPLICATIONS

This application claims priority to Provisional Application No. 62/429,014, filed Dec. 1, 2016; Provisional Application No. 62/429,009, filed Dec. 1, 2016; Provisional Application No. 62/429,007, filed Dec. 1, 2016; Provisional Application No. 62/429,004, filed Dec. 1, 2016; and Provisional Application No. 62/433,095, filed Dec. 12, 2016, the disclosures of which are incorporated by reference in their entirety.

SEQUENCE LISTING

The instant application contains a Sequence Listing with 62 sequences which has been submitted via EFS-Web and is hereby incorporated by reference in its entirety. Said ASCII copy, created on Nov. 29, 2017, is named 39062_US_10105_Sequence_Listing.txt, and is 83,418 bytes in size.

FIELD OF THE INVENTION

This invention relates to compositions and methods for improving traits, for example nutritional quality traits, of seeds, particularly seeds of agricultural plants, for example maize, wheat, cotton, soybean. For example, this invention describes microbes that are capable of living within or heterologously disposed to a plant, which are used to impart improved traits to seeds grown from plants with which they are or have been heterologously disposed. The disclosed invention also describes methods of improving seed characteristics by introducing microbes to parental plants. Further, this invention also provides methods of treating seeds and other plant elements with microbes that are capable of living within a plant, particularly maize, spring wheat, cotton, soybean, to impart improved agronomic characteristics, particularly modulated nutritional quality traits, to progeny seeds.

BACKGROUND OF THE INVENTION

According the United Nations Food and Agricultural Organization (UN FAO), the world's population will exceed 9.6 billion people by the year 2050, which will require significant improvements in agricultural to meet growing food demands. There is a need for improved agricultural plants that will enable the nearly doubled food production demands with fewer resources and more environmentally sustainable inputs, for plants with improved responses to various biotic and abiotic stresses, as well as improved nutritional composition.

Today, crop performance is optimized primarily via technologies directed towards the interplay between crop genotype (e.g., plant breeding, genetically-modified (GM) crops) and its surrounding environment (e.g., fertilizer, synthetic herbicides, pesticides). While these paradigms have assisted in doubling global food production in the past fifty years, yield growth rates have stalled in many major crops and shifts in the climate have been linked to production instability and declines in important crops, driving an urgent need for novel solutions to crop yield improvement. In addition to their long development and regulatory timelines, public fears of GM-crops and synthetic chemicals have challenged their use in many key crops and countries, resulting in a lack of acceptance for many GM traits and the exclusion of GM crops and many synthetic chemistries from some global markets. Thus, there is a significant need for innovative, effective, environmentally-sustainable, and publicly-acceptable approaches to improving the characteristics of crop plants.

Like humans, who utilize a complement of beneficial microbial symbionts, plants have been purported to derive a benefit from the vast array of bacteria and fungi that live both within and around their tissues in order to support the plant's health and growth. Endophytes are symbiotic organisms (typically bacteria or fungi) that live within plants, and inhabit various plant tissues, often colonizing the intercellular spaces of host leaves, stems, flowers, fruits, seeds, or roots. To date, only a small number of symbiotic endophyte-host relationships have been analyzed in limited studies to provide fitness benefits to model host plants within controlled laboratory settings.

Efforts to modulate compositions, such as fats or proteins, in seeds of crop plants have been largely unsuccessful, as changes in one specific component are often at the expense of another, or at the expense of total plant yield. Thus, there remains an outstanding need for compositions and methods that can modulate levels of individual seed nutrients (e.g., protein, fat, carbohydrate, fiber, moisture, ash, or Calories) without negatively impacting yield (i.e., no statistical negative impact to yield).

There remains a great need to develop better plant-endophyte systems to confer benefits to a variety of agriculturally-important plants, for example to provide improved nutritional quality traits in the seeds produced from such plants. Provided herein are methods of improving the nutritional profile of seeds grown from plants heterologously disposed to endophytes.

SUMMARY OF THE INVENTION

Figure 1A:
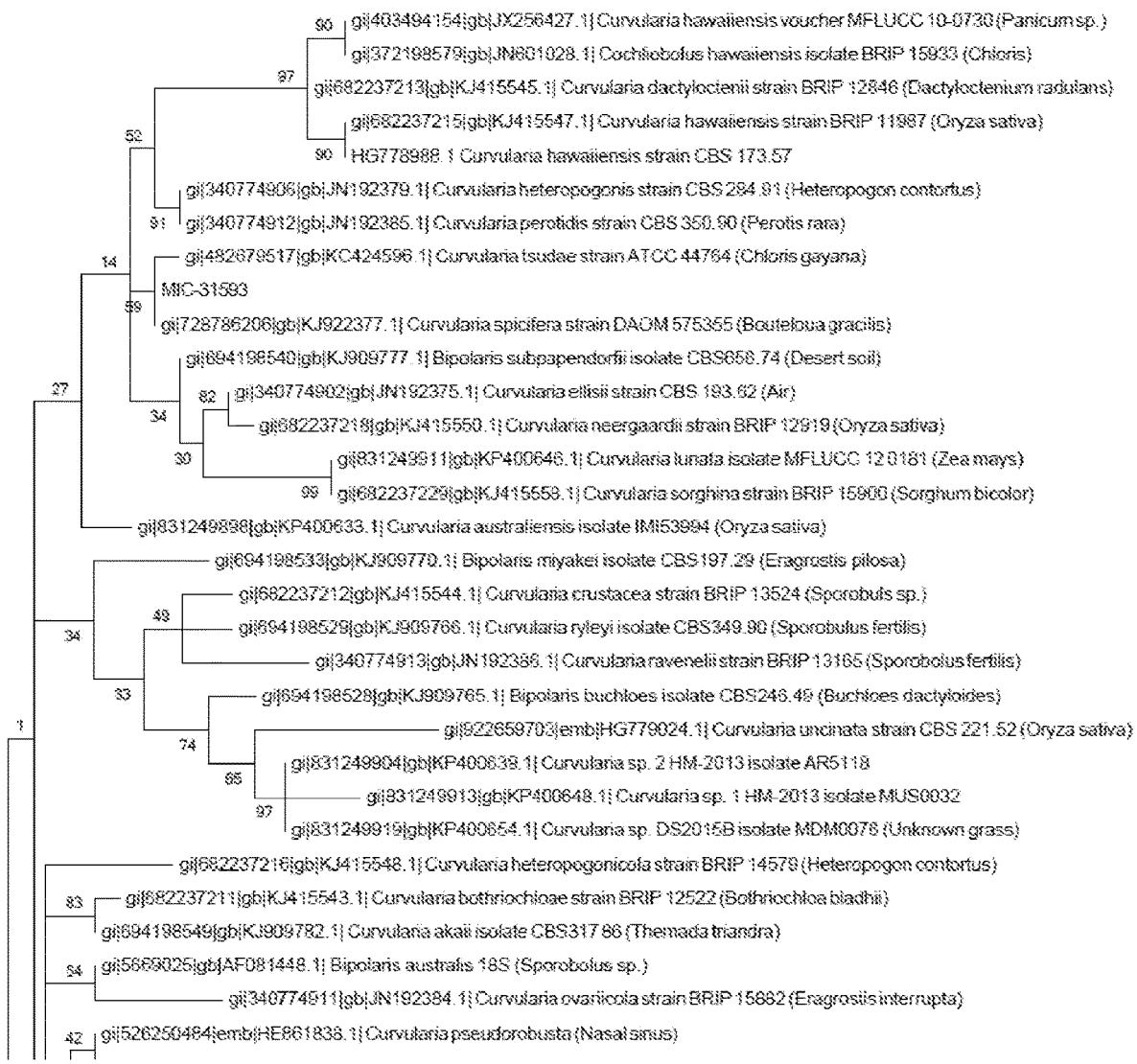
FIG. 1A depicts part 1 of 2 of an exemplary molecular phylogenetic analysis of MIC-07010 and MIC-31593 by the Maximum Likelihood method.

In one aspect, the invention provides a method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte.

In one aspect, the invention provides a method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte.

In one aspect, the invention provides a method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte, wherein the endophyte comprises a polynucleotide sequence that is at least 97% identical to a polynucleotide sequence selected from the group consisting of SEQ ID NOs. 16, 17, 26, 27, 28, 29, 30, 31, 32 and 33.

In one aspect, the invention provides a method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte, wherein the endophyte is a *Curvularia spicifera* as deposited under NRRL Culture Deposit No. NRRL-67467, or a modified endophyte derived from the deposit that retains the ability to increase fat composition of a seed produced by a plant element heterologously disposed with the endophyte.

In one aspect, the invention provides a method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in carbohydrate composition as compared to a reference soybean plant element not further comprising the endophyte.

In one aspect, the invention provides a method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in carbohydrate composition as compared to a reference soybean plant element not further comprising the endophyte, wherein the endophyte comprises a polynucleotide sequence that is at least 97% identical to a polynucleotide sequence selected from the group consisting of SEQ ID NOs. 20, 21, 24, and 25.

In one aspect, the invention provides an animal feed derived from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte.

In one aspect, the invention provides an animal feed derived from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte.

In one aspect, the invention provides an animal feed derived from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte, wherein the endophyte comprises a polynucleotide sequence that is at least 97% identical to a polynucleotide sequence selected from the group consisting of SEQ ID NOs. 16, 17, 26, 27, 28, 29, 30, 31, 32 and 33.

In one aspect, the invention provides an animal feed derived from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte, wherein the endophyte is a *Curvularia spicifera* as deposited under NRRL Culture Deposit No. NRRL-67467, or a modified endophyte derived from the deposit that retains the ability to increase fat composition of a seed produced by a plant element heterologously disposed with the endophyte.

In one aspect, the invention provides an animal feed derived from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in carbohydrate composition as compared to a reference soybean plant element not further comprising the endophyte.

In one aspect, the invention provides an animal feed derived from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in carbohydrate composition as compared to a reference soybean plant element not further comprising the endophyte, wherein the endophyte comprises a polynucleotide sequence that is at least 97% identical to a polynucleotide sequence selected from the group consisting of SEQ ID NOs. 20, 21, 24, and 25.

In one aspect, the invention provides a soybean for oil extraction comprising the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte.

In one aspect, the invention provides a soybean for oil extraction comprising the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte.

In one aspect, the invention provides a soybean for oil extraction comprising the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte, wherein the endophyte comprises a polynucleotide sequence that is at least 97% identical to a polynucleotide sequence selected from the group consisting of SEQ ID NOs. 16, 17, 26, 27, 28, 29, 30, 31, 32 and 33.

In one aspect, the invention provides a soybean for oil extraction comprising the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte, wherein the endophyte is a *Curvularia spicifera* as deposited under NRRL Culture Deposit No. NRRL-67467, or a modified endophyte derived from the deposit that retains the ability to increase fat composition of a seed produced by a plant element heterologously disposed with the endophyte.

In one aspect, the invention provides a human food product derived from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte.

In one aspect, the invention provides a human food product derived from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte.

In one aspect, the invention provides a human food product derived from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte, wherein the endophyte comprises a polynucleotide sequence that is at least 97% identical to a polynucleotide sequence selected from the group consisting of SEQ ID NOs. 16, 17, 26, 27, 28, 29, 30, 31, 32 and 33.

In one aspect, the invention provides a human food product from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte, wherein the endophyte is a *Curvularia spicifera* as deposited under NRRL Culture Deposit No. NRRL-67467, or a modified endophyte derived from the deposit that retains the ability to increase fat composition of a seed produced by a plant element heterologously disposed with the endophyte.

In one aspect, the invention provides a human food product derived from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in carbohydrate composition as compared to a reference soybean plant element not further comprising the endophyte.

In one aspect, the invention provides a human food product derived from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in carbohydrate composition as compared to a reference soybean plant element not further comprising the endophyte, wherein the endophyte comprises a polynucleotide sequence that is at least 97% identical to a polynucleotide sequence selected from the group consisting of SEQ ID NOs. 20, 21, 24, and 25.

In one aspect, the invention provides a soybean for oil extraction comprising the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte.

In one aspect, the invention provides a soybean for oil extraction comprising the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte.

In one aspect, the invention provides a soybean for oil extraction comprising the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte, wherein the endophyte comprises a polynucleotide sequence that is at least 97% identical to a polynucleotide sequence selected from the group consisting of SEQ ID NOs. 16, 17, 26, 27, 28, 29, 30, 31, 32 and 33.

In one aspect, the invention provides a soybean for oil extraction comprising the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte, wherein the endophyte is a *Curvularia spicifera* as deposited under NRRL Culture Deposit No. NRRL-67467, or a modified endophyte derived from the deposit that retains the ability to increase fat composition of a seed produced by a plant element heterologously disposed with the endophyte.

In one aspect, the invention provides an industrial product derived from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte.

In one aspect, the invention provides an industrial product derived from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte.

In one aspect, the invention provides an industrial product derived from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte, wherein the endophyte comprises a polynucleotide sequence that is at least 97% identical to a polynucleotide sequence selected from the group consisting of SEQ ID NOs. 16, 17, 26, 27, 28, 29, 30, 31, 32 and 33.

In one aspect, the invention provides an industrial product from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in fat composition as compared to a reference soybean plant element not further comprising the endophyte, wherein the endophyte is a *Curvularia spicifera* as deposited under NRRL Culture Deposit No. NRRL-67467, or a modified endophyte derived from the deposit that retains the ability to increase fat composition of a seed produced by a plant element heterologously disposed with the endophyte.

In one aspect, the invention provides an industrial product derived from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in carbohydrate composition as compared to a reference soybean plant element not further comprising the endophyte.

In one aspect, the invention provides an industrial product derived from the modulated soybean seed produced by the method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the seed produced by the plant element heterologously disposed with the endophyte exhibits an increase in carbohydrate composition as compared to a reference soybean plant element not further comprising the endophyte, wherein the endophyte comprises a polynucleotide sequence that is at least 97% identical to a polynucleotide sequence selected from the group consisting of SEQ ID NOs. 20, 21, 24, and 25.

In one aspect, the invention provides a method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte.

In one aspect, the invention provides a method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits an increase in total digestible nutrients as compared to a reference corn plant element not further comprising the endophyte.

In one aspect, the invention provides a method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits an increase in total digestible nutrients as compared to a reference corn plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides a method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits a decrease in acid detergent fiber as compared to a reference corn plant element not further comprising the endophyte.

In one aspect, the invention provides a method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits a decrease in acid detergent fiber as compared to a reference corn plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides a method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte.

In one aspect, the invention provides a method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte, wherein the endophyte comprises a polynucleotide sequence that is at least 97% identical to a polynucleotide sequence selected from the group consisting of SEQ ID NOs. 18 and 19.

In one aspect, the invention provides an animal feed derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte.

In one aspect, the invention provides an animal feed derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits an increase in total digestible nutrients as compared to a reference corn plant element not further comprising the endophyte.

In one aspect, the invention provides an animal feed derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits an increase in total digestible nutrients as compared to a reference corn plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides an animal feed derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits a decrease in acid detergent fiber as compared to a reference corn plant element not further comprising the endophyte.

In one aspect, the invention provides an animal feed derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits a decrease in acid detergent fiber as compared to a reference corn plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides an animal feed derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte.

In one aspect, the invention provides an animal feed derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte, wherein the endophyte comprises a polynucleotide sequence that is at least 97% identical to a polynucleotide sequence selected from the group consisting of SEQ ID NOs. 18 and 19.

In one aspect, the invention provides a human food product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte.

In one aspect, the invention provides a human food product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits an increase in total digestible nutrients as compared to a reference corn plant element not further comprising the endophyte.

In one aspect, the invention provides a human food product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits an increase in total digestible nutrients as compared to a reference corn plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides a human food product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits a decrease in acid detergent fiber as compared to a reference corn plant element not further comprising the endophyte.

In one aspect, the invention provides a human food product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits a decrease in acid detergent fiber as compared to a reference corn plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides a human food product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte.

In one aspect, the invention provides a human food product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte, wherein the endophyte comprises a polynucleotide sequence that is at least 97% identical to a polynucleotide sequence selected from the group consisting of SEQ ID NOs. 18 and 19.

In one aspect, the invention provides an industrial product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte.

In one aspect, the invention provides an industrial product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits an increase in total digestible nutrients as compared to a reference corn plant element not further comprising the endophyte.

In one aspect, the invention provides an industrial product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits an increase in total digestible nutrients as compared to a reference corn plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides an industrial product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits a decrease in acid detergent fiber as compared to a reference corn plant element not further comprising the endophyte.

In one aspect, the invention provides an industrial product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits a decrease in acid detergent fiber as compared to a reference corn plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides an industrial product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte.

In one aspect, the invention provides an industrial product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte, wherein the endophyte comprises a polynucleotide sequence that is at least 97% identical to a polynucleotide sequence selected from the group consisting of SEQ ID NOs. 18 and 19.

In one aspect, the invention provides an industrial product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the product is ethanol.

In one aspect, the invention provides an industrial product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits an increase in total digestible nutrients as compared to a reference corn plant element not further comprising the endophyte, wherein the product is ethanol.

In one aspect, the invention provides an industrial product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits an increase in total digestible nutrients as compared to a reference corn plant element not further comprising the endophyte, wherein the endophyte comprises a polynucleotide sequence that is at least 97% identical to a polynucleotide sequence selected from the group consisting of SEQ ID NOs. 18 or 19, wherein the product is ethanol.

In one aspect, the invention provides an industrial product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits a decrease in acid detergent fiber as compared to a reference corn plant element not further comprising the endophyte, wherein the product is ethanol.

In one aspect, the invention provides an industrial product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced by the plant element heterologously disposed with the endophyte exhibits a decrease in acid detergent fiber as compared to a reference corn plant element not further comprising the endophyte, wherein the endophyte comprises a polynucleotide sequence that is at least 97% identical to a polynucleotide sequence selected from the group consisting of SEQ ID NOs. 18 or 19, wherein the product is ethanol.

In one aspect, the invention provides an industrial product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte, wherein the product is ethanol.

In one aspect, the invention provides an industrial product derived from the modulated corn seed produced by the method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte, wherein the endophyte comprises a polynucleotide sequence that is at least 97% identical to a polynucleotide sequence selected from the group consisting of SEQ ID NOs. 18 and 19, wherein the product is ethanol.

In one aspect, the invention provides a method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte.

In one aspect, the invention provides a method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte, wherein the seed produced by the plant element heterologously disposed with the endophyte exhibits an increase in fat composition as compared to a reference wheat plant element not further comprising the endophyte.

In one aspect, the invention provides a method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte, wherein the seed produced by the plant element heterologously disposed with the endophyte exhibits an increase in fat composition as compared to a reference wheat plant element not further comprising the endophyte, wherein the endophyte comprises a polynucleotide sequence that is at least 97% identical to a polynucleotide sequence selected from the group consisting of SEQ ID NOs. 22 and 23.

In one aspect, the invention provides a method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte, wherein the seed produced by the plant element heterologously disposed with the endophyte exhibits an increase in fat composition as compared to a reference wheat plant element not further comprising the endophyte, wherein the endophyte is an *Enterobacter cowanii* as deposited under NRRL Culture Deposit No. as NRRL-B67465, or a modified endophyte derived from the deposit that retains the ability to increase fat composition of a seed produced by a plant element heterologously disposed with the endophyte.

In one aspect, the invention provides an animal feed derived from the modulated wheat seed produced by the method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte.

In one aspect, the invention provides an animal feed derived from the modulated wheat seed produced by the method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte, wherein the seed produced by the plant element heterologously disposed with the endophyte exhibits an increase in fat composition as compared to a reference wheat plant element not further comprising the endophyte.

In one aspect, the invention provides an animal feed derived from the modulated wheat seed produced by the method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte, wherein the seed produced by the plant element heterologously disposed with the endophyte exhibits an increase in fat composition as compared to a reference wheat plant element not further comprising the endophyte, wherein the endophyte comprises a polynucleotide sequence that is at least 97% identical to a polynucleotide sequence selected from the group consisting of SEQ ID NOs. 22 and 23.

In one aspect, the invention provides an animal feed derived from the modulated wheat seed produced by the method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte, wherein the seed produced by the plant element heterologously disposed with the endophyte exhibits an increase in fat composition as compared to a reference wheat plant element not further comprising the endophyte, wherein the endophyte is an *Enterobacter cowanii* as deposited under NRRL Culture Deposit No. as NRRL-B67465, or a modified endophyte derived from the deposit that retains the ability to increase fat composition of a seed produced by a plant element heterologously disposed with the endophyte.

In one aspect, the invention provides a human food product derived from the modulated wheat seed produced by the method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte.

In one aspect, the invention provides a human food product derived from the modulated wheat seed produced by the method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte, wherein the seed produced by the plant element heterologously disposed with the endophyte exhibits an increase in fat composition as compared to a reference wheat plant element not further comprising the endophyte.

In one aspect, the invention provides a human food product derived from the modulated wheat seed produced by the method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte, wherein the seed produced by the plant element heterologously disposed with the endophyte exhibits an increase in fat composition as compared to a reference wheat plant element not further comprising the endophyte, wherein the endophyte comprises a polynucleotide sequence that is at least 97% identical to a polynucleotide sequence selected from the group consisting of SEQ ID NOs. 22 and 23.

In one aspect, the invention provides a human food product derived from the modulated wheat seed produced by the method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte, wherein the seed produced by the plant element heterologously disposed with the endophyte exhibits an increase in fat composition as compared to a reference wheat plant element not further comprising the endophyte, wherein the endophyte is an *Enterobacter cowanii* as deposited under NRRL Culture Deposit No. as NRRL-B67465, or a modified endophyte derived from the deposit that retains the ability to increase fat composition of a seed produced by a plant element heterologously disposed with the endophyte.

In one aspect, the invention provides an industrial product derived from the modulated wheat seed produced by the method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte.

In one aspect, the invention provides an industrial product derived from the modulated wheat seed produced by the method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte, wherein the seed produced by the plant element heterologously disposed with the endophyte exhibits an increase in fat composition as compared to a reference wheat plant element not further comprising the endophyte.

In one aspect, the invention provides an industrial product derived from the modulated wheat seed produced by the method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte, wherein the seed produced by the plant element heterologously disposed with the endophyte exhibits an increase in fat composition as compared to a reference wheat plant element not further comprising the endophyte, wherein the endophyte comprises a polynucleotide sequence that is at least 97% identical to a polynucleotide sequence selected from the group consisting of SEQ ID NOs. 22 and 23.

In one aspect, the invention provides an industrial product derived from the modulated wheat seed produced by the method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte, wherein the seed produced by the plant element heterologously disposed with the endophyte exhibits an increase in fat composition as compared to a reference wheat plant element not further comprising the endophyte, wherein the endophyte is an *Enterobacter cowanii* as deposited under NRRL Culture Deposit No. as NRRL-B67465, or a modified endophyte derived from the deposit that retains the ability to increase fat composition of a seed produced by a plant element heterologously disposed with the endophyte.

In one aspect, the invention provides a method of modulating the composition of a seed produced by a cotton plant, comprising heterologously disposing an endophyte to a cotton plant element in an amount effective to alter the composition of the seed produced by the plant element relative to seed produced by a reference cotton plant element not further comprising the endophyte.

In one aspect, the invention provides a method of modulating the composition of a seed produced by a cotton plant, comprising heterologously disposing an endophyte to a cotton plant element in an amount effective to alter the composition of the seed produced by the plant element relative to seed produced by a reference cotton plant element not further comprising the endophyte, wherein the seed produced by the plant element heterologously disposed with the endophyte exhibits an increase in ash composition as compared to a reference cotton plant element not further comprising the endophyte.

In one aspect, the invention provides a method of modulating the composition of a seed produced by a cotton plant, comprising heterologously disposing an endophyte to a cotton plant element in an amount effective to alter the composition of the seed produced by the plant element relative to seed produced by a reference cotton plant element not further comprising the endophyte, wherein the seed produced by the plant element heterologously disposed with the endophyte exhibits an increase in ash composition as compared to a reference cotton plant element not further comprising the endophyte, wherein the endophyte comprises a polynucleotide sequence that is at least 97% identical to a polynucleotide sequence selected from the group consisting of SEQ ID NOs. 34, 35, 36, and 37.

In one aspect, the invention provides an animal feed derived from the modulated cotton seed produced by the method of modulating the composition of a seed produced by a cotton plant, comprising heterologously disposing an endophyte to a cotton plant element in an amount effective to alter the composition of the seed produced by the plant element relative to seed produced by a reference cotton plant element not further comprising the endophyte.

In one aspect, the invention provides an animal feed derived from the modulated cotton seed produced by the method of modulating the composition of a seed produced by a cotton plant, comprising heterologously disposing an endophyte to a cotton plant element in an amount effective to alter the composition of the seed produced by the plant element relative to seed produced by a reference cotton plant element not further comprising the endophyte, wherein the seed produced by the plant element heterologously disposed with the endophyte exhibits an increase in ash composition as compared to a reference cotton plant element not further comprising the endophyte.

In one aspect, the invention provides an animal feed derived from the modulated cotton seed produced by the method of modulating the composition of a seed produced by a cotton plant, comprising heterologously disposing an endophyte to a cotton plant element in an amount effective to alter the composition of the seed produced by the plant element relative to seed produced by a reference cotton plant element not further comprising the endophyte, wherein the seed produced by the plant element heterologously disposed with the endophyte exhibits an increase in ash composition as compared to a reference cotton plant element not further comprising the endophyte, wherein the endophyte comprises a polynucleotide sequence that is at least 97% identical to a polynucleotide sequence selected from the group consisting of SEQ ID NOs. 34, 35, 36, and 37.

In one aspect, the invention provides a human food product derived from the modulated cotton seed produced by the method of modulating the composition of a seed produced by a cotton plant, comprising heterologously disposing an endophyte to a cotton plant element in an amount effective to alter the composition of the seed produced by the plant element relative to seed produced by a reference cotton plant element not further comprising the endophyte.

In one aspect, the invention provides a human food product derived from the modulated cotton seed produced by the method of modulating the composition of a seed produced by a cotton plant, comprising heterologously disposing an endophyte to a cotton plant element in an amount effective to alter the composition of the seed produced by the plant element relative to seed produced by a reference cotton plant element not further comprising the endophyte, wherein the seed produced by the plant element heterologously disposed with the endophyte exhibits an increase in ash composition as compared to a reference cotton plant element not further comprising the endophyte.

In one aspect, the invention provides a human food product derived from the modulated cotton seed produced by the method of modulating the composition of a seed produced by a cotton plant, comprising heterologously disposing an endophyte to a cotton plant element in an amount effective to alter the composition of the seed produced by the plant element relative to seed produced by a reference cotton plant element not further comprising the endophyte, wherein the seed produced by the plant element heterologously disposed with the endophyte exhibits an increase in ash composition as compared to a reference cotton plant element not further comprising the endophyte, wherein the endophyte comprises a polynucleotide sequence that is at least 97% identical to a polynucleotide sequence selected from the group consisting of SEQ ID NOs. 34, 35, 36, and 37.

In one aspect, the invention provides an industrial product derived from the modulated cotton seed produced by the method of modulating the composition of a seed produced by a cotton plant, comprising heterologously disposing an endophyte to a cotton plant element in an amount effective to alter the composition of the seed produced by the plant element relative to seed produced by a reference cotton plant element not further comprising the endophyte.

In one aspect, the invention provides an industrial product derived from the modulated cotton seed produced by the method of modulating the composition of a seed produced by a cotton plant, comprising heterologously disposing an endophyte to a cotton plant element in an amount effective to alter the composition of the seed produced by the plant element relative to seed produced by a reference cotton plant element not further comprising the endophyte, wherein the seed produced by the plant element heterologously disposed with the endophyte exhibits an increase in ash composition as compared to a reference cotton plant element not further comprising the endophyte.

In one aspect, the invention provides an industrial product derived from the modulated cotton seed produced by the method of modulating the composition of a seed produced by a cotton plant, comprising heterologously disposing an endophyte to a cotton plant element in an amount effective to alter the composition of the seed produced by the plant element relative to seed produced by a reference cotton plant element not further comprising the endophyte, wherein the seed produced by the plant element heterologously disposed with the endophyte exhibits an increase in ash composition as compared to a reference cotton plant element not further comprising the endophyte, wherein the endophyte comprises a polynucleotide sequence that is at least 97% identical to a polynucleotide sequence selected from the group consisting of SEQ ID NOs. 34, 35, 36, and 37.

In one aspect, the invention provides a method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the plant element heterologously disposed with the endophyte is capable of producing an average seed yield at least 97% of the average seed yield of a reference plant element not further comprising the endophyte.

In one aspect, the invention provides a method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the plant element heterologously disposed with the endophyte is capable of producing an average seed yield at least 97% of the average seed yield of a reference plant element not further comprising the endophyte.

In one aspect, the invention provides a method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte, wherein the plant element heterologously disposed with the endophyte is capable of producing an average seed yield at least 97% of the average seed yield of a reference plant element not further comprising the endophyte.

In one aspect, the invention provides a method of modulating the composition of a seed produced by a cotton plant, comprising heterologously disposing an endophyte to a cotton plant element in an amount effective to alter the composition of the seed produced by the plant element relative to seed produced by a reference cotton plant element not further comprising the endophyte, wherein the plant element heterologously disposed with the endophyte is capable of producing an average seed yield at least 97% of the average seed yield of a reference plant element not further comprising the endophyte.

In one aspect, the invention provides a method of modulating the composition of a seed produced by a soybean plant, comprising heterologously disposing an endophyte to a soybean plant element in an amount effective to alter the composition of the seed produced by the soybean plant element relative to seed produced by a reference soybean plant element not further comprising the endophyte, wherein the plant element is modified.

In one aspect, the invention provides a method of modulating the composition of a seed produced by a corn plant, comprising heterologously disposing an endophyte to a corn plant element in an amount effective to alter the composition of the seed produced by the plant element relative to seed produced by a reference corn plant element not further comprising the endophyte, wherein the plant element is modified.

In one aspect, the invention provides a method of modulating the composition of a seed produced by a wheat plant, comprising heterologously disposing an endophyte to a wheat plant element in an amount effective to alter the composition of the seed produced by the plant element relative to seed produced by a reference wheat plant element not further comprising the endophyte, wherein the plant element is modified.

In one aspect, the invention provides a method of modulating the composition of a seed produced by a cotton plant, comprising heterologously disposing an endophyte to a cotton plant element in an amount effective to alter the composition of the seed produced by the plant element relative to seed produced by a reference cotton plant element not further comprising the endophyte, wherein the plant element is modified.

In one aspect, the invention provides a synthetic composition, comprising a soybean plant element and an endophyte heterologously disposed to the plant element, wherein the endophyte is capable of altering the composition of seed produced by the plant element relative to seed produced by a reference soybean plant element not further comprising the endophyte.

In one aspect, the invention provides a synthetic composition, comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed produced from the plant element heterologously disposed with the endophyte exhibits an increase in fat composition as compared to a reference plant element not further comprising the endophyte.

In one aspect, the invention provides a synthetic composition, comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed produced from the plant element heterologously disposed with the endophyte exhibits an increase in fat composition as compared to a reference plant element not further comprising the endophyte, wherein the endophyte comprises a polynucleotide sequence that is at least 97% identical to a polynucleotide sequence selected from the group consisting of SEQ ID NOs. 16, 17, 26, 27, 28, 29, 30, 31, 32 and 33.

In one aspect, the invention provides a synthetic composition, comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed produced from the plant element heterologously disposed with the endophyte exhibits an increase in fat composition as compared to a reference plant element not further comprising the endophyte, wherein the endophyte is a *Curvularia spicifera* as deposited under NRRL Culture Deposit No. NRRL-67467, or a modified endophyte derived from the deposit that retains the ability to increase fat composition of a seed produced by a plant element heterologously disposed with the endophyte.

In one aspect, the invention provides a synthetic composition, comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed exhibits an increase in carbohydrate composition as compared to a reference soybean plant element not further comprising the endophyte.

In one aspect, the invention provides a synthetic composition, comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed exhibits an increase in carbohydrate composition as compared to a reference soybean plant element not further comprising the endophyte, wherein the endophyte comprises a polynucleotide sequence that is at least 97% identical to a polynucleotide sequence selected from the group consisting of SEQ ID NOs. 20, 21, 24, and 25.

In one aspect, the invention provides an animal feed derived from a soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte.

In one aspect, the invention provides an animal feed derived from a soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed produced from the plant element heterologously disposed with the endophyte exhibits an increase in fat composition as compared to a reference plant element not further comprising the endophyte.

In one aspect, the invention provides an animal feed derived from a soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed produced from the plant element heterologously disposed with the endophyte exhibits an increase in fat composition as compared to a reference plant element not further comprising the endophyte, wherein the endophyte comprises a polynucleotide sequence that is at least 97% identical to a polynucleotide sequence selected from the group consisting of SEQ ID NOs. 16, 17, 26, 27, 28, 29, 30, 31, 32 and 33.

In one aspect, the invention provides an animal feed derived from a soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed produced from the plant element heterologously disposed with the endophyte exhibits an increase in fat composition as compared to a reference plant element not further comprising the endophyte, wherein the endophyte is a *Curvularia spicifera* as deposited under NRRL Culture Deposit No. NRRL-67467, or a modified endophyte derived from the deposit that retains the ability to increase fat composition of a seed produced by a plant element heterologously disposed with the endophyte.

In one aspect, the invention provides an animal feed derived from a soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed exhibits an increase in carbohydrate composition as compared to a reference soybean plant element not further comprising the endophyte.

In one aspect, the invention provides an animal feed derived from a soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed exhibits an increase in carbohydrate composition as compared to a reference soybean plant element not further comprising the endophyte, wherein the endophyte comprises a polynucleotide sequence that is at least 97% identical to a polynucleotide sequence selected from the group consisting of SEQ ID NOs. 20, 21, 24, and 25.

In one aspect, the invention provides a soybean for oil extraction comprising the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte.

In one aspect, the invention provides a soybean for oil extraction comprising the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed produced from the plant element heterologously disposed with the endophyte exhibits an increase in fat composition as compared to a reference plant element not further comprising the endophyte.

In one aspect, the invention provides a soybean for oil extraction comprising the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed produced from the plant element heterologously disposed with the endophyte exhibits an increase in fat composition as compared to a reference plant element not further comprising the endophyte, wherein the endophyte comprises a polynucleotide sequence that is at least 97% identical to a polynucleotide sequence selected from the group consisting of SEQ ID NOs. 16, 17, 26, 27, 28, 29, 30, 31, 32 and 33.

In one aspect, the invention provides a soybean for oil extraction comprising the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed produced from the plant element heterologously disposed with the endophyte exhibits an increase in fat composition as compared to a reference plant element not further comprising the endophyte, wherein the endophyte is a *Curvularia spicifera* as deposited under NRRL Culture Deposit No. NRRL-67467, or a modified endophyte derived from the deposit that retains the ability to increase fat composition of a seed produced by a plant element heterologously disposed with the endophyte.

In one aspect, the invention provides a soybean for oil extraction comprising the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed exhibits an increase in carbohydrate composition as compared to a reference soybean plant element not further comprising the endophyte.

In one aspect, the invention provides a soybean for oil extraction comprising the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed exhibits an increase in carbohydrate composition as compared to a reference soybean plant element not further comprising the endophyte, wherein the endophyte comprises a polynucleotide sequence that is at least 97% identical to a polynucleotide sequence selected from the group consisting of SEQ ID NOs. 20, 21, 24, and 25.

In one aspect, the invention provides a human food product derived from the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte.

In one aspect, the invention provides a human food product derived from the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed produced from the plant element heterologously disposed with the endophyte exhibits an increase in fat composition as compared to a reference plant element not further comprising the endophyte.

In one aspect, the invention provides a human food product derived from the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed produced from the plant element heterologously disposed with the endophyte exhibits an increase in fat composition as compared to a reference plant element not further comprising the endophyte, wherein the endophyte comprises a polynucleotide sequence that is at least 97% identical to a polynucleotide sequence selected from the group consisting of SEQ ID NOs. 16, 17, 26, 27, 28, 29, 30, 31, 32 and 33.

In one aspect, the invention provides a human food product derived from the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed produced from the plant element heterologously disposed with the endophyte exhibits an increase in fat composition as compared to a reference plant element not further comprising the endophyte, wherein the endophyte is a *Curvularia spicifera* as deposited under NRRL Culture Deposit No. NRRL-67467, or a modified endophyte derived from the deposit that retains the ability to increase fat composition of a seed produced by a plant element heterologously disposed with the endophyte.

In one aspect, the invention provides a human food product derived from the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed exhibits an increase in carbohydrate composition as compared to a reference soybean plant element not further comprising the endophyte.

In one aspect, the invention provides a human food product derived from the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed exhibits an increase in carbohydrate composition as compared to a reference soybean plant element not further comprising the endophyte, wherein the endophyte comprises a polynucleotide sequence that is at least 97% identical to a polynucleotide sequence selected from the group consisting of SEQ ID NOs. 20, 21, 24, and 25.

In one aspect, the invention provides an industrial product derived from the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte.

In one aspect, the invention provides an industrial product derived from the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed produced from the plant element heterologously disposed with the endophyte exhibits an increase in fat composition as compared to a reference plant element not further comprising the endophyte.

In one aspect, the invention provides an industrial product derived from the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed produced from the plant element heterologously disposed with the endophyte exhibits an increase in fat composition as compared to a reference plant element not further comprising the endophyte, wherein the endophyte comprises a polynucleotide sequence that is at least 97% identical to a polynucleotide sequence selected from the group consisting of SEQ ID NOs. 16, 17, 26, 27, 28, 29, 30, 31, 32 and 33.

In one aspect, the invention provides an industrial product derived from the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed produced from the plant element heterologously disposed with the endophyte exhibits an increase in fat composition as compared to a reference plant element not further comprising the endophyte, wherein the endophyte is a *Curvularia spicifera* as deposited under NRRL Culture Deposit No. NRRL-67467, or a modified endophyte derived from the deposit that retains the ability to increase fat composition of a seed produced by a plant element heterologously disposed with the endophyte.

In one aspect, the invention provides an industrial product derived from the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed exhibits an increase in carbohydrate composition as compared to a reference soybean plant element not further comprising the endophyte.

In one aspect, the invention provides an industrial product derived from the modulated soybean seed produced by a synthetic composition, the composition comprising a soybean plant element and an endophyte heterologously disposed to the plant element, wherein the endophyte is capable of altering the composition of seed produced by the plant element relative to seed produced by a reference soybean plant element not further comprising the endophyte, wherein the seed exhibits an increase in carbohydrate composition as compared to a reference soybean plant element not further comprising the endophyte, wherein the endophyte comprises a polynucleotide sequence that is at least 97% identical to a polynucleotide sequence selected from the group consisting of SEQ ID NOs. 20, 21, 24, and 25.

In one aspect, the invention provides a synthetic composition, comprising a corn plant element and an endophyte heterologously disposed to the plant element, wherein the endophyte is capable of altering the composition of seed produced by the plant element relative to seed produced by a reference corn plant element not further comprising the endophyte.

In one aspect, the invention provides a synthetic composition, comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients as compared to a reference plant element not further comprising the endophyte.

In one aspect, the invention provides a synthetic composition, comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients as compared to a reference plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides a synthetic composition, comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits a decrease in acid detergent fiber as compared to a reference plant element not further comprising the endophyte.

In one aspect, the invention provides a synthetic composition, comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits a decrease in acid detergent fiber as compared to a reference plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides a synthetic composition, comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte.

In one aspect, the invention provides a synthetic composition, comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides an animal feed derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte.

In one aspect, the invention provides an animal feed derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients as compared to a reference plant element not further comprising the endophyte.

In one aspect, the invention provides an animal feed derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients as compared to a reference plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides an animal feed derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits a decrease in acid detergent fiber as compared to a reference plant element not further comprising the endophyte.

In one aspect, the invention provides an animal feed derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits a decrease in acid detergent fiber as compared to a reference plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides an animal feed derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte.

In one aspect, the invention provides an animal feed derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides a human food product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte.

In one aspect, the invention provides a human food product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients as compared to a reference plant element not further comprising the endophyte.

In one aspect, the invention provides a human food product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients as compared to a reference plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides a human food product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits a decrease in acid detergent fiber as compared to a reference plant element not further comprising the endophyte.

In one aspect, the invention provides a human food product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits a decrease in acid detergent fiber as compared to a reference plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides a human food product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte.

In one aspect, the invention provides a human food product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides an industrial product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte.

In one aspect, the invention provides an industrial product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients as compared to a reference plant element not further comprising the endophyte.

In one aspect, the invention provides an industrial product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients as compared to a reference plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides an industrial product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits a decrease in acid detergent fiber as compared to a reference plant element not further comprising the endophyte.

In one aspect, the invention provides an industrial product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits a decrease in acid detergent fiber as compared to a reference plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides an industrial product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte.

In one aspect, the invention provides an industrial product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte, wherein the endophyte comprises a polynucleotide sequence that is at least 97% identical to a polynucleotide sequence selected from the group consisting of SEQ ID NOs. 18 or 19.

In one aspect, the invention provides an industrial product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the product is ethanol.

In one aspect, the invention provides an industrial product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients as compared to a reference plant element not further comprising the endophyte, wherein the product is ethanol.

In one aspect, the invention provides an industrial product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients as compared to a reference plant element not further comprising the endophyte, wherein the endophyte comprises a polynucleotide sequence that is at least 97% identical to a polynucleotide sequence selected from the group consisting of SEQ ID NOs. 18 or 19, wherein the product is ethanol.

In one aspect, the invention provides an industrial product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits a decrease in acid detergent fiber as compared to a reference plant element not further comprising the endophyte, wherein the product is ethanol.

In one aspect, the invention provides an industrial product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits a decrease in acid detergent fiber as compared to a reference plant element not further comprising the endophyte, wherein the endophyte comprises a polynucleotide sequence that is at least 97% identical to a polynucleotide sequence selected from the group consisting of SEQ ID NOs. 18 or 19, wherein the product is ethanol.

In one aspect, the invention provides an industrial product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte, wherein the product is ethanol.

In one aspect, the invention provides an industrial product derived from the modulated corn seed produced by a synthetic composition, the composition comprising a corn plant element and an endophyte heterologously disposed to the plant element, wherein the endophyte is capable of altering the composition of seed produced by the plant element relative to seed produced by a reference corn plant element not further comprising the endophyte, wherein the seed produced from the plant element heterologously disposed with the endophyte exhibits an increase in total digestible nutrients and a decrease in acid detergent fiber as compared to a reference plant element not further comprising the endophyte, wherein the endophyte comprises a polynucleotide sequence that is at least 97% identical to a polynucleotide sequence selected from the group consisting of SEQ ID NOs. 18 or 19, wherein the product is ethanol.

In one aspect, the invention provides a synthetic composition, comprising a wheat plant element and an endophyte heterologously disposed to the plant element, wherein the endophyte is capable of altering the composition of seed produced by the plant element relative to seed produced by a reference wheat plant element not further comprising the endophyte.

In one aspect, the invention provides a synthetic composition, comprising a wheat plant element and an endophyte heterologously disposed to the plant element, wherein the endophyte is capable of altering the composition of seed produced by the plant element relative to seed produced by a reference wheat plant element not further comprising the endophyte, wherein the seed produced from the plant element heterologously disposed with the endophyte exhibits an increase in fat composition as compared to a reference plant element not further comprising the endophyte.

In one aspect, the invention provides a synthetic composition, comprising a wheat plant element and an endophyte heterologously disposed to the plant element, wherein the endophyte is capable of altering the composition of seed produced by the plant element relative to seed produced by a reference wheat plant element not further comprising the endophyte, wherein the seed produced from the plant element heterologously disposed with the endophyte exhibits an increase in fat composition as compared to a reference plant element not further comprising the endophyte, wherein the endophyte comprises a polynucleotide sequence that is at least 97% identical to a polynucleotide sequence selected from the group consisting of SEQ ID NOs. 22 or 23.

In one aspect, the invention provides a synthetic composition, comprising a wheat plant element and an endophyte heterologously disposed to the plant element, wherein the endophyte is capable of altering the composition of seed produced by the plant element relative to seed produced by a reference wheat plant element not further comprising the endophyte, wherein the seed produced from the plant element heterologously disposed with the endophyte exhibits an increase in fat composition as compared to a reference plant element not further comprising the endophyte, wherein the endophyte is an *Enterobacter cowanii* as deposited under NRRL Culture Deposit No. as NRRL-B67465, or a modified endophyte derived from the deposit that retains the ability to increase in fat composition in a seed produced by a plant element heterologously disposed with the endophyte.

In one aspect, the invention provides an animal feed derived from the modulated wheat seed produced by a synthetic composition, the composition comprising a wheat plant element and an endophyte heterologously disposed to the plant element, wherein the endophyte is capable of altering the composition of seed produced by the plant element relative to seed produced by a reference wheat plant element not further comprising the endophyte.

In one aspect, the invention provides an animal feed derived from the modulated wheat seed produced by a synthetic composition, the composition comprising a wheat plant element and an endophyte heterologously disposed to the plant element, wherein the endophyte is capable of altering the composition of seed produced by the plant element relative to seed produced by a reference wheat plant element not further comprising the endophyte, wherein the seed produced from the plant element heterologously disposed with the endophyte exhibits an increase in fat composition as compared to a reference plant element not further comprising the endophyte.

In one aspect, the invention provides an animal feed derived from the modulated wheat seed produced by a synthetic composition, the composition comprising a wheat plant element and an endophyte heterologously disposed to the plant element, wherein the endophyte is capable of altering the composition of seed produced by the plant element relative to seed produced by a reference wheat plant element not further comprising the endophyte, wherein the seed produced from the plant element heterologously disposed with the endophyte exhibits an increase in fat composition as compared to a reference plant element not further comprising the endophyte, wherein the endophyte comprises a polynucleotide sequence that is at least 97% identical to a polynucleotide sequence selected from the group consisting of SEQ ID NOs. 22 or 23.

In one aspect, the invention provides an animal feed derived from the modulated wheat seed produced by a synthetic composition, the composition comprising a wheat plant element and an endophyte heterologously disposed to the plant element, wherein the endophyte is capable of altering the composition of seed produced by the plant element relative to seed produced by a reference wheat plant element not further comprising the endophyte, wherein the seed produced from the plant element heterologously disposed with the endophyte exhibits an increase in fat composition as compared to a reference plant element not further comprising the endophyte, wherein the endophyte is an *Enterobacter cowanii* as deposited under NRRL Culture Deposit No. as NRRL-B67465, or a modified endophyte derived from the deposit that retains the ability to increase in fat composition in a seed produced by a plant element heterologously disposed with the endophyte.

In one aspect, the invention provides a human food product derived from the modulated wheat seed produced by a synthetic composition, the composition comprising a wheat plant element and an endophyte heterologously disposed to the plant element, wherein the endophyte is capable of altering the composition of seed produced by the plant element relative to seed produced by a reference wheat plant element not further comprising the endophyte.

In one aspect, the invention provides a human food product derived from the modulated wheat seed produced by a synthetic composition, the composition comprising a wheat plant element and an endophyte heterologously disposed to the plant element, wherein the endophyte is capable of altering the composition of seed produced by the plant element relative to seed produced by a reference wheat plant element not further comprising the endophyte, wherein the seed produced from the plant element heterologously disposed with the endophyte exhibits an increase in fat composition as compared to a reference plant element not further comprising the endophyte.

In one aspect, the invention provides a human food product derived from the modulated wheat seed produced by a synthetic composition, the composition comprising a wheat plant element and an endophyte heterologously disposed to the plant element, wherein the endophyte is capable of altering the composition of seed produced by the plant element relative to seed produced by a reference wheat plant element not further comprising the endophyte, wherein the seed produced from the plant element heterologously disposed with the endophyte exhibits an increase in fat composition as compared to a reference plant element not further comprising the endophyte, wherein the endophyte comprises a polynucleotide sequence that is at least 97% identical to a polynucleotide sequence selected from the group consisting of SEQ ID NOs. 22 or 23.

In one aspect, the invention provides a human food product derived from the modulated wheat seed produced by a synthetic composition, the composition comprising a wheat plant element and an endophyte heterologously disposed to the plant element, wherein the endophyte is capable of altering the composition of seed produced by the plant element relative to seed produced by a reference wheat plant element not further comprising the endophyte, wherein the seed produced from the plant element heterologously disposed with the endophyte exhibits an increase in fat composition as compared to a reference plant element not further comprising the endophyte, wherein the endophyte is an *Enterobacter cowanii* as deposited under NRRL Culture Deposit No. as NRRL-B67465, or a modified endophyte derived from the deposit that retains the ability to increase in fat composition in a seed produced by a plant element heterologously disposed with the endophyte.

In one aspect, the invention provides an industrial product derived from the modulated wheat seed produced by a synthetic composition, the composition comprising a wheat plant element and an endophyte heterologously disposed to the plant element, wherein the endophyte is capable of altering the composition of seed produced by the plant element relative to seed produced by a reference wheat plant element not further comprising the endophyte.

In one aspect, the invention provides an industrial product derived from the modulated wheat seed produced by a synthetic composition, the composition comprising a wheat plant element and an endophyte heterologously disposed to the plant element, wherein the endophyte is capable of altering the composition of seed produced by the plant element relative to seed produced by a reference wheat plant element not further comprising the endophyte, wherein the seed produced from the plant element heterologously disposed with the endophyte exhibits an increase in fat composition as compared to a reference plant element not further comprising the endophyte.

In one aspect, the invention provides an industrial product derived from the modulated wheat seed produced by a synthetic composition, the composition comprising a wheat plant element and an endophyte heterologously disposed to the plant element, wherein the endophyte is capable of altering the composition of seed produced by the plant element relative to seed produced by a reference wheat plant element not further comprising the endophyte, wherein the seed produced from the plant element heterologously disposed with the endophyte exhibits an increase in fat composition as compared to a reference plant element not further comprising the endophyte, wherein the endophyte comprises a polynucleotide sequence that is at least 97% identical to a polynucleotide sequence selected from the group consisting of SEQ ID NOs. 22 or 23.

In one aspect, the invention provides an industrial product derived from the modulated wheat seed produced by a synthetic composition, the composition comprising a wheat plant element and an endophyte heterologously disposed to the plant element, wherein the endophyte is capable of altering the composition of seed produced by the plant element relative to seed produced by a reference wheat plant element not further comprising the endophyte, wherein the seed produced from the plant element heterologously disposed with the endophyte exhibits an increase in fat composition as compared to a reference plant element not further comprising the endophyte, wherein the endophyte is an *Enterobacter cowanii* as deposited under NRRL Culture Deposit No. as NRRL-B67465, or a modified endophyte derived from the deposit that retains the ability to increase in fat composition in a seed produced by a plant element heterologously disposed with the endophyte.

In one aspect, the invention provides a synthetic composition, comprising a cotton plant element and an endophyte heterologously disposed to the plant element, wherein the endophyte is capable of altering the composition of seed produced by the plant element relative to seed produced by a reference cotton plant element not further comprising the endophyte.

In one aspect, the invention provides a synthetic composition, comprising a cotton plant element and an endophyte heterologously disposed to the plant element, wherein the endophyte is capable of altering the composition of seed produced by the plant element relative to seed produced by a reference cotton plant element not further comprising the endophyte, wherein the seed produced from the plant element heterologously disposed with the endophyte exhibits an increase in ash composition as compared to a reference plant element not further comprising the endophyte.

In one aspect, the invention provides a synthetic composition, comprising a cotton plant element and an endophyte heterologously disposed to the plant element, wherein the endophyte is capable of altering the composition of seed produced by the plant element relative to seed produced by a reference cotton plant element not further comprising the endophyte, wherein the seed produced from the plant element heterologously disposed with the endophyte exhibits an increase in ash composition as compared to a reference plant element not further comprising the endophyte, wherein the endophyte comprises a polynucleotide sequence that is at least 97% identical to a polynucleotide sequence selected from the group consisting of SEQ ID NOs. 34, 35, 36, or 37.

In one aspect, the invention provides an animal feed derived from the modulated cotton seed produced by a synthetic composition, the composition comprising a cotton plant element and an endophyte heterologously disposed to the plant element, wherein the endophyte is capable of altering the composition of seed produced by the plant element relative to seed produced by a reference cotton plant element not further comprising the endophyte.

In one aspect, the invention provides an animal feed derived from the modulated cotton seed produced by a synthetic composition, the composition comprising a cotton plant element and an endophyte heterologously disposed to the plant element, wherein the endophyte is capable of altering the composition of seed produced by the plant element relative to seed produced by a reference cotton plant element not further comprising the endophyte, wherein the seed produced from the plant element heterologously disposed with the endophyte exhibits an increase in ash composition as compared to a reference plant element not further comprising the endophyte.

In one aspect, the invention provides an animal feed derived from the modulated cotton seed produced by a synthetic composition, the composition comprising a cotton plant element and an endophyte heterologously disposed to the plant element, wherein the endophyte is capable of altering the composition of seed produced by the plant element relative to seed produced by a reference cotton plant element not further comprising the endophyte, wherein the seed produced from the plant element heterologously disposed with the endophyte exhibits an increase in ash composition as compared to a reference plant element not further comprising the endophyte, wherein the endophyte comprises a polynucleotide sequence that is at least 97% identical to a polynucleotide sequence selected from the group consisting of SEQ ID NOs. 34, 35, 36, or 37.

In one aspect, the invention provides a human food product derived from the modulated cotton seed produced by a synthetic composition, the composition comprising a cotton plant element and an endophyte heterologously disposed to the plant element, wherein the endophyte is capable of altering the composition of seed produced by the plant element relative to seed produced by a reference cotton plant element not further comprising the endophyte.

In one aspect, the invention provides a human food product derived from the modulated cotton seed produced by a synthetic composition, the composition comprising a cotton plant element and an endophyte heterologously disposed to the plant element, wherein the endophyte is capable of altering the composition of seed produced by the plant element relative to seed produced by a reference cotton plant element not further comprising the endophyte, wherein the seed produced from the plant element heterologously disposed with the endophyte exhibits an increase in ash composition as compared to a reference plant element not further comprising the endophyte.

In one aspect, the invention provides a human food product derived from the modulated cotton seed produced by a synthetic composition, the composition comprising a cotton plant element and an endophyte heterologously disposed to the plant element, wherein the endophyte is capable of altering the composition of seed produced by the plant element relative to seed produced by a reference cotton plant element not further comprising the endophyte, wherein the seed produced from the plant element heterologously disposed with the endophyte exhibits an increase in ash composition as compared to a reference plant element not further comprising the endophyte, wherein the endophyte comprises a polynucleotide sequence that is at least 97% identical to a polynucleotide sequence selected from the group consisting of SEQ ID NOs. 34, 35, 36, or 37.

In one aspect, the invention provides an industrial product derived from the modulated cotton seed produced by a synthetic composition, the composition comprising a cotton plant element and an endophyte heterologously disposed to the plant element, wherein the endophyte is capable of altering the composition of seed produced by the plant element relative to seed produced by a reference cotton plant element not further comprising the endophyte.

In one aspect, the invention provides an industrial product derived from the modulated cotton seed produced by a synthetic composition, the composition comprising a cotton plant element and an endophyte heterologously disposed to the plant element, wherein the endophyte is capable of altering the composition of seed produced by the plant element relative to seed produced by a reference cotton plant element not further comprising the endophyte, wherein the seed produced from the plant element heterologously disposed with the endophyte exhibits an increase in ash composition as compared to a reference plant element not further comprising the endophyte.

In one aspect, the invention provides an industrial product derived from the modulated cotton seed produced by a synthetic composition, the composition comprising a cotton plant element and an endophyte heterologously disposed to the plant element, wherein the endophyte is capable of altering the composition of seed produced by the plant element relative to seed produced by a reference cotton plant element not further comprising the endophyte, wherein the seed produced from the plant element heterologously disposed with the endophyte exhibits an increase in ash composition as compared to a reference plant element not further comprising the endophyte, wherein the endophyte comprises a polynucleotide sequence that is at least 97% identical to a polynucleotide sequence selected from the group consisting of SEQ ID NOs. 34, 35, 36, or 37.

In one aspect, the invention provides a synthetic composition, comprising a soybean plant element and an endophyte heterologously disposed to the plant element, wherein the endophyte is capable of altering the composition of seed produced by the plant element relative to seed produced by a reference soybean plant element not further comprising the endophyte, wherein the plant element heterologously disposed with the endophyte is capable of producing an average seed yield at least 97% of the average seed yield of a reference plant element not further comprising the endophyte.

In one aspect, the invention provides a synthetic composition, comprising a corn plant element and an endophyte heterologously disposed to the plant element, wherein the endophyte is capable of altering the composition of seed produced by the plant element relative to seed produced by a reference corn plant element not further comprising the endophyte, wherein the plant element heterologously disposed with the endophyte is capable of producing an average seed yield at least 97% of the average seed yield of a reference plant element not further comprising the endophyte.

In one aspect, the invention provides a synthetic composition, comprising a wheat plant element and an endophyte heterologously disposed to the plant element, wherein the endophyte is capable of altering the composition of seed produced by the plant element relative to seed produced by a reference wheat plant element not further comprising the endophyte, wherein the plant element heterologously disposed with the endophyte is capable of producing an average seed yield at least 97% of the average seed yield of a reference plant element not further comprising the endophyte.

In one aspect, the invention provides a synthetic composition, comprising a cotton plant element and an endophyte heterologously disposed to the plant element, wherein the endophyte is capable of altering the composition of seed produced by the plant element relative to seed produced by a reference cotton plant element not further comprising the endophyte, wherein the plant element heterologously disposed with the endophyte is capable of producing an average seed yield at least 97% of the average seed yield of a reference plant element not further comprising the endophyte.

In one aspect, the invention provides a synthetic composition, comprising a soybean plant element and an endophyte heterologously disposed to the plant element, wherein the endophyte is capable of altering the composition of seed produced by the plant element relative to seed produced by a reference soybean plant element not further comprising the endophyte, wherein the plant element is modified.

In one aspect, the invention provides a synthetic composition, comprising a corn plant element and an endophyte heterologously disposed to the plant element, wherein the endophyte is capable of altering the composition of seed produced by the plant element relative to seed produced by a reference corn plant element not further comprising the endophyte, wherein the plant element is modified.

In one aspect, the invention provides a synthetic composition, comprising a wheat plant element and an endophyte heterologously disposed to the plant element, wherein the endophyte is capable of altering the composition of seed produced by the plant element relative to seed produced by a reference wheat plant element not further comprising the endophyte, wherein the plant element is modified.

In one aspect, the invention provides a synthetic composition, comprising a cotton plant element and an endophyte heterologously disposed to the plant element, wherein the endophyte is capable of altering the composition of seed produced by the plant element relative to seed produced by a reference cotton plant element not further comprising the endophyte, wherein the plant element is modified.

DETAILED DESCRIPTION OF THE INVENTION

Terms used in the claims and specification are defined as set forth below unless otherwise specified.

It must be noted that, as used in the specification and the appended claims, the singular forms "a," "an" and "the" include plural referents unless the context clearly dictates otherwise.

As demonstrated herein, the nutritional composition of seeds of agricultural plants such as maize, wheat, cotton, soybean are altered or modulated by application of a treatment comprising one or more endophytes. In some embodiments, endophytes of the present invention may modulate the nutritional composition of progeny seeds produced by a parental maize, wheat, cotton, or soybean plant. Progeny seeds produced by a parental plant is alternately and equivalently stated as seeds produced by a plant. An "endophyte" is an organism capable of living on a plant element (e.g., rhizoplane or phylosphere) or within a plant element, or in close physical proximity with a plant element, e.g., the rhizosphere, or e.g., on a seed. Endophytes can occupy the intracellular or extracellular spaces of plant tissue, including the leaves, stems, flowers, fruits, seeds, or roots. A "beneficial" endophytes does not cause disease or harm the host plant otherwise. An endophyte can be a fungus or a bacterium. As used herein, the term "microbe" is sometimes used to describe an endophyte.

In some embodiments, a treatment is applied to a plant or plant element by heterologously disposing the treatment to the plant or plant element. A "plant element" is intended to generically reference either a whole plant or a plant component, including but not limited to plant tissues and regions thereof, plant parts and regions thereof, and to plant cell types. A plant element is preferably one of the following: whole plant, seedling, meristematic tissue, ground tissue, vascular tissue, dermal tissue, seed, leaf, root, shoot, stem, flower, fruit, stolon, bulb, tuber, corm, keikis, shoot, bud.

As used herein, an "agricultural seed" is a seed used to grow a plant typically used in agriculture (an "agricultural plant"). The seed may be of a monocot or dicot plant, and may be planted for the production of an agricultural product, for example feed, food, fiber, fuel, industrial uses, etc. As used herein, an agricultural seed is a seed that is prepared for planting, for example, in farms for growing.

"Agricultural plants," or "plants of agronomic importance," include plants that are cultivated by humans for food, feed, fiber, fuel, and/or industrial purposes. Agricultural plants include, but are not limited to, monocotyledonous species such as: maize (*Zea mays* including subspecies such as *Zea mays indenata*, *Zea mays indurata*, *Zea mays amylacea*, *Zea mays saccharata*, and *Zea mays everta*), wheat (genus *Triticum* including species such as *Triticum aestivum*, *Triticum spelta*, *Triticum monococcum*, *Triticum dicoccum*, *Triticum durum*, *Triticum turgidum*, and *Triticum rigidum*), and dicotyledonous species such as: soybean (*Glycine max*) and cotton (genus *Gossypium* including species such as *Gossypium arboretum*, *Gossypium herbaceum*, *Gossypium hirsutum*, *Gossypium barbadense*). As used herein the terms "maize" and "corn" are equivalent and used interchangeably. A "population of plants" or "plant population" refers to more than one plant, that are of the same taxonomic category, typically be of the same species, and will also typically share a common genetic derivation.

In one embodiment, it is contemplated that the plant of the present invention is corn (*Zea* spp.), in particular *Zea mays* ssp. such as *Zea mays indenata*, *Zea mays indurata*, *Zea mays amylacea*, *Zea mays saccharata*, and *Zea mays everta*. In one embodiment, it is contemplated that the plant of the present invention is the corn variety Stine 9734, or a closely related variety. In some embodiments, the present invention contemplates the use of endophytes that can confer a beneficial agronomic trait upon a corn plant element or corn plant to which it is heterologously disposed.

Figure 2:
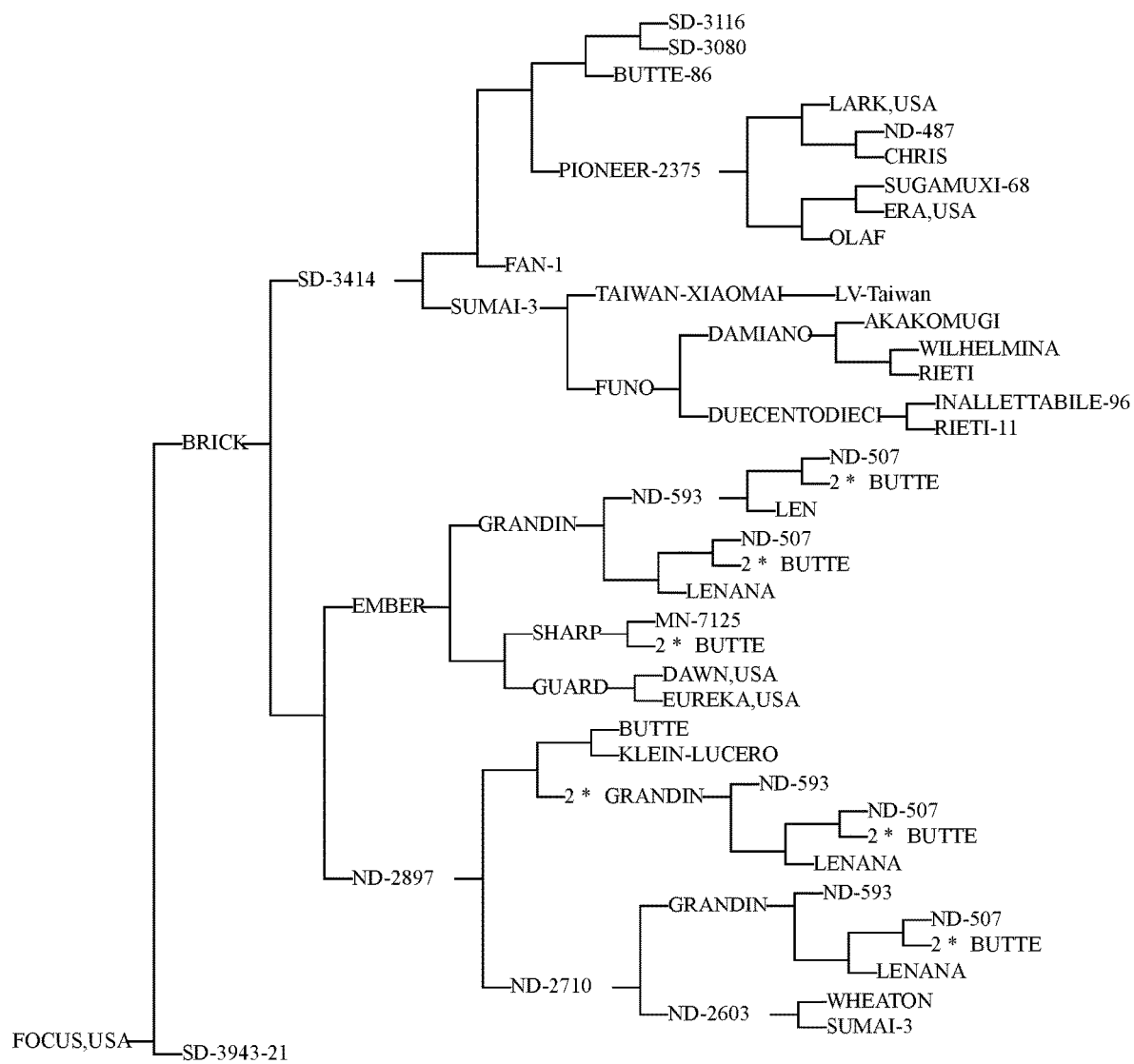
FIG. 2 shows the pedigree of the wheat variety SDSU Focus.
Figure 3:
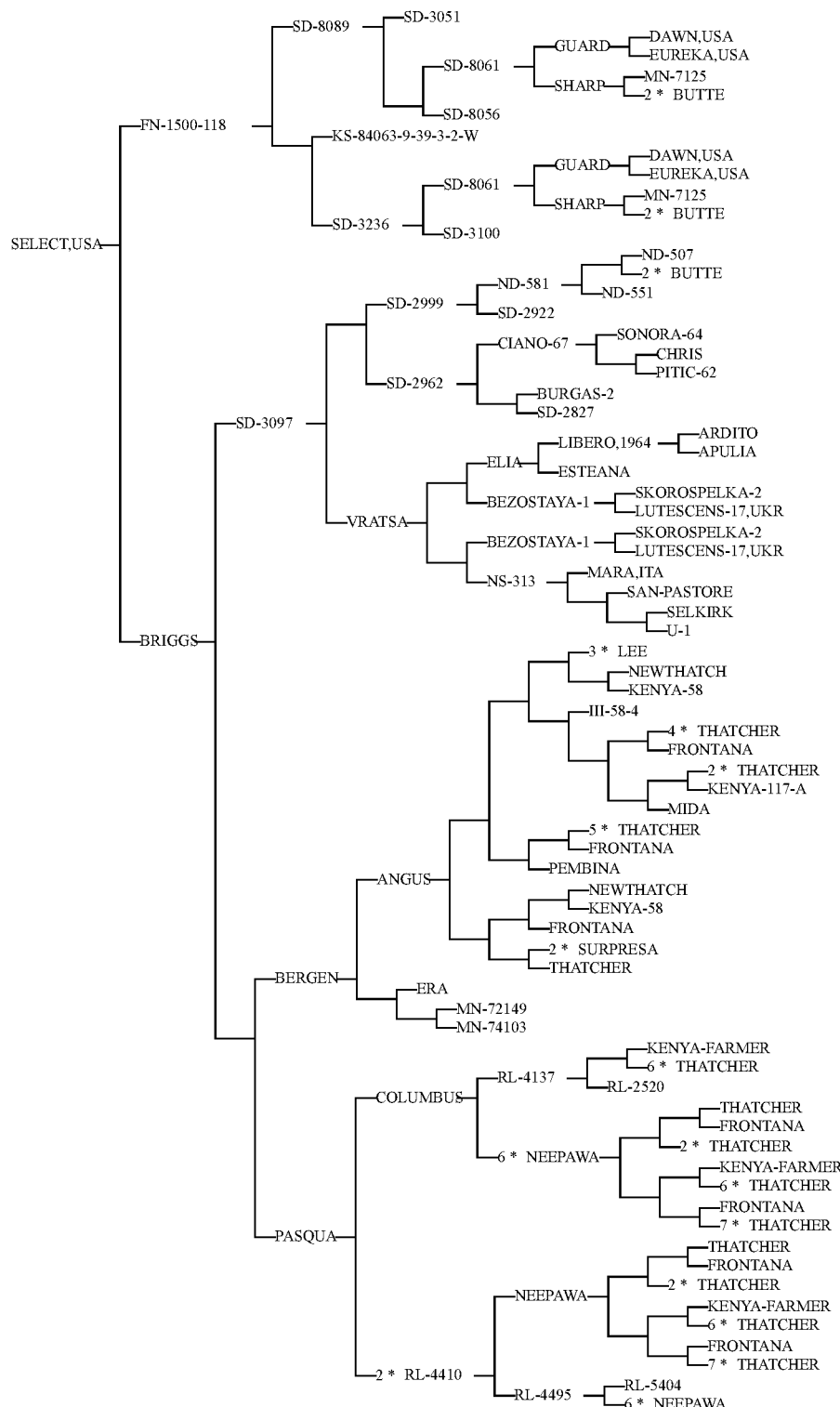
FIG. 3 shows the pedigree of the wheat variety SDSU Select.

In one embodiment, it is contemplated that the plant of the present invention is wheat (*Triticum* spp.) including species *T. aestivum* and *T. durum*. In one embodiment, it is contemplated that the plant of the present invention is hard red winter (HRW), hard red spring (HRS), hard white (HW), durum, soft white (SW), or soft red winter (SRW). In one embodiment, it is contemplated that the plant of the present invention is the wheat variety SDSU Focus, SDSU Select, or a closely related variety. FIG. 2 shows an exemplary pedigree of the wheat variety SDSU Focus. FIG. 3 shows an exemplary pedigree of the wheat variety SDSU Select. In some embodiments, the present invention contemplates the use of endophytes that can confer a beneficial agronomic trait upon a wheat plant element or wheat plant to which it is heterologously disposed.

In one embodiment, it is contemplated that the plant of the present invention is soy (*Glycine max*). In one embodiment, it is contemplated that the plant of the present invention is the soy variety Dairyland DSR1808R2Y, Pfister 38R25, Stine 3920, Stine 33E22, or a closely related variety. In some embodiments, the present invention contemplates the use of endophytes that can confer a beneficial agronomic trait upon a soy plant element or soy plant to which it is heterologously disposed.

In some embodiments, plant elements of the present invention include wild plants and domesticated varieties of the genera *Zea*, *Triticum*, *Glycine*, *Gossypium*. Plants elements may developed by any technique, including but not limited to directed evolution, selection, marker assisted selection, hybridization, outcrossing, backcrossing, in-breeding, polyploidization, reverse breeding, doubled haploids, induced mutation, other genetic or epigenetic modifications, and combinations thereof.

In some embodiments, a treatment may comprise a modified microbe or plant or plant element. A microbe or plant or plant element is "modified" when it comprises an artificially introduced genetic or epigenetic modification. In some embodiments, the modification is introduced by a genome engineering technology. In some embodiments, the modification is introduced by a targeted nuclease. In some embodiments, targeted nucleases include, but are not limited to, transcription activator-like effector nuclease (TALEN), zinc finger nuclease (ZNF), clustered regulatory interspaced short palindromic repeats (CRISPR), CRISPR/Cas9, CRISPR/CPF1, and combinations thereof. In some embodiments, the modification is an epigenetic modification. In some embodiments, the modification is introduced by treatment with a DNA methyltransferase inhibitor such as 5-azacytidine, or a histone deacetylase inhibitor such as 2-amino-7-methoxy-3H-phenoxazin-3-one. In some embodiments, the modification is introduced via tissue culture. In some embodiments, a modified microbe or plant or plant element comprises a transgene.

A treatment is "heterologously disposed" when mechanically or manually applied, artificially inoculated or disposed onto or into a plant element, seedling, plant or onto or into a plant growth medium or onto or into a treatment formulation so that the treatment exists on or in the plant element, seedling, plant, plant growth medium, or formulation in a manner not found in nature prior to the application of the treatment, e.g., said combination which is not found in nature in that plant variety, at that stage in plant development, in that plant tissue, in that abundance, or in that growth environment (for example, drought). In some embodiments, such a manner is contemplated to be selected from the group consisting of: the presence of the endophyte; presence of the endophyte in a different number of cells, concentration, or amount; the presence of the endophyte in a different plant element, tissue, cell type, or other physical location in or on the plant; the presence of the endophyte at different time period, e.g. developmental phase of the plant or plant element, time of day, time of season, and combinations thereof. In some embodiments, "heterologously disposed" means that the endophyte being applied to a different tissue or cell type of the plant element than that in which the endophyte is naturally found. In some embodiments, "heterologously disposed" means that the endophyte is applied to a developmental stage of the plant element, seedling, or plant in which said endophyte is not naturally associated, but may be associated at other stages. For example, if an endophyte is normally found at the flowering stage of a plant and no other stage, an endophyte applied at the seedling stage may be considered to be heterologously disposed. In some embodiments, an endophyte is heterologously disposed the endophyte is normally found in the root tissue of a plant element but not in the leaf tissue, and the endophyte is applied to the leaf. In another non-limiting example, if an endophyte is naturally found in the mesophyll layer of leaf tissue but is being applied to the epithelial layer, the endophyte would be considered to be heterologously disposed. In some embodiments, "heterologously disposed" means that the native plant element, seedling, or plant does not contain detectable levels of the microbe in that same plant element, seedling, or plant. In some embodiments, "heterologously disposed" means that the endophyte being applied is at a greater concentration, number, or amount of the plant element, seedling, or plant, than that which is naturally found in said plant element, seedling, or plant. For example, an endophyte is heterologously disposed when present at a concentration that is at least 1.5 times greater, between 1.5 and 2 times greater, 2 times greater, between 2 and 3 times greater, 3 times greater, between 3 and 5 times greater, 5 times greater, between 5 and 7 times greater, 7 times greater, between 7 and 10 times greater, 10 times greater, or even greater than 10 times higher number, amount, or concentration than the concentration that was present prior to the disposition of said endophyte. In another non-limiting example, an endophyte that is naturally found in a leaf tissue of a cupressaceous tree would be considered heterologous to leaf tissue of a maize, wheat, cotton, soybean plant. In another example, an endophyte that is naturally found in leaf tissue of a maize, spring wheat, cotton, soybean plant is considered heterologous to a leaf tissue of another maize, spring wheat, cotton, soybean plant that naturally lacks said endophyte.

The inventors herein have conceived of using endophytes to modulate (e.g., improve) the nutritional composition of seeds produced by agricultural plants heterologously disposed with one or more endophytes of the present invention. The seed progeny of parental plants that have been heterologously disposed to an endophyte or a plurality of endophytes at some point during said host plant's life cycle exhibit modulated nutritional composition as compared to seeds produced by reference plants not heterologously disposed to one or more endophytes. In part, the present invention describes methods of improving the nutritional quality trait(s) of seeds obtained from parental plants which have been grown from seeds treated with endophytes.

A "host plant" includes any plant, particularly a plant of agronomic importance, within which or onto which a microbe, such as an endophyte, is heterologously disposed. As used herein, a microbe is said to colonize a plant, plant element, or seed, when it can exist as an endophyte in relationship with a plant or plant element during at least part of either the plant's or the microbe's life cycle. In some embodiments, an endophyte is said to "colonize" a plant or plant element when it can be stably detected within the plant or plant element over a period time, such as one or more days, weeks, months or years. Some of the compositions and methods described herein involve a heterologous disposition of a plurality of endophytes or population of endophytes in an amount effective to colonize a plant.

In some embodiments, the present invention contemplates the establishment of an endophyte in a plant element. In some embodiments, endophyte establishment results in a detectable change to the plant element, in particular the progeny seed of a host plant that itself was heterologously disposed to one or more endophytes at some point in its life cycle. The detectable change can be an improvement in one or more nutritional quality traits of the progeny seed. As used herein, an endophyte is considered to have conferred an improved agricultural trait when the improved trait arose from the plant, the endophyte, concerted action between the plant and endophyte, or combinations thereof.

It is contemplated that the modulation, or improvement, of nutritional quality trait in the seed may be due to any number of potential mechanisms of action. For example, seed nutritional quality trait may be altered due to the presence of the associated endophyte directly in the seed tissue. In another example, seed nutritional quality trait may be altered due to the direct influence of the endophyte on the host plant's metabolic or other biochemical pathways. In another example, seed nutritional quality trait may be altered due to the indirect action of the endophyte, for example, via production of a substance that induces another endophyte to directly influence the host plant's metabolic or other biochemical pathway, to induce altered seed nutritional composition.

In some embodiments, the endophyte-associated plant (e.g., one or more endophytes have been heterologously disposed with a plant or plant element) is able to produce a detectable change in the content of at least one nutritional quality trait in the seed produced by the plant. In some embodiments, the endophyte-associated plant or part thereof contains at least one increased nutritional quality trait when compared with reference agricultural plants. In some embodiments, the endophyte-associated plant or part thereof contains at least one decreased nutritional quality trait when compared with reference agricultural plants. In some embodiments, the endophyte modulates the level of the nutritional quality trait directly (e.g., the microbe itself produces the nutritional quality trait, resulting in an overall increase in the level of the nutritional quality trait found in the seed). In other cases, the agricultural plant, as a result of the heterologously disposed endophytic microbe, exhibits a modulated level of the nutritional quality trait (e.g., the plant reduces the expression of a biosynthetic enzyme responsible for production of the nutritional quality trait as a result of the endophyte inoculation). In still other cases, the modulation in the level of the metabolite is a consequence of the activity of both the endophyte and the plant (e.g., the plant produces increased amounts of the nutritional quality trait when compared with a reference agricultural plant, and the endophytic microbe also produces the metabolite). Therefore, as used herein, a modulation in the level of a metabolite can be an alteration in the metabolite level through the actions of the endophyte and/or the inoculated plant. The levels of a nutritional quality trait can be measured in a seed, and compared with the levels of the nutritional quality trait in a seed from a reference agricultural plant not comprising the endophyte.

As used herein, the phrase "modulating the composition of a seed" refers to modulating the nutritional composition of a seed or nutrients within a seed. "Nutrient", "seed nutrient" or "nutritional quality trait" refers to any composition of the associated plant element, most particularly compositions providing benefit to other organisms that consume or utilize said plant element. Seed nutrients, include but are not limited to, protein, fat, fiber, carbohydrate, moisture, ash, total digestible nutrients and Calories. In some embodiments, fiber is acid detergent fiber (ADF). ADF represents the highly indigestible fiber portion of a seed; it includes lignin, cellulose, silica, and insoluble form of Nitrogen (not hemicellulose). Total digestible nutrients is a measure of the sum of nutrients in a seed that are capable of supplying energy, namely the digestible fiber, protein, lipid, and carbohydrate components of seed. Net energy values are calculated based on the variability in energy utilization of mammals that are maintaining their body mass (maintenance), increasing body mass (gain) or lactating (lactation). The net energy values reported herein are net energy values for lactation, and are derived from the calculation described in Example 7. Ash refers to the inorganic residue that remains after either complete oxidation of organic matter or ignition in food material "Modulated seeds" are seeds wherein one or more nutrients are increased or decreased by at least 0.1%, at least 0.5%, at least 1%, at least 2%, at least 3%, between 3% and 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with a reference plant. In some embodiments, the modulated seeds are modulated soybean seeds, modulated maize seeds, modulated wheat seeds, or modulated cotton seeds.

A "reference plant", "reference plant element", "reference agricultural plant" or "reference seed" is a similarly situated plant or seed of the same species, strain, or cultivar to which a treatment, formulation, composition or endophyte preparation as described herein is not administered or contacted. A reference plant, therefore, is identical to the treated plant except for the presence of the active ingredient (e.g. endophyte) to be tested and can serve as a control for detecting the effects of the treatment (e.g. active ingredient) conferred to the plant. A plurality of reference plants may be referred to as a "reference population".

A "reference environment" refers to the environment, treatment or condition of the plant in which a measurement is made. For example, production of a compound in a plant heterologously disposed to an endophyte can be measured in a reference environment of drought stress, and compared with the levels of the compound in a reference agricultural plant under the same conditions of drought stress. Alternatively, the levels of a compound in plant heterologously disposed to an endophyte and reference agricultural plant can be measured under identical conditions of no stress.

In some embodiments, a treatment is heterologously disposed on a plant element in an amount effective to improve plant health. In some embodiments, treatments capable of improving plant health are applied in an amount effective to improve a trait of agronomic importance or tolerance by at least 0.1%, at least 0.5%, at least 1%, at least 2%, at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, as compared to a reference plant element not further comprising said endophyte.

"Plant health" is demonstrated by the presence or improvement of a trait of agronomic importance found in a plant or plant element as compared to a reference plant or plant element. Traits of agronomic importance include, but are not limited to improved disease resistance, improved drought tolerance, improved heat tolerance, improved cold tolerance, improved salinity tolerance, improved metal tolerance, improved herbicide tolerance, improved water use efficiency, improved nitrogen utilization, improved nitrogen fixation, improved pest resistance, improved herbivore resistance, improved pathogen resistance, yield improvement, health enhancement, vigor improvement, growth improvement, photosynthetic capability improvement, nutrient use efficiency enhancement, increased biomass, increased shoot length, increased root length, increased root biomass, increased root area, improved root architecture, modulation of a metabolite, modulation of the proteome, increased seed weight, modulation of seed carbohydrate composition, modulation of seed oil composition, modulation of seed protein content, modulation of seed oil content, modulation of seed ash content, modulation of seed net energy content, modulation of seed Caloric content, modulation of seed total digestible nutrient content, modulation of seed fiber composition, modulation of seed acid detergent fiber content, modulation of seed nutrient composition, and combinations thereof.

The presence or improvement of a trait of agronomic importance can be assessed with physiological parameters including, but not limited to, increased height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, wilt recovery, turgor pressure, or any combination thereof, as compared to a reference plant grown under similar conditions.

As used herein, the terms "water-limited condition" and "drought condition," or "water-limited" and "drought," may be used interchangeably. For example, a method or composition for improving a plant's ability to grow under drought conditions means the same as the ability to grow under water-limited conditions. In such cases, the plant can be further said to display improved tolerance to drought stress. As used herein, the terms "normal watering" and "well-watered" are used interchangeably, to describe a plant grown under typical growth conditions with no water restriction. High molecular weight polyethylene glycol (PEG) can be used to create highly controlled, water limited experimental conditions that decrease the water potential similarly to drying soils.

Additionally, "altered metabolic function" or "altered enzymatic function" may include, but not be limited to, the following: altered production of an auxin, altered nitrogen fixation, altered production of an antimicrobial compound, altered production of a siderophore, altered mineral phosphate solubilization, altered production of a cellulase, altered production of a chitinase, altered production of a xylanase, altered production of acetoin, altered utilization of a carbon source.

"Agronomic trait potential" is intended to mean a capability of a plant element for exhibiting a phenotype, preferably an improved agronomic trait, at some point during its life cycle, or conveying said phenotype to another plant element with which it is associated in the same plant. For example, a plant element may comprise an endophyte that will provide benefit to leaf tissue of a plant from which the plant element is grown; in such case, the plant element comprising such endophyte has the agronomic trait potential for a particular phenotype (for example, increased biomass in the plant) even if the plant element itself does not display said phenotype.

"Biomass" means the total mass or weight (fresh or dry), at a given time, of a plant tissue, plant tissues, an entire plant, or population of plants. Biomass is usually given as weight per unit area. The term may also refer to all the plants or species in the community (community biomass).

As used herein, an endophyte is considered to have conferred an improved agricultural trait when the improved trait arose from the plant, the endophyte, concerted action between the plant and endophyte, or combinations thereof. As used herein an "agricultural trait" and a "trait of agronomic importance" are used interchangeably.

A "non-host target" means an organism or chemical compound that is altered in some way after contacting a host plant that comprises an endophyte, as a result of a property conferred to the host plant by the endophyte.

The terms "decreased," "fewer," "slower" and "increased", "faster", "enhanced", "improved", "greater" as used herein refers to a decrease or increase in a characteristic of the endophyte treated plant element or resulting plant compared to a reference plant element or resulting plant. For example, a decrease in a characteristic may be at least 0.1%, 0.5%, at least 1%, at least 2%, at least about 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least about 60%, between 60% and 70%, between 70% and 80%, at least 75%, at least about 80%, between 80% and 90%, at least about 90%, between 90% and 100%, at least 100%, between 100% and 200%, at least 200%, at least about 300%, at least about 400% or more lower than a reference plant and an increase may be at least 0.1%, 0.5%, at least 1%, at least 2%, at least about 3%, at least 4%, at least 5%, between 5% and 10%, at least 10%, between 10% and 20%, at least 15%, at least 20%, between 20% and 30%, at least 25%, at least 30%, between 30% and 40%, at least 35%, at least 40%, between 40% and 50%, at least 45%, at least 50%, between 50% and 60%, at least about 60%, between 60% and 70%, between 70% and 80%, at least 75%, at least about 80%, between 80% and 90%, at least about 90%, between 90% and 100%, at least 100%, between 100% and 200%, at least 200%, at least about 300%, at least about 400% or more higher than a reference plant.

In some embodiments, the endophyte is capable of effecting changes in a trait of agronomic importance at concentrations detected on the treated plant element of at least $10^2$ CFU or spores per plant element, between $10^2$ and $10^3$ CFU or spores per plant element, about $10^3$ CFU or spores per plant element, between $10^3$ and $10^4$ CFU or spores per plant element, about $10^4$ CFU or spores per plant element, or between $10^4$, of about $10^5$ CFU or spores per plant element, at least $10^5$ CFU or spores per plant element, between $10^5$ and $10^6$ CFU or spores per plant element, about $10^6$ CFU or spores per plant element, between $10^6$ and $10^7$ CFU or spores per plant element, about $10^7$ CFU or spores per plant element, between $10^7$ and $10^8$ CFU or spores per plant element, about $10^8$ CFU or spores per plant element, or even greater than $10^8$ CFU or spores per plant element. In some embodiments, the plant element is a seed. In some embodiments of any of the methods or compositions described herein, CFU or spores per plant element are determined per unit of surface area or mass of a plant element, as a non-limiting example: at least $10^2$, at least $10^3$, at least $10^4$, about $10^4$, at least $10^5$, about $10^5$, at least $10^6$, about $10^6$, at least $10^7$, about $10^7$, at least $10^8$, or about $10^8$ CFU or spores per square inch of leaf area.

In some embodiments, a treatment is heterologously disposed on a plant element in an amount effective to alter the nutrient composition of a seed produced by the plant element. In some embodiments, treatments capable of altering the nutrient composition of a seed are applied in an amount effective to modulate nutrient composition of a seed by at least 0.1%, at least 0.5%, at least 1%, at least 2%, at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, as compared to a reference plant element not further comprising said endophyte.

In some embodiments, the endophyte is capable of effecting changes in seed nutritional quality trait at concentrations detected on or in the treated plant element of at least $10^2$ CFU or spores per plant element, between $10^2$ and $10^3$ CFU or spores per plant element, about $10^3$ CFU or spores per plant element, between $10^3$ and $10^4$ CFU or spores per plant element, about $10^4$ CFU or spores per plant element, or between $10^4$, of about $10^5$ CFU or spores per plant element, at least $10^5$ CFU or spores per plant element, between $10^5$ and $10^6$ CFU or spores per plant element, about $10^6$ CFU or spores per plant element, between $10^6$ and $10^7$ CFU or spores per plant element, about $10^7$ CFU or spores per plant element, between $10^7$ and $10^8$ CFU or spores per plant element, about $10^8$ CFU or spores per plant element, or even greater than $10^8$ CFU or spores per plant element. In some embodiments, the plant element is a seed.

A surprising aspect of the present invention is that the compositions and methods described herein demonstrate modulated levels of individual seed nutrients with no adverse impact to yield, for example, no statistical negative impact to seed yield. An increased "seed yield" can refer to any increase in seed or fruit weight, size, or abundance per a unit of measure, for example, per plant, per number of plants, per mass of plants, per acre planted, per acre harvested. In some embodiments, seed yield is reported as pounds or bushels of seed produced per acre harvested. The terms seed and grain are used interchangeably herein. Yield may also refer to the recovery of a particular component of a plant tissue upon processing, for example, the amount of oil which can be extracted per unit of seed. Typically, the particular characteristic is designated when referring to increased yield, e.g., increased seed yield or increased oil yield. Where the characteristic is not specified it may be assumed yield refers to seed yield.

In some embodiments, the seed yield of a plant element is not adversely impacted wherein the plant element heterologously disposed with an endophyte is capable of producing an average seed yield at least 90%, 93%, 95%, 96%, at least 97%, 98%, 99%, 100%, at least 100%, 103%, at least 105% of the average seed yield of a reference plant element not further comprising the endophyte.

Colonization

In some embodiments, the endophytes described herein are capable of colonizing a host plant. Successful colonization can be confirmed by detecting the presence of an endophyte population within the plant. For example, after applying a fungal endophyte to seeds, the endophyte can be detected in one or more plant elements of the plants that germinate from the seeds. Detecting the presence of the endophyte inside the plant can be accomplished by measuring the viability of the endophyte after surface sterilization of the seed or the plant: endophyte colonization results in an internal localization of the endophyte, rendering it resistant to conditions of surface sterilization. The presence and quantity of endophyte can also be established using other means known in the art, for example, immunofluorescence microscopy using endophyte-specific antibodies, or fluorescence in situ hybridization (see, for example, Amann et al. (2001) Current Opinion in Biotechnology 12:231-236). Alternatively, specific nucleic acid probes recognizing conserved sequences from an endophyte can be employed to amplify a region, for example by quantitative PCR, and correlated to CFUs by means of a standard curve.

In some embodiments, the endophytes are selected for their distinct localization in the plant after colonization. For example, an endophyte may preferentially colonize in the host plant reproductive tissue, the root tissue, the leaf tissue, the stem tissue, or the progeny seed. In some cases, different populations of endophytes may selectively or preferentially colonize different plant elements. In particular, an endophyte or combination of endophytes is selected to confer improved nutritional composition levels in seeds of a host plant that has been associated at some point during its life cycle with said endophyte(s).

In another embodiment, the endophyte is disposed, for example, on the surface of a seed of an agricultural plant, in an amount effective to be detectable in the mature agricultural plant. In some embodiments, the endophyte is disposed in an amount effective to be detectable in an amount of at least about 100 CFU or spores, between 100 CFU or spores and 200 CFU or spores, at least about 200 CFU or spores, between 200 CFU or spores and 300 CFU or spores, at least about 300 CFU or spores, between 300 CFU or spores and 500 CFU or spores, at least about 500 CFU or spores, between 500 CFU or spores and 1,000 CFU or spores, at least about 1,000 CFU or spores, between 1,000 CFU or spores and 3,000 CFU or spores, at least about 3,000 CFU or spores, between 3,000 CFU or spores and 10,000 CFU or spores, at least about 10,000 CFU or spores, between 10,000 CFU or spores and 30,000 CFU or spores, at least about 30,000 CFU or spores, between 30,000 CFU or spores and 100,000 CFU or spores, at least about 100,000 CFU or spores or more in the mature agricultural plant.

In some embodiments, the endophyte is capable of colonizing particular plant elements or tissue types of the plant. In some embodiments, the endophyte is heterologously disposed on the seed or seedling in an amount effective to be detectable within a target tissue of the agricultural plant selected from a fruit, a seed, a leaf, or a root, or portion thereof. For example, the endophyte can be detected in an amount of at least about 100 CFU or spores, between 100 CFU or spores and 200 CFU or spores, at least about 200 CFU or spores, between 200 CFU or spores and 300 CFU or spores, at least about 300 CFU or spores, between 300 CFU or spores and 500 CFU or spores, at least about 500 CFU or spores, between 500 CFU or spores and 1,000 CFU or spores, at least about 1,000 CFU or spores, between 1,000 CFU or spores and 3,000 CFU or spores, at least about 3,000 CFU or spores, between 3,000 CFU or spores and 10,000 CFU or spores, at least about 10,000 CFU or spores, between 10,000 CFU or spores and 30,000 CFU or spores, at least about 30,000 CFU or spores, between 30,000 CFU or spores and 100,000 CFU or spores, at least about 100,000 CFU or spores or more, in the target tissue of the agricultural plant.

As used herein, a "colony-forming unit" ("CFU") is used as a measure of viable microorganisms in a sample. A CFU is an individual viable cell capable of forming on a solid medium a visible colony whose individual cells are derived by cell division from one parental cell.

A "spore" or a population of "spores" refers to bacteria or fungi that are generally viable, more resistant to environmental influences such as heat and bactericidal or fungicidal agents than other forms of the same bacteria or fungi, and typically capable of germination and out-growth. Bacteria and fungi that are "capable of forming spores" are those bacteria and fungi comprising the genes and other necessary abilities to produce spores under suitable environmental conditions.

As demonstrated herein, the nutritional composition of seeds are altered or modulated by application of a treatment comprising one or more bacterial or fungal endophytes. In some embodiments of the present invention, the endophyte is a bacterium. In some embodiments of the present invention, the endophyte is a fungus.

As used herein, the term "bacterium" or "bacteria" refers in general to any prokaryotic organism, and may reference an organism from either Kingdom Eubacteria (Bacteria), Kingdom Archaebacteria (Archae), or both. In some cases, bacterial genera have been reassigned due to various reasons (such as, but not limited to, the evolving field of whole genome sequencing), and it is understood that such nomenclature reassignments are within the scope of any claimed genus.

As used herein, the term "fungus" or "fungi" refers in general to any organism from Kingdom Fungi. Historical taxonomic classification of fungi has been according to morphological presentation. Beginning in the mid-1800's, it was recognized that some fungi have a pleomorphic life cycle, and that different nomenclature designations were being used for different forms of the same fungus. With the development of genomic sequencing, it became evident that taxonomic classification based on molecular phylogenetics did not align with morphological-based nomenclature (Shenoy B D, Jeewon R, Hyde K D. Impact of DNA sequence-data on the taxonomy of anamorphic fungi. Fungal Diversity 26(10) 1-54. 2007). Systematics experts have not aligned on common nomenclature for all fungi, nor are all existing databases and information resources inclusive of updated taxonomies. As such, many fungi referenced herein may be described by their anamorph form but it is understood that based on identical genomic sequencing, any pleomorphic state of that fungus may be considered to be the same organism. In some cases, fungal genera have been reassigned due to various reasons, and it is understood that such nomenclature reassignments are within the scope of any claimed genus.

Figure 1B:
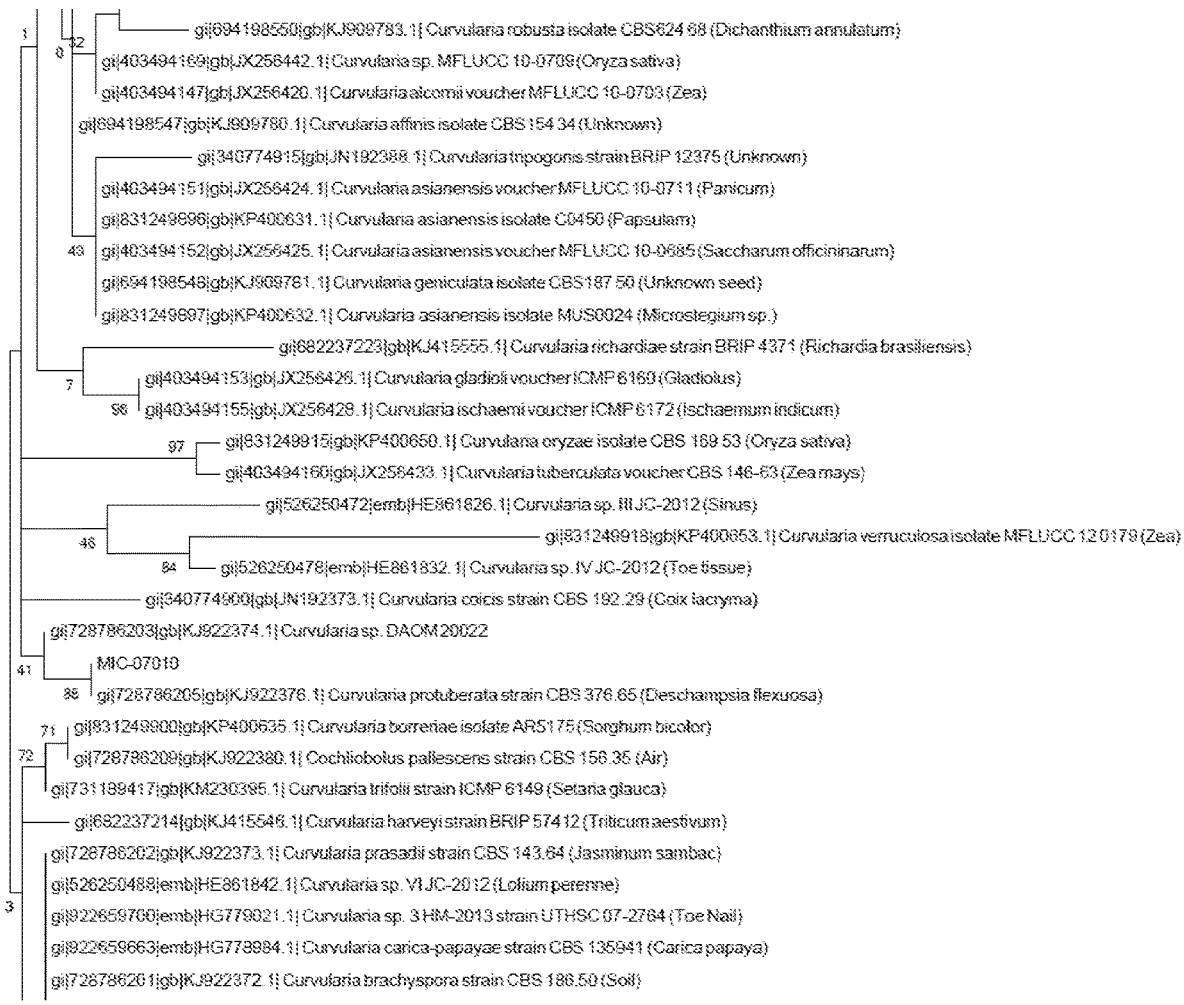
FIG. 1B depicts part 2 of 2 of an exemplary molecular phylogenetic analysis of MIC-07010 and MIC-31593 by the Maximum Likelihood method.

In some embodiments of the present invention, the endophyte is a fungi obtained from one of the following Classes: Dothideomycetes, Sordariomycetes, Eurotiomycetes, or Leotiomycetes; or one of the following Orders: Pleosporales, Hypocreales, Capnodiales, Eurotiales, or Sordariales; or one of the following Families: Pleosporaceae, Cladosporiaceae, Didymosphaeriaceae, Aspergillaceae, Pseudeurotiaceae, or Cephalothecaceae; or one of the following Genera: *Curvularia, Epicoccum, Periconia, Acremonium, Cladosporium, Exserohilum, Paraconiothyrium, Penicillium, Pseudeurotium,* or *Phialemonium*. In some cases, fungal genera have been reassigned due to various reasons, and it is understood that such nomenclature reassignments are within the scope of any claimed genus. For example, the genus *Bipolaris* and the genus *Curvularia* are closely related, but separate anamorphs, although the genus *Cochliobolus* has been described as the teleomorph for both. FIG. 1A and FIG. 1B represents an exemplary description of the phylogenetic relationship between the microbes MIC-07010 and MIC-31593 represented by SEQ ID NO: 53 and SEQ ID NO: 54. It is understood that the genus *Acremonium* is also reported in the literature as genus *Sarocladium* as well as genus *Tilachilidium* (Summerbell R. C., C. Gueidan, H-J. Schroers, G. S. de Hoog, M. Starink, Y. Arocha Rosete, J. Guano and J. A. Scott. *Acremonium* phylogenetic overview and revision of Gliomastix, *Sarocladium*, and Trichothecium. Studies in Mycology 68: 139-162. 2011). Exemplary endophytes of the genus *Acremonium* include endophytes comprising one or more sequences at least 97% identical to SEQ ID NOs: 48 or 49. Further, it is understood that the genus *Cladosporium* is an anamorph of the teleomorph genus *Davidiella* (Bensch K, Braun U, Groenewald J Z, Crous P W. The genus *Cladosporium*. Stud Mycol. 2012 Jun. 15; 72(1): 1-401), and is understood to describe the same organism. Exemplary endophytes of the genus *Cladosporium* include endophytes comprising one or more sequences at least 97% identical to SEQ ID NOs: 50, 51, or 52.

In some embodiments of the present invention, the endophyte is a bacteria obtained from one of the following Phyla: Firmicutes, Proteobacteria, Actinobacteria, or Bacteroidetes; or one of the following Classes: Bacilli, Betaproteobacteria, Actinobacteria, Gammaproteobacteria, Flavobacteriia, or Alphaproteobacteria; Orders: Bacillales, Burkholderiales, Micrococcales, Enterobacterales, Streptomycetales, Pseudomonadales, Flavobacteriales, Rhizobiales, or Sphingomonadales; or one of the following Families: Bacillaceae, Burkholderiaceae, Microbacteriaceae, Enterobacteriaceae, Erwiniaceae, Streptomycetaceae, Moraxellaceae, Flavobacteriaceae, Micrococcaceae, Brucellaceae, Paenibacillaceae, or Sphingomonadaceae; or one of the following Genera: *Bacillus, Burkholderia, Curtobacterium, Enterobacter, Pantoea, Streptomyces, Acinetobacter, Chryseobacterium, Micrococcus, Ochrobactrum, Paenibacillus,* or *Sphingomonas*.

Endophytes of the present invention can be described by genetic sequences. Marker genes are genetic sequences that are particularly useful in classifying organisms. The 16S and ITS polynucleotide sequences are two marker gene sequences by which bacteria (16S) and fungi (ITS) may be specifically identified and assigned taxonomic nomenclature. Additional genomic regions that are useful marker genes include the Beta-tubulin and second largest subunit of RNA polymerase II.

As used herein "polynucleotide sequence", "nucleotide sequence", "nucleic acid sequence", and "sequence" are equivalent and used interchangeably.

The term 16S refers to the DNA sequence of the 16S ribosomal RNA (rRNA) sequence of a bacterium. 16S rRNA gene sequencing is a well-established method for studying phylogeny and taxonomy of bacteria.

"Internal Transcribed Spacer" (ITS) refers to the spacer DNA (non-coding DNA) situated between the small-subunit ribosomal RNA (rRNA) and large-subunit (LSU) rRNA genes in the chromosome or the corresponding transcribed region in the polycistronic rRNA precursor transcript. ITS gene sequencing is a well-established method for studying phylogeny and taxonomy of fungi. In some cases, the "Large SubUnit" (LSU) sequence is used to identify fungi.

As used herein, a nucleic acid has "homology" or is "homologous" to a second nucleic acid if the nucleic acid sequence has a similar sequence to the second nucleic acid sequence. The terms "identity", "percent identity", "percent sequence identity" or "identical" in the context of nucleic acid sequences refer to the nucleotides in the two sequences that are the same when aligned for maximum correspondence. There are different algorithms known in the art that can be used to measure nucleotide sequence identity. Nucleotide sequence identity can be measured by a local or global alignment, preferably implementing an optimal local or optimal global alignment algorithm. For example, a global alignment may be generated using an implementation of the Needleman-Wunsch algorithm (Needleman, S. B. & Wunsch, C. D. (1970) Journal of Molecular Biology. 48(3): 443-53). For example, a local alignment may be generated using an implementation of the Smith-Waterman algorithm (Smith T. F & Waterman, M. S. (1981) Journal of Molecular Biology. 147(1):195-197). Optimal global alignments using the Needleman-Wunsch algorithm and optimal local alignments using the Smith-Waterman algorithm are implemented in USEARCH, for example USEARCH version v8.1.1756_i86osx32.

A gap is a region of an alignment wherein a sequence does not align to a position in the other sequence of the alignment. In global alignments, terminal gaps are discarded before identity is calculated. For both local and global alignments, internal gaps are counted as differences. A terminal gap is a region beginning at the end of a sequence in an alignment wherein the nucleotide in the terminal position of that sequence does not correspond to a nucleotide position in the other sequence of the alignment and extending for all contiguous positions in that sequence wherein the nucleotides of that sequence do not correspond to a nucleotide position in the other sequence of the alignment. An internal gap is a gap in an alignment which is flanked on the 3' and 5' end by positions wherein the aligned sequences are identical.

In some embodiments, the nucleic acid sequence to be aligned is a complete gene. In some embodiments, the nucleic acid sequence to be aligned is a gene fragment. In some embodiments, the nucleic acid sequence to be aligned is an intergenic sequence. In a preferred embodiment, inference of homology from a sequence alignment is make where the region of alignment is at least 85% of the length of the query sequence.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, or at least about 90%, or at least about 95%, 96%, at least 97%, 98%, 99% or 100% of the positions of the alignment, wherein the region of alignment is at least about 50%, 60%, 70%, 75%, 85%, or at least about 90%, or at least about 95%, 96%, 97%, 98%, 99% or 100% of the length of the query sequence. In a preferred embodiment, the region of alignment contains at least 100 positions inclusive of any internal gaps. In some embodiments, the region of alignment comprises at least 100 nucleotides of the query sequence. In some embodiments, the region of alignment comprises at least 200 nucleotides of the query sequence. In some embodiments, the region of alignment comprises at least 300 nucleotides of the query sequence. In some embodiments, the region of alignment comprises at least 400 nucleotides of the query sequence. In some embodiments, the region of alignment comprises at least 500 nucleotides of the query sequence. In some embodiments, the query sequence is selected from the SEQ ID Nos in Table 6.

In some embodiments, the endophyte comprises a nucleotide sequence that is at least 95% identical to a nucleotide sequence selected from the group consisting of SEQ ID NOs. 18-62. In some embodiments, the endophyte comprises a nucleotide sequence that is at least 96% identical to a nucleotide sequence selected from the group consisting of SEQ ID NOs. 18-62. In some embodiments, the endophyte comprises a nucleotide sequence that is at least 97% identical to a nucleotide sequence selected from the group consisting of SEQ ID NOs. 18-62. In some embodiments, the endophyte comprises a nucleotide sequence that is at least 98% identical to a nucleotide sequence selected from the group consisting of SEQ ID NOs. 18-62. In some embodiments, the endophyte comprises a nucleotide sequence that is at least 99% identical to a nucleotide sequence selected from the group consisting of SEQ ID NOs. 18-62. In some embodiments, the endophyte comprises a nucleotide sequence that is 100% identical to a nucleotide sequence selected from the group consisting of SEQ ID NOs. 18-62. In some embodiments, the endophyte comprises at least one, at least two, at least three, at least four, at least five, at least six nucleotide sequences that are at least 97% identical at least one, at least two, at least three, at least four, at least five, at least six nucleotide sequences that are selected from the group consisting of SEQ ID NOs. 18-62. In some embodiments, the endophyte comprises a nucleotide sequence that is at least 97% identical to a nucleotide sequence selected from the group consisting of SEQ ID NOs. 28, 29, 30, 31, 32, 33. In some embodiments, the endophyte is deposited as NRRL-67467. In some embodiments, the endophyte comprises a nucleotide sequence that is at least 97% identical to SEQ ID NO. 23. In some embodiments, the endophyte is deposited as NRRL-B67465. In some embodiments, the endophyte comprises a nucleotide sequence that is at least 97% identical to a nucleotide sequence selected from the group consisting of SEQ ID NOs. 26 and 27. In some embodiments, the endophyte comprises a nucleotide sequence that is at least 97% identical to SEQ ID NO. 22. In some embodiments, the endophyte comprises a nucleotide sequence that is at least 97% identical to a nucleotide sequence selected from the group consisting of SEQ ID NOs. 34, 35, 36, and 37. In some embodiments, the endophyte comprises a nucleotide sequence that is at least 97% identical to a nucleotide sequence selected from the group consisting of SEQ ID NOs. 18 and 19. In some embodiments, the endophyte comprises a nucleotide sequence that is at least 97% identical to a nucleotide sequence selected from the group consisting of SEQ ID NOs. 24 and 25. In some embodiments, the endophyte comprises a nucleotide sequence that is at least 97% identical to a nucleotide sequence selected from the group consisting of SEQ ID NOs. 20 and 21. In some embodiments, the endophyte is deposited as Deposit ID: NRRL-67466. In some embodiments, the endophyte is deposited as Deposit ID: NRRL-67467, Deposit ID: NRRL-B67465, or Deposit ID: NRRL-67466, and thereafter modified. In some embodiments, the modified endophyte retains the ability to modulate the nutrient composition of a seed produced by a plant element heterologously disposed with the modified endophyte.

Pluralities and Populations of Endophytes

As demonstrated herein, the nutritional composition of seeds are altered or modulated by application of a treatment comprising one or more endophytes.

In some embodiments, the one or more endophytes are a "plurality of endophytes". A "plurality of endophytes" means two or more genetically distinct endophytes, e.g., of bacteria or fungi, or combinations thereof. In some embodiments, the two or more genetically distinct endophytes comprise a first and second endophyte. In other embodiments, the two or more genetically distinct endophytes are two or more species of endophytes. In yet other embodiments, the two or more genetically distinct endophytes are two or more genera of endophytes. In yet other embodiments, the two or more genetically distinct endophytes are two or more families of endophytes. In yet other embodiments, the two or more types of endophyte entities are two or more orders of endophytes. In some embodiments, the plurality of endophytes comprises a first bacterial endophyte and a second bacterial endophyte, wherein the second endophyte comprises a 16S sequence less than 97% identical to a 16S sequence of the first endophyte. In some embodiments, the plurality of endophytes comprises a first fungal endophyte and a second fungal endophyte, wherein the second endophyte comprises a ITS sequence less than 97% identical to a ITS sequence of the first endophyte. In some embodiments, the 16S or ITS sequence of the second endophyte is less than 95% identical to the 16S or ITS sequence of the first endophyte.

In some embodiments, the one or more endophytes are a "population of endophytes" or an "endophyte population". A "population of endophytes" or an "endophyte population" is a plurality of endophytes that share a common genetic derivation, i.e., a plurality of endophytes of identical taxonomy. In some embodiments, a population of endophytes refers to a plurality of endophytes of the same genus. In some embodiments, a population of endophytes refers to a plurality of endophytes each comprising 16S or ITS sequences having at least 97% identity to the other, or each having at least 97% identity to a third 16S or ITS sequence.

In some embodiments of the present invention, it is contemplated that combinations of endophytes can provide an increased benefit or different benefits to the host plant, as compared to that conferred by a single endophyte, by virtue of additive effects. For example, one endophyte that induces a benefit in the host plant may induce such benefit equally well in a plant that is also colonized with a different endophyte that also induces the same benefit in the host plant. The host plant thus exhibits the same total benefit from the plurality of different endophytes as the additive benefit to individual plants colonized with each individual endophyte of the plurality. In one example, a plant is colonized with two different endophytes: one provides a 1× increase in seed protein content when heterologously disposed to the plant, and the other provides a 2× increase in seed protein content when heterologously disposed to a different plant. When both endophytes are heterologously disposed to the same plant, that plant would experience a 3× (additive of 1×+2× single effects) increase in seed protein content. Additive effects are a surprising aspect of the present invention, as non-compatibility of endophytes may result in a cancellation of the beneficial effects of both endophytes.

In some embodiments, it is contemplated that a combination of endophytes can provide an increased benefit to the host plant, as compared to that conferred by a single endophyte, by virtue of synergistic effects. For example, one endophyte that induces a benefit in the host plant may induce such benefit beyond additive effects in a plant that is also colonized with a different endophyte that also induces that benefit in the host plant. The host plant thus exhibits the greater total benefit from the plurality of different endophytes than would be expected from the additive benefit of individual plants colonized with each individual endophyte of the plurality. In one example, a plant is colonized with two different endophytes: one provides a 1× increase in seed protein content when heterologously disposed to a plant, and the other provides a 2× increase in seed protein content when heterologously disposed to a different plant. When both endophytes are heterologously disposed to the same plant, that plant would experience a 5× (greater than an additive of 1×+2× single effects) increase in seed protein content. Synergistic effects are a surprising aspect of the present invention.

Beneficial Attributes of Synthetic Combinations of Plant Elements and Endophytes The trait of the seed can be altered without known genetic modification of the plant genome, and comprises the following steps. First, a preparation of an isolated endophyte that is heterologous to the seed of the host plant is provided, and optionally processed to produce an endophyte formulation. The endophyte formulation is then contacted with the host plant. The plants are then allowed to go to seed, and the progeny seeds are collected.

The term "isolated" is intended to specifically reference an organism, cell, tissue, polynucleotide, or polypeptide that is removed from its original source and purified from additional components with which it was originally associated. For example, an endophyte may be considered isolated from a seed if it is removed from that seed source and purified so that it is isolated from any additional components with which it was originally associated. Similarly, an endophyte may be removed and purified from a plant or plant element so that it is isolated and no longer heterologously disposed to its source plant or plant element.

As used herein, an isolated endophyte or microbe is an endophyte or microbe that has been removed from its natural milieu. "Pure cultures" or "isolated cultures" are cultures in which the organisms present are only of one particular genus and species. This is in contrast to "mixed cultures," which are cultures in which more than one genus and/or species of microorganism are present. As such, the term "isolated" does not necessarily reflect the extent to which the microbe has been purified. A "substantially pure culture" of the microbe refers to a culture which contains substantially no other endophytes or microbes than the desired endophyte or microbe. In other words, a substantially pure endophyte or microbe culture is substantially free of other contaminants, which can include microbial contaminants. Further, as used herein, "biologically pure" is intended to mean the endophyte or microbe separated from materials with which it is normally associated in nature. A microbe or endophyte heterologously disposed to other microbes or endophytes, or with compounds or materials that it is not normally found with in nature, is still defined as "biologically pure." A monoculture is, of course, "biologically pure." As used herein, the term "enriched culture" of an isolated microbe or endophyte refers to a culture that contains more that 50%, 60%, 70%, 80%, 90%, or 95% of the isolated endophyte or microbe.

Uses of Modulated Seed

Modulated seeds of the present invention may be used to improve the composition or production of a food product for human consumption, a feed for animal consumption, a fuel, a fiber, or other food or industrial product. In some embodiments, use of a modulated seed in a food or feed product improves the nutrition available to the organism directly or indirectly metabolizing the modulated seed. In some embodiments, the organism metabolizing the modulated seed is a mammal, fish, bird, amphibian, reptile, crustacean, mollusc, aquatic plant, algae, bacteria, fungi, or other living organism. In some embodiments, use of a modulated seed in a food or feed product improves the efficiency or reduces the cost of producing the food or feed. In some embodiments, use of a modulated seed in a food or feed product enhances the value of a by-product of production of the food, feed or industrial product.

Human food products include but are not limited to vegetable oils (including oils for baking, cooking, frying, flavoring, and storing foods), extracted or enriched plant proteins (including tofu, protein powders, and protein flakes), milled products and derivates thereof (including flours, meals, germs, and brans).

Animal feeds include, but are not limited, to whole, crushed and rolled seeds, and more highly processed seeds such as oilseed meals, dried distillers grains, and middlings.

A seed for oil extraction is a seed comprising fatty acids which can be extracted. Methods of oil extraction include, but are not limited to, mechanical pressing and solvent extraction. In preferred embodiments, seeds for oil extraction are soybean seeds, corn seeds, cotton seeds, or wheat seeds. As used herein, "oil" and "fat" are used interchangeably.

Industrial products are manufactured products not primarily intended for consumption by a living organism. Industrial products include, but are not limited to, biocomposites, adhesives, lubricants, solvents, waxes, oils, foams, and biofuels such as ethanol and biodiesel.

Synthetic Compositions and Treatment Formulations

A "synthetic composition" comprises one or more endophytes combined by human endeavor with a heterologously disposed plant element or a heterologously disposed treatment formulation, said combination which is not found in nature. In some embodiments, a synthetic composition comprises both one or more plant elements and one or more formulation components combined by human endeavor with an isolated, purified endophyte composition. In some embodiments, said purified endophyte composition is mechanically or manually applied, artificially inoculated or disposed on a plant element in a manner that is not found on or in the plant element before application of the purified endophyte composition, e.g., said combination or association which is not found in nature.

The synthetic compositions provided herein are preferably stable. The endophyte may be shelf-stable, where at least 0.01%, of the CFUs are viable after storage in desiccated form (i.e., moisture content of 30% or less) for 1, 2, 3, 4, 5, 6, 7, 8, 9, 10 or greater than 10 weeks at 4° C. or at room temperature. Optionally, a shelf-stable formulation is in a dry formulation, a powder formulation, or a lyophilized formulation. In some embodiments, the formulation is formulated to provide stability for the population of endophytes. In an embodiment, the formulation is substantially stable at temperatures between about −20° C. and about 50° C. for at least about 1, 2, 3, 4, 5, or 6 days, or 1, 2, 3 or 4 weeks, or 1, 2, 3, 4, 5, 6, 7, 8, 9, 10, 11 or 12 months, or one or more years. In another embodiment, the formulation is substantially stable at temperatures between about 4° C. and about 37° C. for at least about 5, 10, 15, 20, 25, 30 or greater than 30 days.

A "treatment formulation" refers to a mixture of chemicals that facilitate the stability, storage, and/or application of the endophyte composition(s). Treatment formulations may comprise any one or more agents such as: surfactant, a buffer, a carrier, a tackifier, a microbial stabilizer, a fungicide, an anticomplex agent, an herbicide, a nematicide, an insecticide, a plant growth regulator, a rodenticide, a desiccant, a nutrient, an excipient, a wetting agent, a salt.

In some embodiments, an "agriculturally compatible carrier" can be used to formulate a treatment formulation or other composition that includes a purified endophyte preparation. As used herein an "agriculturally compatible carrier" refers to any material, other than water, that can be added to a plant element without causing or having an adverse effect on the plant element (e.g., reducing seed germination) or the plant that grows from the plant element, or the like.

The carrier can be a solid carrier or liquid carrier, and in various forms including microspheres, powders, emulsions and the like. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in a composition of the invention. Water-in-oil emulsions can also be used to formulate a composition that includes the purified population (see, for example, U.S. Pat. No. 7,485,451). Suitable formulations that may be prepared include wettable powders, granules, gels, agar strips or pellets, thickeners, biopolymers, and the like, microencapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil. When such formulations are used as wettable powders, biologically compatible dispersing agents such as non-ionic, anionic, amphoteric, or cationic dispersing and emulsifying agents can be used.

In some embodiments, the agricultural carrier may be soil or a plant growth medium. Other agricultural carriers that may be used include water, fertilizers, plant-based oils, humectants, or combinations thereof. Liquid carriers include vegetable oils such as soybean oil, neem oil, cottonseed oil, and other compositions such as glycerol, ethylene glycol, polyethylene glycol, propylene glycol, polypropylene glycol, etc. In some embodiments, the agricultural carrier may be a solid, such as diatomaceous earth, loam, silica, alginate, clay, bentonite, vermiculite, seed cases, peat, wheat, bran, talc, fuller's earth, pasteurized soil, other plant, animal, or abiogenic products, or combinations thereof, including granules, pellets, or suspensions. In some embodiments, the solid carriers of a treatment formulation include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used solid carriers. Mixtures of any of the aforementioned ingredients are also contemplated as carriers, such as but not limited to, pesta (flour and kaolin clay), agar or flour-based pellets in loam, sand, or clay, etc. Formulations may include food sources for the cultured organisms, such as barley, rice, wheat or other biological materials such as seed, plant elements, sugar cane bagasse, hulls or stalks from grain processing, ground plant material or wood from building site refuse, sawdust or small fibers from recycling of paper, fabric, or wood. Other suitable formulations will be known to those skilled in the art.

In some cases, a flowability polymer, also referred to as a plantability polymer such as Flo Rite® e.g., Flo-Rite® 1706 (BASF, Ludwigshafen, Germany). In some embodiments, a flowability or plantability polymer is DISCO™ AG (Incotec, Enkhuizen, the Netherlands). In some embodiments, a flowability or plantability polymer is Kannar® Universal Wonder (Kannar Earth Science, Ltd., Buford, Ga.).

In an embodiment, the formulation can include a tackifier or adherent. Such agents are useful for combining the complex population of the invention with carriers that can contain other compounds (e.g., control agents that are not biologic), to yield a coating composition. Such compositions help create coatings around the plant or plant element to maintain contact between the endophyte and other agents with the plant or plant element. In some embodiments, adherents are selected from the group consisting of: alginate, gums, starches, lecithins, formononetin, polyvinyl alcohol, alkali formononetinate, hesperetin, polyvinyl acetate, cephalins, Gum Arabic, Xanthan Gum, carragennan, PGA, other biopolymers, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and polyoxyethylene-polyoxybutylene block copolymers. Other examples of adherent compositions that can be used in the synthetic preparation include those described in EP 0818135, CA 1229497, WO 2013090628, EP 0192342, WO 2008103422 and CA 1041788.

It is also contemplated that the formulation may further comprise an anti-caking agent.

The formulation can also contain a surfactant, wetting agent, emulsifier, stabilizer, or anti-foaming agent. Non-limiting examples of surfactants include nitrogen-surfactant blends such as Prefer 28 (Cenex), Surf-N (US), Inhance (Brandt), P-28 (Wilfarm) and Patrol (Helena); esterified seed oils include Sun-It II (AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic (Helena), Sylgard 309 (Wilbur-Ellis) and Century (Precision), polysorbate 20, polysorbate 80, Tween 20, Tween 80, Scattics, Alktest TW20, Canarcel, Peogabsorb 80, Triton X-100, Conco NI, Dowfax 9N, Igebapl CO, Makon, Neutronyx 600, Nonipol NO, Plytergent B, Renex 600, Solar NO, Sterox, Serfonic N, T-DET-N, Tergitol NP, Triton N, IGEPAL CA-630, Nonident P-40, Pluronic. In some embodiments, the surfactant is present at a concentration of between 0.01% v/v to 10% v/v. In another embodiment, the surfactant is present at a concentration of between 0.1% v/v to 1% v/v. An example of an anti-foaming agent would be Antifoam-C.

In certain cases, the formulation includes a microbial stabilizer. Such an agent can include a desiccant. As used herein, a "desiccant" can include any compound or mixture of compounds that can be classified as a desiccant regardless of whether the compound or compounds are used in such concentrations that they in fact have a desiccating effect on the liquid inoculant. Such desiccants are ideally compatible with the population used, and should promote the ability of an endophyte population to survive application on the seeds and to survive desiccation. Examples of suitable desiccants include one or more of trehalose, sucrose, glycerol, and methylene glycol. Other suitable desiccants include, but are not limited to, non-reducing sugars and sugar alcohols (e.g., mannitol or sorbitol). The amount of desiccant introduced into the formulation can range from about 5% to about 50% by weight/volume, for example, between about 10% to about 40%, between about 15% and about 35%, or between about 20% and about 30%. In some embodiments, components of a sugar-based microbial stabilizer include, but are not limited to, glucose, sucrose, polyvinylpyrrolidone K 30 (PVP30K), mineral oil, soy lecithin, peptone, monopotassium phosphate (KH2PO4) and dipotassium phosphate (K2HPO4). In an alternate embodiment, components of a non-sugar based microbial stabilizer include, but are not limited to, polyvinylpyrrolidone K 30 (PVP30K), polyvinylpyrrolidone/vinyl acetate (PVP-VA), soy lecithin, peptone, mineral oil, hydroxypropyl-guar (HP-Guar), monopotassium phosphate (KH2PO4) and dipotassium phosphate (K2HPO4). Components of exemplary microbial stabilizers for use with the invention described herein are depicted in Table 1 and Table 2.

TABLE 1

Exemplary sugar based microbial stabilizer

| Component | Percentage (%), by weight |
|---|---|
| Glucose | 11.4 |
| Sucrose | 11.4 |
| PVP30K | 2.8 |
| Mineral oil | 5.7 |
| Soy lecithin | 0.3 |
| Peptone | 11.4 |
| KH2PO4 | 0.78 |
| K2HPO4 | 0.99 |
| Non-chlorinated water | 55 |

TABLE 2

Exemplary non-sugar based microbial stabilizer

| Component | Percentage (%), by weight |
|---|---|
| PVP30K | 3.8 |
| PVP-VA | 3.8 |
| Soy lecithin | 0.4 |
| Peptone | 15.4 |
| Mineral oil | 6.0 |
| HP-Guar | 0.2 |
| KH2PO4 | 0.96 |
| K2HPO4 | 1.23 |
| Non-chlorinated water | 68 |

In some cases, it is advantageous for the formulation to contain agents such as a fungicide, an anticomplex agent, an herbicide, a nematicide, an insecticide, a plant growth regulator, a rodenticide, a bactericide, a virucide, or a nutrient. Such agents are ideally compatible with the agricultural plant element or seedling onto which the formulation is applied (e.g., it should not be deleterious to the growth or health of the plant). Furthermore, the agent is ideally one which does not cause safety concerns for human, animal or industrial use (e.g., no safety issues, or the compound is sufficiently labile that the commodity plant product derived from the plant contains negligible amounts of the compound).

The endophyte populations herein can be combined with one or more of the agents described above to yield a treatment formulation suitable for combining with an agricultural plant element, seedling, or other plant element. Endophyte populations can be obtained from growth in culture, for example, using a synthetic growth medium. In addition, endophytes can be cultured on solid media, for example on petri dishes, scraped off and suspended into the preparation. Endophytes at different growth phases can be used. For example, endophytes at lag phase, early-log phase, mid-log phase, late-log phase, stationary phase, early death phase, or death phase can be used. Endophytic spores may be used for the present invention, for example but not limited to: arthospores, sporangispores, conidia, chlamadospores, pycnidiospores, endospores, zoospores.

The formulations comprising endophyte populations typically contains between about 0.1 to 95% by weight, for example, between about 1% and 90%, between about 3% and 75%, between about 5% and 60%, between about 10% and 50% in wet weight of the population. It is preferred that the formulation contains at least about $10^3$ CFU per ml of formulation, for example, at least about $10^4$, at least about $10^5$, at least about $10^6$, at least about $10^7$ CFU, at least about $10^8$ CFU per ml of formulation. It is preferred that the formulation be applied to the plant element at about $10^2$ CFU/seed, between $10^2$ and $10^3$ CFU, at least about $10^3$ CFU, between $10^3$ and $10^4$ CFU, at least about $10^4$ CFU, between $10^4$ and $10^5$ CFU, at least about $10^5$ CFU, between $10^5$ and $10^6$ CFU, at least about $10^6$ CFU, between $10^6$ and $10^7$ CFU, at least about $10^7$ CFU, between $10^7$ and $10^8$ CFU, or even greater than $10^8$ CFU per seed.

In some cases, the present invention contemplates the use of compositions that are "compatible" with agricultural chemicals, including but not limited to, a fungicide, an anticomplex compound, a bactericide, a virucide, an herbicide, a nematicide, a parasiticide, a pesticide, or any other agent widely used in agricultural which has the effect of killing or otherwise interfering with optimal growth of another organism. As used herein, a composition is "compatible" with an agricultural chemical when the organism is modified, such as by genetic modification, e.g., contains a transgene that confers resistance to an herbicide, or is adapted to grow in, or otherwise survive, the concentration of the agricultural chemical used in agriculture. For example, an endophyte disposed on the surface of a plant element is compatible with the fungicide metalaxyl if it is able to survive the concentrations that are applied on the plant element surface.

In some embodiments, the endophytes display tolerance to an agrichemical selected from the group consisting of: Aeris®, Avicta® DuoCot 202, Cruiser®, Syntenta CCB® (A), Clariva®, Albaugh, Dynasty®, Apron®, Maxim®, Gaucho®, Provoke® ST, Syngenta CCB®, Trilex®, WG Purple, WG Silver, Azoxystrobin, Carboxin, Difenoconazole, Fludioxonil, fluxapyroxad, Ipconazole, Mefenoxam, Metalaxyl, Myclobutanil, Penflufen, pyraclostrobin, Sedaxane, TCMTB, Tebuconazole, Thiram, Triadimenol (Baytan®), Trifloxystrobin, Triticonazole, Tolclofos-methyl, PCNB, Abamectin, Chlorpyrifos, Clothianidin, Imidacloprid, Thiamethoxam, Thiodicarb.

Agricultural chemical compatible endophytes can also be isolated by selection on liquid medium. The culture of endophytes can be plated on petri dishes without any forms of mutagenesis; alternatively, endophytes can be mutagenized using any means known in the art. For example, endophyte cultures can be exposed to UV light, gamma-irradiation, or chemical mutagens such as ethylmethanesulfonate (EMS), ethidium bromide (EtBr) dichlovos (DDVP), methyl methane sulphonale (MMS), triethylphosphate (TEP), trimethylphosphate (TMP), nitrous acid, or DNA base analogs, prior to selection on fungicide comprising media. Finally, where the mechanism of action of a particular chemical is known, the target gene can be specifically mutated (either by gene deletion, gene replacement, site-directed mutagenesis, etc.) to generate an endophyte that is resilient against that particular chemical.

Compatibility with an antimicrobial agent can be determined by a number of means known in the art, including the comparison of the minimal inhibitory concentration of the unmodified and modified endophytes. In some embodiments, the present invention discloses an isolated modified endophyte, wherein the endophyte is modified such that it exhibits at least 3 fold greater, for example, at least 5 fold greater, between 5 and 10 fold greater, at least 10 fold greater, between 10 and 20 fold greater, at least 20 fold greater, between 20 and 30 fold greater, at least 30 fold greater or more minimal inhibitory concentration to an antimicrobial agent when compared with the unmodified endophyte.

Candidate isolates can be tested to ensure that the selection for agrichemical compatibility did not result in loss of a desired bioactivity. Isolates of endophytes that are compatible with commonly employed agents can be selected as described above. The resulting compatible endophyte can be compared with the parental endophyte on plants in its ability to promote germination.

The agrichemical compatible endophytes generated as described above can be detected in samples. For example, where a transgene was introduced to render the endophyte compatible with the agrichemical(s), the transgene can be used as a target gene for amplification and detection by PCR. In addition, where point mutations or deletions to a portion of a specific gene or a number of genes results in compatibility with the agrichemical(s), the unique point mutations can likewise be detected by PCR or other means known in the art. Such methods allow the detection of the endophyte even if it is no longer viable. Thus, commodity plant products produced using the agrichemical compatible endophytes described herein can readily be identified by employing these and related methods of nucleic acid detection.

In some embodiments, a synthetic composition is applied mechanically or manually or artificially inoculated to a plant element in a seed treatment, root wash, seedling soak, foliar application, soil inocula, in-furrow application, sidedress application, soil pre-treatment, wound inoculation, drip tape irrigation, vector-mediation via a pollinator, injection, osmopriming, hydroponics, aquaponics, aeroponics, and combinations thereof. Application to the plant may be achieved, for example, as a powder for surface deposition onto plant leaves, as a spray to the whole plant or selected plant element, as part of a drip to the soil or the roots, or as a coating onto the plant element prior to or after planting. Such examples are meant to be illustrative and not limiting to the scope of the invention.

The invention will be further described in the following examples, which do not limit the scope of the invention described in the claims.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Example 1. Isolation and Identification of Endophytes

Isolation and cultivation of endophytic microbes from agricultural plants was performed using methods well known in the art. MIC—was isolated from the [tissue] of [Genus species variety]. DNA was extracted from the ground tissues using the DNeasy DNA extraction kit (Qiagen, Hilden, Germany) according to the manufacturer's instructions. The endophytes were characterized by the sequences of genomic regions, these sequences include SEQ ID NOs: 18-62. Primers that amplify genomic regions of the endophytes of the present invention are listed in Table 3. Additional isolation and cultivation of endophytic microbes from agricultural plants was performed using methods well known in the art.

TABLE 3

Primer sequences useful in identifying microbes of the present invention

| Primers | Genomic locus |
|---|---|
| 27f (5'-AGAGTTTGATYMTGGCTCAG-3') (SEQ ID NO: 1)<br>1492r (5'-GGTTACCTTGTTACGACTT-3') (SEQ ID NO: 2) | 16S |
| 515f (5'-GTGYCAGCMGCCGCGGTAA-3') (SEQ ID NO: 3)<br>806r (5'-GGACTACNVGGGTWTCTAAT-3') (SEQ ID NO: 4) | 16S |
| ITS_1 (5'-CTTGGTCATTTAGAGGAAGTAA-3') (SEQ ID NO: 5)<br>LR5 (5'-TCCTGAGGGAAACTTCG-3') (SEQ ID NO: 8) | ITS |
| ITS_2 (5'-GCTGCGTTCTTCATCGATGC-3') (SEQ ID NO: 6)<br>ITS_3 (5'-GCATCGATGAAGAACGCAGC-3') (SEQ ID NO: 7) | ITS |
| Btub2Fd, beta-tubulin, primer-amplicon F (5'-GTBCACCTYCARACCGGYCARTG-3') (SEQ ID NO: 9)<br>Btub4Rd, beta-tubulin, primer-amplicon R (5'-CCRGAYTGRCCRAARACRAAGTTGTC-3') (SEQ ID NO: 10) | Beta-tubulin |
| fRPB2-5F (5'-GAYGAYMGWGATCAYTTYGG-3') (SEQ ID NO: 13)<br>bRPB2-7.1R (5'-CCCATRGCYTGYTTMCCCATDGC-3') (SEQ ID NO: 11) | second largest subunit of RNA polymerase II |
| fRPB2-5F (5'-GAYGAYMGWGATCAYTTYGG-3') (SEQ ID NO: 13)<br>bRPB2-7R (5'-CCCATRGCYTGYTTMCCCATDGC-3') (SEQ ID NO: 12) | second largest subunit of RNA polymerase II |
| MIC-15870-F01, unique genomic region, primer-amplicon F (5'-TGGTCAACTAGCGAACGTGT-3') (SEQ ID NO: 14)<br>MIC-15870-R01, unique genomic region, primer-amplicon R (5'-AGAGGCGAACGGGTACACT-3') (SEQ ID NO: 15) | unique genomic region |
| MIC-84414-F01, unique genomic region, primer-amplicon F (5'-AAATGTTGTTCATGCGACCA-3') (SEQ ID NO: 16)<br>MIC-84414-R01, unique genomic region, primer-amplicon R (5'-TCTCCCAGGAGCTTTCGTTA-3') (SEQ ID NO: 17) | unique genomic region |

MIC-15870 was deposited with the Agricultural Research Service Culture Collection (NRRL), at the U.S. Department of Agriculture, 1815 North University Street, Peoria, Ill. 61604, under the terms of the Budapest Treaty, as Deposit ID: NRRL-67466.

MIC-84414 was deposited with the Agricultural Research Service Culture Collection (NRRL), at the U.S. Department of Agriculture, 1815 North University Street, Peoria, Ill. 61604, under the terms of the Budapest Treaty, as Deposit ID: NRRL-67467.

MIC-82330 was deposited with the Agricultural Research Service Culture Collection (NRRL), at the U.S. Department of Agriculture, 1815 North University Street, Peoria, Ill. 61604, under the terms of the Budapest Treaty, as Deposit ID: NRRL-B67465.

Example 2: Identification of Endophytes Using Marker Gene Sequences

The fungal endophytes of the present invention can be identified by the sequence of one or more of the following loci: second largest subunit of RNA polymerase II (RPB2), beta-tubulin. PCR amplification of second largest subunit of RNA polymerase II (RPB2) using primer sequences fRPB2-5F (SEQ ID NO: 13) and bRPB2-7.1R (SEQ ID NO: 11) is described in Riess K, Oberwinkler F, Bauer R, Garnica S. High genetic diversity at the regional scale and possible speciation in Sebacina epigaea and S. incrustans. BMC Evolutionary Biology. 2013; 13:102. doi:10.1186/1471-2148-13-102. PCR amplification of second largest subunit of RNA polymerase II (RPB2) using primer sequences fRPB2-5F (SEQ ID NO: 13) and fRPB2-7R (SEQ ID NO: 12) is described in Liu Y, Whelen S, Hall B. Phylogenetic relationships among ascomycetes: evidence from an RNA polymerase II subunit. Mol. Biol. Evol. 1999. 16(12): 1799-1808. PCR amplification of beta-tubulin using primer sequences Btub2Fd (SEQ ID NO: 9) and Btub4Rd (SEQ ID NO: 10) is described in Aveskamp et al. (2009) DNA phylogeny reveals polyphyly of *Phoma* section Peyronellaea and multiple taxonomic novelties Mycologia, 101(3):363-382.

MIC-84414 can be identified by the sequence of one or more of the following: its RPB2 sequence (SEQ ID NO: 28), RPB2 sequence (SEQ ID NO: 29), beta-tubulin sequence (SEQ ID NO: 30).

MIC-68178 can be identified by the sequence of its beta-tubulin sequence (SEQ ID NO: 37).

Example 3: Identification of Bacterial and Fungal Endophytes Using 16S and ITS Sequences Classification of the Bacterial Strains Using 16S Sequence To accurately characterize isolated bacterial endophytes, colonies were submitted for marker gene sequencing, and the sequences were analyzed to provide taxonomic classifications. Colonies were subjected to 16S rRNA gene PCR amplification using a primer pair 27f (5'-AGAGTTT-GATYMTGGCTCAG-3') (SEQ ID NO: 1) and 1492r (5'-GGTTACCTTGTTACGACTT-3') (SEQ ID NO: 2). Sequencing reactions were performed using primers: 27f (5'-AGAGTTTGATYMTGGCTCAG-3') (SEQ ID NO: 1), 515f (5'-GTGYCAGCMGCCGCGGTAA-3') (SEQ ID NO: 3), 806r (5'-GGACTACNVGGGTWTCTAAT-3') (SEQ ID NO: 4), and 1492r (5'-GGTTACCTTGTTACGACTT-3') (SEQ ID NO: 2). Preferably sequencing primers are chosen so that overlapping regions are sequenced. Sanger sequencing of was performed at Genewiz (South Plainfield, N.J.). Raw chromatograms were converted to sequences, and corresponding quality scores were assigned using Trace-Tuner v3.0.6beta (U.S. Pat. No. 6,681,186). These sequences were quality filtered, aligned and a consensus sequence generated using Geneious v 8.1.8 (Biomatters Limited, Auckland NZ).

Taxonomic classifications were assigned to the sequences using the highest probability of assignment based on the results of industry standard taxonomic classification tools: LCA (runs USEARCH (Edgar, R. C., 2010) with option search_global, then for all best match hits, returns lowest taxonomic rank shared by all best hits for a query), RDP Naive Bayesian rRNA Classifier version 2.11, September 2015 (Wang et al., 2007), SPINGO version 1.3 (32 bit) (Allard et al. (2015) BMC Bioinformatics 16:324 DOI: 10.1186/s12859-015-0747-1), and UTAX version v8.1.1861_i86linux64 (Edgar, R. C. (2016) available online at drive5.com/usearch/manual/utax_algo.html), using reference databases: RDP 16S rRNA training set 15 (Cole et al., 2014), and SILVA version 119 (Quast et al., 2013). The classifier and database combinations listed in Table 4 were used to assign taxonomy to bacterial sequences.

TABLE 4

The classifier and database combinations used to classify 16S sequences

| Classifier | Database |
|---|---|
| LCA | SILVA, version 119 |
| RDP | RDP, 16S rRNA training set 15 |
| SPINGO | RDP, 16S rRNA training set 15 |
| UTAX | RDP, 16S rRNA training set 15 |
| | SILVA, version 119 |

Classification of the Fungal Strain Using ITS Sequences

Total genomic DNA was extracted from individual fungal isolates, using the DNeasy Plant Mini Kit (Qiagen, Germantown, Md.). Polymerase Chain Reaction (PCR) was used to amplify a genomic region including the nuclear ribosomal internal transcribed spacers (ITS) using a primer pair ITS_1 (5'-CTTGGTCATTTAGAGGAAGTAA-3') (SEQ ID NO: 5) and LR5 (5'-TCCTGAGGGAAACTTCG-3') (SEQ ID NO: 8). Each 25 microliter-reaction mixture included 22.5 microliters of Invitrogen Platinum Taq supermix, 0.5 microliter of each primer (10 uM), and 1.5 microliters of DNA template (~2-4 ng). Cycling reactions were run with MJ Research PTC thermocyclers and consisted of 94° C. for 5 min, 35 cycles of 94° C. for 30 s, 54° C. for 30 s, and 72° C. for 1 min, and 72° C. for 10 min. Sanger sequencing of was performed at Genewiz (South Plainfield, N.J.) using primers: ITS_1 (5'-CTTGGTCATTTAGAGGAAGTAA-3') (SEQ ID NO: 5), ITS_2 (5'-GCTGCGTTCTTCATC-GATGC-3') (SEQ ID NO: 6), ITS_3 (5'-GCATCGAT-GAAGAACGCAGC-3') (SEQ ID NO:7), and LR5 (5'-TCCTGAGGGAAACTTCG-3') (SEQ ID NO: 8). Sequencing primers were chosen so that overlapping regions were sequenced. Raw chromatograms were converted to sequences, and corresponding quality scores were assigned using TraceTuner v3.0.6beta (U.S. Pat. No. 6,681,186). These sequences were quality filtered, aligned and a consensus sequence generated using Geneious v 8.1.8 (Biomatters Limited, Auckland NZ).

Taxonomic classifications were assigned to the sequences using the highest probability of assignment based on the results of industry standard taxonomic classification tools: LCA (runs USEARCH (Edgar, R. C., 2010) with option search_global, then for all best match hits, returns lowest taxonomic rank shared by all best hits for a query), SPINGO (Allard et al., 2015), and UTAX (Edgar, R. C., 2016), using the WARCUP Fungal ITS trainset 1 (Deshpande et al. (2016) Mycologia 108(1):1-5) and UNITE (Koljalg et al., 2013). The classifier and database combinations listed in Table 5 were used to assign taxonomy to fungal sequences.

TABLE 5

The classifier and database combinations used to classify ITS sequences.

| Classifier | Database |
|---|---|
| LCA | UNITE, Fungal ITS trainset Jul. 4, 2014 |
| RDP | UNITE, Fungal ITS trainset Jul. 4, 2014 |
| | WARCUP, Fungal ITS trainset 1 |
| SPINGO | UNITE, Fungal ITS trainset Jul. 4, 2014 |
| UTAX | UNITE, Fungal ITS trainset Jul. 4, 2014 |
| | WARCUP, Fungal ITS trainset 1 |

TABLE 6

Taxonomic classification of endophytes of the present invention

| SEQ ID NOs | MIC ID | Kingdom | Phylum | Class | Order |
|---|---|---|---|---|---|
| 18, 19 | MIC-93265 | Bacteria | Firmicutes | Bacilli | Bacillales |
| 20, 21 | MIC-19621 | Bacteria | Proteobacteria | Betaproteobacteria | Burkholderiales |
| 22 | MIC-99849 | Bacteria | Actinobacteria | Actinobacteria | Micrococcales |
| 23 | MIC-82330 | Bacteria | Proteobacteria | Gammaproteobacteria | Enterobacterales |
| 24, 25 | MIC-78123 | Bacteria | Proteobacteria | Gammaproteobacteria | Enterobacterales |
| 26, 27 | MIC-38013 | Bacteria | Actinobacteria | Actinobacteria | Streptomycetales |
| 28, 29, 30, 31, 32, 33 | MIC-84414 | Fungi | Ascomycota | Dothideomycetes | Pleosporales |
| 34, 35, 36, 37 | MIC-68178 | Fungi | Ascomycota | Dothideomycetes | Pleosporales |
| 38, 39 | MIC-15870 | Fungi | Ascomycota | Dothideomycetes | Pleosporales |
| 40 | MIC-43662 | Bacteria | Proteobacteria | Gammaproteobacteria | Pseudomonadales |
| 41 | MIC-56418 | Bacteria | Bacteroidetes | Flavobacteriia | Flavobacteriales |
| 42 | MIC-69189 | Bacteria | Actinobacteria | Actinobacteria | Micrococcales |
| 43, 44 | MIC-01424 | Bacteria | Actinobacteria | Actinobacteria | Micrococcales |
| 45 | MIC-14459 | Bacteria | Proteobacteria | Alphaproteobacteria | Rhizobiales |

TABLE 6-continued

Taxonomic classification of endophytes of the present invention

| | | | | | |
|---|---|---|---|---|---|
| 46 | MIC-54707 | Bacteria | Firmicutes | Bacilli | Bacillales |
| 47 | MIC-14715 | Bacteria | Proteobacteria | Alphaproteobacteria | Sphingomonadales |
| 48 | MIC-89612 | Fungi | Ascomycota | Sordariomycetes | Hypocreales |
| 49 | MIC-96038 | Fungi | Ascomycota | Sordariomycetes | Hypocreales |
| 50, 51 | MIC-61256 | Fungi | Ascomycota | Dothideomycetes | Capnodiales |
| 52 | MIC-50414 | Fungi | Ascomycota | Dothideomycetes | Capnodiales |
| 53 | MIC-07010 | Fungi | Ascomycota | Dothideomycetes | Pleosporales |
| 54 | MIC-31593 | Fungi | Ascomycota | Dothideomycetes | Pleosporales |
| 55, 56 | MIC-68390 | Fungi | Ascomycota | Dothideomycetes | Pleosporales |
| 57 | MIC-40075 | Fungi | Ascomycota | Dothideomycetes | Pleosporales |
| 58, 59 | MIC-33228 | Fungi | Ascomycota | Eurotiomycetes | Eurotiales |
| 60 | MIC-72917 | Fungi | Ascomycota | Leotiomycetes | incertae sedis |
| 61 | MIC-50989 | Fungi | Ascomycota | Sordariomycetes | Sordariales |
| 62 | MIC-70076 | Bacteria | Proteobacteria | Gammaproteobacteria | Enterobacterales |

| SEQ ID NOs | Family | Genus | Species |
|---|---|---|---|
| 18, 19 | Bacillaceae | *Bacillus* | *simplex* |
| 20, 21 | Burkholderiaceae | *Burkholderia* | |
| 22 | Microbacteriaceae | *Curtobacterium* | |
| 23 | Enterobacteriaceae | *Enterobacter* | *cowanii* |
| 24, 25 | Erwiniaceae | *Pantoea* | |
| 26, 27 | Streptomycetaceae | *Streptomyces* | *kathirae* |
| 28, 29, 30, 31, 32, 33 | Pleosporaceae | *Curvularia* | *spicifera* |
| 34, 35, 36, 37 | Pleosporaceae | *Epicoccum* | *nigrum* |
| 38, 39 | Pleosporaceae | *Periconia* | *macrospinosa* |
| 40 | Moraxellaceae | *Acinetobacter* | *lwoffii* |
| 41 | Flavobacteriaceae | *Chryseobacterium* | |
| 42 | Microbacteriaceae | *Curtobacterium* | |
| 43, 44 | Micrococcaceae | *Micrococcus* | |
| 45 | Brucellaceae | *Ochrobactrum* | |
| 46 | Paenibacillaceae | *Paenibacillus* | *taichungensis* |
| 47 | Sphingomonadaceae | *Sphingomonas* | |
| 48 | incertae sedis | *Acremonium* | *strictum* |
| 49 | incertae sedis | *Acremonium* | *alternatum* |
| 50, 51 | Cladosporiaceae | *Cladosporium* | |
| 52 | Cladosporiaceae | *Cladosporium* | *oxysporum* |
| 53 | Pleosporaceae | *Curvularia* | |
| 54 | Pleosporaceae | *Curvularia* | *spicifera* |
| 55, 56 | Pleosporaceae | *Exserohilum* | |
| 57 | Didymosphaeriaceae | *Paraconiothyrium* | |
| 58, 59 | Aspergillaceae | *Penicillium* | |
| 60 | Pseudeurotiaceae | *Pseudeurotium* | *bakeri* |
| 61 | Cephalothecaceae | *Phialemonium* | *inflatum* |
| 62 | Enterobacteriaceae | *Enterobacter* | *cowanii* |

Example 4. Assessment of Improved Plant Characteristics, Seedling Vigor

Assay of Soy Seedling Vigor

Seed Preparation:

The lot quality of soybean seeds is first assessed by testing germination of 100 seeds. Seeds are placed, 8 seeds per petri dish, on filter paper in petri dishes, 12 mL of water is added to each plate and plates are incubated for 3 days at 24° C. The percent germination is greater than 95%. One thousand soybean seeds are then surface sterilized by co-incubation with chlorine gas in a 20×30 cm container placed in a chemical fume hood for 16 hours. Percent germination of 50 seeds, per sterilization batch, is tested as above and confirmed to be greater than 95%.

Preparation and Heterologous Disposition of Endophytes:

Spore solutions are made by rinsing and scraping spores from agar slants which have been growing for about 1 month. Rinsing is done with 0.05% Silwet. Solutions are passed through Miracloth to filter out mycelia. Spores per ml are counted under a microscope using a hemocytometer. The stock suspension is then diluted into 10^6 spores/ml utilizing water. 3 μl of spore suspension is used per seed (~10^3 CFUs/seed is obtained). Control treatments are prepared by adding equivalent volumes of sterile water to seeds.

Assay of Seedling Vigor:

Two rolled pieces of germination paper are placed in a sterile glass gar with 50 mL sterile water, then removed when completely saturated. Then the papers are separated and inoculated seeds are placed at approximately 1 cm intervals along the length of one sheet of moistened germination paper, at least 2.5 cm from the top of the paper and 3.8 cm from the edge of the paper. The second sheet of is placed on top of the seeds and the layered papers and seeds are loosely rolled into a tube. Each tube is secured with a rubber band around the middle and placed in a single sterile glass jar and covered loosely with a lid. For each treatment, three jars with 15 seeds per jar are prepared. The position of jars with the growth chamber is randomized. Jars are incubated at 60% relative humidity, and 22° C. day, 18° C. night with 12 hours light and 12 hours dark for 4 days and then the lids are removed and the jars incubated for an additional 7 days. Then the germinated seedlings are weighed and photographed and root length and root surface area scored as follows.

Dirt, excess water, seed coats and other debris is removed from seedlings to allow accurate scanning of the roots. Individual seedlings are laid out on clear plastic trays and trays are arranged on an Epson Expression 11000XL scanner (Epson America, Inc., Long Beach Calif.). Roots are manually arranged to reduce the amount of overlap. For root measurements, shoots are removed if the shape of the shoot causes it to overlap the roots.

The WinRHIZO software version *Arabidopsis* Pro2016a (Regents Instruments, Quebec Canada) is used with the following acquisition settings: greyscale 4000 dpi image, speed priority, overlapping (1 object), Root Morphology: Precision (standard), Crossing Detection (normal). The scanning area is set to the maximum scanner area. When the scan is completed, the root area is selected and root length and root surface area are measured.

Statistical analysis is performed using R (R Core Team, 2016. R: A language and environment for statistical computing. R Foundation for Statistical Computing, Vienna, Austria. R-project.org/).

Assay of Corn Seedling Vigor

Seed Preparation:

The lot quality of corn seeds is first evaluated for germination by transfer of 100 seeds and with 3.5 mL of water to a filter paper lined petri dish. Seeds are incubated for 3 days at 24° C., and to ensure that percent germination is greater than 95%. One thousand corn seeds are then surface sterilized by co-incubation with chlorine gas in a 20×30 cm container in a chemical fume hood for 12 hours. Percent germination of 50 seeds, per sterilization batch, is tested as above and confirmed to be greater than 95%.

Optional Reagent Preparation:

7.5% PEG 6000 (Calbiochem, San Diego, Calif.) is prepared by adding 75 g of PEG to 1000 mL of water, then stirred on a warm hot plate until the PEG is fully dissolved. The solution is then autoclaved.

Preparation and Heterologous Disposition of Endophytes:

Spore solutions are made by rinsing and scraping spores from agar slants which have been growing for about 1 month. Rinsing is done with 0.05% Silwet. Solutions are passed through Miracloth to filter out mycelia. Spores per ml are counted under a microscope using a hemocytometer. The stock suspension is then diluted into $10^6$ spores/ml utilizing water. 3 µl of spore suspension is used per seed (~$10^3$ CFUs/seed is obtained). Control treatments are prepared by adding equivalent volumes of sterile water to seeds.

Assay of Seedling Vigor:

Either 25 ml of sterile water (or optionally, 25 ml of PEG solution as prepared above) is added to each Cyg™ germination pouch (Mega International, Newport, Minn.) and place into pouch rack (Mega International, Newport, Minn.). Sterile forceps are used to place seeds prepared as above into every other perforation in the germination pouch. Seeds are fitted snugly into each perforation to ensure they did not shift when moving the pouches. Before and in between treatments forceps are sterilized using ethanol and flame and workspace wiped down with 70% ethanol. For each treatment, three pouches with 15 seeds per pouch are prepared. The germination racks with germination pouches are placed into plastic tubs, and covered with perforated plastic wrap to prevent drying. Tubs are incubated at 60% relative humidity, and 22° C. day, 18° C. night with 12 hours light and 12 hours dark for 6 days to allow for germination and root length growth. Placement of pouches within racks and racks/tubs within the growth chamber is randomized to minimize positional effect. At the end of 6 days the seeds are scored manually for germination, root and shoot length.

Statistical analysis is performed using R (R Core Team, 2016. R: A language and environment for statistical computing. R Foundation for Statistical Computing, Vienna, Austria. R-project.org/).

Assay of Wheat Seedling Vigor

Seed Preparation:

The lot of wheat seeds is first evaluated for germination by transfer of 100 seeds and with 8 mL of water to a filter paper lined petri dish. Seeds are incubated for 3 days at 24° C., and percent germination was greater than 95%. Wheat seeds are then surface sterilized by co-incubation with chlorine gas in a 20×30 cm container in a chemical fume hood for 12 hours. Percent germination of 50 seeds, per sterilization batch, is tested as above and confirmed to be greater than 95%.

Optional Reagent Preparation:

7.5% polyethylene glycol (PEG) is prepared by adding 75 g of PEG to 1000 mL of water, then stirring on a warm hot plate until the PEG is fully dissolved. The solution is then autoclaved.

Preparation and Heterologous Disposition of Endophytes:

Spore solutions are made by rinsing and scraping spores from agar slants which have been growing for about 1 month. Rinsing is done with 0.05% Silwet. Solutions are passed through Miracloth to filter out mycelia. Spores per ml are counted under a microscope using a hemocytometer. The stock suspension is then diluted into $10^6$ spores/ml utilizing water. 3 µl of spore suspension is used per seed (~$10^3$ CFUs/seed is obtained). Seeds and spores are combined a 50 mL falcon tube and gently shaken for 5-10 seconds until thoroughly coated. Control treatments are prepared by adding equivalent volumes of sterile water to seeds.

Assay of Seedling Vigor:

Petri dishes are prepared by adding four sheets of sterile heavy weight seed germination paper, then adding 50 mL sterile water (or optionally, 50 ml of PEG solution as prepared above) to each plate then allowing the liquid to thoroughly soak into all sheets. The sheets are positioned and then creased so that the back of the plate and one side wall are covered, two sheets are then removed and placed on a sterile surface. Along the edge of the plate across from the covered side wall 15 inoculated seeds are placed evenly at least one inch from the top of the plate and half an inch from the sides. Seeds are placed smooth side up and with the pointed end of the seed pointing toward the side wall of the plate covered by germination paper. The seeds are then covered by the two reserved sheets, the moist paper layers smoothed together to remove air bubbles and secure the seeds, and then the lid is replaced. For each treatment, at least three plates with 15 seeds per plate are prepared. The plates are then randomly distributed into stacks of 8-12 plates and a plate without seeds is placed on the top. The stacks are incubated at 60% relative humidity, and 22° C. day, 18° C. night with 12 hours light and 12 hours dark for 24 hours, then each plate is turned to a semi-vertical position with the side wall covered by paper at the bottom. The plates are incubated for an additional 5 days, then scored manually for germination, root and shoot length.

Statistical analysis is performed using R (R Core Team, 2016. R: A language and environment for statistical computing. R Foundation for Statistical Computing, Vienna, Austria. R-project.org/).

Example 5. Assessment of Improved Plant Characteristics, Field Trials

Preparation of Bacterial Endophytes

An agar plug of each bacterial strain was transferred using a transfer tube to 4 mL of potato dextrose broth (PDB) in a 24 well plate and incubated at room temperature at 675 rpm on a shaker for 3 days. After growth of bacteria in broth, 200 µl was transferred into a spectrophotometer reading plate and bacteria OD was read at 600 nm absorbance. All bacteria strains were then normalized to 0.05 OD utilizing PBS 1× buffer. Once desired dilutions were made, 3 µl of the bacteria solution was applied per seed, and mixed well by shaking in a sterile Falcon tube for 5-10 seconds.

Preparation of Fungal Endophytes

Preparation of molasses broth and potato dextrose agar: Molasses broth was prepared by dissolving 30 g molasses and 5 g yeast extract per liter deionized water in an autoclavable container and autoclaving (15 psi, 121° C.) for 45 min. Potato dextrose agar (PDA) plates were prepared by dissolving 39.0 g PDA powder per liter deionized water in an autoclavable container and autoclaving (15 psi, 121° C.) for 45 min. The agar was allowed to cool to 50-60° C., before pouring into sterile petri plates (30 mL per 90 mm plate).

Liquid biomass: All equipment and consumables were thoroughly sterilized and procedures performed in a biosafety cabinet. The inoculant is prepared by placing 1 plug from a cryopreserved stock on a fresh PDA plate, sealing the plate with Parafilm® and incubating at room temperature in the dark for 5-10 days. Then ~5×5 mm plugs were cut from the PDA plates and 10-12 plugs were transferred into flasks containing the sterile molasses broth, covered, secured in a shaker and incubated for at least 10 days with shaking at ~130 rpm. Then the culture was placed in a blender for 5 seconds and 1 mL of the blended was centrifuged and the supernatant was discarded and the pellet resuspended in 0.5 mL 1× Phosphate Buffered Saline (PBS) to generate inoculum.

Dry biomass: All equipment and consumables were thoroughly sterilized and procedures performed in a biosafety cabinet. The inoculant is prepared by placing 1 plug from a cryopreserved stock on a fresh PDA plate, sealing the plate with Parafilm® and incubating at room temperature in the dark for 5-10 days. Then ~5×5 mm plugs were cut from the PDA plates and 10-12 plugs were transferred into flasks containing the sterile molasses broth, covered, secured in a shaker and incubated for at least 10 days with shaking at ~130 rpm. In sterile conditions, the liquid culture was carefully decanted using 150 mm sterile filter paper on a sterilized Buchner funnel over a sterile flask. Once all liquid had passed through the funnel, the pellet was rinsed with sterile water until the filtrate ran clear. When dry, the pellet was transferred to a drying cabinet and dried until brittle. The pellet was then ground into a fine powder, and sample used to generate CFU counts.

Preparation of Sodium Alginate and Talc for Seed Treatments

A 2% weight/volume solution of sodium alginate for the seed coatings is prepared by the following method. An Erlenmeyer flask is filled with the appropriate volume of deionized water and warmed to 50 degrees Celsius on a heat plate with agitation using a stir bar. The appropriate mass of sodium alginate powder for the desired final concentration solution is slowly added until dissolved. The solution is autoclaved at 121 degrees Celsius at 15 PSI for 30 minutes to sterilize.

Talcum powder for the powdered seed coatings is prepared by the following method. Talcum powder is aliquoted into Ziploc bags or 50 mL Falcon tubes, and autoclaved in dry cycle (121 degrees Celsius at 15 PSI for 30 minutes) to sterilize.

Heterologous Disposition of Endophytes on Wheat Seeds

Endophyte treatment was heterologously disposed to wheat seeds according to the following seed treatment protocols for liquid or dry formulation.

Liquid formulation: The 2% sodium alginate solution prepared above was added to the seeds at a rate of 15 ml per kg of seeds. Liquid fungal culture as prepared in above was added to the seeds at a rate of 8.3 ml per kg of seeds. Control treatments were prepared using equivalent volumes of sterile broth. The seeds were then agitated to disperse the solution evenly on the seeds.

Then 12.5 g of talc powder per kg of seed was added and the seeds were agitated to disperse the powder evenly on the seeds. Then 17 ml per kg of seed of Flo-Rite® 1706 (BASF, Ludwigshafen, Germany) was added and the seeds were agitated to disperse the powder evenly on the seeds. The final concentration of endophyte was targeted to be at least $10^4$ CFU. Treated seeds were allowed to dry overnight in a well-ventilated space before planting.

Dry formulation: The 2% sodium alginate solution prepared above was added to the seeds at a rate of 20 ml per kg of seeds. Equal parts of the fungal dry biomass prepared above and the talc prepared above were mixed. The solution is applied to the prepared seeds so that an equivalent of 12.5 g of fungal dry biomass was applied per kg of seeds. Control treatments were prepared using equivalent volumes of talc. The seeds were then agitated to disperse the solution evenly on the seeds.

Then 17 ml per kg of seed of Flo-Rite® 1706 (BASF, Ludwigshafen, Germany) was added and the seeds were agitated to disperse the powder evenly on the seeds. The final concentration of endophyte was targeted to be at least $10^4$ CFU. Treated seeds were allowed to dry overnight in a well-ventilated space before planting.

Heterologous Disposition of Endophytes on Soy Seeds

Endophyte treatment was heterologously disposed to soy seeds according to the following seed treatment protocols for liquid or dry formulation.

Liquid formulation: The 2% sodium alginate solution prepared above was added to the seeds at a rate of 8.3 ml per kg of seeds. Liquid fungal culture as prepared above was added to the seeds at a rate of 8.3 (fungal endophytes) or 8.4 (bacterial endophytes) ml per kg of seeds. Control treatments were prepared using equivalent volumes of sterile broth. The seeds were then agitated to disperse the solution evenly on the seeds. For fungal endophytes, 15 g per kg of seed of the talc powder prepared above was added and the seeds were agitated to disperse the powder evenly on the seeds. Then 13.3 (for fungal endophyte treatments) or 2.7 (for bacterial endophyte treatments) ml per kg of seed of Flo-Rite® 1706 (BASF, Ludwigshafen, Germany) was added and the seeds were agitated to disperse the powder evenly on the seeds. The final concentration of endophyte was targeted to be at least $10^4$ CFU. Treated seeds were allowed to dry overnight in a well-ventilated space before planting.

Dry fungal formulation: The 2% sodium alginate solution prepared in Example 8 was added to the seeds at a rate of 16.6 ml per kg of seeds. Equal parts of the dry fungal biomass prepared above and the talc prepared in above were mixed. The solution was applied so that an equivalent of 10 g of dry fungal biomass was applied per kg of seeds. Control treatments were prepared using equivalent volumes of talc. The seeds were then agitated to disperse the solution evenly on the seeds.

Then 13.3 ml per kg of seed of Flo-Rite® 1706 (BASF, Ludwigshafen, Germany) was added and the seeds were agitated to disperse the powder evenly on the seeds. The final concentration of endophyte was targeted to be at least $10^4$ CFU. Treated seeds were allowed to dry overnight in a well-ventilated space before planting.

Heterologous Disposition of Endophytes on Corn Seeds

Endophyte treatment was heterologously disposed to corn seeds according to the following seed treatment protocol.

Dry fungal formulation: The 2% sodium alginate solution prepared above was added to the seeds at a rate of 23 ml per kg of seeds. Equal parts of the dry fungal biomass prepared in above and the talc prepared above were mixed. The solution was applied so that an equivalent of 10 g of fungal powder was applied per kg of seeds. Control treatments were prepared using equivalent volumes of talc. The seeds were then agitated to disperse the solution evenly on the seeds.

Then 16.6 ml per kg of seed of Flo-Rite® 1706 (BASF, Ludwigshafen, Germany) was added and the seeds were agitated to disperse the powder evenly on the seeds. The final concentration of endophyte was targeted to be at least $10^4$ CFU. Treated seeds were allowed to dry overnight in a well-ventilated space before planting.

Liquid formulation: Liquid culture as prepared above was added to the seeds at a rate of 23 (for fungal endophyte treatments) or 8.4 (for bacterial endophyte treatments) ml per kg of seeds, with equivalent volumes of the prepared sodium alginate. Control treatments were prepared using equivalent volumes of sterile broth. The seeds were then agitated to disperse the solution evenly on the seeds. For fungal endophytes, 15 g per kg of seed of the talc powder prepared in sterile was added and the seeds were agitated to disperse the powder evenly on the seeds. Then 16.6 ml (for fungal endophyte treatments) or 2.4 ml (for bacterial endophyte treatments) per kg of seed of Flo-Rite® 1706 (BASF, Ludwigshafen, Germany) was added and the seeds were agitated to disperse the powder evenly on the seeds. The final concentration of endophyte was targeted to be at least $10^4$ CFU. Treated seeds were allowed to dry overnight in a well-ventilated space before planting.

Assay of Seed Yield Under Field Conditions, Wheat

Field trials were conducted under non-irrigated (dryland) conditions at multiple locations, preferably in diverse geographic regions. Wheat seeds were treated with commercial fungicidal and insecticidal treatment. Seeds were heterologously disposed with the endophyte formulations described above and untreated seeds (lacking formulation and endophyte) were also planted. Seeds were sown in regularly spaced rows in soil at 1.2 million seeds/acre seeding density. At each location, at least 3 replicate plots were planted for each endophyte or control treatment in a randomized complete block design. Each plot consisted of seven, 15.24 m (40 ft.) rows.

At the end of the field trial employing endophyte treatment and control treatment plants, plots were machine harvested with a 5-ft research combine and yield calculated by the on-board computer.

The endophyte treatments, each comprising one of the following microbes: MIC-68390, MIC-68178, MIC-07010, MIC-31593, MIC-96038, or MIC-50414, resulted in average increases in yield of 7-15% in the wheat variety SDSU Focus. The endophyte treatments, each comprising one of the following microbes: MIC-68390, MIC-68178, MIC-07010, MIC-31593, MIC-96038, or MIC-50414, resulted in average increases in yield of 15-22% in the wheat variety SDSU Select.

TABLE 7

Average yield of wheat treated with endophytes in field trials

| | SDSU Focus, Variety 3 | | SDSU Select, Variety 4 | |
|---|---|---|---|---|
| | Average yield (BU/acre) | % difference Untreated | Average yield (BU/acre) | % difference Untreated |
| Untreated control | 36.9 | 0 | 37.7 | 0% |
| MIC-68390 | 39.3 | 7% | 45.0 | 19% |
| MIC-68178 | 40.9 | 11% | 46.1 | 22% |
| MIC-07010 | 41.1 | 11% | 43.9 | 16% |
| MIC-31593 | 42.1 | 14% | 44.3 | 18% |
| MIC-96038 | 42.6 | 15% | 43.4 | 15% |
| MIC-50414 | 40.0 | 8% | 45.7 | 21% |

Assay of Seed Yield Under Field Conditions, Corn

Field trials were conducted at multiple locations, preferably in diverse geographic regions. Plots were non-irrigated (dryland) or maintained with suboptimal irrigation at a rate to target approximately 25% reduction in yield. Seeds were prepared with the endophyte formulations (dry) and formulation control (dry, lacking any endophyte) as described in Example 11, untreated seeds (lacking formulation and endophyte) were also planted. Seeds were sown in regularly spaced rows in soil at planting densities typical for each region. At each location 3 replicate plots were planted per endophyte or control treatment in a randomized complete block design. Each plot consisted of four 15.24 m (40 ft.) rows, each separated by 76.2 cm (30 in).

At the end of the field trial employing endophyte treatment and control treatment plants, plots were machine harvested with a 5-ft research combine and yield calculated by the on-board computer. Only the middle two rows of the 4 row plots were harvested to prevent border effects.

The endophyte treatments comprising MIC-68390 resulted in average increases in yield of 0.9% relative to formulation control and average increases in yield of 1.0% relative to the untreated control, in the corn variety Stine 9734.

TABLE 8

Average yield of corn variety Stine 9734 treated with endophytes in field trials

| | Stine 9734, Variety 2 | | |
|---|---|---|---|
| | Average yield (BU/acre) | % difference Formulation control | % difference Untreated control |
| Untreated | 185.5 | | 0.0% |
| Formulation control (dry) | 185.7 | 0.0% | |
| MIC-68390 | 187.4 | 0.9% | 1.0% |

Assay of Seed Yield Under Field Conditions, Soy

Field trials were conducted under non-irrigated (dryland) conditions at multiple locations, preferably in diverse geographic regions. Seeds were prepared with the endophyte formulations as described above and untreated seeds (lacking formulation and endophyte) were also planted. MIC-68178 was formulated with the dry formulation; MIC-68390, MIC-07010, MIC-96038, and MIC-50414 were formulated with the liquid formulation.

Seeds were sown in regularly spaced rows in soil at 40,000 seeds/acre seeding density. At each location, at least 3 replicate plots were planted per endophyte or control treatment in a randomized complete block design. Each plot consisted of four 15.24 m (40 ft.) rows, each separated by 76.2 cm (30 in).

At the end of the field trial employing endophyte treatment and control treatment plants, plots were machine harvested with a 5-ft research combine and yield calculated by the on-board computer. Only the middle two rows of the 4 row plots were harvested to prevent border effects.

The endophyte treatment comprising MIC-68390 resulted in average increases in yield of 3.5% in the soy variety Dairyland DSR1808R2Y. The endophyte treatments, each comprising one of the following microbes: MIC-68390, MIC-68178, MIC-07010, MIC-31593, MIC-96038, or MIC-50414 resulted in average increases in yield of 3.5-10.2% in the soy variety Pfister 38R25. The endophyte treatments, each comprising one of the following microbes: MIC-68390, MIC-68178, MIC-07010, or MIC-50414, resulted in average increases in yield of 1.1-4.9% in the soy variety Stine 3920.

TABLE 9

Average yield of soy variety Dairyland DSR1808R2Y treated with endophytes in field trials

| | Dairyland DSR1808R2Y, Variety 1 | |
| --- | --- | --- |
| | Average yield (pounds/acre) | % difference Untreated control |
| Untreated control | 33.9 | 0.0% |
| MIC-68390 | 35.1 | 3.5% |

TABLE 10

Average yield of soy variety Pfister 38R25 treated with endophytes in field trials

| | Pfister 38R25, Variety 2 | |
| --- | --- | --- |
| Row Labels | Average yield (pounds/acre) | % difference Untreated control |
| Untreated control | 56.8 | 0% |
| MIC-68390 | 58.8 | 3.5% |
| MIC-68178 | 60.0 | 5.6% |
| MIC-07010 | 60.0 | 5.6% |
| MIC-96038 | 61.2 | 7.7% |
| MIC-50414 | 62.6 | 10.2% |

TABLE 11

Average yield of soy variety Stine 3920 treated with endophytes in field trials

| | Stine 3920, Variety 4 | |
| --- | --- | --- |
| Row Labels | Average yield (pounds/acre) | % difference Untreated control |
| Untreated control | 56.9 | 0% |
| MIC-68390 | 58.4 | 2.6% |
| MIC-68178 | 59.7 | 4.9% |
| MIC-07010 | 58.9 | 3.5% |
| MIC-50414 | 57.5 | 1.1% |

Example 6. Additional Methods of Mechanical and Manual Application, Artificial Inoculation and Disposition onto or into a Plant Element Osmopriming and Hydropriming A fungal or bacterial endophyte is inoculated onto seeds during the osmopriming (soaking in polyethylene glycol solution to create a range of osmotic potentials) and/or hydropriming (soaking in de-chlorinated water) process. Osmoprimed seeds are soaked in a polyethylene glycol solution containing a bacterial and/or fungal endophyte for one to eight days and then air dried for one to two days. Hydroprimed seeds are soaked in water for one to eight days containing a bacterial and/or fungal endophyte and maintained under constant aeration to maintain a suitable dissolved oxygen content of the suspension until removal and air drying for one to two days. Talc and or flowability polymer are added during the drying process.

Foliar Application

A fungal or bacterial endophyte is inoculated onto aboveground plant tissue (leaves and stems) as a liquid suspension in dechlorinated water containing adjuvants, sticker-spreaders and UV protectants. The suspension is sprayed onto crops with a boom or other appropriate sprayer.

Soil Inoculation

A fungal or bacterial endophyte is inoculated onto soils in the form of a liquid suspension either; pre-planting as a soil drench, during planting as an in furrow application, or during crop growth as a side-dress. A fungal or bacterial endophyte is mixed directly into a fertigation system via drip tape, center pivot or other appropriate irrigation system.

Hydroponic and Aeroponic Inoculation

A fungal or bacterial endophyte is inoculated into a hydroponic or aeroponic system either as a powder or liquid suspension applied directly to the rockwool substrate, or applied to the circulating or sprayed nutrient solution.

Vector-Mediated Inoculation

A fungal or bacterial endophyte is introduced in power form in a mixture containing talc or other bulking agent to the entrance of a beehive (in the case of bee-mediation) or near the nest of another pollinator (in the case of other insects or birds)). The pollinators pick up the powder when exiting the hive and deposit the inoculum directly to the crop's flowers during the pollination process.

Root Wash

The method includes contacting the exterior surface of a plant's roots with a liquid inoculant formulation containing a purified bacterial population, a purified fungal population, or a mixture of purified bacteria and fungi. The plant's roots are briefly passed through standing liquid microbial formulation or liquid formulation is liberally sprayed over the roots, resulting in both physical removal of soil and microbial debris from the plant roots, as well as inoculation with microbes in the formulation.

Seedling Soak

The method includes contacting the exterior surfaces of a seedling with a liquid inoculant formulation containing a purified bacterial population, a purified fungal population, or a mixture of purified bacteria and fungi. The entire seedling is immersed in standing liquid microbial formulation for at least 30 seconds, resulting in both physical removal of soil and microbial debris from the plant roots, as well as inoculation of all plant surfaces with microbes in the formulation. Alternatively, the seedling can be germinated from seed in or transplanted into media soaked with the microbe(s) of interest and then allowed to grow in the media, resulting in soaking of the plantlet in microbial formulation for much greater time totaling as much as days or weeks. Endophytic microbes likely need time to colonize and enter the plant, as they explore the plant surface for cracks or wounds to enter, so the longer the soak, the more likely the microbes will successfully be installed in the plant.

Wound Inoculation

The method includes contacting the wounded surface of a plant with a liquid or solid inoculant formulation containing a purified bacterial population, a purified fungal population, or a mixture of purified bacteria and fungi. Plant surfaces are designed to block entry of microbes into the endosphere, since pathogens attempting to infect plants in this way. In order to introduce beneficial endophytic microbes to plant endospheres, access to the interior of the plant is opened by wounding the plant. This wound can take a number of forms, including pruned roots, pruned branches, puncture wounds in the stem breaching the bark and cortex, puncture wounds in the tap root, puncture wounds in leaves, and puncture wounds seed allowing entry past the seed coat. Wounds can be made using needles, hammer and nails, knives, drills, etc. The wound can then be contacted the microbial inoculant as liquid, as powder, inside gelatin capsules, in a pressurized capsule injection system, in a pressurized reservoir and tubing injection system, allowing entry and colonization by microbes into the endosphere. Alternatively, the entire wounded plant can be soaked or washed in the microbial inoculant for at least 30 seconds, giving more microbes a chance to enter the wound, as well as inoculating other plant surfaces with microbes in the formulation—for example pruning seedling roots and soaking them in inoculant before transplanting is a very effective way to introduce endophytes into the plant.

Injection

The method includes injecting microbes into a plant in order to successfully install them in the endosphere. Plant surfaces are designed to block entry of microbes into the endosphere, since pathogens attempting to infect plants in this way. In order to introduce beneficial endophytic microbes to endospheres, access to the interior of the plant is opened by puncturing the plant surface with a needle and injecting microbes into the inside of the plant. Different parts of the plant can be inoculated this way including the main stem or trunk, branches, tap roots, seminal roots, buttress roots, and even leaves. The injection can be made with a hypodermic needle, a drilled hole injector, or a specialized injection system, and through the puncture wound can then be contacted the microbial inoculant as liquid, as powder, inside gelatin capsules, in a pressurized capsule injection system, in a pressurized reservoir and tubing injection system, allowing entry and colonization by microbes into the endosphere.

Example 7: Method of Determining Seed Nutritional Quality Trait Component

Preparation of Endophytes

The following methods were used to produce endophytes for field trial seed treatments.

The thawed contents of a cryo-vial containing the isolated endophyte was added to 100 mL of growth media in a 250 mL Erlenmeyer flask with a vented cap. For fungal endophytes, the flask was incubated at 24 C for 3 days on a shaker set at approximately 130 revolutions per minute (RPM). For bacterial endophytes, the flask was incubated at 24 C for 2 days on a shaker set at approximately 130 revolutions per minute (RPM). An aliquot of the culture was the collected and the purity of the culture assayed by DNA sequencing and taxonomic identification, for example, as described in Examples 1, 2 and 3.

For bacterial endophytes, a 1% inoculum was prepared from the endophyte culture and 1 L of sterile media in a Fernbach Flask. For fungal endophytes, a 3% inoculum was prepared from the endophyte culture and 1 L of sterile media in a Fernbach Flask. An Airotop Seal was on top of the Fernbach Flask. The Fernbach Flask is then incubated at 24 C on a shaker set at 130 RPM for 5-7 days (fungal endophytes) or 1-5 days (bacterial endophytes).

Heterologous Disposition of Endophytes on Wheat Seeds

Endophyte treatments were heterologously disposed to wheat seeds according to the following seed treatment protocol.

Liquid culture as prepared above was added to the seeds at a rate of 8.3 (fungal endophytes) or 8.4 (bacterial endophytes) ml per kg of seeds. Control treatments were prepared using equivalent volumes of sterile broth. The seeds were then agitated to disperse the solution evenly on the seeds. For fungal endophytes, 12.5 g of talc powder per kg of seed was added and the seeds were agitated to disperse the powder evenly on the seeds. Then 17 ml (fungal endophytes) or 2 ml (bacterial endophytes) per kg of seed of Flo-Rite® 1706 (BASF, Ludwigshafen, Germany) was added and the seeds were agitated to disperse the powder evenly on the seeds. The final concentration of endophyte was targeted to be at least $10^4$ CFU. Treated seeds were allowed to dry overnight in a well-ventilated space before planting.

Heterologous Disposition of Endophytes on Soy Seeds

Endophyte treatments were heterologously disposed soy seeds according to the following seed treatment protocol.

Liquid culture as prepared above was added to the seeds at a rate of 8.3 (fungal endophytes) or 8.4 (bacterial endophytes) ml per kg of seeds. Control treatments were prepared using equivalent volumes of sterile broth. The seeds were then agitated to disperse the solution evenly on the seeds. Then 13.3 (fungal endophytes) or 2.7 (bacterial endophytes) ml per kg of seed of Flo-Rite® 1706 (BASF, Ludwigshafen, Germany) was added and the seeds were agitated to disperse the powder evenly on the seeds. The final concentration of endophyte was targeted to be at least $10^4$ CFU. Treated seeds were allowed to dry overnight in a well-ventilated space before planting.

Heterologous Disposition of Endophytes on Corn Seeds

Endophyte treatments were heterologously disposed to corn seeds according to the following seed treatment protocol.

Liquid culture as prepared above was added to the seeds at a rate of 23 (for fungal endophyte treatments) or 8.4 (for bacterial endophyte treatments) ml per kg of seeds. Control treatments were prepared using equivalent volumes of sterile broth. The seeds were then agitated to disperse the solution evenly on the seeds. For fungal endophytes, 15 g per kg of seed of the talc powder prepared in sterile was added and the seeds were agitated to disperse the powder evenly on the seeds. Then 16.6 ml (for fungal endophyte treatments) or 2.4 ml (for bacterial endophyte treatments) per kg of seed of Flo-Rite® 1706 (BASF, Ludwigshafen, Germany) was added and the seeds were agitated to disperse the powder evenly on the seeds. The final concentration of endophyte was targeted to be at least $10^4$ CFU. Treated seeds were allowed to dry overnight in a well-ventilated space before planting.

Heterologous Disposition of Endophytes on Cotton Seeds

Endophyte treatments were heterologously disposed to cotton seeds according to the following seed treatment protocol.

Liquid culture as prepared above was added to the seeds at a rate of 8.3 (fungal endophytes) or 8.4 (bacterial endophytes) ml per kg of seeds. Control treatments were prepared using equivalent volumes of sterile broth. The seeds were then agitated to disperse the solution evenly on the seeds. For fungal endophytes, 15 g per kg of seed of the talc powder prepared in sterile was added and the seeds were agitated to disperse the powder evenly on the seeds. Then 13.3 ml (fungal endophytes) or 2.7 ml (bacterial endophytes) per kg of seed of Flo-Rite® 1706 (BASF, Ludwigshafen, Germany) was added and the seeds were agitated to disperse the powder evenly on the seeds. The final concentration of endophyte was targeted to be at least $10^{\wedge}4$ CFU. Treated seeds were allowed to dry overnight in a well-ventilated space before planting.

Wheat Trial Design

Field trials were conducted under non-irrigated (dryland) conditions at multiple locations, preferably in diverse geographic regions. Wheat seeds were treated with commercial fungicidal and insecticidal treatment. Seeds were heterologously disposed with the endophyte formulations described above and untreated seeds (lacking formulation and endophyte) were also planted. Seeds were sown in regularly spaced rows in soil at 1.2 million seeds/acre seeding density. At each location, at least 3 replicate plots were planted for each endophyte or control treatment in a randomized complete block design. Each plot consisted of seven, 15.24 m (40 ft.) rows.

At the end of the field trial employing endophyte treatment and control treatment plants, plots were machine harvested with a 5-ft research combine and yield calculated by the on-board computer.

Soy Trial Design

Field trials were conducted under non-irrigated (dryland) conditions at multiple locations, preferably in diverse geographic regions. Seeds were prepared with the endophyte formulations as described above and untreated seeds (lacking formulation and endophyte) were also planted.

Seeds were sown in regularly spaced rows in soil at 40,000 seeds/acre seeding density. At each location, at least 3 replicate plots were planted per endophyte or control treatment in a randomized complete block design. Each plot consisted of four 15.24 m (40 ft.) rows, each separated by 76.2 cm (30 in).

At the end of the field trial employing endophyte treatment and control treatment plants, plots were machine harvested with a 5-ft research combine and yield calculated by the on-board computer. Only the middle two rows of the 4 row plots were harvested to prevent border effects.

Corn Trial Design

Field trials were conducted at multiple locations, preferably in diverse geographic regions. Plots were non-irrigated (dryland) or maintained with suboptimal irrigation at a rate to target approximately 25% reduction in yield. Seeds were prepared with the endophyte formulations and formulation control as described above, untreated seeds (lacking formulation and endophyte) were also planted. Seeds were sown in regularly spaced rows in soil at planting densities typical for each region. At each location 3 replicate plots were planted per endophyte or control treatment in a randomized complete block design. Each plot consisted of four 15.24 m (40 ft.) rows, each separated by 76.2 cm (30 in).

At the end of the field trial employing endophyte treatment and control treatment plants, plots were machine harvested with a 5-ft research combine and yield calculated by the on-board computer. Only the middle two rows of the 4 row plots were harvested to prevent border effects.

Cotton Trial Design

Field trials were conducted under non-irrigated (dryland) conditions at multiple locations, preferably in diverse geographic regions. Seeds were prepared with the endophyte formulations as described above and untreated seeds (lacking formulation and endophyte) were also planted.

Seeds were sown in regularly spaced rows in soil at 40,000 seeds/acre seeding density. At each location, at least 3 replicate plots were planted per endophyte or control treatment in a randomized complete block design. Each plot consisted of four 15.24 m (40 ft.) rows.

At the end of the field trial employing endophyte treatment and control treatment plants, plots were machine harvested and the seed de-linted.

Seed Nutritional Analysis

Figure 4:
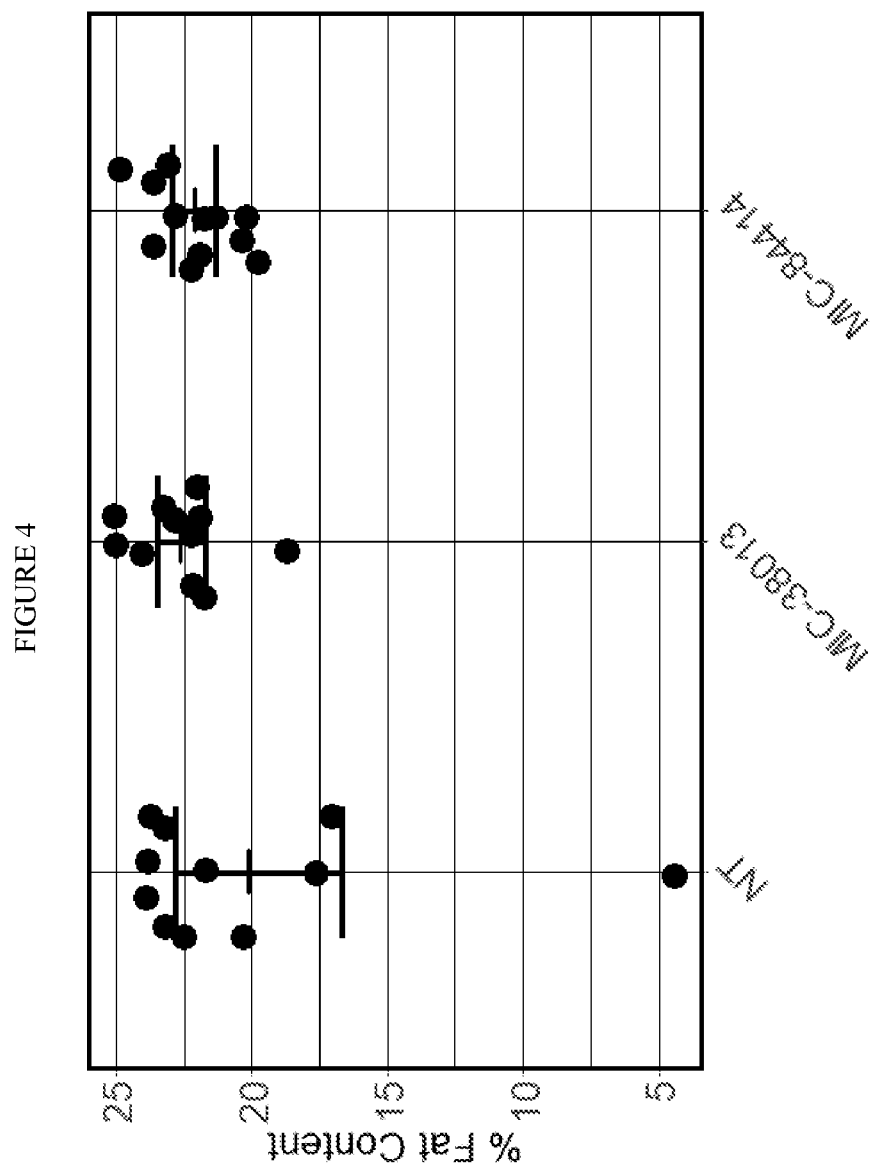
FIG. 4 shows exemplary results of endophyte treatments on the percentage fat composition of soybean seeds; NT represents untreated controls (seeds not heterologously disposed with a treatment formulation), also shown are treatments comprising MIC-38013 and MIC-84414. The experimental conditions and methods are described in Example 7.
Figure 7:
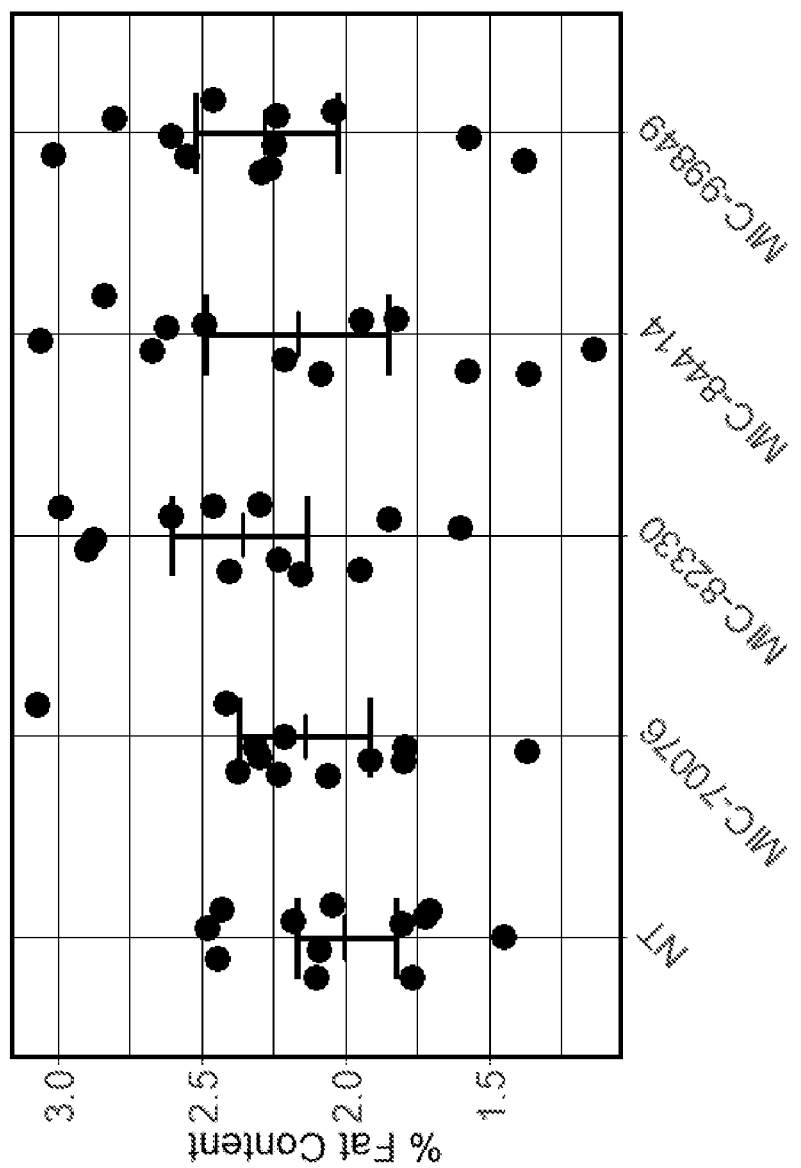
FIG. 7 shows exemplary results of endophyte treatments on the percentage fat composition of wheat seeds; NT represents untreated controls (seeds not heterologously disposed with a treatment formulation), also shown are treatments comprising MIC-70076, MIC-82330, MIC-84414, and MIC-99849. The experimental conditions and methods are described in Example 7.

Fat: Seed samples from harvested plants were obtained as described above in this Example and also as from plants grown as described in Example 5. Analysis of fat was conducted on replicate samples according to the Association of Official Agricultural Chemists Reference Method AOAC 920.39, of the Official Methods Of Analysis of AOAC International, 20th Edition (2016). Samples were weighed onto filter paper, dried, and extracted in hot hexane for 4 hrs using a Soxlhet system. Oil was recovered in pre-weighed glassware, and % fat was measured gravimetrically. Mean percent changes between the treatment (endophyte-treated seed) and untreated control (seed treated not heterologously disposed with a treatment formulation) were calculated for seeds produced by the methods of this Example. Mean percent changes between the treatment (endophyte-treated seed) and formulation control (seeds treated with a formulation not comprising an endophyte) were calculated for seeds produced by the methods of Example 5. The percent crude fat composition of endophyte treated soy seeds and untreated controls are shown in FIG. 4 and Table 12. The percent crude fat composition of endophyte treated wheat seeds and untreated controls are shown in FIG. 7 and Table 13.

TABLE 12

Average crude fat content as % of soy seed composition for seeds produced by endophyte treated and untreated control plants.

| Treatment | Mean | Std Dev | Std Error | % over NT |
|---|---|---|---|---|
| Untreated control (NT) | 20.11 | 5.74 | 1.73 | 0.00 |
| MIC-84414 | 22.12 | 1.53 | 0.44 | 9.98 |
| MIC-38013 | 22.63 | 1.68 | 0.49 | 12.55 |

TABLE 13

Average crude fat content as % of wheat seed composition for seeds produced by endophyte treated and untreated control plants.

| Treatment | mean | Std Dev | Std Error | % over NT |
|---|---|---|---|---|
| Untreated control (NT) | 2.00 | 0.33 | 0.10 | 0.00 |
| MIC-84414 | 2.16 | 0.62 | 0.18 | 8.12 |
| MIC-82330 | 2.36 | 0.43 | 0.12 | 17.82 |
| MIC-70076 | 2.14 | 0.42 | 0.12 | 6.91 |
| MIC-99849 | 2.28 | 0.47 | 0.14 | 14.03 |

Figure 8:
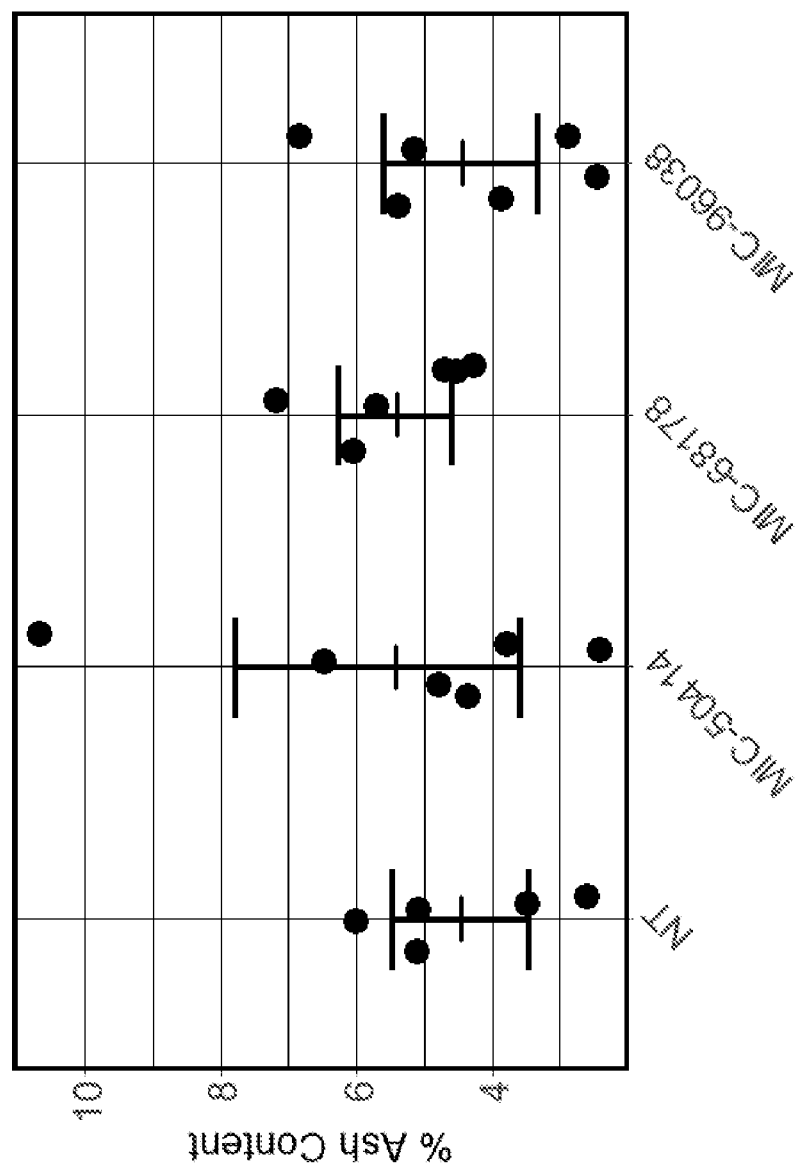
FIG. 8 shows exemplary results of endophyte treatments on the percentage ash composition of cotton seeds; NT represents untreated controls (seeds not heterologously disposed with a treatment formulation), also shown are treatments comprising MIC-50414, MIC-68178, and MIC-96038. The experimental conditions and methods are described in Example 7.

Ash: Replicate seed samples from harvested plants were obtained as described above in this Example and also as from plants grown as described in Example 5. Analysis of ash was conducted on replicate samples according to the Association of Official Agricultural Chemists Reference Method AOAC 942.05, of the Official Methods Of Analysis of AOAC International, 20$^{th}$ Edition (2016). Samples were weighed into pre-weighed crucibles, and ashed in a furnace at 600° C. for 3 hrs. Weight loss on ashing was calculated as % ash. Mean percent changes between the treatment (endophyte-treated seed) and untreated control (seed treated not heterologously disposed with a treatment formulation) were calculated for seeds produced by the methods of this Example. Mean percent changes between the treatment (endophyte-treated seed) and formulation control (seeds treated with a formulation not comprising an endophyte) were calculated for seeds produced by the methods of Example 5. The percent ash composition of endophyte treated cotton seeds and untreated controls are shown in FIG. 8 and Table 14.

TABLE 14

Average ash content as % of cotton seed composition for seeds produced by endophyte treated and untreated control plants.

| Treatment | mean | Std Dev | Std Error | % over NT |
|---|---|---|---|---|
| Untreated control (NT) | 4.46 | 1.38 | 0.62 | 0.00 |
| MIC-68178 | 5.40 | 1.11 | 0.45 | 21.08 |
| MIC-96038 | 4.43 | 1.63 | 0.67 | −0.60 |
| MIC-50414 | 5.42 | 2.91 | 1.19 | 21.45 |

Figure 6:
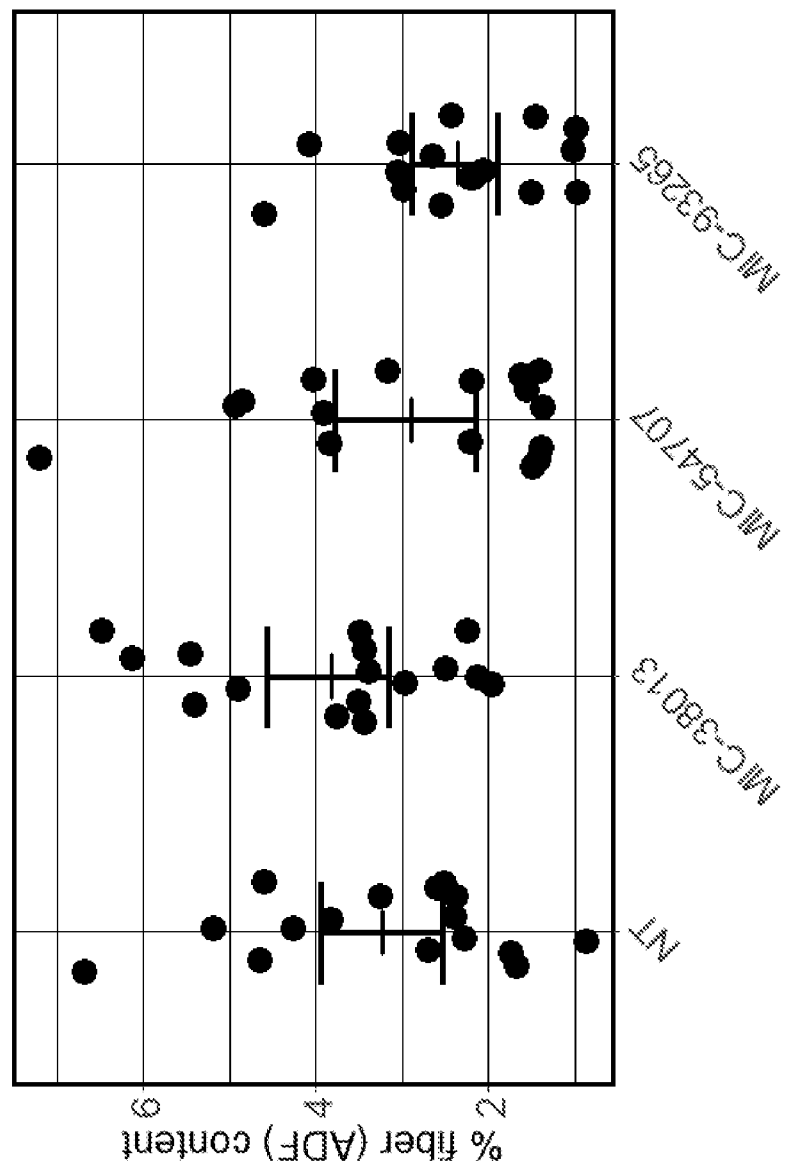
FIG. 6 shows exemplary results of endophyte treatments on the percentage acid detergent fiber composition of corn seeds; NT represents untreated controls (seeds not heterologously disposed with a treatment formulation), also shown are treatments comprising MIC-38013, MIC-54707 and MIC-93265. The experimental conditions and methods are described in Example 7.

Fiber: Replicate seed samples from harvested plants were obtained as described above in this Example and also as from plants grown as described in Example 5. Analysis of fiber was conducted on replicate samples according to the Association of Official Agricultural Chemists Reference Method AOAC 978.10, of the Official Methods Of Analysis of AOAC International, 20$^{th}$ Edition (2016). Samples were weighed into filter paper, defatted and dried, and hydrolyzed first in acid, then in alkali solution. The recovered portion was dried, weighed, ashed at 600°, and weighed again. The loss on ashing was calculated as % Fiber. Mean percent changes between the treatment (endophyte-treated seed) and untreated control (seed treated not heterologously disposed with a treatment formulation) were calculated for seeds produced by the methods of this Example. Mean percent changes between the treatment (endophyte-treated seed) and formulation control (seeds treated with a formulation not comprising an endophyte) were calculated for seeds produced by the methods of Example 5. The percent ADF composition of endophyte treated corn seeds and untreated controls are shown in FIG. 6 and Table 15.

TABLE 15

Average ADF content as % of corn seed composition for seeds produced by endophyte treated and untreated control plants.

| Treatment | mean | Std Dev | Std Error | % over NT |
|---|---|---|---|---|
| Untreated control (NT) | 3.23 | 1.52 | 0.38 | 0.00 |
| MIC-38013 | 3.83 | 1.44 | 0.36 | 18.60 |
| MIC-93265 | 2.36 | 1.05 | 0.26 | −26.94 |
| MIC-54707 | 2.90 | 1.73 | 0.43 | −10.08 |

Moisture: Replicate seed samples from harvested plants were obtained as described above in this Example and also as from plants grown as described in Example 5. Analysis of moisture was conducted on replicate samples according to the Association of Official Agricultural Chemists Reference Method AOAC 930.15, of the Official Methods Of Analysis of AOAC International, 20$^{th}$ Edition (2016). Samples were weighed into pre-weighed aluminum dishes, and dried at 135° C. for 2 hrs. Weight loss on drying was calculated as % Moisture. Mean percent changes between the treatment (endophyte-treated seed) and untreated control (seed treated not heterologously disposed with a treatment formulation) were calculated for seeds produced by the methods of this Example. Mean percent changes between the treatment (endophyte-treated seed) and formulation control (seeds treated with a formulation not comprising an endophyte) were calculated for seeds produced by the methods of Example 5.

Protein: Replicate seed samples from harvested plants were obtained as described in above in this Example and also as from plants grown as described in Example 5. Analysis of protein was conducted on replicate samples according to the Association of Official Agricultural Chemists Reference Method AOAC 990.03, of the Official Methods Of Analysis of AOAC International, 20th Edition (2016). Samples were combusted and nitrogen gas is measured using a combustion nitrogen analyzer (Dumas). Nitrogen was multiplied by 6.25 to calculate % protein. Mean percent changes between the treatment (endophyte-treated seed) and untreated control (seed treated not heterologously disposed with a treatment formulation) were calculated for seeds produced by the methods of this Example. Mean percent changes between the treatment (endophyte-treated seed) and formulation control (seeds treated with a formulation not comprising an endophyte) were calculated for seeds produced by the methods of Example 5.

Total Carbohydrate: Replicate seed samples from harvested plants were obtained as described in Example 5. Analysis of carbohydrate was determined for replicate samples as a calculation according to the following formula:

Total Carbohydrate=100%−% (Protein+Ash+Fat+Moisture+Fiber)

Figure 10:
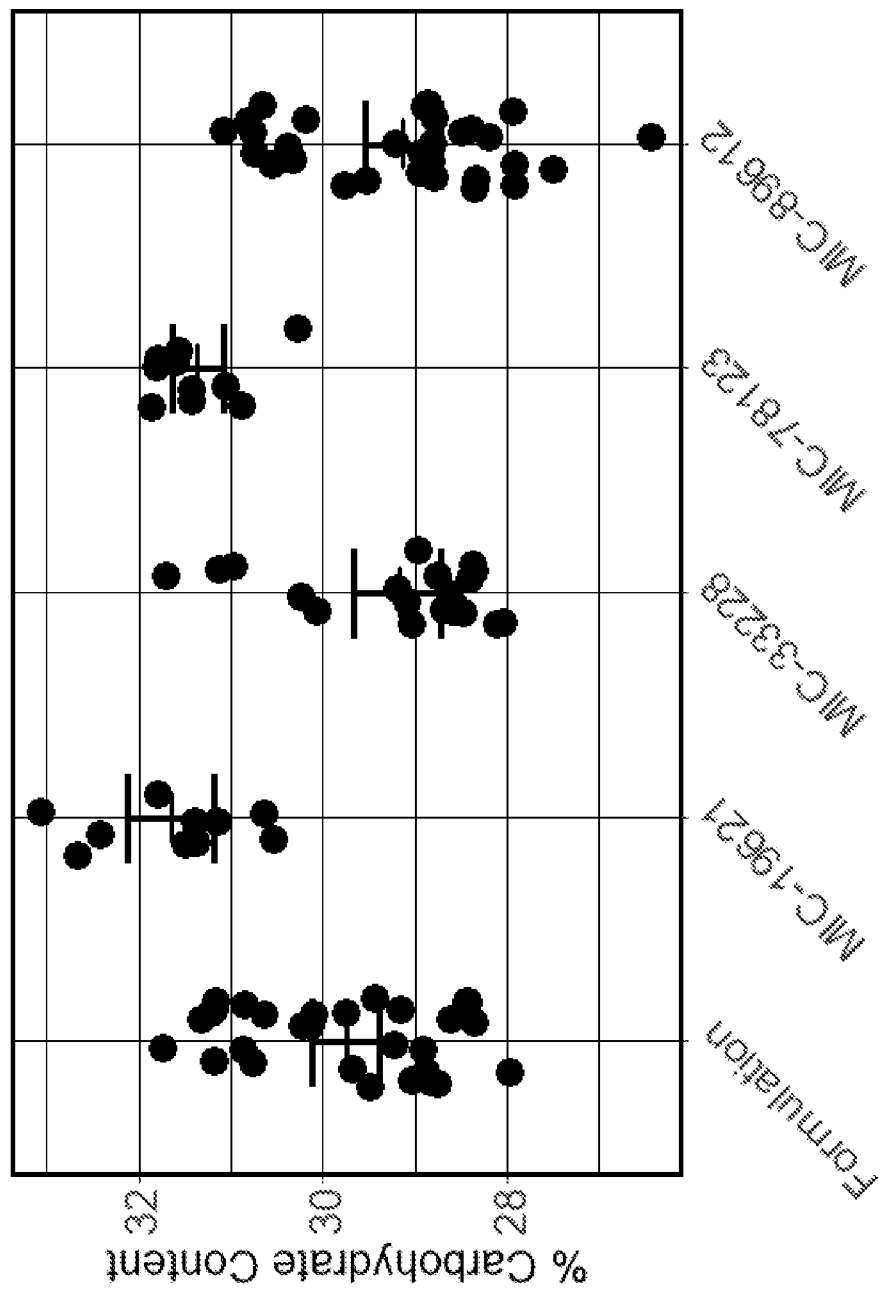
FIG. 10 shows exemplary results of endophyte treatments on the percentage carbohydrate composition of soy seeds; Formulation represents formulations controls (seeds treated with a formulation not comprising an endophyte), also shown are treatments comprising MIC-78123, MIC-19621, MIC-89612 and MIC-33228. The experimental conditions and methods are described in Example 7.

The % Protein, % Ash, % Fat, % Moisture, % Fiber was determined according to the methods described in this Example. Mean percent changes between the treatment (endophyte-treated seed) and formulation control (seeds treated with a formulation not comprising an endophyte) were calculated for seeds produced by the methods of Example 5. The percent carbohydrate composition of endophyte treated soy seeds and formulation controls are shown in FIG. 10 and Table 16.

TABLE 16

Average total carbohydrates as % of soybean seed composition for seeds produced by endophyte treated and formulation control plants.

| Treatment | mean | Std Dev | Std Error | % over Formulation |
|---|---|---|---|---|
| Formulation | 29.75 | 1.11 | 0.20 | 0.00 |
| MIC-14715 | 30.90 | 0.78 | 0.25 | 3.87 |
| MIC-78123 | 31.37 | 0.50 | 0.16 | 5.44 |
| MIC-19621 | 31.64 | 0.84 | 0.26 | 6.34 |
| MIC-89612 | 29.13 | 1.16 | 0.21 | −2.08 |
| MIC-33228 | 29.16 | 1.07 | 0.24 | −1.99 |

Total Calories: Replicate seed samples from harvested plants were obtained as described in Example 5. Analysis of Calories was determined for replicate samples as a calculation according to the following formula:

Total Calories=(Calories from protein)+(Calories from carbohydrate)+Calories from fat)

Where Calories from protein are calculated as 4 Calories per gram of protein, Calories from carbohydrate are calculated as 4 Calories per gram of carbohydrate, and Calories from fat are calculated as 9 Calories per gram of fat. Mean percent changes between the treatment (endophyte-treated seed) and untreated control (seed treated not heterologously disposed with a treatment formulation) were calculated for seeds produced by the methods of this Example. Mean percent changes between the treatment (endophyte-treated seed) and formulation control (seeds treated with a formulation not comprising an endophyte) were calculated for seeds produced by the methods of Example 5.

Total digestible nutrients: Replicate seed samples from harvested plants were obtained as described above in this Example. Total digestible nutrients (TDN) was determined for replicate samples as a calculation according to the following formula:

TDN=81.41−(0.48*ADF)

Figure 5:
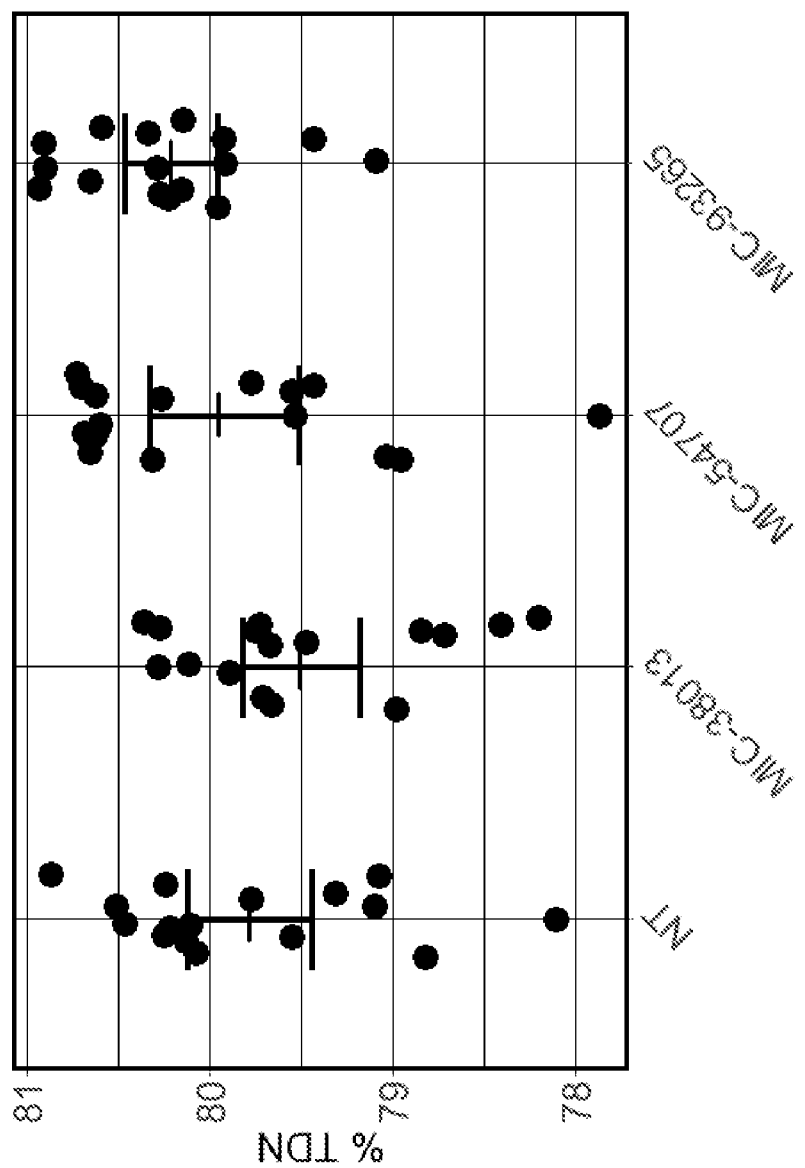
FIG. 5 shows exemplary results of endophyte treatments on the percentage total digestible nutrient (TDN) composition of corn seeds; NT represents untreated controls (seeds not heterologously disposed with a treatment formulation), also shown are treatments comprising MIC-38013, MIC-54707 and MIC-93265. The experimental conditions and methods are described in Example 7.

Mean percent changes between the treatment (endophyte-treated seed) and untreated control (seed treated not heterologously disposed with a treatment formulation) were calculated for seeds produced by the methods of this Example. The percent total digestible nutrient composition of endophyte treated corn seeds and untreated controls are shown in FIG. 5 and Table 17.

TABLE 17

Average total digestible nutrients content as % of corn seed composition for seeds produced by endophyte treated and untreated control plants.

| Treatment | mean | Std Dev | Std Error | % over NT |
|---|---|---|---|---|
| Untreated control (NT) | 79.78 | 0.74 | 0.18 | 0.00 |
| MIC-38013 | 79.51 | 0.69 | 0.17 | −0.34 |

TABLE 17-continued

Average total digestible nutrients content as % of corn seed composition for seeds produced by endophyte treated and untreated control plants.

| Treatment | mean | Std Dev | Std Error | % over NT |
|---|---|---|---|---|
| MIC-93265 | 80.21 | 0.51 | 0.13 | 0.54 |
| MIC-54707 | 79.95 | 0.83 | 0.21 | 0.21 |

Net energy: Replicate seed samples from harvested plants were obtained as described above in this Example. Net energy was determined for replicate samples as a calculation according to the following formula:

Net energy (Mcal/lb)=(TDN %×0.01114)−0.054

Figure 9:
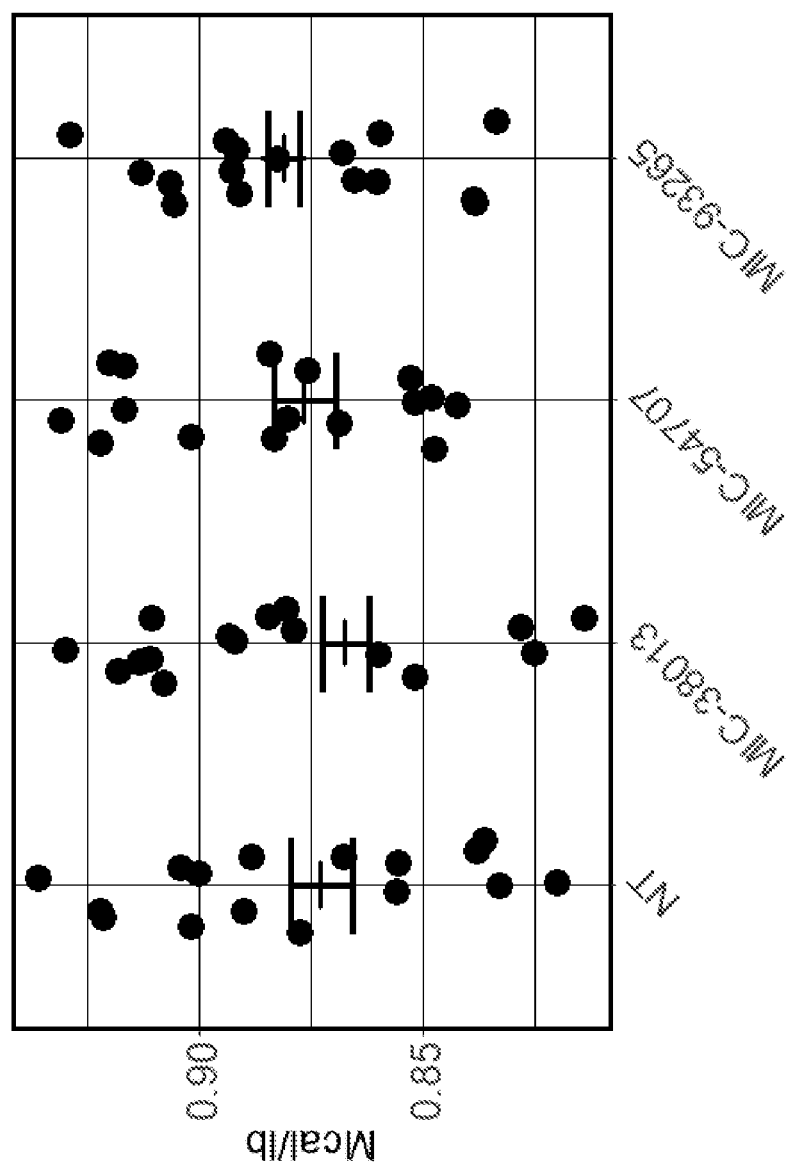
FIG. 9 shows exemplary results of endophyte treatments on the net energy composition as Mcal/lb of corn seeds; NT represents untreated controls (seeds not heterologously disposed with a treatment formulation), also shown are treatments comprising MIC-38013, MIC-54707 and MIC-93265. The experimental conditions and methods are described in Example 7.

Mean percent changes between the treatment (endophyte-treated seed) and untreated control (seed treated not heterologously disposed with a treatment formulation) were calculated. The net energy composition of endophyte treated corn seeds and untreated controls are shown in FIG. 9 and Table 18.

TABLE 18

Average net energy content (Mcal/lb) of corn seed produced by endophyte treated and untreated control plants.

| Treatment | mean | Std Dev | Std Error | % over NT |
|---|---|---|---|---|
| Untreated control (NT) | 0.87 | 0.01 | 0.00 | 0.00 |
| MIC-38013 | 0.87 | 0.01 | 0.00 | −0.64 |
| MIC-93265 | 0.88 | 0.01 | 0.00 | 0.93 |
| MIC-54707 | 0.88 | 0.01 | 0.00 | 0.43 |

Having illustrated and described the principles of the present invention, it should be apparent to persons skilled in the art that the invention can be modified in arrangement and detail without departing from such principles. It is to be understood that while the invention has been described in conjunction with the detailed description thereof, the foregoing description is intended to illustrate and not limit the scope of the invention, which is defined by the scope of the appended claims. Other embodiments, advantages, and modifications are within the scope of the following claims.

We claim:

1. A method of increasing crude fat content of a seed produced by a soybean plant, comprising mechanically or manually inoculating a soybean plant seed with a treatment formulation comprising an agriculturally compatible carrier and a purified fungal population that comprises a seed fungal endophyte of the genus *Curvularia* that is heterologous to the soybean plant seed and comprises a polynucleotide sequence having at least 97% nucleotide sequence identity to the polynucleotide sequence as set forth in SEQ ID NO: 31, wherein the endophyte is heterologously disposed to the soybean plant seed in an amount effective to colonize a soybean plant germinated from the inoculated soybean plant seed, wherein a seed obtained from the colonized soybean plant exhibits an increase in crude fat content as compared to a reference soybean plant seed obtained from a reference soybean plant lacking the colonized endophyte of the genus *Curvularia* comprising at least 97% nucleotide sequence identity to SEQ ID NO: 31, and wherein said reference soybean plant is germinated from a reference soybean plant seed lacking the colonized endophyte of the genus *Curvularia* comprising at least 97% nucleotide sequence identity to SEQ ID NO: 31.

2. The method of claim 1, wherein the endophyte is a *Curvularia spicifera* as deposited under NRRL Culture Deposit No. NRRL-67467.

* * * * *

SEQUENCE LISTING

```
<160> NUMBER OF SEQ ID NOS: 62

<210> SEQ ID NO 1
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 1
agagtttgat ymtggctcag                                        20

<210> SEQ ID NO 2
<211> LENGTH: 19
<212> TYPE: DNA
<213> ORGANISM: Artificial sequence
<220> FEATURE:
<223> OTHER INFORMATION: Synthetic Polynucleotide

<400> SEQUENCE: 2
```

```
ggttaccttg ttacgactt                                                   19
```

<210> SEQ ID NO 3
<211> LENGTH: 19
<212> TYPE: DNA
<213> ORGANISM: Artificial sequence
<220> FEATURE:
<223> OTHER INFORMATION: Synthetic Polynucleotide

<400> SEQUENCE: 3

```
gtgycagcmg ccgcggtaa                                                   19
```

<210> SEQ ID NO 4
<211> LENGTH: 20
<212> TYPE: DNA
<213> ORGANISM: Artificial sequence
<220> FEATURE:
<223> OTHER INFORMATION: Synthetic Polynucleotide
<220> FEATURE:
<221> NAME/KEY: misc_feature
<222> LOCATION: (8)..(8)
<223> OTHER INFORMATION: n is a, c, g, or t

<400> SEQUENCE: 4

```
ggactacnvg ggtwtctaat                                                  20
```

<210> SEQ ID NO 5
<211> LENGTH: 22
<212> TYPE: DNA
<213> ORGANISM: Artificial sequence
<220> FEATURE:
<223> OTHER INFORMATION: Synthetic Polynucleotide

<400> SEQUENCE: 5

```
cttggtcatt tagaggaagt aa                                               22
```

<210> SEQ ID NO 6
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 6

```
gctgcgttct tcatcgatgc                                                  20
```

<210> SEQ ID NO 7
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 7

```
gcatcgatga agaacgcagc                                                  20
```

<210> SEQ ID NO 8
<211> LENGTH: 17
<212> TYPE: DNA
<213> ORGANISM: Artificial sequence
<220> FEATURE:
<223> OTHER INFORMATION: Synthetic Polynucleotide

<400> SEQUENCE: 8

```
tcctgaggga aacttcg                                                     17
```

```
<210> SEQ ID NO 9
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 9
gtbcacctyc araccggyca rtg                                               23

<210> SEQ ID NO 10
<211> LENGTH: 26
<212> TYPE: DNA
<213> ORGANISM: Artificial sequence
<220> FEATURE:
<223> OTHER INFORMATION: Synthetic Polynucleotide

<400> SEQUENCE: 10
ccrgaytgrc craaracraa gttgtc                                            26

<210> SEQ ID NO 11
<211> LENGTH: 23
<212> TYPE: DNA
<213> ORGANISM: Artificial sequence
<220> FEATURE:
<223> OTHER INFORMATION: Synthetic Polynucleotide

<400> SEQUENCE: 11
cccatrgcyt gyttmcccat dgc                                               23

<210> SEQ ID NO 12
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 12
cccatwgcyt gcttmcccat                                                   20

<210> SEQ ID NO 13
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 13
gaygaymgwg atcayttygg                                                   20

<210> SEQ ID NO 14
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 14
tggtcaacta gcgaacgtgt                                                   20

<210> SEQ ID NO 15
<211> LENGTH: 19
<212> TYPE: DNA
<213> ORGANISM: Artificial sequence
<220> FEATURE:
<223> OTHER INFORMATION: Synthetic Polynucleotide
```

<400> SEQUENCE: 15
agaggcgaac gggtacact                                                19

<210> SEQ ID NO 16
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 16
aaatgttgtt catgcgacca                                               20

<210> SEQ ID NO 17
<211> LENGTH: 20
<212> TYPE: DNA
<213> ORGANISM: Artificial sequence
<220> FEATURE:
<223> OTHER INFORMATION: Synthetic Polynucleotide

<400> SEQUENCE: 17
tctcccagga gctttcgtta                                               20

<210> SEQ ID NO 18
<211> LENGTH: 1479
<212> TYPE: DNA
<213> ORGANISM: Bacillus simplex

<400> SEQUENCE: 18
ggctcaggac gaacgctggc ggcgtgccta atacatgcaa gtcgagcgaa tcgatgggag    60
cttgctccct gagattagcg gcggacgggt gagtaacacg tgggcaacct gcctataaga   120
ctgggataac ttcgggaaac cggagctaat accggataca ttcttttctc gcatgagaga   180
agatggaaag acggtttacg ctgtcactta tagatgggcc cgcggcgcat tagctagttg   240
gtgaggtaat ggctcaccaa ggcgacgatg cgtagccgac ctgagagggt gatcggccac   300
actgggactg agacacggcc cagactccta cgggaggcag cagtagggaa tcttccgcaa   360
tggacgaaag tctgacggag caacgccgcg tgaacgaaga aggccttcgg gtcgtaaagt   420
tctgttgtta gggaagaaca agtaccagag taactgctgg taccttgacg gtacctaacc   480
agaaagccac ggctaactac gtgccagcag ccgcggtaat acgtaggtgg caagcgttgt   540
ccggaattat tgggcgtaaa gcgcgcgcag gtggttcctt aagtctgatg tgaaagccca   600
cggctcaacc gtggagggtc attggaaact ggggaacttg agtgcagaag aggaaagtgg   660
aattccaagt gtagcggtga atgcgtaga gatttggagg aacaccagtg gcgaaggcga   720
ctttctggtc tgtaactgac actgaggcgc gaaagcgtgg ggagcaaaca ggattagata   780
ccctggtagt ccacgccgta aacgatgagt gctaagtgtt agagggtttc cgccctttag   840
tgctgcagct aacgcattaa gcactccgcc tggggagtac ggccgcaagg ctgaaactca   900
aaggaattga cggggcccg cacaagcggt ggagcatgtg gtttaattcg aagcaacgcg   960
aagaacctta ccaggtcttg acatcctctg acaaccctag atagggct ttccccttcg    1020
ggggacagag tgacaggtgg tgcatggttg tcgtcagctc gtgtcgtgag atgttgggtt  1080
aagtcccgca acgagcgcaa cccttgatct tagttgccag cattcagttg gcactctaa   1140
ggtgactgcc ggtgacaaac cggaggaagg tggggatgac gtcaaatcat catgcccctt  1200
atgacctggg ctacacacgt gctacaatgg atggtacaaa gggctgcaaa cctgcgaagg  1260
taagcgaatc ccataaagcc attctcagtt cggattgcag gctgcaactc gcctgcatga  1320

| | |
|---|---|
| agccggaatc gctagtaatc gcggatcagc atgccgcggt gaatacgttc ccgggccttg | 1380 |
| tacacaccgc ccgtcacacc acgagagttt gtaacacccg aagtcggtga ggtaaccttc | 1440 |
| atggagccag ccgcctaagg tgggacagat gattggggt | 1479 |

<210> SEQ ID NO 19
<211> LENGTH: 1421
<212> TYPE: DNA
<213> ORGANISM: Bacillus simplex

<400> SEQUENCE: 19

| | |
|---|---|
| atgcagtcga gcgaatcgat gggagcttgc tccctgagat tagcggcgga cgggtgagta | 60 |
| acacgtgggc aacctgccta taagactggg ataacttcgg gaaaccggag ctaataccgg | 120 |
| atacgttctt ttctcgcatg agagaagatg gaaagacgct tacgctgtc acttatagat | 180 |
| gggcccgcgg cgcattagct agttggtgag gtaatggctc accaaggcga cgatgcgtag | 240 |
| ccgacctgag agggtgatcg gccacactgg gactgagaca cggcccagac tcctacggga | 300 |
| ggcagcagta gggaatcttc cgcaatggac gaaagtctga cggagcaacg ccgcgtgaac | 360 |
| gaagaaggcc ttcgggtcgt aaagttctgt tgttagggaa gaacaagtac cagagtaact | 420 |
| gctggtacct tgacggtacc taaccagaaa gccacggcta actacgtgcc agcagccgcg | 480 |
| gtaatacgta ggtggcaagc gttgtccgga attattgggc gtaaagcgcg cgcaggtggt | 540 |
| tccttaagtc tgatgtgaaa gcccacggct caaccgtgga gggtcattgg aaactgggga | 600 |
| acttgagtgc agaagaggaa agtggaattt ccaagtgtag cggtgaaatg cgtagagatt | 660 |
| tggaggaaca ccagtggcga aggcgacttt ctggtctgta actgacactg aggcgcgaaa | 720 |
| gcgtggggag caaacaggat tagataccct ggtagtccac gccgtaaacg atgagtgcta | 780 |
| agtgttagag ggtttccgcc ctttagtgct gcagctaacg cattaagcac tccgcctggg | 840 |
| gagtacggcc gcaaggctga aactcaaagg aattgacggg ggcccgcaca agcggtggag | 900 |
| catgtggttt aattcgaacg atcccgttct accttaccag gtgatgacat cctctgacaa | 960 |
| ccctagagat agggctttcc ccttcggggg acagagtgac aggtggtgca tggttgtcgt | 1020 |
| cagctcgtgt cgtgagatgt tgggttaagt cccgcaacga gcgcaaccct tgatcttagt | 1080 |
| tgccagcatt cagttgggca ctctaaggtg actgccggtg acaaaccgga ggaaggtggg | 1140 |
| gatgacgtca atcatcatg ccccttatga cctgggctac acacgtgcta caatggatgg | 1200 |
| tacaaagggc tgcaaacctg cgaaggtaag cgaatcccat aaagccattc tcagttcgga | 1260 |
| ttgcaggctg caactcgcct gcatgaagcc ggaatcgcta gtaatcgcgg atcagcatgc | 1320 |
| cgcggtgaat acgttcccgg gccttgtaca caccgcccgt cacaccacga gagtttgtaa | 1380 |
| cacccgaagt cggtgaggta accttcatgg agccagccgc c | 1421 |

<210> SEQ ID NO 20
<211> LENGTH: 1459
<212> TYPE: DNA
<213> ORGANISM: Unknown
<220> FEATURE:
<223> OTHER INFORMATION: Kingdom: Bacteria, Phylum: Proteobacteria,
      Class: Betaproteobacteria, Order: Burkholderiales,
      Family: Burkholderiaceae, Genus: Burkholderia

<400> SEQUENCE: 20

| | |
|---|---|
| tcagattgaa cgctggcggc atgccttaca catgcaagtc gaacggcagc acgggagcaa | 60 |
| tcctggtggc gagtggcgaa cgggtgagta atacatcgga acgtgtcctg tagtggggga | 120 |

```
tagcccggcg aaagccggat taataccgca tacgatctgt ggatgaaagc gggggatcct    180
tcgggacctc gcgctacagg ggcggccgat ggcagattag ctagttggtg gggtaaaggc    240
ctaccaaggc gacgatctgt agctggtctg agaggacgac cagccacact gggactgaga    300 cacgcccag actcctacgg gaggcagcag tggggaattt tggacaatgg gcgaaagcct    360
gatccagcaa tgccgcgtgt gtgaagaagg ccttcgggtt gtaaagcact tttgtccgga    420
aagaaaacct cgtggttaat acccgtgggg atgacggta ccggaagaat aagcaccggc    480
taactacgtg ccagcagccg cggtaatacg tagggtgcaa gcgttaatcg gaattactgg    540
gcgtaaagcg tgcgcaggcg gtccgctaag acagatgtga atccccggg cttaacctgg    600 gaactgcatt tgtgactggc gggctagagt atggcagagg ggggtagaat tccacgtgta    660
gcagtgaaat gcgtagagat gtggaggaat accgatggcg aaggcagccc cctgggccaa    720
tactgacgct catgcacgaa agcgtgggga gcaaacagga ttagataccc tggtagtcca    780
cgccctaaac gatgtcaact agttgttggg gattcatttc cttagtaacg tagctaacgc    840
gtgaagttga ccgcctgggg agtacggtcg caagattaaa actcaaagga attgacgggg    900
acccgcacaa gcggtggatg atgtggatta attcgatgca acgcgaaaaa ccttacctac    960
ccttgacatg tatggaacct ggctgagagg tcggggtgcc cgaaagggag ccataacaca    1020
ggtgctgcat ggctgtcgtc agctcgtgtc gtgagatgtt gggttaagtc ccgcaacgag    1080
cgcaaccctt gtccctagtt gctacgcaag agcactctag gagactgcc ggtgacaaac    1140 cggaggaagg tggggatgac gtcaagtcct catggccctt atgggtaggg cttcacacgt    1200
catacaatgg tcgaacaga gggtcgccaa cccgcgaggg ggagccaatc ccagaaaacc    1260
gatcgtagtc cggatcgcac tctgcaactc gagtgcgtga agctggaatc gctagtaatc    1320
gcggatcagc atgccgcggt gaatacgttc ccgggtcttg tacacaccgc ccgtcacacc    1380
atgggagtgg gttttaccag aagtggctag tctaaccgca aggaggacgg tcaccacggt    1440
agattcatga ctgggtgaa                                                 1459
```

<210> SEQ ID NO 21
<211> LENGTH: 1377
<212> TYPE: DNA
<213> ORGANISM: Unknown
<220> FEATURE:
<223> OTHER INFORMATION: Kingdom: Bacteria, Phylum: Proteobacteria,
      Class: Betaproteobacteria, Order: Burkholderiales,
      Family: Burkholderiaceae, Genus: Burkholderia

<400> SEQUENCE: 21

```
tagcaatcct ggtggcgagt ggcgaacggg tgagtaatac atcggaacgt gtcctgtagt    60
gggggatagc ccggcgaaag ccggattaat accgcatacg atctgtggat gaaagcgggg    120
gatccttcgg gacctcgcgc tacaggggcg ccgatggca gattagctag ttggtgggt    180 aaaggcctac caaggcgacg atctgtagct ggtctgagag gacgaccagc cacactggga    240
ctgagacacg gcccagactc ctacgggagg cagcagtggg gaattttgga caatgggcga    300
aagcctgatc ccagcaatgc cgcgtgtgtg aagaaggcct cgggttgta aagcactttt    360 gtccggaaag aaaacctcgt ggttaatacc cgtgggggat gacggtaccg gaagaataag    420
caccggctaa ctacgtgcca gcagccgcgg taatacgtag ggtgcaagcg ttaatcggaa    480
ttactgggcg taaagcgtgc gcaggcggtc cgctaagaca gatgtgaaat ccccgggctt    540
aacctgggaa ctgcatttgt gactgcggg ctagagtatg gcagaggggg gtagaattcc    600
acgtgtagca gtgaaatgcg tagagatgtg gaggaatacc gatggcgaag gcagccccct    660
```

```
gggccaatac tgacgctcat gcacgaaagc gtggggagca acaggatta gataccctgg    720 tagtccacgc cctaaacgat gtcaactagt tgttggggat tcatttcctt agtaacgtag    780
ctaacgcgtg aagttgaccg cctggggagt acggtcgcaa gattaaaact caaaggaatt    840 gacgggacc cgcacaagcg gtggatgatg tggattaatt cgatgcaacg cgaaaaacct    900
tacctaccct tgacatgtat ggaacctggc tgagaggtcc gggtgcccga aagggagcca    960
taacacaggg tgctgcatgg ctgtcgtcag ctcgtgtcgt gagatgttgg gataagtccc    1020
gcaacgagcg caaccccttgt ccctagttgc tacgcaagag cactctaggg agactgccgg    1080
tgacaaaccg gaggaaggtg gggatgacgt caagtcctca tggcccttat gggtagggct    1140
tcacacgtca tacaatggtc ggaacagagg gtcgccaacc cgcgagggg agccaatccc    1200 agaaaaccga tcgtagtccg gatcgcactc tgcaactcga gtgcgtgaag ctggaatcgc    1260
tagtaatcgc ggatcagcat gccgcggtga atacgttccc gggtcttgta cacaccgccc    1320
gtcacaccat gggagtgggt tttaccagaa gtggctagtc taaccgcaag gaggacg    1377
```

<210> SEQ ID NO 22
<211> LENGTH: 1395
<212> TYPE: DNA
<213> ORGANISM: Unknown
<220> FEATURE:
<223> OTHER INFORMATION: Kingdom: Bacteria, Phylum: Actinobacteria,
      Class: Actinobacteria, Order: Micrococcales, Family:
      Microbacteriaceae, Genus: Curtobacterium

<400> SEQUENCE: 22

```
tgcagtcgaa cgatgatgcc cagcttgctg ggtggattag tggcgaacgg gtgagtaaca    60
cgtgagtaac ctgcccctga ctctgggata agcgttggaa acgacgtcta atactggata    120
tgactgccgg ccgcatggtc tggtggtgga aagatttttt ggttggggat ggactcgcgg    180
cctatcagct tgttggtgag gtaatggctc accaaggcga cgacgggtag ccggcctgag    240
agggtgaccg gccacactgg gactgagaca cggcccagac tcctacggga ggcagcagtg    300
gggaatattg cacaatgggc gaaagcctga tgcagcaacg ccgcgtgagg gatgacggcc    360
ttcgggttgt aaacctcttt tagtagggaa gaagcgtaag tgacggtacc tgcagaaaaa    420
gcaccggcta actacgtgcc agcagccgcg gtaatacgta gggtgcaagc gttgtccgga    480
attattgggc gtaaagagct cgtaggcggt ttgtcgcgtc tgctgtgaaa tcccgaggct    540
caacctcggg cttgcagtgg gtacgggcag actagagtgc ggtagggag attggaattc    600 ctggtgtagc ggtggaatgc gcagatatca ggaggaacac cgatggcgaa ggcagatctc    660
tgggccgtaa ctgacgctga ggagcgaaag cgtggggagc gaacaggatt agataccctg    720
gtagtccacg ccgtaaacgt tgggcgctag atgtagggac cttccacgg tttctgtgtc    780 gtagctaacg cattaagcgc cccgcctggg gagtacggcc gcaaggctaa aactcaaagg    840
aattgacggg ggcccgcaca agcggcggag catgcggatt aattcgatgc aacgcgaaga    900
accttaccaa ggcttgacat acaccggaaa cggccagaga tggttgcccc cttgtggtcg    960
gtgtacaggt ggtgcatggt tgtcgtcagc tcgtgtcgtg agatgttggg ttaagtcccg    1020
caacgagcgc aaccctcgtt ctatgttgcc agcgcgttat ggcggggact cataggagac    1080
tgccggggtc aactcggagg aaggtgggga tgacgtcaaa tcatcatgcc ccttatgtct    1140
tgggcttcac gcatgctaca atggccgta caaaggctg cgataccgta aggtggagcg    1200
aatcccaaaa agccggtctc agttcggatt gaggtctgca actcgacctc atgaagtcgg    1260
```

| | |
|---|---|
| agtcgctagt aatcgcagat cagcaacgct gcggtgaata cgttcccggg ccttgtacac | 1320 |
| accgcccgtc aagtcatgaa agtcggtaac acccgaagcc ggtggcctaa cccttgtgga | 1380 |
| aggagccgtc gaagg | 1395 |

<210> SEQ ID NO 23
<211> LENGTH: 1465
<212> TYPE: DNA
<213> ORGANISM: Enterobacter cowanii

<400> SEQUENCE: 23

| | |
|---|---|
| tgctcagatt tgaacgctgg cggcaggcct aacacatgca agtcgaacgg taacaggaag | 60 |
| cagcttgctg cttcgctgac gagtggcgga cgggtgagta atgtctggga aactgcctga | 120 |
| tggaggggga taactactgg aaacggtagc taataccgca taacgtcgca agaccaaaga | 180 |
| gggggacctt cgggcctctt gccatcagat gtgcccagat gggattagct agtaggtggg | 240 |
| gtaacggctc acctaggcga cgatccctag ctggtctgag aggatgacca gccacactgg | 300 |
| aactgagaca cggtccagac tcctacggga ggcagcagtg gggaatattg cacaatgggc | 360 |
| gcaagcctga tgcagccatg ccgcgtgtat gaagaaggcc ttcgggttgt aaagtacttt | 420 |
| cagcggggag gaaggcgatg tggttaataa ccgcgtcgat tgacgttacc cgcagaagaa | 480 |
| gcaccggcta actccgtgcc agcagccgcg gtaatacgga gggtgcaagc gttaatcgga | 540 |
| attactgggc gtaaagcgca cgcaggcggt ctgtcaagtc ggatgtgaaa tccccgggct | 600 |
| caacctggga actgcatccg aaactggcag gcttgagtct cgtagagggg gtagaattc | 660 |
| caggtgtagc ggtgaaatgc gtagagatct ggaggaatac cggtggcgaa ggcggccccc | 720 |
| tggacgaaga ctgacgctca ggtgcgaaag cgtgggagc aaacaggatt agataccctg | 780 |
| gtagtccacg ccgtaaacga tgtcgacttg gaggttgtgc ccttgaggcg tggcttccgg | 840 |
| agctaacgcg ttaagtcgac cgcctgggga gtacggccgc aaggttaaaa ctcaaatgaa | 900 |
| ttgacggggg cccgcacaag cggtggagca tgtggtttaa ttcgatgcaa cgcgaagaac | 960 |
| cttacctggt cttgacatcc acagaacttt ccagagatgg attggtgcct tcgggaactg | 1020 |
| tgagacaggt gctgcatggc tgtcgtcagc tcgtgttgtg aaatgttggg ttaagtcccg | 1080 |
| caacgagcgc aacccttatc ctttgttgcc agcggtccgg ccgggaactc aaaggagact | 1140 |
| gccagtgata aactggagga aggtggggat gacgtcaagt catcatggcc ttacgacca | 1200 |
| gggctacaca cgtgctacaa tggcgcatac aaagagaagc aaactcgcga gagccagcgg | 1260 |
| acctcataaa gtgcgtcgta gtccggattg gagtctgcaa ctcgactcca tgaagtcgga | 1320 |
| atcgctagta atcgtgaatc agaatgtcac ggtgaatacg ttcccgggcc ttgtacacac | 1380 |
| cgcccgtcac accatgggag tgggttgcaa agaagtagg tagcttaacc ttcgggaggg | 1440 |
| cgcttaccac tttgtgatca tgact | 1465 |

<210> SEQ ID NO 24
<211> LENGTH: 1471
<212> TYPE: DNA
<213> ORGANISM: Unknown
<220> FEATURE:
<223> OTHER INFORMATION: Kingdom: Bacteria, Phylum: Proteobacteria,
    Class: Gammaproteobacteria, Order: Enterobacterales,
    Family: Erwiniaceae, Genus: Pantoea

<400> SEQUENCE: 24

| | |
|---|---|
| ctcagattga acgctggcgg caggcctaac acatgcaagt cgaacggcag cacagaagag | 60 |
| cttgctcttt gggtggcgag tggcggacgg gtgagtaatg tctgggaaac tgcccgatgg | 120 |

```
aggggggataa ctactggaaa cggtagctaa taccgcataa cgtcgcaaga ccaaagtggg       180
ggaccttcgg gcctcacacc atcggatgtg cccagatggg attagctagt aggtggggta       240
atggctcacc taggcgacga tccctagctg gtctgagagg atgaccagcc acactggaac       300
tgagacacgg tccagactcc tacggggagg cagcagtggg gaatattgca caatgggcgca      360 agcctgatgc agccatgccg cgtgtatgaa gaaggccttc gggttgtaaa gtactttcag       420
cggggaggaa ggcggtgagg ttaataacct tgccgattga cgttacccgc agaagaagca       480
ccggctaact ccgtgccagc agccgcggta atacggaggg tgcaagcgtt aatcggaatt       540
actgggcgta aagcgcacgc aggcggtctg ttaagtcaga tgtgaaatcc ccgggcttaa       600
cctgggaact gcatttgaaa ctggcaggct tgagtctcgt agagggggt agaattccag        660 gtgtagcggt gaaatgcgta gagatctgga ggaataccgg tggcgaaggc ggccccctgg       720
acgaagactg acgctcaggt gcgaaagcgt ggggagcaaa caggattaga taccctggta      780
gtccacgccg taaacgatgt cgacttggag gttgtgccct tgaggcgtgg cttccggagc      840
taacgcgtta agtcgaccgc ctggggagta cggccgcaag gttaaaactc aaatgaattg      900
acggggcccc gcacaagcgg tggagcatgt ggtttaattc gatgcaacgc gaagaacctt      960
acctggcctt gacatccaga gaacttagca gagatgcttt ggtgccttcg ggaactctga     1020
gacaggtgct gcatggctgt cgtcagctcg tgttgtgaaa tgttgggtta agtcccgcaa     1080
cgagcgcaac ccttatcctt tgttgccagc ggctcggccg ggaactcaaa ggagactgcc     1140
ggtgataaac cggaggaagg tgggggatgac gtcaagtcat catggccctt acggccaggg    1200
ctacacacgt gctacaatgg cgcatacaaa gagaagcgac ctcgcgagag caagcggacc     1260
tcataaagtg cgtcgtagtc cggattggag tctgcaactc gactccatga agtcggaatc     1320
gctagtaatc gtagatcaga atgctacggt gaatacgttc ccgggccttg tacacaccgc     1380
ccgtcacacc atgggagtgg gttgcaaaag aagtaggtag cttaaccttc gggagggcgc     1440
ttaccacttt gtgattcatg actggggtga a                                    1471
```

<210> SEQ ID NO 25
<211> LENGTH: 1418
<212> TYPE: DNA
<213> ORGANISM: Unknown
<220> FEATURE:
<223> OTHER INFORMATION: Kingdom: Bacteria, Phylum: Proteobacteria,
      Class: Gammaproteobacteria, Order: Enterobacterales,
      Family: Erwiniaceae, Genus: Pantoea

<400> SEQUENCE: 25

```
catgcagtcg aacggcagca cagaagagct tgctctttgg gtggcgagtg gcggacgggt        60
gagtaatgtc tgggaaactg cccgatggag ggggataact actggaaacg gtagctaata      120
ccgcataacg tcgcaagacc aaagtggggg accttcgggc ctcacaccat cggatgtgcc      180
cagatgggat tagctagtag gtggggtaat ggctcaccta ggcgacgatc cctagctggt      240
ctgagaggat gaccagccac actggaactg agacacggtc cagactccta cggggaggcag     300 cagtggggaa tattgcacaa tgggcgcaag cctgatgcag ccatgccgcg tgtatgaaga      360
aggccttcgg gttgtaaagt actttcagcg gggaggaagg cggtgaggtt aataaccttg      420
ccgattgacg ttacccgcag aagaagcacc ggctaactcc gtgccagcag ccgcggtaat      480
acggagggtg caagcgttaa tcggaattac tgggcgtaaa gcgcacgcag gcggtctgtt      540
aagtcagatg tgaaatcccc gggcttaacc tgggaactgc atttgaaact ggcaggcttg      600
```

| | |
|---|---|
| agtctcgtag aggggggtag aattccaggt gtagcggtga aatgcgtaga gatctggagg | 660 |
| aataccggtg gcgaaggcgg cccctggac gaagactgac gctcaggtgc gaaagcgtgg | 720 |
| ggagcaaaca ggattagata ccctggtagt ccacgccgta aacgatgtcg acttggaggt | 780 |
| tgtgcccttg aggcgtggct tccggagcta acgcgttaag tcgaccgcct ggggagtacg | 840 |
| ggccgcaagg ttaaaactca aatgaattga cgggggccc gcacaagcgg tggagcatgt | 900 |
| ggtttaattc gatgcaacgc gaagaacctt acctggcctt gacatccaga gaacttagca | 960 |
| gagatgcttt ggtgccttcg ggaactctga dacaggtgct gcatggctgt cgtcagctcg | 1020 |
| tgttcacaaa tgttgggtta agtcccgcaa cgagcgcaac ccttatcctt tgttgccagc | 1080 |
| ggctcggccg ggaactcaaa ggagactgcc ggtgataaac cggaggaagg tggggatgac | 1140 |
| gtcaagtcat catggccctt acggccaggg ctacacacgt gctacaatgg cgcatacaaa | 1200 |
| gagaagcgac ctcgcgagag caagcggacc tcataaagtg cgtcgtagtc cggattggag | 1260 |
| tctgcaactc gactccatga agtcggaatc gctagtaatc gtagatcaga atgctacggt | 1320 |
| gaatacgttc ccgggccttg tacacaccgc ccgtcacacc atgggagtgg gttgcaaaag | 1380 |
| aagtaggtag cttaaccttc gggagggcgc taccacct | 1418 |

<210> SEQ ID NO 26
<211> LENGTH: 1426
<212> TYPE: DNA
<213> ORGANISM: Streptomyces kathirae

<400> SEQUENCE: 26

| | |
|---|---|
| cgaacgctgg cggcgtgctt aacacatgca agtcgaacga tgaagccctt cggggtggat | 60 |
| tagtggcgaa cgggtgagta acacgtgggc aatctgccct tcactctggg acaagccctg | 120 |
| gaaacggggt ctaataccgg atacgacgcg ctcgggcatc cgatgtgcgt ggaaagctcc | 180 |
| ggcggtgaag gatgagcccg cggcctatca gcttgttggt gaggtaatgg ctcaccaagg | 240 |
| cgacgacggg tagccggcct gagagggcga ccggccacac tgggactgag acacggccca | 300 |
| gactcctacg ggaggcagca gtgggaata ttgcacaatg ggcgcaagcc tgatgcagcg | 360 |
| acgccgcgtg agggatgacg gccttcgggt tgtaaacctc tttcagcagg gaagaagcgc | 420 |
| aagtgacggt acctgcagaa gaagcgccgg ctaactacgt gccagcagcc gcggtaatac | 480 |
| gtagggcgca agcgttgtcc ggaattattg ggcgtaaaga gctcgtaggc ggcttgtcac | 540 |
| gtcgattgtg aaagcccgag gcttaacctc gggtctgcag tcgatacggg caggctagag | 600 |
| tgtggtaggg gagatcggaa ttcctggtgt agcggtgaaa tgcgcagata tcaggaggaa | 660 |
| caccggtggc gaaggcggat ctctgggcca ttactgacgc tgaggagcga aagcgtgggg | 720 |
| agcgaacagg attagatacc ctggtagtcc acgccgtaaa cggtgggaac taggtgttgg | 780 |
| cgacattcca cgtcgtcggt gccgcagcta acgcattaag ttccccgcct ggggagtacg | 840 |
| gccgcaaggc taaaactcaa aggaattgac ggggcccgc acaagcggcg gagcatgtgg | 900 |
| cttaattcga cgcaacgcga agaaccttac caaggcttga catacaccgg aaacatccag | 960 |
| agatgggtgc cccttgtgg tcggtgtaca ggtggtgcat ggctgtcgtc agctcgtgtc | 1020 |
| gtgagatgtt gggttaagtc ccgcaacgag cgcaaccctt gttctgtgtt gccagcatgc | 1080 |
| ccttcgggt gatggggact cacaggagac cgccgggtc aactcggagg aaggtgggga | 1140 |
| cgacgtcaag tcatcatgcc ccttatgtct tgggctgcac acgtgctaca atggccggta | 1200 |
| caatgagctg cgataccgtg aggtggacg aatctcaaaa agccggtctc agttcggatt | 1260 |
| ggggtctgca actcgacccc atgaagtcgg agtcgctagt aatcgcagat cagcagtgct | 1320 |

```
gcggtgaata cgttcccggg ccttgtacac accgcccgtc acgtcacgaa agtcggtaac   1380
acccgaagcc ggtggcccaa ccccctgcggg agggagctgt cgaaag              1426
```

<210> SEQ ID NO 27
<211> LENGTH: 880
<212> TYPE: DNA
<213> ORGANISM: Streptomyces kathirae

<400> SEQUENCE: 27

```
cgctggacca actccttcgg gaggcagcag tggggaatat tgcacaatgg gcgcaagcct     60
gatgcagcga cgccgcgtga gggatgacgg ccttcgggtt gtaaacctct ttcagcaggg    120
aagaagcgca agtgacggta cctgcagaag aagcgccggc taactacgtg ccagcagccg    180
cggtaatacg tagggcgcaa cgttgtccg gaattattgg gcgtaaagag ctcgtaggcg    240
gcttgtcacg tcgattgtga agcccgagg cttaacctcg gtctgcagt cgatacgggc    300 aggctagagt gtggtagggg agatcggaat tcctggtgta gcggtgaaat gcgcagatat    360
caggaggaac accggtggcg aaggcggatc tctgggccat tactgacgct gaggagcgaa    420
agcgtgggga gcgaacagga ttagataccc tggtagtcca cgccgtaaac ggtgggaact    480
aggtgttggc gacattccac gtcgtcggtg ccgcagctaa cgcattaagt tccccgcctg    540
gggagtacgg ccgcaaggct aaaactcaaa ggaattgacg ggggcccgca caagcggcgg    600
agcatgtggc ttaattcgac gcaacgcgaa gaaccttacc aaggcttgac atacaccgga    660
aacatccaga gatgggtgcc cccttgtggt cggcgtacag gtcgtgcatg gctgtcgtca    720
gctcgtgtcg tgagatgttg ggtaagtccc gcaacgagcg caaccttgtt ctggtgctgc    780
cagcatgccc ttcgggtgat gggacttcac cacggagacc gcggctccac tccgacgagg    840
tgggggacga cgtcagtcat catgccctaa tgtctggctg                         880
```

<210> SEQ ID NO 28
<211> LENGTH: 1197
<212> TYPE: DNA
<213> ORGANISM: Curvularia spicifera

<400> SEQUENCE: 28

```
cccatagctt gcttacccat ggcagattgg tatgtgttac ggggcgactg gttgtgatct     60
gggaagggaa tgatactagc gcaaatacccc aagatcatag ctgggtgaat ctcacaatgg    120
gtgtaggcgt ggatgcgagg atccggtagt ggcttgaggc ggcggagtcg atccttgcct    180
tcagtagatc gctcagctgc gggcaagccc atcttcattt ctcgccattc ttccaaatcc    240
tcgggagaga atgttatcat tgcagtttct tcttcctcgg catcgaggta ttcaacgaca    300
ccgtcttgaa tgagacctct ccagccgtat gtagcctgct cgacttcctc ttgactccag    360
ccttgtcttg tgctggtctc ttgctgttca gccttgagct tgttgctgat tccttggta    420 aagatgaggt ggttccggtt tggcttccga atatcgtttt ctacgacgaa caaaggcctc    480
atgacacgac ccgcatctgt gaagatcttg aactctctgt cgcgaatatc acgaatcaaa    540
ctcatctcgt aagacagagt accattgcgg cgaagctcct gcacgactgt gacaagctgc    600
tgagcatttg aatgaacacc aacccagaca ccgttaacga agaccttggt cgcatccggg    660
ttctgattct ggtcgtactc ctcgagaagt tgcatgttac gttgtgtcat gaagtcgata    720
atgggcgatg catcgctacc aacactgaca taacacataa gagacaagtt cttgaccaga    780
ccgcaagcct gtccttcggg cgtctcagca gggcagacaa gaccccaatg agagttgtga    840
```

```
agctgtcgcg gctttgccaa cttaccatca cgtccaacgg gggtgttcgt tcgacgcaga    900
tgggacagtg tggaggcata ggtgtatcgg ttcaacacct gcgaaacacc agccttggca    960
gatgcagcct tcttctgatc accccaattg cctgtagcca gagagtactt caggccgttt   1020
gtgatgatgc tggctttcac agccatttga acgttgaagt cttggttgtt ttccacgcac   1080
cgctggaggt acttgtagac atccttggtg agcttcagga acaagattcg gaacaagttg   1140
gcaatcagag gtccagccag atctagtcgc ttctttccaa agtgatcacg atcgtcc      1197
```

<210> SEQ ID NO 29
<211> LENGTH: 1197
<212> TYPE: DNA
<213> ORGANISM: Curvularia spicifera

<400> SEQUENCE: 29

```
cccatagctt gcttacccat ggcagattgg tatgtgttac ggggcgactg gttgtgatct     60
gggaagggaa tgatactagc gcaaataccc aagatcatag ctgggtgaat ctcacaatgg    120
gtgtaggcgt ggatgcgagg atccggtagt ggcttgaggc ggcggagtcg atccttgcct    180
tcagtagatc gctcagctgc gggcaagccc atcttcattt ctcgccattc ttccaaatcc    240
tcgggagaga atgttatcat tgcagtttct tcttcctcgg catcgaggta ttcaacgaca    300
ccgtcttgaa tgagacctct ccagccgtat gtagcctgct cgacttcctc ttgactccag    360
ccttgtcttg tgctggtctc ttgctgttca gccttgagct tgttgctgat tccttggta    420 aagatgaggt ggttccggtt tggcttccga atatcgtttt ctacgacgaa caaaggcctc    480
atgacacgac ccgcatctgt gaagatcttg aactctctgt cgcgaatatc acgaatcaaa    540
ctcatctcgt aagacagagt accattgcgg cgaagctcct gcacgactgt gacaagctgc    600 tgagcattg aatgaacacc aacccagaca ccgttaacga agaccttggt cgcatccggg    660
ttctgattct ggtcgtactc ctcgagaagt tgcatgttac gttgtgtcat gaagtcgata    720
atgggcgatg catcgctacc aacactgaca taacacataa gagacaagtt cttgaccaga    780
ccgcaagcct gtccttcggg cgtctcagca gggcagacaa gaccccaatg agagttgtga    840
agctgtcgcg gctttgccaa cttaccatca cgtccaacgg gggtgttcgt tcgacgcaga    900
tgggacagtg tggaggcata ggtgtatcgg ttcaacacct gcgaaacacc agccttggca    960
gatgcagcct tcttctgatc accccaattg cctgtagcca gagagtactt caggccgttt   1020
gtgatgatgc tggctttcac agccatttga acgttgaagt cttggttgtt ttccacgcac   1080
cgctggaggt acttgtagac atccttggtg agcttcagga acaagattcg gaacaagttg   1140
gcaatcagag gtccagccag atctagtcgc ttctttccaa agtgatcacg atcgtcc      1197
```

<210> SEQ ID NO 30
<211> LENGTH: 387
<212> TYPE: DNA
<213> ORGANISM: Curvularia spicifera

<400> SEQUENCE: 30

```
cccgactggc cgaagacgaa gttgtcgggg cggaagagct gaccaaaggg accagcgcgg     60
acagcgtcca tggtacccgg gctcgagatcg acgaggacgg cacggggcac gaacttgttg    120
ttggaagcct gctgcacatc agtattggtc ttttgtctgt tggggcttca ccgagggacg    180
tacttcgttg aagtagacgt tcatgcgctc gagctgaagg tcagaggtgc cgttgtagac    240
accagagccg tcgaggccat gctcgccgga aatggtctgc cagaaggcgg caccaatttg    300
gttaccctgt agcggctgtt agcagtcgtt cccgtggtgt tttcaggcgg cgcgagactt    360
```
acgcattgac cggtctggag gtgaacc                                          387

<210> SEQ ID NO 31
<211> LENGTH: 622
<212> TYPE: DNA
<213> ORGANISM: Curvularia spicifera

<400> SEQUENCE: 31
aaatgttgtt catgcgacca atggatttgc aagtcatctt gtacccggcc tccgcaagaa      60
gatcgtaggc gcacgagcgc acatgtcggc tcagcgacca ggggaactat tccctaacag     120
tggtggcatg cgctcatgga gtgtgattta tggtggggag tttgactatg tcacccaacg     180
gccttccgcg gacggtgata tccaaggaga tatcatgctt ggaggcggct ttatgcggtc     240
gctaaagaag ggcgtcgacc aaattggact ttatgacgac ggtgatattc ttgagcctct     300
gaccatttcg catatctcag gcgtgtttcc tgcagttttc catcccagat ggggtgctgg     360
tggcggttg aaacaagtgt ggtctggaat tctgggattg actggtgatt tacttcctct     420
ggtgggccgg ctggatacaa aattgacagg tcgaaattct ccgagtcagc acggcgtagt     480
ggatgcaaag agcagttgtg gagagtgggt gcagccggc ttctgcgggg aaggcatggt     540
ctgggcctgg ctttgtggag ttgctcttgg aattatggtc gctggaactg aggaacacga     600
tgtaacgaaa gctcctggga ga                                              622

<210> SEQ ID NO 32
<211> LENGTH: 1465
<212> TYPE: DNA
<213> ORGANISM: Curvularia spicifera

<400> SEQUENCE: 32
tcttggtcat ttagaggaag taaaagtcgt aacaaggtct ccgtaggtga acctgcggag      60
ggatcattac acaataaaat acgaaggccg ttcgcggctg gactatttat tacccttgtc     120
ttttgcgcac ttgttgtttc ctgggcgggt tcgctcgcca ccaggaccac aatataaacc     180
tttttatgc agttgcaatc agcgtcagta taacaaatgt aaatcattta caactttcaa     240
caacggatct cttggttctg catcgatga agaacgcagc gaaatgcgat acgtagtgtg     300
aattgcagaa ttcagtgaat catcgaatct tgaacgcac attgcgccct tggtattcc     360
aaagggcatg cctgttcgag cgtcatttgt accctcaagc tttgcttggt gttgggcgtt     420
tttgtctttg gcccgccaaa gactcgcctt aaaatgattg gcagccggcc tactggtttc     480
gcagcgcagc acatttttgc gcttgcaatc agcaaaagag gacggcaatc catcaagact     540
ccttctcacg tttgacctcg gatcaggtag ggatacccgc tgaacttaag catatcaata     600
agcggaggaa aagaaaccaa cagggattgc cctagtaacg gcgagtgaag cggcaacagc     660
tcaaatttga atctggctc tttcagagtc cgagttgtaa tttgcagagg gcgctttggc      720
tttggcagcg gtccaagttc cttggaacag gacgtcacag agggtgagaa tcccgtacgt     780
ggtcgctagc tattgccgtg taaagcccct tcgacgagtc gagttgtttg ggaatgcagc     840
tctaaatggg aggtaaattt cttctaaagc taaatattgg ccagagaccg atagcgcaca     900
agtagagtga tcgaaagatg aaaagcactt tggaaagaga gtcaaacagc acgtgaaatt     960
gttgaaaggg aagcgcttgc agccagactt gcttgcagtt gctcatccgg gcttttgccc    1020
ggtgcactct tctgcaggca ggccagcatc agtttgggcg gtgggataaa ggtctctgtc    1080
acgtaccttc cttcgggttg gccttatagg ggagacgcca taccaccagc ctggactgag    1140

```
gtccgcgcat ctgctaggat gctggcgtaa tggctgtaag cggcccgtct tgaaacacgg      1200
accaaggagt ctaacatcta tgcgagtgtt tgggtgtcaa gcccgagcgc gtaatgaaag      1260
tgaacggagg tgggaacccg caagggtgca ccatcgaccg atcctgaagt ttacggaagg      1320
atttgagtaa gagcatggct gttgggaccc gaaagatggt gaactatgct tgaatagggt      1380
gaagccagag gaaactctgg tggaggctcg cagcggttct gacgtgcaaa tcgatcgtca      1440
aatttgggca tagggggcgaa agact                                            1465

<210> SEQ ID NO 33
<211> LENGTH: 1472
<212> TYPE: DNA
<213> ORGANISM: Curvularia spicifera

<400> SEQUENCE: 33
tccgtaggtg aacctgcgga gggatcatta cacaataaaa tacgaaggcc gttcgcggct       60
ggactattta ttaccttgt cttttgcgca cttgttgttt cctgggcggg ttcgctcgcc      120
accaggacca caatataaac cttttttatg cagttgcaat cagcgtcagt ataacaaatg      180
taaatcattt acaactttca caacggatc tcttggttct ggcatcgatg aagaacgcag      240
cgaaatgcga tacgtagtgt gaattgcaga attcagtgaa tcatcgaatc tttgaacgca      300
cattgcgccc tttggtattc caaagggcat gcctgttcga gcgtcatttg taccctcaag      360
cttttgcttg gtgttgggcgt ttttgtcttt ggcccgccaa agactcgcct taaaatgatt      420
ggcagccggc ctactggttt cgcagcgcag cacatttttg cgcttgcaat cagcaaaaga      480
ggacggcaat ccatcaagac tccttctcac gtttgacctc ggatcaggta gggatacccg      540
ctgaacttaa gcatatcaat aagcggagga aagaaacca acagggattg ccctagtaac      600
ggcgagtgaa gcggcaacag ctcaaatttg aaatctggct cttttcagag tccgagttgta      660 atttgcagag ggcgctttgg ctttggcagc ggtccaagtt ccttggaaca ggacgtcaca      720
gagggtgaga atcccgtacg tggtcgctag ctattgccgt gtaaagcccc ttcgacgagt      780
cgagttgttt gggaatgcag ctctaaatgg gaggtaaatt tcttctaaag ctaaatattg      840
gccagagacc gatagcgcac aagtagagtg atcgaaagat gaaaagcact ttggaaagag      900
agtcaaacag cacgtgaaat tgttgaaagg gaagcgcttg cagccagact tgcttgcagt      960
tgctcatccg ggcttttgcc cggtgcactc ttctgcaggc aggccagcat cagtttgggc     1020
ggtgggataa aggtctctgt cacgtacctt ccttcgggtt ggccttatag gggagacgcc     1080
ataccaccag cctggactga ggtccgcgca tctgctagga tgctggcgta atggctgtaa     1140
gcggcccgtc ttgaaacacg gaccaaggag tctaacatct atgcgagtgt ttgggtgtca     1200
agcccgagcg cgtaatgaaa gtgaacggag gtgggaaccc gcaagggtgc accatcgacc     1260
gatcctgaag tttacggaag gatttgagta agagcatggc tgttgggacc cgaaagatgg     1320
tgaactatgc ttgaataggg tgaagccaga ggaaactctg gtggaggctc gcagcggttc     1380
tgacgtgcaa atcgatcgtc aaatttgggc atagggggcga agactaatc gaactatcta     1440 gtagctggtt cctgccgaag tttccctcag ga                                    1472

<210> SEQ ID NO 34
<211> LENGTH: 1439
<212> TYPE: DNA
<213> ORGANISM: Epicoccum nigrum

<400> SEQUENCE: 34
tcttggtcat ttagaggaag taaaagtcgt aacaaggttt ccgtaggtga acctgcggaa       60
```

```
ggatcattac ctagagtttg tggacttcgg tctgctacct cttacccatg tcttttgagt    120
accttcgttt cctcggcggg tccgcccgcc ggttggacaa cattcaaacc ctttgcagtt    180
gcaatcagcg tctgaaaaaa cttaatagtt acaactttca acaacggatc tcttggttct    240
ggcatcgatg aagaacgcag cgaaatgcga taagtagtgt gaattgcaga attcagtgaa    300
tcatcgaatc tttgaacgca cattgcgccc ttggtattc  catggggcat gcctgttcga    360
gcgtcatttg taccttcaag ctctgcttgg tgttgggtgt tttgtctcgc ctccgcgcgc    420
agactcgcct taaaacaatt ggcagccggc gtattgattt cggagcgcag tacatctcgc    480
gctttgcact cataacgacg acgtccaaaa gtacattttt acactcttga cctcggatca    540
ggtagggata cccgctgaac ttaagcatat caataagcgg aggaaaagaa accaacaggg    600
attgccctag taacggcgag tgaagcggca acagctcaaa tttgaaatct ggcgtctttg    660
gcgtccgagt tgtaatttgc agagggcgct ttggcattgg cagcggtcca agttccttgg    720
aacaggacgt cacagagggt gagaatcccg tacgtggtcg ctagccttta ccgtgtaaag    780
ccccttcgac gagtcgagtt gtttgggaat gcagctctaa atgggaggta aatttcttct    840
aaagctaaat actggccaga gaccgatagc gcacaagtag agtgatcgaa agatgaaaag    900
cactttggaa agagagttaa aaagcacgtg aaattgttga aagggaagcg cttgcagcca    960
gacttgcctg tagttgctca tccgggtttc tacccggtgc actcttctac gggcaggcca   1020
gcatcagttt gggcggttgg ataaaggtct ctgtcatgta cctcccttcg gggagatctt   1080
ataggggaga cgacatgcaa ccagcctgga ctgaggtccg cgcatctgct aggatgctgg   1140
cgtaatggct gtaagcggcc cgtcttgaaa cacggaccaa ggagtctaac atctatgcga   1200
gtgtttgggt gtcaagcccg agcgcgtaat gaaagtgaac ggaggtggga acctttcggg   1260
gtgcaccatc gaccgatcct gatgtcttcg gatggatttg agtaagagca tagctgttgg   1320
gacccgaaag atggtgaact atgcttgaat agggtgaagc cagaggaaac tctggtggag   1380
gctcgcagcg gttctgacgt gcaaatcgat cgtcaaattt gggcataggg gcgaaagac    1439
```

<210> SEQ ID NO 35
<211> LENGTH: 1447
<212> TYPE: DNA
<213> ORGANISM: Epicoccum nigrum

<400> SEQUENCE: 35

```
tccgtaggtg aacctgcgga aggatcatta cctagagttt gtggacttcg gtctgctacc     60
tcttacccat gtcttttgag taccttcgtt tcctcggcgg gtccgcccgc cggttggaca    120
acattcaaac cctttgcagt tgcaatcagc gtctgaaaaa acttaatagt tacaactttc    180
aacaacggat ctcttggttc tggcatcgat gaagaacgca gcgaaatgcg ataagtagtg    240
tgaattgcag aattcagtga atcatcgaat ctttgaacgc acattgcgcc ccttggtatt    300 ccatgggca  tgcctgttcg agcgtcattt gtaccttcaa gctctgcttg gtgttgggtg    360
ttttgtctcg cctccgcgcg cagactcgcc ttaaaacaat tggcagccgg cgtattgatt    420
tcggagcgca gtacatctcg cgctttgcac tcataacgac gacgtccaaa agtacatttt    480
tacactcttg acctcggatc aggtagggat acccgctgaa cttaagcata tcaataagcg    540
gaggaaaaga accaacagg  gattgccctag taacggcga  gtgaagcggc aacagctcaa    600
atttgaaatc tggcgtcttt ggcgtccgag ttgtaatttg cagagggcgc tttggcattg    660
gcagcggtcc aagttccttg gaacaggacg tcacagaggg tgagaatccc gtacgtggtc    720
```

```
gctagccttt accgtgtaaa gccccttcga cgagtcgagt tgtttgggaa tgcagctcta    780
aatgggaggt aaatttcttc taaagctaaa tactggccag agaccgatag cgcacaagta    840
gagtgatcga agatgaaaa gcactttgga aagagagtta aaaagcacgt gaaattgttg     900
aaagggaagc gcttgcagcc agacttgcct gtagttgctc atccgggttt ctacccggtg    960
cactcttcta cgggcaggcc agcatcagtt tgggcggttg gataaaggtc tctgtcatgt   1020
acctcccttc ggggagatct tataggggag acgacatgca accagcctgg actgaggtcc   1080
gcgcatctgc taggatgctg gcgtaatggc tgtaagcggc ccgtcttgaa acacggacca   1140
aggagtctaa catctatgcg agtgtttggg tgtcaagccc gagcgcgtaa tgaaagtgaa   1200
cggaggtggg aaccttttcgg ggtgcaccat cgaccgatcc tgatgtcttc ggatggattt   1260
gagtaagagc atagctgttg ggacccgaaa gatggtgaac tatgcttgaa tagggtgaag   1320
ccagaggaaa ctctggtgga ggctcgcagc ggttctgacg tgcaaatcga tcgtcaaatt   1380
tgggcatagg ggcgaaagac taatcgaact atctagtagc tggttcctgc cgaagtttcc   1440
ctcagga                                                              1447

<210> SEQ ID NO 36
<211> LENGTH: 483
<212> TYPE: DNA
<213> ORGANISM: Epicoccum nigrum

<400> SEQUENCE: 36
tggacttcgg tctgctacct cttacccatg tcttttgagt accttcgttt cctcggcggg     60
tccgcccgcc ggttggacaa cattcaaacc ctttgcagtt gcaatcagcg tctgaaaaaa    120
cttaatagtt acaactttca acaacggatc tcttggttct ggcatcgatg aagaacgcag    180
cgaaatgcga taagtagtgt gaattgcaga attcagtgaa tcatcgaatc tttgaacgca    240
cattgcgccc cttggtattc catggggcat gcctgttcga gcgtcatttg taccttcaag    300
ctctgcttgg tgttgggtgt tttgtctcgc ctccgcgcgc agactcgcct taaaacaatt    360
ggcagccggc gtattgattt cggagcgcag tacatctcgc gctttgcact cataacgacg    420
acgtccaaaa gtacattttt acactcttga cctcggatca ggtagggata cccgctgaac    480
tta                                                                   483

<210> SEQ ID NO 37
<211> LENGTH: 383
<212> TYPE: DNA
<213> ORGANISM: Epicoccum nigrum

<400> SEQUENCE: 37
ccagactggc cgaagacgaa gttatcggga cggaagagct ggccgaaggg gccggcgcgg     60
acagcgtcca ttgtaccggg ctccaagtcg acgaggacgg cacggggaac gaacttgttg    120
ccagaggcct gcgggaggtc agcactcgca gtccgtctca ggaaagcgtg tcgtttctag    180
tacctcgttg aagtagacgt tcatgcgctc gagctggagg tccgaggtgc cgttgtagac    240
accggagccg tcgaggccat gctcgccgga gatggtctgc cagaaggcag caccgatttg    300
gttaccctgt cccttgtgag ctgccgtcca tgagagaaca tgcaagtggt gtacttacgc    360
actgaccggt ctggaggtga acc                                             383

<210> SEQ ID NO 38
<211> LENGTH: 1456
<212> TYPE: DNA
<213> ORGANISM: Periconia macrospinosa
```

<400> SEQUENCE: 38

```
tcttggtcat ttagaggaag taaaagtcgt aacaaggttt ccgtaggtga acctgcggaa        60
ggatcattac acattcgggg cgcttcggcg ctccttatac acccaccctc tgcctacgtg       120
tacctctata gcttcctcgg cgggctcgcc cgccgccagg aacccacgaa accccttgca       180
ttatacgcga aaacttctga taacaaacct aaattatcac aactttcaac aatggatctc       240
ttggttctgg catcgatgaa gaacgcagcg aaatgcgata agtagtgtga attgcagaat       300
tcagtgaatc atcgaatctt tgaacgcaca ttgcggccat aggtattcct ttggccatgc       360
ctgttcgagc gtcatttaca ccctcaagcc tagcttggtg ttgggcgtct gtcccgccgt       420
tctcgcgcgc ggactcgcct caaagtcatt ggcggcggtc gtgccggccc cctcgcgcag       480
cacatttgcg cttctcggag gcccggcgga tccgcgctcc agcaagacct ttcacgactt       540
gacctcggat caggtaggga tacccgctga acttaagcat atcaataagc ggaggaaaag       600
aaaccaacag ggattgccct agtaacggcg agtgaagcgg caacagctca aatttgaaat       660
ctggcccctt tggggtccga gttgtaattt gcagagggtg ctttggcgtt ggcggcggtc       720
taagttcctt ggaacaggac atcgcagagg gtgagaatcc cgtatgtggt cgcatgcctt       780
cgccgtgtaa agccccttcg acgagtcgag ttgtttggga atgcagctct aaatgggagg       840
taaatttctt ctaaagctaa ataccggcca gagaccgata gcgcacaagt agagtgatcg       900
aaagatgaaa agcactttgg aaagagagtc aaacagcacg tgaaattgtt gaaagggaag       960
cgcttgcagc cagacttgcc tgtagttgct cacccgggct cctgcccggg gcactcttct      1020
gcaggcaggc cagcatcagt ttgggcggtc ggataaaggg ctctgacacg tacttcccct      1080
cggggttgac atacagggga gccgcaatgc gaccagcccg gactgaggtc cgcgcatctg      1140
ctaggatgct ggcgtaatgg ctgtaagcgg cccgtcttga acacggacc aaggagtcta       1200
acatctatgc gagtgtttgg gtgtcaagcc cgagcgcgca atgaaagtga acggaggtgg      1260
gagcccctcg gggtgcacca tcgaccgatc ctgatgtctt cggatggatt tgagtaagag      1320
catagctgtt gggacccgaa agatggtgaa ctatgcttga ataggtgaa gccagaggaa       1380
actctggtgg aggctcgcag cggttctgac gtgcaaatcg atcgtcaaat ttgggcatag      1440
gggcgaaaga ctaatc                                                     1456
```

<210> SEQ ID NO 39
<211> LENGTH: 599
<212> TYPE: DNA
<213> ORGANISM: Periconia macrospinosa

<400> SEQUENCE: 39

```
tggtcaacta gcgaacgtgt ttggccgcag gtctcctctt atttattgcg ttgcgctttt        60
cgctttgggg agtgggattg ctggaggcgc ccataatcct ggaatgttaa tatctggacg       120
tacagtacaa ggtgtaggcg caggaggcat atatgtcctc cttgatatcg tgtgctgcga       180
tctggtacca ctccgcgagc gtggaaaata tgtcggccta atgaactcat gggccggtgt       240
tgctgctgga attgggcctg tcataggtgg agccttggcc gatactaact ggcgctggat       300
attctatctc aatcttccga tctgtgggct ggcgttaggc gtggttttgc ttttcatgcg       360
aatgaaaact ggtacgcagg gcgaaggcgt gttgaagctt cgccaaattg attatctggg       420
gagttttatt ttcataccga gtatgatcgc acttctatac ggcttgatca ctggaggcat       480
tcaatatccg tggtcatcgt ggcggattat tctcccattg gtgattggcg ttgccggctg       540
```

| | |
|---|---|
| gatactattc cacatccaac agttcttcac ggacgtccca agtgtacccg ttcgcctct | 599 |

<210> SEQ ID NO 40
<211> LENGTH: 1420
<212> TYPE: DNA
<213> ORGANISM: Acinetobacter lwoffii

<400> SEQUENCE: 40

| | |
|---|---|
| cacatgcagt cgagcgggga gagtagcttg ctacttgacc tagcggcgga cgggtgagta | 60 |
| atgcttagga atctgcctat tagtggggga caacatctcg aaagggatgc taataccgca | 120 |
| tacgtcctac gggagaaagc aggggacctt cgggccttgc gctaatagat gagcctaagt | 180 |
| cggattagct agttggtggg gtaaaggcct accaaggcga cgatctgtag cgggtctgag | 240 |
| aggatgatcc gccacactgg gactgagaca cggcccagac tcctacggga ggcagcagtg | 300 |
| gggaatattg gacaatgggg gaaccctga tccagccatg ccgcgtgtgt gaagaaggcc | 360 |
| ttttggttgt aaagcacttt aagcgaggag gaggctaccg agattaatac tcttggatag | 420 |
| tggacgttac tcgcagaata agcaccggct aactctgtgc cagcagccgc ggtaatacag | 480 |
| agggtgcaag cgttaatcgg atttactggg cgtaaagcgc gcgtaggtgg ccaattaagt | 540 |
| caaatgtgaa atccccgagc ttaacttggg aattgcattc gatactggtt ggctagagta | 600 |
| tgggagagga tggtagaatt ccaggtgtag cggtgaaatg cgtagagatc tggaggaata | 660 |
| ccgatggcga aggcagccat ctggcctaat actgacactg aggtgcgaaa gcatgggag | 720 |
| caaacaggat tagataccct ggtagtccat gccgtaaacg atgtctacta gccgttgggg | 780 |
| cctttgctgg ctttagtggc gcagctaacg cgataagtag accgcctggg gagtacggtc | 840 |
| gcaagactaa aactcaaatg aattgacggg ggcccgcaca agcggtggag catgtggttt | 900 |
| aattcgatgc aacgcgaagt agcttacctg gtcttgacat agtatcttct ttccagagat | 960 |
| ggattggtgc cttcgggaac ttacatacag gtgctgcatg gctgtcgtca gctcgtgtcg | 1020 |
| tgagatgttg ggttaagtcc cgcaacgagc gcaacccttt tccttatttg ccagcgggtt | 1080 |
| aagccgggaa ctttaaggat actgccagtg acaaactgga ggaaggcggg gacgacgtca | 1140 |
| agtcatcatg gcccttacga ccagggctac acacgtgcta caatggtcgg tacaaagggt | 1200 |
| tgctacctcg cgagaggatg ctaatctcaa aaagccgatc gtagtccgga ttggagtctg | 1260 |
| caactcgact ccatgaagtc ggaatcgcta gtaatcgcgg atcagaatgc cgcggtgaat | 1320 |
| acgttcccgg gccttgtaca caccgcccgt cacaccatgg gagtttgttg caccagaagt | 1380 |
| agggtaggtc cttaacgtct aagggaggac gctaccacgg | 1420 |

<210> SEQ ID NO 41
<211> LENGTH: 1384
<212> TYPE: DNA
<213> ORGANISM: Unknown
<220> FEATURE:
<223> OTHER INFORMATION: Kingdom: Bacteria, Phylum: Bacteroidetes,
    Class: Flavobacteriia, Order: Flavobacteriales, Family:
    Flavobacteriaceae, Genus: Chryseobacterium

<400> SEQUENCE: 41

| | |
|---|---|
| agccgagcgg tatttcttct tcggaagaga gagagcggcg tacgggtgcg aacacgtgt | 60 |
| gcaacctacc tttatcaggg ggatagcctt tcgaaaggaa gattaatacc ccataatata | 120 |
| ttgaatggca tcatttaata ttgaaaactc cggtggatag agatgggcac gcgcaagatt | 180 |
| agatagttgg tgaggtaacg gctcaccaag tcaatgatct ttaggggggcc tgagagggtg | 240 |
| atcccccaca ctggtactga gacacggacc agactcctac gggaggcagc agtgaggaat | 300 |

```
attggacaat gggtgaaagc ctgatccagc catcccgcgt gaaggacgac ggccctatgg      360
gttgtaaact tcttttgtac agggataaac ctttccacgt gtggaaagct gaaggtactg      420
tacgaataag caccggctaa ctccgtgcca gcagccgcgg taatacggag ggtgcaagcg      480
ttatccggat ttattgggtt taaagggtcc gtaggcggac ctgtaagtca gtggtgaaat      540
ctcatagctt aactatgaaa ctgccattga tactgcaggt cttgagtaaa tttgaagtgg      600
ctggaataag tagtgtagcg gtgaaatgca tagatattac ttagaacacc aattgcgaag      660
gcaggtcact aagatttaac tgacgctgag ggacgaaagc gtggggagcg aacaggatta      720
gataccctgg tagtccacgc cgtaaacgat gctaactcgt ttttggattt tcggattcag      780
agaccaagcg aaagtgataa gttagccacc tggggagtac gtccgcaagg atgaaactca      840
aaggaattga cgggggcccg cacaagcggt ggattatgtg gtttaattcg atgatacgcg      900
aggaacctta ccaagactta aatgggaaat gacagattta gaaatagatc cttcttcgga      960 cattttcaa ggtgctgcat ggttgtcgtc agctcgtgcc gtgaggtgtt aggttaagtc     1020
ctgcaacgag cgcaacccct gtcactagtt gctaacattc agttgaggac tctagtgaga     1080
ctgcctacgc aagtagagag gaaggtgggg atgacgtcaa atcatcacgg cccttacgtc     1140
ttgggccaca cacgtaatac aatggccggt acagagggca gctacacagc gatgtgatgc     1200
aaatctcgaa agccggtctc agttcggatt ggagtctgca actcgactct atgaagctgg     1260
aatcgctagt aatcgcgcat cagccatggc gcggtgaata cgttcccggg ccttgtacac     1320
accgcccgtc aagccatgga agtttggggt acctgaagtc ggtgaccgta aaaggagctg     1380
ccta                                                                 1384
```

<210> SEQ ID NO 42
<211> LENGTH: 1404
<212> TYPE: DNA
<213> ORGANISM: Unknown
<220> FEATURE:
<223> OTHER INFORMATION: Kingdom: Bacteria, Phylum: Actinobacteria,
      Class: Actinobacteria, Order: Micrococcales, Family:
      Microbacteriaceae, Genus: Curtobacterium

<400> SEQUENCE: 42

```
cacatgcagt cgaacgatga tgcccagctt gctgggtgga ttagtggcga acgggtgagt       60
aacacgtgag taacctgccc ctgactctgg gataagcgtt ggaaacgacg tctaatactg      120
gatatgactg ccggccgcat ggtctggtgg tggaaagatt ttttggttgg ggatggactc      180
gcggcctatc agcttgttgg tgaggtaatg gctcaccaag cgacgacgg gtagccggcc       240 tgagagggtg accggccaca ctgggactga cacggccc agactcctac gggaggcagc       300
agtggggaat attgcacaat gggcgaaagc ctgatgcagc aacgccgcgt gagggatgac      360
ggccttcggg ttgtaaacct cttttagtag ggaagaagcg taagtgacgg tacctgcaga      420
aaaaagcacc ggctaactac gtgccagcag ccgcggtaat acgtagggtg caagcgttgt      480
ccggaattat tgggcgtaaa gagctcgtag gcggtttgtc gcgtctgctg tgaaatcccg      540
aggctcaacc tcgggcttgc agtgggtacg ggcagactag agtgcggtag gggagattgg      600
aattcctggt gtagcggtgg aatgcgcaga tatcaggagg aacaccgatg gcgaaggcag      660
atctctgggc cgtaactgac gctgaggagc gaaagcgtgg ggagcgaaca ggattagata      720
ccctggtagt ccacgccgta aacgttgggc gctagtgta gggacctttc cacggtttct      780
gtgtcgtagc taacgcatta agcgccccgc ctggggagta cggccgcaag gctaaaactc      840
```

```
aaaggaattg acggggcccc gcacaagcgg cggagcatgc ggattaattc gatgcaacgc    900
gaagaacctt accaaaggct tgacatacac cggaaacggc cagagatggt tgccccgtt    960
gtggtcggtg tacaggtgga gcatggggtt gtcgtcagct cgtgtcgtga gatgttgggt   1020
taagtcccgc aacgagcgca accctcgttc tatgttgcca gcgcgttatg gcggggactc   1080
ataggagact gccggggtca actcggagga aggtggggat gacgtcaaat catcatgccc   1140
cttatgtctt gggcttcacg catgctacaa tggccggtac aaagggctgc gataccgtaa   1200
ggtggagcga atcccaaaaa gccggtctca gttcggattg aggtctgcaa ctcgacctca   1260
tgaagtcgga gtcgctagta atcgcagatc agcaacgctg cggtgaatac gttcccgggc   1320
cttgtacaca ccgcccgtca agtcatgaaa gtcggtaaca cccgaagccg gtggcctaac   1380
ccttgtggaa ggagccgtcg aatg                                          1404

<210> SEQ ID NO 43
<211> LENGTH: 1398
<212> TYPE: DNA
<213> ORGANISM: Unknown
<220> FEATURE:
<223> OTHER INFORMATION: Kingdom: Bacteria, Phylum: Actinobacteria,
      Class: Actinobacteria, Order: Micrococcales, Family:
      Micrococcaceae, Genus: Micrococcus

<400> SEQUENCE: 43
accatgcagt cgaacgatga agcccagctt gctgggtgga ttagtggcga acgggtgagt     60
aacacgtgag taacctgccc ttaactctgg gataagcctg ggaaactggg tctaataccg    120
gataggagcg tccaccgcat ggtgggtgtt ggaaagattt atcggttttg gatggactcg    180
cggcctatca gcttgttggt gaggtaatgg ctcaccaagg cgacgacggg tagccggcct    240
gagagggtga ccggccacac tgggactgag acacggccca gactcctacg ggaggcagca    300
gtggggaata ttgcacaatg ggcgcaagcc tgatgcagcg acgccgcgtg agggatgacg    360
gccttcgggt tgtaaacctc tttcagtagg gaagaagcga agtgacggt acctgcagaa    420
gaagcaccgg ctaactacgt gccagcagcc gcggtaatac gtagggtgcg agcgttatcc    480
ggaattattg ggcgtaaaga gctcgtaggc ggtttgtcgc gtctgtcgtg aaagtccggg    540
gcttaacccc ggatctgcgg tgggtacggg cagactagag tgcagtaggg gagactggaa    600
ttccctggtg tagcggtgga atgcgcagat atcaggagga acaccgatgg cgaaggcagg    660
tctctgggct gtaactgacg ctgaggagcg aaagcatggg gagcgaacag gattagatac    720
cctggtagtc catgccgtaa acgttgggca ctaggtgtgg ggaccattcc acggtttccg    780
cgccgcagct aacgcattaa gtgccccgcc tggggagtac ggccgcaagg ctaaaactca    840
aaggaattga cggggcccg cacaagcgg ggagcatgcg gattaattcg atgcaacgcg    900
aagtagctta ccaaggcttg acatgttctc gatcgccgta gagatacggt tttccctttg    960
gggcgggatc acaggatggt gcatggttgt cgtcagctcg tgtcgtgaga tgttgggtta   1020
agtcccgcaa cgagcgcaac cctcgttcca tgttgccagc acgtaatggt ggggactcat   1080
gggagactgc cggggtcaac tcggaggaag tgaggacga cgtcaaatca tcatgcccct   1140
tatgtcttgg gcttcacgca tgctacaatg gccggtacaa tggttgcga tactgtgagg   1200
tggagctaat cccaaaaagc cggtctcagt tcggattggg gtctgcaact cgaccccatg   1260
aagtcggagt cgctagtaat cgcagatcag caacgctgcg gtgaatacgt tcccgggcct   1320
tgtacacacc gcccgtcaag tcacgaaagt tggtaacacc cgaagccggt ggcctaaccc   1380
ttgtgggggg agccgtcg                                                 1398
```

<210> SEQ ID NO 44
<211> LENGTH: 1443
<212> TYPE: DNA
<213> ORGANISM: Unknown
<220> FEATURE:
<223> OTHER INFORMATION: Kingdom: Bacteria, Phylum: Actinobacteria,
      Class: Actinobacteria, Order: Micrococcales, Family:
      Micrococcaceae, Genus: Micrococcus

<400> SEQUENCE: 44

| | | | | | |
|---|---|---|---|---|---|
| gctcaggatg | aacgctggcg | gcgtgcttaa | cacatgcaag | tcgaacgatg | aagcccagct | 60 |
| tgctgggtgg | attagtggcg | aacgggtgag | taacacgtga | gtaacctgcc | cttaactctg | 120 |
| ggataagcct | gggaaactgg | gtctaatacc | ggataggagc | gtccaccgca | tggtgggtgt | 180 |
| tggaaagatt | tatcggtttt | ggatggactc | gcggcctatc | agcttgttgg | tgaggtaatg | 240 |
| gctcaccaag | gcgacgacgg | gtagccggcc | tgagagggtg | accggccaca | ctgggactga | 300 |
| gacacggccc | agactcctac | gggaggcagc | agtggggaat | attgcacaat | gggcgcaagc | 360 |
| ctgatgcagc | gacgccgcgt | gagggatgac | ggccttcggg | ttgtaaacct | ctttcagtag | 420 |
| ggaagaagcg | aaagtgacgg | tacctgcaga | agaagcaccg | gctaactacg | tgccagcagc | 480 |
| cgcggtaata | cgtagggtgc | gagcgttatc | cggaattatt | gggcgtaaag | agctcgtagg | 540 |
| cggtttgtcg | cgtctgtcgt | gaaagtccgg | ggcttaaccc | cggatctgcg | gtgggtacgg | 600 |
| gcagactaga | gtgcagtagg | ggagactgga | attcctggtg | tagcggtgga | atgcgcagat | 660 |
| atcaggagga | acaccgatgg | cgaaggcagg | tctctgggct | gtaactgacg | ctgaggagcg | 720 |
| aaagcatggg | gagcgaacag | gattagatac | cctggtagtc | catgccgtaa | acgttgggca | 780 |
| ctaggtgtgg | ggaccattcc | acggtttccg | cgccgcagct | aacgcattaa | gtgccccgcc | 840 |
| tggggagtac | ggccgcaagg | ctaaaactca | aaggaattga | cggggcccg | cacaagcggc | 900 |
| ggagcatgcg | gattaattcg | atgcaacgcg | aagaacctta | ccaaggcttg | acatgttctc | 960 |
| gatcgccgta | gagatacggt | ttccccttg | gggcgggttc | acaggtggtg | catggttgtc | 1020 |
| gtcagctcgt | gtcgtgagat | gttgggttaa | gtcccgcaac | gagcgcaacc | ctcgttccat | 1080 |
| gttgccagca | cgtcgtggtg | gggactcatg | ggagactgcc | ggggtcaact | cggaggaagg | 1140 |
| tgaggacgac | gtcaaatcat | catgcccctt | atgtcttggg | cttcacgcat | gctacaatgg | 1200 |
| ccggtacaat | gggttgcgat | actgtgaggt | ggagctaatc | ccaaaaagcc | ggtctcagtt | 1260 |
| cggattgggg | tctgcaactc | gaccccatga | agtcggagtc | gctagtaatc | gcagatcagc | 1320 |
| aacgctgcg | tgaatacgtt | cccgggcctt | gtacaccg | cccgtcaagt | cacgaaagtt | 1380 |
| ggtaacaccc | gaagccggtg | gcctaaccct | tgtgggggga | gccgtcgaag | tgggaccagc | 1440 |
| gat | | | | | | 1443 |

<210> SEQ ID NO 45
<211> LENGTH: 1359
<212> TYPE: DNA
<213> ORGANISM: Unknown
<220> FEATURE:
<223> OTHER INFORMATION: Kingdom: Bacteria, Phylum: Proteobacteria,
      Class: Alphaproteobacteria, Order: Rhizobiales,
      Family: Brucellaceae, Genus: Ochrobactrum

<400> SEQUENCE: 45

| | | | | | |
|---|---|---|---|---|---|
| cacatgcagt | cgagcgcccc | gcaaggggag | cggcagacgg | gtgagtaacg | cgtgggaacg | 60 |
| tacctttgc | tacggaataa | ctcagggaaa | cttgtgctaa | taccgtatgt | gcccttcggg | 120 |

```
ggaaagattt atcggcaaag gatcggcccg cgttggatta gctagttggt gaggtaaagg      180
ctcaccaagg cgacgatcca tagctggtct gagaggatga tcagccacac tgggactgag      240
acacggccca gactcctacg ggaggcagca gtggggaata ttggacaatg ggcgcaagcc      300
tgatccagcc atgccgcgtg agtgatgaag gcccctaggg tgtaaagctc tttcaccggt      360
gaagataatg acggtaaccg gagaagaagc cccggctaac ttcgtgccag cagccgcggt      420
aatacgaagg gggctagcgt tgttcggatt tactgggcgt aaagcgcacg taggcggact      480
tttaagtcag gggtgaaatc ccggggctca accccggaac tgcctttgat actggaagtc      540
ttgagtatgg tagaggtgag tggaattccg agtgtagagg tgaaattcgt agatattcgg      600
aggaacacca gtggcgaagg cggctcactg gaccattact gacgctgagg tgcgaaagcg      660
tggggagcaa acaggattag ataccctggt agtccacgcc gtaaacgatg aatgttagcc      720 gttgggagt ttactcttcg gtggcgcagc taacgcatta acattccgc ctggggagta       780 cggtcgcaag attaaaactc aaaggaattg acggggcccg cacaagcgg tggagcatgt       840 ggtttaattc gaagcaacgc gcagaacctt accagccctt gacataccgg tcgcggacac      900
agagatgtgt ctttcagttc ggctggaccg gatacaggtg ctgcatggct gtcgtcagct      960
cgtgtcgtga gatgttgggt taagtcccgc aacgagcgca accctcgccc ttagttgcca     1020
gcatttagtt gggcactcta agggactgcc ggtgataag ccgagaggaa ggtggggatg      1080
acgtcaagtc ctcatggccc ttacgggctg gctacacac gtgctacaat ggtggtgaca      1140
gtgggcagcg agcacgcgag tgtgagctaa tctccaaaag ccatctcagt tcggattgca     1200
ctctgcaact cgagtgcatg aagttggaat cgctagtaat cgcggatcag catgccgcgg     1260
tgaatacgtt cccgggcctt gtacacaccg cccgtcacac catgggagtt ggttttaccc     1320
gaaggcgctg tgctaaccgc aaggaggcag gcgaccact                             1359
```

<210> SEQ ID NO 46
<211> LENGTH: 1436
<212> TYPE: DNA
<213> ORGANISM: Paenibacillus taichungensis

<400> SEQUENCE: 46

```
atacatgcag tcgagcggac ttgcatgaga agcttgcttc tctgatggtt agcggcggac       60
gggtgagtaa cacgtaggca cctgccctca agcttgggac aactaccgga aacggtagct      120
aataccgaat agttgttttc ttctcctgaa gaaaactgga agacggagc aatctgtcac       180 ttggggatgg gcctgcggcg cattagctag ttggtgggt aacggctcac caaggcgacg       240
atgcgtagcc gacctgagag ggtgatcggc cacactggga ctgagacacg gcccagactc      300
ctacgggagg cagcagtagg gaatcttccg caatgggcga aagcctgacg gagcaatgcc      360
gcgtgagtga tgaaggtttt cggatcgtaa agctctgttg ccaggaagaa acgcttggga     420
gagtaactgc tctcaaggtg acggtacctg agaagaaagc cccggctaac tacgtgccag      480
cagccgcggt aatacgtagg gggcaagcgt tgtccggaat tattgggcgt aaagcgcgcg      540
caggcggtca tttaagtctg tgtttaatc ccggggctca accccggatc gcactggaaa      600
ctgggtgact tgagtgcaga agaggagagt ggaattccac gtgtagcggt gaaatgcgta      660
gatatgtgga ggaacaccag tggcgaagcg cgactctctg gctgtaact gacgctgagg       720 cgcgaaagcg tggggagcaa acaggattag ataccctggt agtccacgcc gtaaacgatg      780
agtgctaggt gttaggggtt tcgatacct tggtgccgaa gttaacacat taagcactcc       840
gcctggggag tacggtcgca agactgaaac tcaaaggaat tgacggggac ccgcacaagc      900
```

```
agtggagtat gtggttttat tcgaagcaac gcgaagaacc ttaccaggtc ttgacatccc      960
tctgaccggt acagagatgt acctttcctt cgggacagag gagacaggtg gtgcatggtt     1020
gtcgtcagct cgtgtcgtga gatgttgggt taagtcccgc aacgagcgca accccttgatc    1080 ttagttgcca gcacttcggg tgggcactct aaggtgactg ccggtgacaa accggaggaa     1140
ggtggggatg acgtcaaatc atcatgcccc ttatgacctg gctacacac gtactacaat      1200 ggccggtaca acgggctgtg aagccgcgag gtggaacgaa tcctaaaaag ccggtctcag     1260
ttcggattgc aggctgcaac tcgcctgcat gaagtcggaa ttgctagtaa tcgcggatca     1320
gcatgccgcg gtgaatacgt tcccgggtct tgtacacacc gcccgtcaca ccacgagagt     1380
ttataacacc cgaagtcggt ggggtaaccg caaggagcca gccgccgaag gtgatc         1436
```

<210> SEQ ID NO 47
<211> LENGTH: 1348
<212> TYPE: DNA
<213> ORGANISM: Unknown
<220> FEATURE:
<223> OTHER INFORMATION: Kingdom: Bacteria, Phylum: Proteobacteria,
    Class: Alphaproteobacteria, Order: Sphingomonadales,
    Family: Sphingomonadaceae, Genus: Sphingomonas

<400> SEQUENCE: 47

```
aacgaaggct tcggccttag tggcgcacgg gtgcgtaacg cgtgggaatc tgcccttttgg     60 ttcggaataa cagctggaaa cggctgctaa taccggatga tgacgaaagt ccaaagattt     120
atcgccagag gatgagcccg cgttggatta ggtagttggt ggggtaaagg cctaccaagc     180
cgacgatcca tagctggtct gagaggatga tcagccacac tgggactgag acacggccca     240
gactcctacg ggaggcagca gtggggaata ttggacaatg gcgaaagcc tgatccagca     300 atgccgcgtg agtgatgaag gccctagggt tgtaaagctc ttttacccgg aagataatg     360 actgtaccgg gagaataagc cccggctaac tccgtgccag cagccgcggt aatacgagg     420 gggctagcgt tgttcggaat tactgggcgt aaagcgcacg taggcggctt tgtaagtcag     480
aggtgaaagc ctggagctca actccagaac tgcctttgag actgcatcgc ttgaatccag    540
gagaggtcag tggaattccg agtgtagagg tgaaattcgt agatattcgg aagaacacca     600
gtggcgaagg cggctgactg gactggtatt gacgctgagg tgcgaaagcg tggggagcaa     660
acaggattag ataccctggt agtccacgcc gtaaacgatg ataactagct gtccgggcac     720
ttggtgcttg ggtggcgcag ctaacgcatt aagttatccg cctgggagt acggccgcaa      780 ggttaaaact caaaggaatt gacggggcc tgcacaagcg gtggagcatg tggtttaatt     840
cgaagcaacg cgcagaacct taccagcgtt tgacatgtcc ggacgatttc cagagatgga    900
tctcttccct tcggggactg gaacacaggt gctgcatggc tgtcgtcagc tcgtgtcgtg     960
agatgttggg ttaagtcccg caacgagcgc aaccctcgcc tttagttacc atcatttagt    1020
tgggtactct aaaggaaccg ccggtgataa gccggaggaa ggtggggatg acgtcaagtc   1080
ctcatggccc ttacgcgctg gctacacac gtgctacaat ggcaactaca gtgggcagcg    1140
accctgcgag ggcgagctaa tcccaaaaag ttgtctcagt tcggattgtt ctctgcaact    1200
cgagagcatg aaggcggaat cgctagtaat cgcggatcag catgccgcgg tgaatacgtt    1260
cccaggcctt gtacacaccg cccgtcacac catgggagtt ggattcaccc gaaggcgttg    1320
cgccaacccg caagggaagc aggcgtac                                        1348
```

<210> SEQ ID NO 48

```
<211> LENGTH: 617
<212> TYPE: DNA
<213> ORGANISM: Acremonium strictum

<400> SEQUENCE: 48
tcttggtcaa tttagaggaa gtaaaagtcg taacaaggtc tccgttggtg aaccagcgga      60
gggttcatta ccagagtgcc ctaggctctc caacccattg tgaacttacc aaacgttccc     120
tcggcgggct cagcgcgcgg tggcctccgg gcctccgggc gtccgccggg gaaaaccaaa     180
ccctgattta atcgtatttc tctgaggggc gaaagcccga aaacaaaatg aatcaaaact     240
ttcaacaacg gatctcttgg ctctggcatc gatgaagaac gcagcgaaat gcgataagta     300
atgtgaattg cagaattcag tgaatcatcg aatctttgaa cgcacattgc gcccgccggc     360
actccggcgg gcatgcctgt ccgagcgtca tttcaacccct caggcccacc cttccggggg     420
agcgggcctg gtgctgggga tcggcggccc tcgcggcccc cgtccctcaa atacagtggc     480
ggtcgcgccg cagcctcccc tgcgtagtag cacaacctcg caccggagag cggaacgacc     540
acgccgtgaa acccccaatt ttttaaggtt gacctcggat caggtaggaa tacccgctga     600
acttaagcat atcaaaa                                                   617

<210> SEQ ID NO 49
<211> LENGTH: 1461
<212> TYPE: DNA
<213> ORGANISM: Acremonium alternatum

<400> SEQUENCE: 49
tccgttggtg aaccagcgga gggatcatta ccgagtgtaa aaactcccaa accattgtga      60
acttaccact gttgcttcgg cggcctcgcc ccgggcgcgt tcgcgcggcc cggacccagg     120
cgtccgccgg aggctccaaa ctcttgtctt ttagtgtatt tctgagtggc ataagcaaat     180
aaatcaaaac tttcagcaac ggatctcttg gttctggcat cgatgaagaa cgcagcaaaa     240
tgcgataagt aatgtgaatt gcagaattca gtgaatcatc gaatctttga acgcacattg     300
cgcccgccag tattctggcg gcatgcctg tctgagcgtc atttcaaccc tcaggacccg     360
ttcgcgggac ctggcgttgg ggatcagcct gcccctggcg cggctggcc ctgaaatcca     420 gtggcggttc cctcgcgaac tcctccgtgc agtaattaaa cctctcgcgg caggatagcg     480
gttgaaccac gccgttaaac cccccacttc tcaaggttga cctcagatca ggtaggaata     540
cccgctgaac ttaagcatat caataagcgg aggaaaagaa accaacaggg attgccctag     600
taacggcgag tgaagcggca acagctcaaa tttgaaatct ggcctcacgg tccgaattgt     660
aatttgtaga ggatgtttct ggcgacgtgt cttccgagtt ccctggaacg ggacgccata     720
gagggtgaga gccccgtccg gtcgtacacc tagcctctgt gaaactcctt cgacgagtcg     780
agtagtttgg gaatgctgct ctaaatggga ggtatacgtc ttctaaagct aaataccggc     840
cagagaccga tagcgcacaa gtagagtgat cgaaagatga aaagcacttt gaaaagaggg     900
ttaaatagta cgtgaaattg ctgaaaggga agcgcttatg accagacttg ggctcggtga     960
atcatccggc gttctcgccg gtgcactttg ccgtcccagg ccagcatcag ttcgcgccgg    1020
gggataaagg tttcgggaat gtagctcctt cgggagtgtt atagcccgtt gcgtaatacc    1080
ctggcgtgga ctgaggtccg cgctctgcaa ggatgctggc gtaatggtca tcagtgaccc    1140
gtcttgaaac acggaccaag gagtcgtctt cgtatgcgag tgttcgggtg tcaaacccct    1200
acgcgtaatg aaagtgaacg taggagagag cttcggcgca tctccgaccg atcctgatgt    1260
tctcggatgg atttgagtaa gagcatacgg ggccggaccc gaaagaaggt gaactatgcc    1320
```

```
tgtatagggt gaagccagag gaaactctgg tggaggctcg cagcggttct gacgtgcaaa    1380
tcgatcgtca aatatgggca tgggggcgaa agactaatcg aaccttctag tagctggttt    1440
ccgccgaagt ttccctcagg a                                              1461
```

<210> SEQ ID NO 50
<211> LENGTH: 591
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Capnodiales, Family: Cladosporiaceae,
      Genus: Cladosporium

<400> SEQUENCE: 50

```
tcttggtcat ttagaggaag taaaagtcgt aacaaggtct ccgtaggtgt acctgcggag     60
ggatcattac aagtgacccc ggtctaacca ccgggatgtt cataacccct tgttgtccga    120
ctctgttgcc tccggggcga ccctgccttc gggcggggc tccgggtgga cacttcaaac    180
tcttgcgtaa ctttgcagtc tgagtaaact taattaataa attaaaactt ttaacaacgg    240
atctcttggt tctggcatcg atgaagaacg cagcgaaatg cgataagtaa tgtgaattgc    300
agaattcagt gaatcatcga atctttgaac gcacattgcg ccccctggta ttccgggggg    360
catgcctgtt cgagcgtcat ttcaccactc aagcctcgct tggtattggg caacgcggtc    420
cgccgcgtgc ctcaaatcga ccggctgggt cttctgtccc taagcgttg tggaaactat     480 tcgctaaagg gtgttcggga ggctacgccg taaaacaacc ccatttctaa ggttgacctc    540
ggatcaggta gggatacccg ctgaacttaa gcatatcaat aagcggagga a              591
```

<210> SEQ ID NO 51
<211> LENGTH: 1445
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Capnodiales, Family: Cladosporiaceae,
      Genus: Cladosporium

<400> SEQUENCE: 51

```
tccgtaggtg aacctgcgga gggatcatta caagtgaccc cggtctaacc accgggatgt     60
tcataaccct tgttgtccg actctgttgc ctccggggcg accctgcctt cgggcggggg    120
ctccgggtgg acacttcaaa ctcttgcgta actttgcagt ctgagtaaac ttaattaata    180
aattaaaact tttaacaacg gatctcttgg ttctggcatc gatgaagaac gcagcgaaat    240
gcgataagta atgtgaattg cagaattcag tgaatcatcg aatctttgaa cgcacattgc    300
gccccctggt attccggggg gcatgcctgt tcgagcgtca tttcaccact caagcctcgc    360
ttggtattgg caacgcggt ccgccgcgtg cctcaaatcg accggctggg tcttctgtcc    420
cctaagcgtt gtgaaacta ttcgctaaag ggtgttcggg aggctacgcc gtaaaacaac    480
cccatttcta aggttgacct cggatcaggt agggataccc gctgaactta agcatatcaa    540
taagcggagg aaaagaaacc aacagggatt gctctagtaa cggcgagtga agcagcaata    600
gctcaaattt gaaatctggc gtcttcgacg tccgagttgt aatttgtaga ggatgcttct    660
gagtaaccac cgacctaagt tccttggaac aggacgtcat agagggtgag aatcccgtat    720
gcggtcggaa agtgctcta tacgtagctc cttcgacgag tcgagttgtt tgggaatgca    780
gctctaaatg ggaggtaaat ttcttctaaa gctaaatatt ggccagagac cgatagcgca    840
```

```
caagtagagt gatcgaaaga tgaaaagcac tttggaaaga gagttaaaaa gcacgtgaaa      900
ttgttaaaag ggaagggatt gcaaccagac ttgctcgcgg tgttccgccg gtcttctgac      960
cggtctactc gccgcgttgc aggccagcat cgtctggtgc cgctggataa gacttgagga     1020
atgtagctcc ctcgggagtg ttatagcctc ttgtgatgca gcgagcgccg ggcgaggtcc     1080
gcgcttcggc taggatgctg gcgtaatggt cgtaatccgc ccgtcttgaa acacggacca     1140
aggagtctaa catctatgcg agtgttcggg tgtcaaaccc ctacgcgtaa tgaaagtgaa     1200
cggaggtgag aaccgcaagg tgcatcatcg accgatcctg atgtcttcgg atggatttga     1260
gtaagagcat agctgttggg acccgaaaga tggtgaacta tgcctgaata gggtgaagcc     1320
agaggaaact ctggtggagg ctcgcagcgg ttctgacgtg caaatcgatc gtcaaatttg     1380
ggtatagggg cgaaagacta atcgaaccat ctagtagctg gttcctgccg aagtttccct     1440
cagga                                                                 1445
```

<210> SEQ ID NO 52
<211> LENGTH: 1445
<212> TYPE: DNA
<213> ORGANISM: Cladosporium oxysporum

<400> SEQUENCE: 52

```
tccgtaggtg aacctgcgga gggatcatta caagtgaccc cggtctaacc accgggatgt       60
tcataaccct tgttgtccg actctgttgc ctccggggcg accctgcctt cgggcggggg       120
ctccgggtgg acacttcaaa ctcttgcgta actttgcagt ctgagtaaac ttaattaata      180
aattaaaact tttaacaacg gatctcttgg ttctggcatc gatgaagaac gcagcgaaat      240
gcgataagta atgtgaattg cagaattcag tgaatcatcg aatctttgaa cgcacattgc      300
gccccctggt attccggggg gcatgcctgt tcgagcgtca tttcaccact caagcctcgc      360
ttggtattgg gcaacgcggt ccgccgcgtg cctcaaatcg accggctggg tcttctgtcc      420
cctaagcgtt gtgaaactat tcgctaaagg gtgctcggg aggctacgcc gtaaaacaaa       480
cccatttcta aggttgacct cggatcaggt agggataccc gctgaactta agcatatcaa      540
taagcggagg aaaagaaacc aacagggatt gctctagtaa cggcgagtga agcagcaata      600
gctcaaattt gaaatctggc gtcttcgacg tccgagttgt aatttgtaga ggatgcttct      660
gagtaaccac cgacctaagt tccttggaac aggacgtcat agagggtgag aatcccgtat      720
gcggtcggaa aggtgctcta tacgtagctc cttcgacgag tcgagttgtt tgggaatgca      780
gctctaaatg ggaggtaaat ttcttctaaa gctaaatatt ggccagagac cgatagcgca      840
caagtagagt gatcgaaaga tgaaaagcac tttggaaaga gagttaaaaa gcacgtgaaa      900
ttgttaaaag ggaagggatt gcaaccagac ttgctcgcgg tgttccgccg gtcttctgac      960
cggtctactc gccgcgttgc aggccagcat cgtctggtgc cgctggataa gacttgagga     1020
atgtagctcc ctcgggagtg ttatagcctc ttgtgatgca gcgagcgccg ggcgaggtcc     1080
gcgcttcggc taggatgctg gcgtaatggt cgtaatccgc ccgtcttgaa acacggacca     1140
aggagtctaa catctatgcg agtgttcggg tgtcaaaccc ctacgcgtaa tgaaagtgaa     1200
cggaggtgag aaccgcaagg tgcatcatcg accgatcctg atgtcttcgg atggatttga     1260
gtaagagcat agctgttggg acccgaaaga tggtgaacta tgcctgaata gggtgaagcc     1320
agaggaaact ctggtggagg ctcgcagcgg ttctgacgtg caaatcgatc gtcaaatttg     1380
ggtatagggg cgaaagacta atcgaaccat ctagtagctg gttcctgccg aagtttccct     1440
cagga                                                                 1445
```

<210> SEQ ID NO 53
<211> LENGTH: 1497
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Pleosporales, Family: Pleosporaceae,
      Genus: Curvularia

<400> SEQUENCE: 53

| | | | | | |
|---|---|---|---|---|---|
| tccgtaggtg | aacctgcgga | gggatcatta | cacaataaca | tatgaaggct | gtacgccgct | 60 |
| gcgcccccgg | gccagttggc | tgaggctgga | ttatttatta | cccttgtctt | ttgcgcactt | 120 |
| gttgtttcct | gggcgggttc | gcccgcctcc | aggaccacac | cataaacctt | ttttatgcag | 180 |
| ttgcaatcag | cgtcagtaca | acaaatgtaa | atcatttaca | actttcaaca | acggatctct | 240 |
| tggttctggc | atcgatgaag | aacgcagcga | aatgcgatac | gtagtgtgaa | ttgcagaatt | 300 |
| cagtgaatca | tcgaatcttt | gaacgcacat | tgcgcccttt | ggtattccaa | agggcatgcc | 360 |
| tgttcgagcg | tcatttgtac | cctcaagctt | tgcttggtgt | tgggcgtttt | tgtctttggt | 420 |
| ttgccaaaga | ctcgccttaa | aacgattggc | agccggcctc | ctggttacgc | agcgcagcac | 480 |
| attttttgcgc | ttgcaatcag | caagagggcg | gcactccatc | aagactcctt | ctcacgtttg | 540 |
| acctcggatc | aggtagggat | acccgctgaa | cttaagcata | tcaataagcg | gaggaaaaga | 600 |
| aaccaacagg | gattgcccta | gtaacggcga | gtgaagcggc | aacagctcaa | atttgaaatc | 660 |
| tggctctttt | agggtccgag | ttgtaatttg | cagagggcgc | tttggctttg | gcagcggtcc | 720 |
| aagttccttg | gaacaggacg | tcacagaggg | tgagaatccc | gtacgtggtc | gctagctatt | 780 |
| gccgtgtaaa | gccccttcga | cgagtcgagt | tgtttgggaa | tgcagctcta | atgggaggt | 840 |
| aaatttcttc | taaagctaaa | tattggccag | agaccgatag | cgcacaagta | gagtgatcga | 900 |
| aagatgaaaa | gcactttgga | aagagagtca | aacagcacgt | gaaattgttg | aaagggaagc | 960 |
| gcttgcagcc | agacttgctt | gcagttgctc | atccgggctt | ttgcccggtg | cactcttctg | 1020 |
| taggcaggcc | agcatcagtt | tgggcggtgg | gataaaggtc | tctgacacgt | tccttccttc | 1080 |
| gggttggcca | tataggggag | acgtcatacc | accagcctgg | actgaggtcc | gcgcatctgc | 1140 |
| taggatgctg | gcgtaatggc | tgtaagcggc | ccgtcttgaa | acacggacca | aggagtctaa | 1200 |
| catctatgcg | agtgtttggg | tgtcaagccc | gagcgcgtaa | tgaaagtgaa | cggaggtggg | 1260 |
| aacccgcaag | ggcgcaccat | cgaccgatcc | tgaagtttac | ggaaggattt | gagtaagagc | 1320 |
| atggctgttg | gacccgaaa | gatggtgaac | tatgcttgaa | tagggtgaag | ccagaggaaa | 1380 |
| ctctggtgga | ggctcgcagc | ggttctgacg | tgcaaatcga | tcgtcaaatt | gggcatagg | 1440 |
| ggcgaaagac | taatcgaact | atctagtagc | tggttcctgc | cgaagtttcc | ctcagga | 1497 |

<210> SEQ ID NO 54
<211> LENGTH: 1472
<212> TYPE: DNA
<213> ORGANISM: Curvularia spicifera

<400> SEQUENCE: 54

| | | | | | |
|---|---|---|---|---|---|
| tccgtaggtg | aacctgcgga | gggatcatta | cacaataaaa | tacgaaggcc | gttcgcggct | 60 |
| ggactattta | ttacccttgt | cttttgcgca | cttgttgttt | cctgggcggg | ttcgctcgcc | 120 |
| accaggacca | caatataaac | cttttttatg | cagttgcaat | cagcgtcagt | ataacaaatg | 180 |
| taaatcattt | acaactttca | acaacggatc | tcttggttct | ggcatcgatg | aagaacgcag | 240 |

-continued

```
cgaaatgcga tacgtagtgt gaattgcaga attcagtgaa tcatcgaatc tttgaacgca      300
cattgcgccc tttggtattc caaagggcat gcctgttcga gcgtcatttg taccctcaag      360 cttttgcttgg tgttgggcgt ttttgtcttt ggcccgccaa agactcgcct taaaatgatt    420
ggcagccggc ctactggttt cgcagcgcag cacattttg cgcttgcaat cagcaaaaga      480
ggacggcaat ccatcaagac tccttctcac gtttgacctc ggatcaggta gggatacccg     540
ctgaacttaa gcatatcaat aagcggagga aaagaaacca acagggattg ccctagtaac     600
ggcgagtgaa gcggcaacag ctcaaatttg aaatctggct ctttcagagt ccgagttgta     660
atttgcagag ggcgctttgg ctttggcagc ggtccaagtt ccttggaaca ggacgtcaca     720
gagggtgaga atcccgtacg tggtcgctag ctattgccgt gtaaagcccc ttcgacgagt     780
cgagttgttt gggaatgcag ctctaaatgg gaggtaaatt tcttctaaag ctaaatattg     840
gccagagacc gatagcgcac aagtagagtg atcgaaagat gaaaagcact ttggaaagag    900
agtcaaacag cacgtgaaat tgttgaaagg gaagcgcttg cagccagact tgcttgcagt    960
tgctcatccg ggcttttgcc cggtgcactc ttctgcaggc aggccagcat cagtttgggc    1020
ggtgggataa aggtctctgt cacgtacctt ccttcgggtt ggccttatag gggagacgcc    1080
ataccaccag cctggactga ggtccgcgca tctgctagga tgctggcgta atggctgtaa   1140
gcggcccgtc ttgaaacacg gaccaaggag tctaacatct atgcgagtgt ttgggtgtca   1200
agcccgagcg cgtaatgaaa gtgaacggag gtgggaaccc gcaagggtgc accatcgacc  1260
gatcctgaag tttacggaag gatttgagta agagcatggc tgttgggacc cgaaagatgg   1320
tgaactatgc ttgaataggg tgaagccaga ggaaactctg gtggaggctc gcagcggttc   1380
tgacgtgcaa atcgatcgtc aaatttgggc ataggggcga agactaatc gaactatcta    1440 gtagctggtt cctgccgaag tttccctcag ga                                 1472
```

<210> SEQ ID NO 55
<211> LENGTH: 1503
<212> TYPE: DNA
<213> ORGANISM: Unknown
<220> FEATURE:
<223> OTHER INFORMATION: Kingdom: Fungi, Phylum: Ascomycota, Class: Dothideomycetes, Order: Pleosporales, Family: Pleosporaceae, Genus: Exserohilum

<400> SEQUENCE: 55

```
tcttggtcat ttagaggaag taaaagtcgt aacaaggtct ccgtaggtga acctgcggag      60
ggatcattac acaacaaaaa tatgagggtg tggtttgctg gcaacagcgt ccgccccaag    120 tattttttcac ccatgtcttt tgcgcacttt ttgtttcctg ggcgagttcg ctcgccacca    180
ggacccaacc ataaacctt ttttatgcag ttgcaatcag cgtcagtata ataattcaat     240
ttattaaaac tttcaacaac ggatctcttg gttctggcat cgatgaagaa cgcagcgaaa    300
tgcgatacgt agtgtgaatt gcagaattca gtgaatcatc gaatctttga acgcacattg    360 cgcccttgg tattccaaag gcatgcctg ttcgagcgtc atttgtaccc tcaagctttg     420
cttggtgttg ggcgtctttt tgtctctccc cttgttgggg gagactcgcc ttaaaacgat    480
tggcagccga cctactggtt tcggagcgc agcacaaatt tgcgccttcc aatccacggg    540
gcggcatcca gcaagccttt gttttctata acaaatccac attttgacct cggatcaggt    600
agggataccc gctgaactta agcatatcaa taagcggagg aaaagaaacc aacagggatt   660
gccctagtaa cggcgagtga agcggcaaca gctcaaattt gaaatctggc ctttcagag     720 tccgagttgt aatttgcaga gggcgctttg gctttggcag cggtccaagt tccttggaac   780
```

```
aggacgtcac agagggtgag aatcccgtac gtggtcgcta gctattgccg tgtaaagccc      840
cttcgacgag tcgagttgtt tgggaatgca gctctaaatg ggaggtaaat ttcttctaaa      900
gctaaatatt ggccagagac cgatagcgca caagtagagt gatcgaaaga tgaaaagcac      960
tttggaaaga gagtcaaaca gcacgtgaaa ttgttgaaag ggaagcgctt gcagccagac     1020
ttgcttgcag ttgctcatcc gggcttttgc ccggtgcact cttctgcagg caggccagca     1080
tcagtttggg cggtgggata aaggtctctg tcatgtacct ctcttcgggg aggccttata     1140
ggggaggcga cataccacca gcctagactg aggtccgcgc atctgctagg atgctggcgt     1200
aatggctgta agcggcccgt cttgaaacac ggaccaagga gtctaacatc tatgcgagtg     1260
tttgggtgtc aagcccgagc gcgtaatgaa agtgaacgga ggtgggaacc cgcaagggtg     1320
caccatcgac cgatcctgaa gtttacgaaa ggatttgagt aagagcatgg ctgttgggac     1380
ccgaaagatg gtgaactatg cttgaatagg gtgaagccag aggaaactct ggtggaggct     1440
cgcagcggtt ctgacgtgca aatcgatcgt caaatttggg catagggggcg aaagactaat     1500 cga                                                                   1503
```

<210> SEQ ID NO 56
<211> LENGTH: 1504
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Pleosporales, Family: Pleosporaceae,
      Genus: Exserohilum

<400> SEQUENCE: 56

```
tccgtaggtg aacctgcgga gggatcatta cacaacaaaa atatgagggt gtggtttgct       60
ggcaacagcg tccgccccaa gtattttcca cccatgtctt ttgcgcactt tttgtttcct      120
gggcgagttc gctcgccacc aggacccaac cataaacctt ttttttatgca gttgcaatca      180 gcgtcagtat aataattcaa tttattaaaa cttttcaacaa cggatctctt ggttctggca      240
tcgatgaaga acgcagcgaa atgcgatacg tagtgtgaat tgcagaattc agtgaatcat      300
cgaatctttg aacgcacatt gcgccctttg gtattccaaa gggcatgcct gttcgagcgt      360
catttgtacc ctcaagcttt gcttggtgtt gggcgtcttt tgtctctctcc ccttgttggg      420 ggagactcgc cttaaaacga ttggcagccg acctactggt tttcggagcg cagcacaaat      480
ttgcgccttc caatccacgg ggcggcatcc agcaagcctt tgttttctat aacaaatcca      540 catttgacc tcggatcagg tagggatacc cgctgaactt aagcatatca ataagcggag      600
gaaaagaaac caacagggat tgccctagta acggcgagtg aagcggcaac agctcaaatt      660
tgaaatctgg ctctttcaga gtccgagttg taatttgcag agggcgcttt ggcttttggca      720 gcggtccaag ttccttggaa caggacgtca cagagggtga gaatcccgta cgtggtcgct      780
agctattgcc gtgtaaagcc ccttcgacga gtcgagttgt ttgggaatgc agctctaaat      840
gggaggtaaa tttcttctaa agctaaatat tggccagaga ccgatagcgc acaagtagag      900
tgatcgaaag atgaaaagca ctttggaaag agagtcaaac agcacgtgaa attgttgaaa      960
gggaagcgct tgcagccaga cttgcttgca gttgctcatc cgggcttttg cccggtgcac     1020
tcttctgcag gcaggccagc atcagtttgg gcggtgggat aaaggtctct gtcatgtacc     1080
tctcttcggg gaggccttat aggggaggcg acataccacc agcctagact gaggtccgcg     1140
catctgctag gatgctggcg taatggctgt aagcggcccg tcttgaaaca cggaccaagg     1200
```

```
agtctaacat ctatgcgagt gtttgggtgt caagcccgag cgcgtaatga aagtgaacgg    1260
aggtgggaac ccgcaagggt gcaccatcga ccgatcctga agtttacgga aggatttgag    1320
taagagcatg gctgttggga cccgaaagat ggtgaactat gcttgaatag ggtgaagcca    1380
gaggaaactc tggtggaggc tcgcagcggt tctgacgtgc aaatcgatcg tcaaatttgg    1440 gcatagggc gaaagactaa tcgaactatc tagtagctgg ttcctgccga agtttccctc     1500
agga                                                                 1504
```

<210> SEQ ID NO 57
<211> LENGTH: 624
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Pleosporales, Family: Didymosphaeriaceae,
      Genus: Paraconiothyrium

<400> SEQUENCE: 57

```
attagaggaa gtaaaagtcg taacaaggtt tccgtaggtg aacctgcgga aggatcatta     60
tccatctcaa ccaggtgcgg tcgcggccct cggggttct ctcccgggtg gtaggggtaa    120
caccctcacg cgccgcattc ctgcatcctt tttttacgag cacctttcgt tctccttcgg   180
cggggcaacc tgccgctgga acttaacaaa accttttttg catctagcat tacctgttct   240
gatacaaaca atcgttacaa cttttcaacaa tggatctctt ggctctggca tcgatgaaga   300
acgcagcgaa atgcgataag tagtgtgaat tgcagaattc agtgaatcat cgaatctttg   360
aacgcacatt gcgccccttg gtattccatg gggcatgcct gttcgagcgt catctacacc   420
ctcaagctct gcttggtgtt gggcgtctgt cccgccttcg cgcgcggact cgccccaaat   480
tcattggcag cggtccttgc ctcctctcgc gcagcacaat tgcgtctgcg ggggggcgtg   540
gcccgcgtcc acgaagcaac attaccgtct ttgacctcgg atcaggtagg gatacccgct   600
gaacttaagc atatcaataa ggcg                                           624
```

<210> SEQ ID NO 58
<211> LENGTH: 624
<212> TYPE: DNA
<213> ORGANISM: Unknown
<220> FEATURE:
<223> OTHER INFORMATION: Kingdom: Fungi, Phylum: Ascomycota, Class:
      Eurotiomycetes, Order: Eurotiales, Family: Aspergillaceae, Genus:
      Penicillium

<400> SEQUENCE: 58

```
tcttggtcat ttagaggaag taaaagtcgt aacaaggttt ccgtaggtga acctgcggaa     60
ggatcattac cgagtgaggg ccctctgggt ccaacctccc accgtgtttt attttacctt   120
gttgcttcgg cgggcccgcc ttaactggcc gcgggggggc ttacgccccc gggcccgcgc   180
ccgccgaaga caccctcgaa ctctgtctga agattgtagt ctgagtgaaa atataaatta   240
tttaaaactt tcaacaacgg atctcttggt tccggcatcg atgaagaacg cagcgaaatg   300
cgatacgtaa tgtgaattgc aaattcagtg aatcatcgag tctttgaacg cacattgcgc   360 ccctggtat tccgggggc atgcctgtcc gagcgtcatt gctgccctca gcacggctt    420 gtgtgttggg ccccgtcctc cgatcccggg ggacgggccc gaaaggcagc ggcggcaccg   480
cgtccggtcc tcgagcgtat ggggctttgt caccgctct gtaggccgg ccggcgcttg   540 ccgatcaacc caaatttta tccaggttga cctcggatca ggtagggata cccgctgaac   600
ttaagcatat caataagcgg agga                                           624
```

-continued

<210> SEQ ID NO 59
<211> LENGTH: 1487
<212> TYPE: DNA
<213> ORGANISM: Unknown
<220> FEATURE:
<223> OTHER INFORMATION: Kingdom: Fungi, Phylum: Ascomycota, Class:
      Eurotiomycetes, Order: Eurotiales, Family: Aspergillaceae, Genus:
      Penicillium

<400> SEQUENCE: 59

```
tccgtaggtg aacctgcgga aggatcatta ccgagtgagg gccctctggg tccaacctcc      60
cacccgtgtt tattttacct tgttgcttcg gcgggcccgc cttaactggc cgccgggggg     120
cttacgcccc cgggcccgcg cccgccgaag acaccctcga actctgtctg aagattgtag     180
tctgagtgaa aatataaatt atttaaaact ttcaacaacg gatctcttgg ttccggcatc     240
gatgaagaac gcagcgaaat gcgatacgta atgtgaattg caaattcagt gaatcatcga     300
gtctttgaac gcacattgcg ccccctggta ttccgggggg catgcctgtc cgagcgtcat     360
tgctgccctc aagcacggct tgtgtgttgg gccccgtcct ccgatcccgg gggacgggcc     420
cgaaaggcag cggcggcacc cgtccggtc ctcgagcgta tggggctttg tcacccgctc     480
tgtaggcccg gccggcgctt gccgatcaac ccaaattttt atccaggttg acctcggatc     540
aggtagggat acccgctgaa cttaagcata tcaataagcg gaggaaaaga aaccaacagg     600
gattgcccca gtaacggcga gtgaagcggc aagagctcaa atttgaaagc tggctccttc     660
ggggtccgca ttgtaatttg tagaggatgc ttcgggagcg gtccccatct aagtgccctg     720
gaacgggacg tcatagaggg tgagaatccc gtatgggatg gggtgtccgc gcccgtgtga     780
agctccttcg acgagtcgag ttgtttggga atgcagctct aaatgggtgg taaatttcat     840
ctaaagctaa atattggccg gagaccgata gcgcacaagt agagtgatcg aaagatgaaa     900
agcactttga aaagagagtt aaaaagcacg tgaaattgtt gaaagggaag cgcttgcgac     960
cagactcgct cgcggggttc agccggcatt cgtgccggtg tacttccccg cgggcgggcc    1020
agcgtcggtt tgggcggtcg gtcaaaggcc ctcggaaggt aacgcccta ggggcgtctt    1080
atagccgagg gtgcaatgcg acctgcctag accgaggaac gcgcttcggc tcggacgctg    1140
gcataatggt cgtaaacgac ccgtcttgaa acacggacca aggagtctaa catctacgcg    1200
agtgttcggg tgtcaaaccc gtgcgcgaag tgaaagcgaa cggaggtggg aaccctcacg    1260
ggtgcaccat cgaccgatcc tgaagtcttc ggatggattt gagtaagagc gtagctgttg    1320
ggacccgaaa gatggtgaac tatgcctgaa tagggcgaag ccagaggaaa ctctggtgga    1380
ggctcgtagc ggttctgacg tgcaaatcga tcgtcgaatt tgggtatagg ggcgaaagac    1440
taatcgaacc atctggtagc tggttcctgc cgaagtttcc ctcagga                 1487
```

<210> SEQ ID NO 60
<211> LENGTH: 1454
<212> TYPE: DNA
<213> ORGANISM: Pseudeurotium bakeri

<400> SEQUENCE: 60

```
tccgtaggtg aacctgcgga aggatcatta aagagacgtt gcccttcggg gtatacctcc      60
caccctttgt ttattatacc tttgttgctt tggcgggccc gtcctcggac caccggcttc     120
ggctggtcag tgcccgccag aggacctaaa actctgtttg ttcatattgt ctgagtacta     180
tataatagtt aaaactttca acaacggatc tcttggttct ggcatcgatg aagaacgcag     240
```

-continued

```
cgaaatgcga taagtaatgt gaattgcaga attcagtgaa tcatcgaatc tttgaacgca      300
cattgcgccc cctggtattc cgggggggcat gcctgttcga gcgtcattac aaccctcaag     360
ctctgcttgg tatttgggctc tgccggtccc ggcaggcctt aaaatcagtg gcggtgccat    420
tcggcttcaa gcgtagtaat tcttctcgct ttggagaccc gggtgcgtgc ttgccagcaa     480
cccccaattt tttcaggttg acctcggatc aggtagggat acccgctgaa cttaagcata     540
tcaataagcg gaggaaaaga accaacagg gattgcctca gtaacggcga gtgaagcggc      600
aacagctcaa atttgaaatc tggcctcacg gtccgagttg taatttgtag aggatgcttc     660
gagcatggtc tggcctaagt tccttggaac aggacgtcat agagggtgag aatcccgtat     720
gcggccaggt gcctacgctc atgtgaagct ccttcgacga gtcgagttgt ttgggaatgc     780
agctcaaaat gggtggtaaa tttcatctaa agctaaatat tggccagaga ccgatagcgc     840
acaagtagag tgatcgaaag atgaaaagca ctttggaaag agagttaaac agtacgtgaa     900
attgttgaaa gggaagcgct tgcaaccaga cttgcgtgcg gccgatcatc cggtgttctc     960
accggtgcac tcggtcgcgc tcaggccagc atcggttttg gtggttggat aaaggcccta   1020
ggaatgtagc ttctctcggg gagtgttata gcctagggtg caatgcagcc caccgggacc   1080
gaggaccgcg cttcggctag gatgctgcg taatggttgt aagcgacccg tcttgaaaca    1140
cggaccaagg agtctaacat ctatgcgagt gtttgggtgt caaacccata cgcgtaatga    1200
aagtgaacga aggtgagaac ccttaagggt gcatcatcga ccgatcctga tgtcttcgga    1260
tggatttgag taagagcata gctgttggga cccgaaagat ggtgaactat gcctgaatag   1320
ggtgaagcca gaggaaactc tggtggaggc tcgcagcggt tctgacgtgc aaatcgatcg   1380
tcaaatttgg gcataggggc gaaagactaa tcgaaccatc tagtagctgg ttcctgccga   1440
agtttccctc agga                                                     1454
```

<210> SEQ ID NO 61
<211> LENGTH: 520
<212> TYPE: DNA
<213> ORGANISM: Phialemonium inflatum

<400> SEQUENCE: 61

```
cattacagag tttaacgact cccaaaccac tgtgaacata cccgtaccgt tgcctcggcg      60
ggcggcccca gggcggggcc gcagcctccc cagcggaggc gcccgccgca ggtcgcaaaa     120
ctataactat atttagtggc atctctgagt aacttccaaa caatcaaaac tttcaacaac     180
ggatctcttg gttctggcat cgatgaagaa cgcagcgaaa tgcgataagt aatgtgaatt     240
gcagaattca gtgaatcatc gaatctttga acgcacattg cgcccgccag cattctggcg     300
ggcatgcctg tccgagcgtc atttcaaccc tcaagccctg cttggtgttg ggcactacg      360 cgcgagcgta ggccctcaaa atcagtggcg gacccgctgg aggtccgggc gtagtaacac     420
atctcgcccg aggtccccag cgtgcccctg ccgttaaacc cccaaattta cagaaggttg     480
acctcggatc aggtaggaat acccgctgaa cttaagcata                            520
```

<210> SEQ ID NO 62
<211> LENGTH: 1480
<212> TYPE: DNA
<213> ORGANISM: Enterobacter cowanii

<400> SEQUENCE: 62

```
tggctcagat tgaacgctgg cggcaggcct aacacatgca agtcgaacgg taacaggaag      60
cagcttgctg cttcgctgac gagtggcgga cgggtgagta atgtctggga aactgcctga    120
```

-continued

```
tggaggggga taactactgg aaacggtagc taataccgca taacgtcgca agaccaaaga    180
gggggacctt cgggcctctt gccatcagat gtgcccagat gggattagct agtaggtggg    240
gtaacggctc acctaggcga cgatccctag ctggtctgag aggatgacca gccacactgg    300
aactgagaca cggtccagac tcctacggga ggcagcagtg gggaatattg cacaatgggc    360
gcaagcctga tgcagccatg ccgcgtgtat gaagaaggcc ttcgggttgt aaagtacttt    420
cagcggggag gaaggcgatg tggttaataa ccgcgtcgat tgacgttacc cgcagaagaa    480
gcaccggcta actccgtgcc agcagccgcg gtaatacgga gggtgcaagc gttaatcgga    540
attactgggc gtaaagcgca cgcaggcggt ctgtcaagtc ggatgtgaaa tccccgggct    600
caacctggga actgcatccg aaactggcag gcttgagtct cgtagagggg ggtagaattc    660
caggtgtagc ggtgaaatgc gtagagatct ggaggaatac cggtggcgaa ggcggccccc    720
tggacgaaga ctgacgctca ggtgcgaaag cgtggggagc aaacaggatt agataccctg    780
gtagtccacg ccgtaaacga tgtcgacttg gaggttgtgc ccttgaggcg tggcttccgg    840
agctaacgcg ttaagtcgac cgcctgggga gtacggccgc aaggttaaaa ctcaaatgaa    900
ttgacggggg cccgcacaag cggtggagca tgtggtttaa ttcgatgcaa cgcgaagaac    960
cttacctggt cttgacatcc acagaacttg ccagagatgg attggtgcct tcgggaactg   1020
tgagacaggt gctgcatggc tgtcgtcagc tcgtgttgtg aaatgttggg ttaagtcccg   1080
caacgagcgc aacccttatc ctttgttgcc agcggtccgg ccgggaactc aaaggagact   1140
gccagtgata aactggagga aggtggggat gacgtcaagt catcatggcc cttacgacca   1200
gggctacaca cgtgctacaa tggcgcatac aaagagaagc aatctcgcga gagctagcgg   1260
acctcataaa gtgcgtcgta gtccggattg gagtctgcaa ctcgactcca tgaagtcgga   1320
atcgctagta atcgtgaatc agaatgtcac ggtgaatacg ttcccgggcc ttgtacacac   1380
cgcccgtcac accatgggag tgggttgcaa aagaagtagg tagcttaacc ttcgggaggg   1440
cgcttaccac tttgtgattc atgactgggg tgaagtcgta                          1480
```